United States Patent
Li et al.

(10) Patent No.: US 10,774,315 B2
(45) Date of Patent: *Sep. 15, 2020

(54) ENGINEERED GLUCOSYLTRANSFERASES

(71) Applicant: DUPONT INDUSTRIAL BIOSCIENCES USA, LLC, Wilmington, DE (US)

(72) Inventors: Yougen Li, Pennington, NJ (US); Ellen D. Semke, Newark, DE (US); Mark S. Payne, Wilmington, DE (US); Jared B. Parker, Elkton, MD (US); Susan Marie Hennessey, Avondale, PA (US); Slavko Kralj, Copenhagen K (DK); Veli Alkan, Palo Alto, CA (US); Richard Bott, Palo Alto, CA (US)

(73) Assignee: DUPONT INDUSTRIAL BIOSCIENCES USA, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 16/127,288

(22) Filed: Sep. 11, 2018

(65) Prior Publication Data
US 2019/0078062 A1 Mar. 14, 2019

Related U.S. Application Data
(60) Provisional application No. 62/557,834, filed on Sep. 13, 2017.

(51) Int. Cl.
*C12N 9/10* (2006.01)
*C12P 19/18* (2006.01)
*C12P 19/04* (2006.01)
*C08B 37/00* (2006.01)
*G16B 25/00* (2019.01)

(52) U.S. Cl.
CPC ........ *C12N 9/1048* (2013.01); *C08B 37/0009* (2013.01); *C12N 9/1051* (2013.01); *C12P 19/04* (2013.01); *C12P 19/18* (2013.01); *C12Y 204/01* (2013.01); *G16B 25/00* (2019.02)

(58) Field of Classification Search
CPC ............... C12N 9/1048; C12N 9/1051; C08B 37/0009; C12P 19/04; C12P 19/18; G16B 25/00; C12Y 204/01
See application file for complete search history.

(56) References Cited

U.S. PATENT DOCUMENTS

| | | |
|---|---|---|
| 5,952,205 A | 9/1999 | Catani et al. |
| 6,207,149 B1 | 3/2001 | Fuglsang et al. |
| 6,242,225 B1 | 6/2001 | Catani et al. |
| 6,660,502 B2 | 12/2003 | Catani et al. |
| 7,000,000 B1 | 2/2006 | O'Brien |
| 7,524,645 B2 | 4/2009 | Monsan et al. |
| 8,269,064 B2 | 9/2012 | Kok-Jacon et al. |
| 8,859,848 B2 * | 10/2014 | Jugde ............... C12N 9/1048 435/320.1 |
| 8,871,474 B2 | 10/2014 | Payne et al. |
| 9,228,177 B2 | 1/2016 | Payne et al. |
| 9,260,701 B2 | 2/2016 | Payne et al. |
| 9,260,702 B2 | 2/2016 | Payne et al. |
| 9,284,539 B2 | 3/2016 | Payne et al. |
| 9,284,540 B2 | 3/2016 | Payne et al. |
| 9,296,996 B2 | 3/2016 | Payne et al. |
| 9,296,997 B2 | 3/2016 | Payne et al. |
| 9,399,765 B2 | 7/2016 | Monsan et al. |
| 9,968,910 B2 * | 5/2018 | Behabtu ............... B01J 20/24 |
| 10,301,604 B2 * | 5/2019 | Li ............... C12N 9/1051 |
| 10,308,968 B2 | 6/2019 | Payne et al. |
| 2002/0155568 A1 | 10/2002 | Van Geel-Schutten et al. |
| 2006/0057704 A1 | 3/2006 | Schlothauer et al. |
| 2006/0127328 A1 | 6/2006 | Monsan et al. |
| 2011/0144317 A1 | 6/2011 | Mulard et al. |
| 2013/0036968 A1 | 2/2013 | Suzuki et al. |
| 2013/0096502 A1 | 4/2013 | Kawamoto et al. |
| 2013/0096511 A1 | 4/2013 | MacArthur |
| 2013/0244287 A1 | 9/2013 | O'Brien et al. |
| 2013/0244288 A1 | 9/2013 | O'Brien et al. |
| 2014/0087431 A1 | 3/2014 | Payne et al. |
| 2015/0218532 A1 | 8/2015 | Cote et al. |
| 2015/0232785 A1 | 8/2015 | Paullin et al. |
| 2015/0232819 A1 | 8/2015 | Paullin et al. |
| 2017/0002335 A1 | 1/2017 | Payne et al. |
| 2017/0002336 A1 | 1/2017 | Payne et al. |
| 2017/0166938 A1 | 6/2017 | Nagy et al. |
| 2017/0218093 A1 | 8/2017 | Cheng et al. |
| 2018/0340199 A1 | 11/2018 | Nagy et al. |
| 2019/0078062 A1 | 3/2019 | Li et al. |
| 2019/0078063 A1 * | 3/2019 | Li ............... C12N 9/1048 |

FOREIGN PATENT DOCUMENTS

| | | |
|---|---|---|
| JP | 2000175694 A | 6/2000 |
| WO | 2013/036918 A2 | 3/2013 |
| WO | 2015183714 A1 | 12/2015 |
| WO | 2015183721 A1 | 12/2015 |
| WO | 2015183722 A1 | 12/2015 |
| WO | 2015183724 A1 | 12/2015 |
| WO | 2015183726 A1 | 12/2015 |
| WO | 2015183729 A1 | 12/2015 |
| WO | 2018052942 A1 | 3/2018 |

OTHER PUBLICATIONS

Broun et al., Catalytic plasticity of fatty acid modification enzymes underlying chemical diversity of plant lipids. Science, 1998, vol. 282: 1315-1317. (Year: 1998).*

Chica et al., Semi-rational approaches to engineering enzyme activity: combining the benefits of directed evolution and rational design. Curr. Opi. Biotechnol., 2005, vol. 16: 378-384. (Year: 2005).*

(Continued)

*Primary Examiner* — Ganapathirama Raghu

(57) ABSTRACT

Disclosed herein are glucosyltransferases with modified amino acid sequences. Such engineered enzymes synthesize alpha-glucan products having increased molecular weight. Further disclosed are reactions and methods in which engineered glucosyltransferases are used to produce alpha-glucan.

27 Claims, No Drawings
Specification includes a Sequence Listing.

(56) References Cited

OTHER PUBLICATIONS

Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Database UniProt Accession No. A01A1FOBMZ6, XP002785922, Feb. 15, 2017.
International Search Report and Written Opinion, PCT/US2018/050345, dated Jan. 14, 2019.
Simpson et al., Four Glucosyltransferases, GTFJ, GTFK, GTFL and GTFM, From *Streptococcus salivarius* ATCC 25975, Microbiology, vol. 141 (1995), pp. 1451-1460.
Leemhuis et al., Glucansucrases: Three-Dimensional Structures, Reactions, Mechanism, α-Glucan Analysis and Their Implications in Biotechnology and Food Applications, Journal of Biotechnology, vol. 163 (2013), pp. 250-272.
Monchois et al., Glucansucrases: Mechanism of Action and Structure-Function Relationships, FEMS Microbiology Reviews, vol. 23 (1999), pp. 131-151.
Monchois et al., Isolation of an Active Catalytic Core of *Streptococcus downei* MFE28 GTF-I Glucosyltransferase, Journal of Bacteriology, vol. 181, No. 7 (1999), pp. 2290-2292.
Rogers, Chapter 5: The Molecular Biology of Cariogenic Bacteria, From Molecular Biology, Horizon Scientific Press, Roy RB Russell (2008), pp. 120-122.
Konishi et al., Structure and Enzymatic Properties of Genetically Truncated Forms of the Water-Insoluble Glucan-Synthesizing Glucosyltransferase From *Streptococcus sobrinus*, J. Biochem., vol. 126 (1999), pp. 287-295.
Tsumuraya et al., Structure of the Water-Insoluble α-D-Glucan of *Streptococcus salivarius* HHT, Carbohydrate Research, vol. 74 (1979), pp. 217-225.
Weaver et al., Weighted Intrinsic Viscosity Relationships for Polysaccharide Mixtures in Dilute Aqueous Solutions, Journal of Applied Polymer Science, vol. 35 (1988), pp. 1631-1637.
Yakushiji et al., Inter-Serotype Comparison of Polysaccharides Produced by Extracellular Enzymes From *Streptococcus mutans*, Carbohydrate Research, vol. 127 (1984), pp. 253-266.
Yoshimi et al., Functional Analysis of the α-1,3-Glucan Synthase Genes AGSA and AGSB in Aspergillus Nidulans: AGSB is the Major α-1,3-Glucan Synthase in This Fungus, PLOS One, vol. 8, Issue 1 (2013), pp. 1-16.
Cote and Skory, Effects of mutations at threonine-654 on the insoluble glucan synthesized by Leuconostoc mesenteroides NRRL B-1118 glucansucrase, Appl. Microbiol. Biotechnol., vol. 98, (2014), pp. 6651-6658.
Chia et al., Functional Analyses of a Conserved Region in Glucosyltransferases of *Streptococcus mutans*, Infection and Immunity, vol. 66, No. 10, pp. 4797-4803 (1998).
Meng et al., Characterization of the glucansucrase GTF180 W1065 mutant enzymes producing polysaccharides and oligosaccharides with altered linkage composition, Food Chem., vol. 217, pp. 81-90 (2017).
Meng et al., Characterization of the Functional Roles of Amino Acid Residues in Acceptor-binding Subsite +1 in the Active Site of the Glucansucrase GTF180 from Lactobacillus reuteri 180*, J. Bio. Chem., vol. 290, No. 50, pp. 30131-30141 (2015).
Monchois et al., Mutagenesis of Asp-569 of Glucosyltransferase I Glucansucrase Modulates Glucan and Oligosaccharide Synthesis, Appl. Env. Micro., vol. 66, No. 5, pp. 1923-1927 (2000).
Monchois et al., Characterization of Leuconostoc mesenteroides NRRL B-512F dextransucrase (DSRS) and identification of aminoacid residues playing a key role in enzyme activity, Appl. Micro. Bio. vol. 48, pp. 465-472 (1997).
Van Hijum et al., Structure-Function Relationships of Glucansucrase and Fructansucrase Enzymes from Lactic Acid Bacteria, Micro. Mol. Bio. Rev., vol. 70, No. 1, pp. 157-176 (2006).
Meng et al., Structure-function relationships of family GH70 glucansucrase and 4,6-α-glucanotransferase enzymes, and their evolutionary relationships with family GH13 enzymes, Cell. Mol. Life Sci., vol. 73, pp. 2681-2706 (2016).
Shimamura et al., Identification of Amino Acid Residues in *Streptococcus mutans* Glucosyltransferases Influencing the Structure of the Glucan Product, Journal of Bacteriology, vol. 176, pp. 4845-4850 (1994.
Cote et al., Some Structural Features of an Insoluble-D-Glucan From a Mutant Strain of Leuconostoc Mesenteroides NRRL B-1355, Journal of Industrial Microbiology & Biotechnology, vol. 23 (1999), pp. 656-660.
Meng et al., Residue Leu 940 has a Crucial Role in the Linkage and Reaction Specificity of the Glucansucrase GTF180 of the Probiotic Bacterium *Lactobacillus reuteri* 180, Journal of Biological Chemistry, vol. 289, No. 47 (2014), pp. 32773-32782.
Castillo et al., Synthesis of Levan in Water-Miscible Organic Solvents, Journal of Biotechnology, vol. 114 (2004), pp. 209-217.
Aman et al., Influence of Temperature, Metal Ions and Organic Solvents on Extracellular Glucansucrase Activity of Leuconostoc Mesenteroidses AA1, J. Chem. Soc., vol. 30, No. 6 (2008), pp. 849-853.
Girard et al., Activity and Stability of Dextransucrase From Leuconostoc Mesenteroides NRRL B-512F in the Presence of Organic Solvents, Enzyme and Microbial Technology, vol. 24 (1999), pp. 425-432.
Chambert et al., Study of the Effect of Organic Solvents on the Synthesis of Levan and the Hydrolysis of Sucrose by Bacillus Subtilis Levansucrase, Carbohydrate Research, vol. 191 (1989), pp. 117-123.
Kralj et al., Rational Transformation of Lactobacillus Reuteri 121 Reuteransucrase Into a Dextrasucrase, Biochemistry, vol. 44 (2005), pp. 9206-9216.
Ozimek et al., Single Amino Acid Residue Changes in Subsite-1 of Inulosucrase From Lactobacillus Reuteri 121 Strongly Influence the Size of Products Synthesized, FEBS Journal, vol. 273 (2006), pp. 4104-4113.
Kralj et al., Biochemical and Molecular Characterization of Lactobacillus Reuteri 121 Reuteransucrase, Microbiology, vol. 150 (2004), pp. 2099-2112.
Van Der Veen et al., Hydrophobic Amino Acid Residues in the Acceptor Binding Site are Main Determinants for Reaction Mechanism and Specificity of Cyclodextrin-Glycosyltransferase, the Journal of Biological Chemistry, vol. 276, No. 48 (2001), pp. 4457-44562.
Kralj et al., Role of Asparagine 1134 in Glucosidic Bond and Transglycosylation Specificity of Reuteransucrase From Lactobacillus Reuteri 121, FEBS Journal, vol. 273 (2006), pp. 3735-3742.
Kang et al., Bioengineering of Leuconostoc Mesenteroides Glucansucrases That Gives Selected Bond Formation for Glucan Synthesis and/or Acceptor-Product Synthesis, Journal of Agricultural and Food Chemistry, vol. 59 (2011), pp. 4148-4155.
Irague et al., Combinatorial Engineering of Dextransucrase Specificity, PLOS One, vol. 8, No. 10 (2013), pp. 1-14.
Vujicic-Zagar et al., Crystal Structure of 117 KDA Glucansucrase Fragment Provides Insight Into Evolution and Product Specificity of GH70 Enzymes, PNAS, vol. 107, No. 50 (2010), pp. 21406-21411.
Van Leeuwen et al., Structural Characterization of Bioengineered α-D-Glucans Produced by Mutant Glucansucrase GTF180 Enzymes of Lactobacillus Reuteri Strain 180, Biomacromolecules, vol. 10 (2009), pp. 580-588.

(56) References Cited

OTHER PUBLICATIONS

Van Leeuwen et al., Structural of Bioengineered α-D-Glucan Produced by a Triple Mutant of the Glucansucrase GTF180 Enzyme From Lactobacillus Reuteri Strain 180: Generation of (α1->4) Linkages in a Native (1->3)(1->6)-α-D-Glucan, Biomacromolecules, vol. 9 (2008), pp. 2251-2258.

\* cited by examiner

SEQUENCE LISTING

```
<160> NUMBER OF SEQ ID NOS: 67

<210> SEQ ID NO 1
<211> LENGTH: 4308
<212> TYPE: DNA
<213> ORGANISM: Streptococcus sobrinus

<400> SEQUENCE: 1
atggttgacg gcaaatacta ctattatgat caggacggta acgtaaagaa gaatttcgcg      60
gtgagcgttg gtgacaaaat ctactacttc gatgaaactg gtgcatataa ggataccagc     120
aaagtggacg ccgacaagag cagcagcgcg gttagccaaa acgcgaccat ctttgcggcg     180
aataaccgtg cgtacagcac ctctgcaaag aattttgaag cggtggataa ctacctgacc     240
gcagacagct ggtatcgtcc gaaatccatc ctgaaggacg gcaaaacctg gaccgagagc     300
ggtaaggatg atttccgtcc actgctgatg gcatggtggc ctgacaccga aactaagcgc     360
aactacgtga actatatgaa taaagtggtc ggtattgaca agacgtacac tgcggaaacg     420
tcgcaagcgg atttgaccgc agcggcggag ctggttcaag cgcgtatcga gcagaagatt     480
accagcgaaa acaacaccaa atggctgcgc gaagcaatct ccgcgttcgt taagacgcag     540
cctcagtgga acggcgagtc cgaaaagccg tatgacgatc acttgcagaa cggtgcgctg     600
ctgtttgata ccaaaccgga cctgacgcca gacacccaaa gcaattaccg tttgctgaac     660
cgtaccccga ccaatcagac tggtagcctg gatagccgtt ttacgtataa tccgaatgac     720
ccgttgggcg gctacgattt cttgctggcg aacgacgttg acaatagcaa tccggtcgtc     780
caggctgaac agttgaactg gctgcattat ctgctgaact ttggctctat ttacgctaac     840
gatgccgacg ccaattttga cagcattcgc gttgatgccg tcgataatgt cgatgctgat     900
ctgctgcaaa tcagcagcga ttacctgaaa gcagcgtatg gcatcgacaa gaataacaag     960
aatgcgaaca accatgttag catcgtcgaa gcgtggagcg acaatgatac cccgtatttg    1020
```

```
cacgacgatg gcgataatct gatgaacatg gacaacaaat ttcgcctgtc catgctgtgg   1080
agcctggcaa agccgctgga caaacgtagc ggtttgaacc cgctgattca caatagcctg   1140
gtggaccgcg aggtggacga tcgtgaagtg gaaaccgtgc cgtcctacag ctttgctcgt   1200
gcacatgata gcgaggtgca ggacatcatc cgtgacatta tcaaggctga gattaaccca   1260
aatagctttg ttatagctt cactcaagaa gagatcgagc aagcctttaa gatttacaac   1320
gaggatttga agaaaacgga caagaaatac acccactaca atgtgccgct gagctacacc   1380
ctgctgctga ccaacaaggg cagcatcccg cgtgtgtact atggtgatat gttcaccgat   1440
gatggccaat acatggcaaa caagaccgtc aactacgacg caatcgagag cctgctgaaa   1500
gcccgtatga aatatgtcag cggtggccaa gcaatgcaga actatcaaat tggtaatggc   1560
gagattttga ccagcgtgcg ctatggtaaa ggtgccctga agcagagcga taagggtgac   1620
gcgacgacgc gcactagcgg tgttggcgtg gttatgggta atcagccgaa cttctccctg   1680
gacggtaaag ttgtggccct gaatatgggt gcggcccatg cgaatcaaga ataccgtgca   1740
ctgatggtca gcactaaaga cggtgtggca acttacgcaa ccgatgctga cgcatccaaa   1800
gcgggcctgg tcaagcgtac cgacgagaac ggctacctgt acttcctgaa tgatgatctg   1860
aagggcgtcg cgaaccctca ggtttccggc ttcttgcaag tgtgggttcc agttggtgcc   1920
gccgatgacc aggacattcg cgtcgccgcc agcgacacgg cgagcacgga tggtaaaagc   1980
ctgcatcaag atgcggcgat ggacagccgc gtcatgtttg agggtttcag caattttcaa   2040
tccttcgcga ccaaagaaga agaatacacg aatgttgtta tcgcgaacaa tgtcgataag   2100
ttcgttagct ggggtatcac cgattttgaa atggctccgc agtatgttag cagcaccgac   2160
ggtcagttct tggacagcgt catccagaat ggctatgcgt ttactgatcg ctatgatctg   2220
ggtatgtcca aggcgaacaa gtatggcacg gcagaccaac tggttaaggc aatcaaagcc   2280
ctgcacgcta aaggcctgaa agttatggcg gactgggtcc ggatcaaat gtacacccttt   2340 ccaaaacagg aagttgtgac cgttacccgc accgacaaat tcggtaaacc gatcgccggc   2400
tctcaaatca atcacagctt gtatgtgacc gacaccaaat ccagcggcga cgactaccaa   2460
gcgaagtacg gcggtgcctt cctggatgaa ctgaaagaaa agtacccgga actgttcacg   2520
aaaaagcaaa ttagcacggg ccaagcgatt gatccgagcg tgaaaatcaa gcagtggagc   2580
gcaaaatact tcaatggttc gaatatcctg ggtcgcggtg cggactatgt gctgagcgac   2640
caggtcagca ataagtattt caacgtggcg agcgacacct tgttcctgcc gtccagcctg   2700
ctgggcaagg tcgtggagag cggcattcgt tacgacggca agggttacat ctacaacagc   2760
tccgcgaccg gcgatcaggt caaagcgtct ttcattacgg aagccggtaa cctgtattac   2820
ttcggcaaag acggttacat ggttactggt gcccagacga ttaatggcgc caactacttc   2880
ttcctggaaa acggtacggc actgcgtaat acgatttaca ccgatgctca aggtaatagc   2940
cactattacg cgaatgatgg caaacgctat gaaaatggct atcaacagtt cggtaacgat   3000
tggcgctact ttaaagatgg taacatggca gtcggcctga ccacgttga tggcaacgtg   3060 caatactttg acaaagacgg cgtccaggca aaggataaga ttatcgtcac ccgtgatggc   3120
aaggtccgtt acttcgatca gcacaacggt aacgcggcga ccaacacgtt cattgctgat   3180
aaaactggcc attggtatta cctgggtaaa gatggcgtcg cggtgactgg cgcccagacc   3240
gtcggcaaac aaaaactgta cttcgaggcc aacggtcaac aagttaaagg tgactttgtt   3300
acgtccgatg agggcaaact gtatttctat gacgttgatt ctggtgacat gtggacggac   3360
accttcatcg aggataaggc gggcaactgg ttctatttgg gcaaggatgg tgcggcagtt   3420
```

-continued

```
acgggtgccc aaacgattcg cggtcagaag ctgtacttca aggccaatgg tcaacaggtc    3480
aagggtgaca ttgttaaggg caccgacggt aaaatccgct actatgatgc aaaatccggt    3540
gaacaggtgt tcaacaaaac ggtgaaagct gcggatggca aaacgtatgt tatcggtaat    3600
gatggtgtcg cggtggaccc tagcgtggtt aaaggtcaaa cctttaagga cgcttcgggc    3660
gctctgcgtt tctacaactt gaagggtcaa ctggtcactg cagcggctg gtatgaaacc    3720 gcgaaccatg actgggttta cattcagtcc ggcaaggcac tgaccggcga acagaccatt    3780
aacggtcaac acctgtattt caaagaagat ggtcaccaag tcaagggtca gttggtcacg    3840
ggcaccgatg taaagtgcg ttactatgac gccaacagcg gtgaccaagc attcaacaag    3900
agcgtcactg tgaatggtaa aacctattac tttggcaacg atggtacggc gcagactgct    3960
ggcaacccga agggtcagac gttcaaggat ggctccgaca tccgtttta ctctatggaa    4020 ggccaactgg tgaccggctc gggttggtac gagaacgcgc aaggccagtg gctgtatgtg    4080
aaaaacggta aggtgctgac tggtctgcaa accgttggca gccagcgtgt ttacttcgac    4140
gagaatggta ttcaggccaa gggcaaagca gtgcgtacca gcgatggcaa aattcgttat    4200
ttcgacgaaa acagcggcag catgatcacg aatcaatgga agttcgtcta tggtcagtat    4260
tactactttg gtaacgacgg tgcacgtatt taccgtggtt ggaactaa                 4308
```

<210> SEQ ID NO 2
<211> LENGTH: 1435
<212> TYPE: PRT
<213> ORGANISM: Streptococcus sobrinus

<400> SEQUENCE: 2

```
Met Val Asp Gly Lys Tyr Tyr Tyr Asp Gln Asp Gly Asn Val Lys
  1               5                  10                  15

Lys Asn Phe Ala Val Ser Val Gly Asp Lys Ile Tyr Tyr Phe Asp Glu
                 20                  25                  30

Thr Gly Ala Tyr Lys Asp Thr Ser Lys Val Asp Ala Asp Lys Ser Ser
             35                  40                  45

Ser Ala Val Ser Gln Asn Ala Thr Ile Phe Ala Ala Asn Asn Arg Ala
         50                  55                  60

Tyr Ser Thr Ser Ala Lys Asn Phe Glu Ala Val Asp Asn Tyr Leu Thr
 65                  70                  75                  80

Ala Asp Ser Trp Tyr Arg Pro Lys Ser Ile Leu Lys Asp Gly Lys Thr
                 85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Asn Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Leu Phe Asp Asn Gln Thr Asp Leu
        195                 200                 205

Thr Pro Asp Thr Gln Ser Asn Tyr Arg Leu Leu Asn Arg Thr Pro Thr
```

```
            210                 215                 220
Asn Gln Thr Gly Ser Leu Asp Ser Arg Phe Thr Tyr Asn Pro Asn Asp
225                 230                 235                 240

Pro Leu Gly Gly Tyr Asp Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Asn Asp Ala Asp Ala Asn Phe Asp Ser
            275                 280                 285

Ile Arg Val Asp Ala Val Asp Asn Val Asp Ala Asp Leu Leu Gln Ile
            290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Glu Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
            515                 520                 525

Gly Lys Gly Ala Leu Lys Gln Ser Asp Lys Gly Asp Ala Thr Thr Arg
530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
            595                 600                 605

Glu Asn Gly Tyr Leu Tyr Phe Leu Asn Asp Asp Leu Lys Gly Val Ala
            610                 615                 620

Asn Pro Gln Val Ser Gly Phe Leu Gln Val Trp Val Pro Val Gly Ala
625                 630                 635                 640
```

```
Ala Asp Asp Gln Asp Ile Arg Val Ala Ala Ser Asp Thr Ala Ser Thr
            645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
            675                 680                 685

Tyr Thr Asn Val Val Ile Ala Asn Asn Val Asp Lys Phe Val Ser Trp
            690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
            725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
            755                 760                 765

Met Ala Asp Trp Val Pro Asp Gln Met Tyr Thr Phe Pro Lys Gln Glu
            770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
            805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
            835                 840                 845

Ala Ile Asp Pro Ser Val Lys Ile Lys Gln Trp Ser Ala Lys Tyr Phe
            850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
            885                 890                 895

Pro Ser Ser Leu Leu Gly Lys Val Val Glu Ser Gly Ile Arg Tyr Asp
            900                 905                 910

Gly Lys Gly Tyr Ile Tyr Asn Ser Ser Ala Thr Gly Asp Gln Val Lys
            915                 920                 925

Ala Ser Phe Ile Thr Glu Ala Gly Asn Leu Tyr Tyr Phe Gly Lys Asp
            930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
            965                 970                 975

Gln Gly Asn Ser His Tyr Tyr Ala Asn Asp Gly Lys Arg Tyr Glu Asn
            980                 985                 990

Gly Tyr Gln Gln Phe Gly Asn Asp Trp Arg Tyr Phe Lys Asp Gly Asn
            995                 1000                1005

Met Ala Val Gly Leu Thr Thr Val Asp Gly Asn Val Gln Tyr Phe
            1010                1015                1020

Asp Lys Asp Gly Val Gln Ala Lys Asp Lys Ile Ile Val Thr Arg
            1025                1030                1035

Asp Gly Lys Val Arg Tyr Phe Asp Gln His Asn Gly Asn Ala Ala
            1040                1045                1050
```

```
Thr Asn Thr Phe Ile Ala Asp Lys Thr Gly His Trp Tyr Tyr Leu
1055                1060                1065

Gly Lys Asp Gly Val Ala Val Thr Gly Ala Gln Thr Val Gly Lys
    1070                1075                1080

Gln Lys Leu Tyr Phe Glu Ala Asn Gly Gln Gln Val Lys Gly Asp
    1085                1090                1095

Phe Val Thr Ser Asp Glu Gly Lys Leu Tyr Phe Tyr Asp Val Asp
    1100                1105                1110

Ser Gly Asp Met Trp Thr Asp Thr Phe Ile Glu Asp Lys Ala Gly
    1115                1120                1125

Asn Trp Phe Tyr Leu Gly Lys Asp Gly Ala Ala Val Thr Gly Ala
    1130                1135                1140

Gln Thr Ile Arg Gly Gln Lys Leu Tyr Phe Lys Ala Asn Gly Gln
    1145                1150                1155

Gln Val Lys Gly Asp Ile Val Lys Gly Thr Asp Gly Lys Ile Arg
    1160                1165                1170

Tyr Tyr Asp Ala Lys Ser Gly Glu Gln Val Phe Asn Lys Thr Val
    1175                1180                1185

Lys Ala Ala Asp Gly Lys Thr Tyr Val Ile Gly Asn Asp Gly Val
    1190                1195                1200

Ala Val Asp Pro Ser Val Val Lys Gly Gln Thr Phe Lys Asp Ala
    1205                1210                1215

Ser Gly Ala Leu Arg Phe Tyr Asn Leu Lys Gly Gln Leu Val Thr
    1220                1225                1230

Gly Ser Gly Trp Tyr Glu Thr Ala Asn His Asp Trp Val Tyr Ile
    1235                1240                1245

Gln Ser Gly Lys Ala Leu Thr Gly Glu Gln Thr Ile Asn Gly Gln
    1250                1255                1260

His Leu Tyr Phe Lys Glu Asp Gly His Gln Val Lys Gly Gln Leu
    1265                1270                1275

Val Thr Gly Thr Asp Gly Lys Val Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Asn Asp Gly Thr Ala Gln Thr Ala Gly Asn Pro
    1310                1315                1320

Lys Gly Gln Thr Phe Lys Asp Gly Ser Asp Ile Arg Phe Tyr Ser
    1325                1330                1335

Met Glu Gly Gln Leu Val Thr Gly Ser Gly Trp Tyr Glu Asn Ala
    1340                1345                1350

Gln Gly Gln Trp Leu Tyr Val Lys Asn Gly Lys Val Leu Thr Gly
    1355                1360                1365

Leu Gln Thr Val Gly Ser Gln Arg Val Tyr Phe Asp Glu Asn Gly
    1370                1375                1380

Ile Gln Ala Lys Gly Lys Ala Val Arg Thr Ser Asp Gly Lys Ile
    1385                1390                1395

Arg Tyr Phe Asp Glu Asn Ser Gly Ser Met Ile Thr Asn Gln Trp
    1400                1405                1410

Lys Phe Val Tyr Gly Gln Tyr Tyr Tyr Phe Gly Asn Asp Gly Ala
    1415                1420                1425

Arg Ile Tyr Arg Gly Trp Asn
    1430                1435
```

<210> SEQ ID NO 3
<211> LENGTH: 4026
<212> TYPE: DNA
<213> ORGANISM: Streptococcus salivarius SK126

<400> SEQUENCE: 3

```
atgatcgacg gcaaatacta ttatgttaat gaggacggta gccacaaaga aaactttgcg      60
attacggtta atggtcaact gctgtatttc ggtaaggacg gcgcactgac ctctagcagc     120
acttacagct ttaccccagg tacgacgaac atcgtggatg gcttttctat caacaaccgc     180
gcgtatgact ccagcgaagc gtcctttgaa ctgattgatg gctacttgac tgccgactcc     240
tggtatcgtc cggcttccat catcaaggac ggtgtcacgt ggcaggccag caccgcagag     300
gactttcgcc cgctgctgat ggcgtggtgg ccaaacgtgg atacccaggt gaactatctg     360
aactacatgt ctaaagtgtt taacctggac gcaaagtata gcagcaccga taaacaagag     420
actctgaagg ttgcagctaa ggatattcag attaagatcg agcagaaaat tcaggcggag     480
aaaagcaccc aatggctgcg cgaaacgatc agcgcttttg tgaaaaccca accacagtgg     540
aacaaagaga ctgagaatta ctcgaaaggt ggtggtgagg atcatctgca aggcggtgca     600
ctgctgtacg tgaatgatag ccgtaccccg tgggcaaata gcgattatcg ccgcctgaac     660
cgcaccgcta ccaatcaaac gggtacgatt gacaagtcca ttctggacga gcagagcgac     720
ccaaatcaca tgggcggttt cgacttcctg ctggcgaatg atgttgacct gtccaacccg     780
gttgtgcagg cagagcagct gaaccagatt cactacttga tgaattgggg ctctatcgtg     840
atgggtgaca agacgcaaa ctttgatggt atccgtgtcg atgcagttga caacgtcgat     900
gccgacatgc tgcaactgta taccaactac ttccgtgaat actacggtgt taacaaaagc     960
gaagcgaacg cactggcgca cattagcgtt ttggaagcgt ggagcttgaa tgataatcac    1020
tacaacgaca aaaccgatgg tgcagcattg gcgatggaga ataagcagcg tctggcgctg    1080
ctgtttagcc tggctaaacc gattaaagag cgcacccccgg cagtgagccc gctgtataac    1140
aacaccttca atacgaccca acgcgatgag aaaaccgact ggatcaataa agacggttct    1200
aaggcctata cgaggatgg tactgtgaag cagagcacca ttggtaagta caatgaaaaa    1260
tatggtgatg catcgggcaa ttatgtgttc atccgtgccc atgataacaa tgtccaagac    1320
atcattgcgg agatcattaa gaaagaaatc aacccgaaaa gcgatggttt caccatcact    1380
gacgccgaaa tgaacaagc gttcgagatt acaataagg acatgctgag cagcgacaag    1440
aagtacaccc tgaataacat cccggcagct tatgccgtga tgttgcagaa catggaaacg    1500 attcccgtg tctattatgg tgacctgtac accgacgacg ccactacat ggaaaccaag    1560 tccccgtatt acgacaccat cgttaacctg atgaaaagcc gtatcaagta cgtcagcggt    1620
ggccaggccc aacgtagcta ctggctgccg accgacggca agatggacaa tagcgacgtt    1680
gagctgtatc gcaccaacga agtgtatacc agcgtccgtt acggtaaaga cattatgacc    1740
gcgaacgata ccgagggtag caagtacagc cgcaccagcg gccaggtcac cctggttgca    1800
aacaacccga agctgaccct ggaccagagc gcgaagctga atgtggaaat gggtaagatt    1860
cacgcgaatc agaaataccg tgccctgatt gtgggcacgg ctgacggtat caagaatttc    1920
accagcgacg cagatgctat gcgcggcagc tacgtgaaag aaaccgactc aatggccgtt    1980
ctgacttttg gcgctaatga catcaaaggt tatgaaacct tcgacatgtc cggctttgtt    2040
gctgtttggg tgccggtcgg cgcgagcgat gatcaggaca ttcgtgtcgc tcctagcact    2100
gaggccaaga aagagggtga attgaccctg aaagcgaccg aagcatacga ttcccagctg    2160
```

```
atctatgaag gttttagcaa ttttcaaacc atcccggatg gtagcgaccc gagcgtgtac    2220
accaatcgca agatcgcaga gaacgtggac ctgttcaagt cctggggtgt tacctcgttt    2280
gaaatggcac cgcagttcgt ttccgcagat gatggcactt ttctggactc tgtgatccaa    2340
aacggctatg cgtttgccga tcgttacgat ttggcgatga gcaagaacaa caaatacggc    2400
agcaaagagg acttgcgtga cgcgctgaaa gccctgcata agcaggcat ccaggcgatt     2460 gcagactggg tcccggacca gatttatcag ttgccgggca agaagtggt cacggcgact     2520 cgcaccgacg gcgcaggccg taaaatcgcg gacgcgatca ttgatcatag cctgtacgtt    2580
gcgaacacta agagcagcgg caaagattac caggcgaagt acggtggtga gttcttggcg    2640
gagctgaagg ccaagtaccc ggagatgttc aaagtgaaca tgatttctac cggcaaaccg    2700
attgatgaca cgtcaaaact gaaacagtgg aaagcagaat actttaacgg caccaacgtc    2760
ttggagcgcg gtgtgggtta tgtcctgagc gatgaagcca cgggtaaata ctttaccgtc    2820
acgaaggatg caacttcat tccgttgcag ctgacgggta tgagaaagt cgtgaccggc      2880 tttagcaatg atggcaaagg tatcacctac ttcggtacga gcggcactca agcgaaatct    2940
gcgttcgtta cgttcaatgg taatacttac tattttgacg ctcgtggtca catggttacg    3000
aacggcgagt attcgccgaa cggtaaggat gtttaccgtt tcctgccgaa tggtattatg    3060
ctgtctaacg ctttttacgt tgatgcaaat ggtaacacgt acctgtacaa cagcaagggc    3120
caaatgtaca aggcggtta caccaaattt gacgttaccg aaacggacaa agatggtaag     3180
gaaagcaagg tggtgaagtt cgttactttt acgaacgaag gtgtcatggc aaaaggcgtt    3240
accgtgattg acggcttcac gcaatacttt ggtgaagatg gtttccaagc gaaagacaag    3300
ctggtcacgt tcaagggcaa gacgtactac ttcgatgcac acaccggcaa tgcgatcaag    3360
gacacctggc gtaatatcaa tggcaagtgg tatcatttcg acgcgaacgg cgttgcagcg    3420
accggcgctc aggtcatcaa tggccaaaaa ctgtatttca cgaggacgg cagccaagtg     3480 aaaggcggtg ttgtcaaaaa cgcggacggt acgtattcta aatacaaaga gggttctggt    3540
gaactggtta ccaacgagtt cttcacgacg gatggcaatg tttggtacta cgcaggcgcg    3600
aatggcaaga ccgttacggg tgcccaggtg attaacggcc aacacctgta cttcaatgcg    3660
gacggttcgc aagtgaaggg cggtgtggtc aagaacgcgg atggcaccta tagcaaatat    3720
gatgcgtcta ccggcgaacg cctgaccaat gagttttttca ccacgggtga taacaactgg   3780
tactacattg gcgcaaacgg caagagcgtg acgggcgagg tcaagatcgg tgacgatacc    3840
tatttctttg ccaaagatgg caagcaagtt aagggtcaaa ctgtcagcgc gggtaacggt    3900
cgtattagct actactatgg tgatagcggt aagcgtgcgg tgagcacttg gatcgaaatc    3960
caaccgggtg tttatgtcta cttcgacaag aacggcattg cctatccgcc tcgtgtgctg    4020
aattaa                                                                4026
```

<210> SEQ ID NO 4
<211> LENGTH: 1341
<212> TYPE: PRT
<213> ORGANISM: Streptococcus salivarius SK126

<400> SEQUENCE: 4

Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Ser Thr Tyr Ser Phe Thr Pro Gly Thr

```
                35                  40                  45
Thr Asn Ile Val Asp Gly Phe Ser Ile Asn Asn Arg Ala Tyr Asp Ser
 50                  55                  60

Ser Glu Ala Ser Phe Glu Leu Ile Asp Gly Tyr Leu Thr Ala Asp Ser
 65                  70                  75                  80

Trp Tyr Arg Pro Ala Ser Ile Ile Lys Asp Gly Val Thr Trp Gln Ala
                 85                  90                  95

Ser Thr Ala Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
            115                 120                 125

Leu Asp Ala Lys Tyr Ser Ser Thr Asp Lys Gln Glu Thr Leu Lys Val
        130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
            195                 200                 205

Thr Pro Trp Ala Asn Ser Asp Tyr Arg Arg Leu Asn Arg Thr Ala Thr
        210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
                260                 265                 270

Leu Met Asn Trp Gly Ser Ile Val Met Gly Asp Lys Asp Ala Asn Phe
            275                 280                 285

Asp Gly Ile Arg Val Asp Ala Val Asp Asn Val Asp Ala Asp Met Leu
        290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
    450                 455                 460
```

```
Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
        515                 520                 525

Asn Leu Met Lys Ser Arg Ile Lys Tyr Val Ser Gly Gln Ala Gln
530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Thr Leu Asp
        595                 600                 605

Gln Ser Ala Lys Leu Asn Val Glu Met Gly Lys Ile His Ala Asn Gln
610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Asp His Ser Leu Tyr Val Ala Asn Thr Lys
850                 855                 860

Ser Ser Gly Lys Asp Tyr Gln Ala Lys Tyr Gly Gly Glu Phe Leu Ala
865                 870                 875                 880
```

```
            Glu Leu Lys Ala Lys Tyr Pro Glu Met Phe Lys Val Asn Met Ile Ser
                            885                 890                 895

Thr Gly Lys Pro Ile Asp Asp Ser Val Lys Leu Lys Gln Trp Lys Ala
                        900                 905                 910

Glu Tyr Phe Asn Gly Thr Asn Val Leu Glu Arg Gly Val Gly Tyr Val
                        915                 920                 925

Leu Ser Asp Glu Ala Thr Gly Lys Tyr Phe Val Thr Lys Asp Gly
                    930                 935                 940

Asn Phe Ile Pro Leu Gln Leu Thr Gly Asn Glu Lys Val Val Thr Gly
            945                 950                 955                 960

Phe Ser Asn Asp Gly Lys Gly Ile Thr Tyr Phe Gly Thr Ser Gly Thr
                            965                 970                 975

Gln Ala Lys Ser Ala Phe Val Thr Phe Asn Gly Asn Thr Tyr Tyr Phe
                        980                 985                 990

Asp Ala Arg Gly His Met Val Thr  Asn Gly Glu Tyr Ser  Pro Asn Gly
                        995                 1000                1005

Lys Asp  Val Tyr Arg Phe Leu  Pro Asn Gly Ile Met  Leu Ser Asn
                    1010                1015                1020

Ala Phe  Tyr Val Asp Ala Asn  Gly Asn Thr Tyr Leu  Tyr Asn Ser
                    1025                1030                1035

Lys Gly  Gln Met Tyr Lys Gly  Gly Tyr Thr Lys Phe  Asp Val Thr
                    1040                1045                1050

Glu Thr  Asp Lys Asp Gly Lys  Glu Ser Lys Val Val  Lys Phe Arg
                    1055                1060                1065

Tyr Phe  Thr Asn Glu Gly Val  Met Ala Lys Gly Val  Thr Val Ile
                    1070                1075                1080

Asp Gly  Phe Thr Gln Tyr Phe  Gly Glu Asp Gly Phe  Gln Ala Lys
                    1085                1090                1095

Asp Lys  Leu Val Thr Phe Lys  Gly Lys Thr Tyr  Phe Asp Ala
                    1100                1105                1110

His Thr  Gly Asn Ala Ile Lys  Asp Thr Trp Arg Asn  Ile Asn Gly
                    1115                1120                1125

Lys Trp  Tyr His Phe Asp Ala  Asn Gly Val Ala Ala  Thr Gly Ala
                    1130                1135                1140

Gln Val  Ile Asn Gly Gln Lys  Leu Tyr Phe Asn Glu  Asp Gly Ser
                    1145                1150                1155

Gln Val  Lys Gly Gly Val Val  Lys Asn Ala Asp Gly  Thr Tyr Ser
                    1160                1165                1170

Lys Tyr  Lys Glu Gly Ser Gly  Glu Leu Val Thr Asn  Glu Phe Phe
                    1175                1180                1185

Thr Thr  Asp Gly Asn Val Trp  Tyr Tyr Ala Gly Ala  Asn Gly Lys
                    1190                1195                1200

Thr Val  Thr Gly Ala Gln Val  Ile Asn Gly Gln His  Leu Tyr Phe
                    1205                1210                1215

Asn Ala  Asp Gly Ser Gln Val  Lys Gly Gly Val Val  Lys Asn Ala
                    1220                1225                1230

Asp Gly  Thr Tyr Ser Lys Tyr  Asp Ala Ser Thr Gly  Glu Arg Leu
                    1235                1240                1245

Thr Asn  Glu Phe Phe Thr Thr  Gly Asp Asn Asn Trp  Tyr Tyr Ile
                    1250                1255                1260

Gly Ala  Asn Gly Lys Ser Val  Thr Gly Glu Val Lys  Ile Gly Asp
                    1265                1270                1275

Asp Thr  Tyr Phe Phe Ala Lys  Asp Gly Lys Gln Val  Lys Gly Gln
```

```
                    1280              1285              1290
Thr Val Ser Ala Gly Asn Gly Arg Ile Ser Tyr Tyr Tyr Gly Asp
    1295              1300              1305

Ser Gly Lys Arg Ala Val Ser Thr Trp Ile Glu Ile Gln Pro Gly
    1310              1315              1320

Val Tyr Val Tyr Phe Asp Lys Asn Gly Ile Ala Tyr Pro Pro Arg
    1325              1330              1335

Val Leu Asn
    1340

<210> SEQ ID NO 5
<211> LENGTH: 3744
<212> TYPE: DNA
<213> ORGANISM: Streptococcus salivarius

<400> SEQUENCE: 5
atgccaagcc acattaagac catcaacggc aaacaatact acgtggagga tgacggtacg      60
attcgcaaga attacgtcct ggagcgtatc ggtggcagcc aatactttaa tgcagaaacc     120
ggtgaactgt ctaatcagaa agagtatcgt ttcgacaaaa atggtggtac tggtagcagc     180
gcggacagca cgaacaccaa cgtgactgtg aacggtgaca aaaacgcatt ttacggtacc     240
acggacaaag acattgagct ggtcgacggc tatttcaccg cgaacacctg gtatcgcccg     300
aaagaaatcc tgaaagacgg caaagaatgg accgccagca cggagaacga taaacgcccg     360
ctgctgaccg tctggtggcc tagcaaagca atccaggcgt cttatctgaa ctacatgaaa     420
gagcaaggcc tgggtaccaa ccaaacgtac acgagcttct ccagccaaac ccaaatggat     480
caagcagccc tggaagtgca aaagcgtatt gaagagcgca tcgcacgcga gggcaatacc     540
gactggctgc gcacgaccat caagaacttc gtgaaaaccc aaccggggttg aacagcacc     600
tctgaaaatc tggacaataa tgatcatctg caaggtggcg ccctgctgta caataacgac     660
tcccgcacga gccacgcgaa cagcgactat cgcctgctga tcgtacgcc gaccagccag     720
accggcaaac acaatccgaa atacaccaaa gataccagca tggtggtttt cgaatttctg     780
ctggcgaacg acatcgataa ctctaatccg gcggttcaag cagagcaact gaactggctg     840
cattacatta tgaacatcgg taccatcacg ggcggttctg aggatgaaaa cttcgacggc     900
gttcgtgttg acgctgtgga taatgtgaat gcggatctgc tgcaaatcgc gagcgactat     960
ttcaaagcaa atacggtgc tgatcaaagc caagatcagg cgatcaaaca cttgagcatc    1020
ctggaagcgt ggtcccataa cgacgcctac tataacgaag ataccaaagg cgcgcagttg    1080
ccgatggatg atccgatgca cctggctctg gtctactcgc tgctgcgtcc gatcggcaat    1140
cgcagcggtg tggaaccgct gatttccaac agcctgaatg accgtagcga gtccggtaag    1200
aacagcaaac gtatggcgaa ctacgcgttc gtacgcgcgc atgatagcga ggtgcaatcg    1260
attattggcc agatcatcaa aaacgagatc aatccgcaaa gcaccggtaa tacgttcacc    1320
ctggatgaga tgaagaaagc gttttgagatt tacaacaagg atatgcgtag cgcgaataag    1380
cagtatacgc agtacaacat cccgagcgcg tatgcgttga tgctgaccca aaggataccc    1440
gttccgcgtg tgtattacgg tgatatgtat acggacgacg tcagtacat ggcgcaaaag    1500
agcccatact atgatgcgat cgaaacgctg ctgaaaggtc gcatccgcta tgccgcaggt    1560
ggtcaggaca tgaaggtcaa ctatattggt tacggtaaca ctaacggctg ggatgctgcg    1620
ggcgtgctga ccagcgtacg ttatggcacg ggcgcaaata cgccagcga tacgggtacc    1680
gccgaaacgc gtaatcaagg tatggcagtg attgttagca accaaccggc gctgcgtctg    1740
```

```
actagcaatt tgaccattaa catgggtgcc gcacaccgta atcaggctta ccgtccgctg    1800
ctgctgacga ccaacgatgg cgtcgcgacc tatttgaacg atagcgatgc gaatggtatc    1860
gttaagtaca ccgacggtaa tggtaatctg accttctccg caaacgagat tcgtggcatc    1920
cgtaacccgc aagttgatgg ctatctggcc gtctgggttc cggtaggtgc gtcggagaat    1980
caggatgttc gtgtggcgcc gagcaaagag aagaacagct ccggtctggt ttacgagagc    2040
aatgctgccc tggatagcca agttatctac gaaggcttca gcaacttcca ggacttcgtt    2100
cagaatccga gccagtatac caacaaaaag attgcagaga atgcaaattt gttcaaatcc    2160
tggggtatta ccagctttga atttgcgccg cagtacgtga gctcggatga tggtagcttc    2220
ctggacagcg ttattcagaa cggttatgcg tttacggacc gctacgacat tggtatgagc    2280
aaagacaaca aatatggttc gctggcggat ttgaaggcag cactgaagag cttgcatgcc    2340
gttggtatta gcgcaatcgc ggattgggtt cctgatcaga tctacaatct gccaggcgac    2400
gaggtcgtca ccgcaacccg cgttaacaac tacggcgaaa ccaaagatgg tgcaatcatt    2460
gatcactctt tgtacgcggc caaaacccgt acttttggta acgactacca gggtaagtat    2520
ggtggtgcgt tcctggacga gctgaaacgt ctgtatccgc agatctttga ccgcgttcag    2580
atttctaccg gtaagcgcat gaccacggac gagaagatca cccaatggtc tgcaaagtat    2640
atgaacggta cgaacatctt ggaccgtggc tctgaatacg tttttgaagaa tggtctgaat    2700 ggttactatg gcaccaatgg tggcaaagtt tcgctgccga agttgtggg tagcaatcaa    2760 agcacgaatg cgacaatca aaacggcgac ggtagcggca agtttgaaaa agcgtctgttc    2820 agcgtgcgtt accgttataa caatggccag tacgcgaaaa atgcctttat caaagataac    2880
gacggcaatg tttactattt cgacaatagc ggtcgtatgg ctgtcggtga aaaacgatt     2940 gacggcaagc agtacttctt cctggctaat ggcgttcagc tgcgtgacgg ctaccgtcaa    3000
aatcgtcgcg gtcaggtgtt ttactacgac cagaatggtg tgctgaacgc aaacggtaaa    3060
caagacccga agcctgacaa caataacaat gcgagcggcc gtaatcaatt cgtccagatc    3120
ggtaacaacg tgtgggcgta ttatgatggc aatggtaaac gtgtcaccgg tcaccagaac    3180
atcaacggtc aggagttgtt tttcgataac aacggtgtcc aggttaaggg tcgtacggtg    3240
aatgagaacg gtgcaattcg ctactatgac gcgaatagcg gtgagatggc acgcaatcgt    3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tggcaacctg cgctattacg acgttaacag cggtgagctg    3480
taccgtaatc gtttccacga aatcgacggc agctggtatt actttgatgg taacggtaat    3540
gcggtgaagg tatggtcaa tatcaacggc caaaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagcccag ttggtgggt ttactttgac    3720 ggtgaaggtc gtggtcagat ctaa                                         3744
```

<210> SEQ ID NO 6
<211> LENGTH: 1247
<212> TYPE: PRT
<213> ORGANISM: Streptococcus salivarius

<400> SEQUENCE: 6

Met Pro Ser His Ile Lys Thr Ile Asn Gly Lys Gln Tyr Tyr Val Glu
1               5                   10                  15

```
Asp Asp Gly Thr Ile Arg Lys Asn Tyr Val Leu Glu Arg Ile Gly Gly
            20                  25                  30

Ser Gln Tyr Phe Asn Ala Glu Thr Gly Glu Leu Ser Asn Gln Lys Glu
        35                  40                  45

Tyr Arg Phe Asp Lys Asn Gly Gly Thr Gly Ser Ser Ala Asp Ser Thr
50                  55                  60

Asn Thr Asn Val Thr Val Asn Gly Asp Lys Asn Ala Phe Tyr Gly Thr
65                  70                  75                  80

Thr Asp Lys Asp Ile Glu Leu Val Asp Gly Tyr Phe Thr Ala Asn Thr
                85                  90                  95

Trp Tyr Arg Pro Lys Glu Ile Leu Lys Asp Gly Lys Glu Trp Thr Ala
            100                 105                 110

Ser Thr Glu Asn Asp Lys Arg Pro Leu Leu Thr Val Trp Trp Pro Ser
        115                 120                 125

Lys Ala Ile Gln Ala Ser Tyr Leu Asn Tyr Met Lys Glu Gln Gly Leu
130                 135                 140

Gly Thr Asn Gln Thr Tyr Thr Ser Phe Ser Ser Gln Thr Gln Met Asp
145                 150                 155                 160

Gln Ala Ala Leu Glu Val Gln Lys Arg Ile Glu Glu Arg Ile Ala Arg
                165                 170                 175

Glu Gly Asn Thr Asp Trp Leu Arg Thr Thr Ile Lys Asn Phe Val Lys
            180                 185                 190

Thr Gln Pro Gly Trp Asn Ser Thr Ser Glu Asn Leu Asp Asn Asn Asp
        195                 200                 205

His Leu Gln Gly Gly Ala Leu Leu Tyr Asn Asn Asp Ser Arg Thr Ser
210                 215                 220

His Ala Asn Ser Asp Tyr Arg Leu Leu Asn Arg Thr Pro Thr Ser Gln
225                 230                 235                 240

Thr Gly Lys His Asn Pro Lys Tyr Thr Lys Asp Thr Ser Asn Gly Gly
                245                 250                 255

Phe Glu Phe Leu Leu Ala Asn Asp Ile Asp Asn Ser Asn Pro Ala Val
            260                 265                 270

Gln Ala Glu Gln Leu Asn Trp Leu His Tyr Ile Met Asn Ile Gly Thr
        275                 280                 285

Ile Thr Gly Gly Ser Glu Asp Glu Asn Phe Asp Gly Val Arg Val Asp
290                 295                 300

Ala Val Asp Asn Val Asn Ala Asp Leu Leu Gln Ile Ala Ser Asp Tyr
305                 310                 315                 320

Phe Lys Ala Lys Tyr Gly Ala Asp Gln Ser Gln Asp Gln Ala Ile Lys
                325                 330                 335

His Leu Ser Ile Leu Glu Ala Trp Ser His Asn Asp Ala Tyr Tyr Asn
            340                 345                 350

Glu Asp Thr Lys Gly Ala Gln Leu Pro Met Asp Asp Pro Met His Leu
        355                 360                 365

Ala Leu Val Tyr Ser Leu Leu Arg Pro Ile Gly Asn Arg Ser Gly Val
370                 375                 380

Glu Pro Leu Ile Ser Asn Ser Leu Asn Asp Arg Ser Glu Ser Gly Lys
385                 390                 395                 400

Asn Ser Lys Arg Met Ala Asn Tyr Ala Phe Val Arg Ala His Asp Ser
                405                 410                 415

Glu Val Gln Ser Ile Ile Gly Gln Ile Ile Lys Asn Glu Ile Asn Pro
            420                 425                 430
```

```
Gln Ser Thr Gly Asn Thr Phe Thr Leu Asp Glu Met Lys Lys Ala Phe
            435                 440                 445
Glu Ile Tyr Asn Lys Asp Met Arg Ser Ala Asn Lys Gln Tyr Thr Gln
    450                 455                 460
Tyr Asn Ile Pro Ser Ala Tyr Ala Leu Met Leu Thr His Lys Asp Thr
465                 470                 475                 480
Val Pro Arg Val Tyr Tyr Gly Asp Met Tyr Thr Asp Asp Gly Gln Tyr
                485                 490                 495
Met Ala Gln Lys Ser Pro Tyr Tyr Asp Ala Ile Glu Thr Leu Leu Lys
            500                 505                 510
Gly Arg Ile Arg Tyr Ala Ala Gly Gly Gln Asp Met Lys Val Asn Tyr
    515                 520                 525
Ile Gly Tyr Gly Asn Thr Asn Gly Trp Asp Ala Ala Gly Val Leu Thr
530                 535                 540
Ser Val Arg Tyr Gly Thr Gly Ala Asn Ser Ala Ser Asp Thr Gly Thr
545                 550                 555                 560
Ala Glu Thr Arg Asn Gln Gly Met Ala Val Ile Val Ser Asn Gln Pro
            565                 570                 575
Ala Leu Arg Leu Thr Ser Asn Leu Thr Ile Asn Met Gly Ala Ala His
    580                 585                 590
Arg Asn Gln Ala Tyr Arg Pro Leu Leu Leu Thr Thr Asn Asp Gly Val
595                 600                 605
Ala Thr Tyr Leu Asn Asp Ser Asp Ala Asn Gly Ile Val Lys Tyr Thr
            610                 615                 620
Asp Gly Asn Gly Asn Leu Thr Phe Ser Ala Asn Glu Ile Arg Gly Ile
625                 630                 635                 640
Arg Asn Pro Gln Val Asp Gly Tyr Leu Ala Val Trp Val Pro Val Gly
                645                 650                 655
Ala Ser Glu Asn Gln Asp Val Arg Val Ala Pro Ser Lys Glu Lys Asn
            660                 665                 670
Ser Ser Gly Leu Val Tyr Glu Ser Asn Ala Ala Leu Asp Ser Gln Val
    675                 680                 685
Ile Tyr Glu Gly Phe Ser Asn Phe Gln Asp Phe Val Gln Asn Pro Ser
690                 695                 700
Gln Tyr Thr Asn Lys Lys Ile Ala Glu Asn Ala Asn Leu Phe Lys Ser
705                 710                 715                 720
Trp Gly Ile Thr Ser Phe Glu Phe Ala Pro Gln Tyr Val Ser Ser Asp
                725                 730                 735
Asp Gly Ser Phe Leu Asp Ser Val Ile Gln Asn Gly Tyr Ala Phe Thr
            740                 745                 750
Asp Arg Tyr Asp Ile Gly Met Ser Lys Asp Asn Lys Tyr Gly Ser Leu
    755                 760                 765
Ala Asp Leu Lys Ala Ala Leu Lys Ser Leu His Ala Val Gly Ile Ser
770                 775                 780
Ala Ile Ala Asp Trp Val Pro Asp Gln Ile Tyr Asn Leu Pro Gly Asp
785                 790                 795                 800
Glu Val Val Thr Ala Thr Arg Val Asn Asn Tyr Gly Glu Thr Lys Asp
                805                 810                 815
Gly Ala Ile Ile Asp His Ser Leu Tyr Ala Ala Lys Thr Arg Thr Phe
            820                 825                 830
Gly Asn Asp Tyr Gln Gly Lys Tyr Gly Gly Ala Phe Leu Asp Glu Leu
    835                 840                 845
Lys Arg Leu Tyr Pro Gln Ile Phe Asp Arg Val Gln Ile Ser Thr Gly
```

```
                    850                 855                 860
Lys Arg Met Thr Thr Asp Glu Lys Ile Thr Gln Trp Ser Ala Lys Tyr
865                 870                 875                 880

Met Asn Gly Thr Asn Ile Leu Asp Arg Gly Ser Glu Tyr Val Leu Lys
                    885                 890                 895

Asn Gly Leu Asn Gly Tyr Tyr Gly Thr Asn Gly Gly Lys Val Ser Leu
                900                 905                 910

Pro Lys Val Val Gly Ser Asn Gln Ser Thr Asn Gly Asp Asn Gln Asn
            915                 920                 925

Gly Asp Gly Ser Gly Lys Phe Glu Lys Arg Leu Phe Ser Val Arg Tyr
        930                 935                 940

Arg Tyr Asn Asn Gly Gln Tyr Ala Lys Asn Ala Phe Ile Lys Asp Asn
945                 950                 955                 960

Asp Gly Asn Val Tyr Tyr Phe Asp Asn Ser Gly Arg Met Ala Val Gly
                965                 970                 975

Glu Lys Thr Ile Asp Gly Lys Gln Tyr Phe Phe Leu Ala Asn Gly Val
            980                 985                 990

Gln Leu Arg Asp Gly Tyr Arg Gln Asn Arg Arg Gly Gln  Val Phe Tyr
        995                 1000                1005

Tyr Asp  Gln Asn Gly Val Leu  Asn Ala Asn Gly Lys  Gln Asp Pro
    1010                1015                1020

Lys Pro  Asp Asn Asn Asn  Ala Ser Gly Arg Asn  Gln Phe Val
    1025                1030                1035

Gln Ile  Gly Asn Asn Val Trp  Ala Tyr Tyr Asp Gly  Asn Gly Lys
    1040                1045                1050

Arg Val  Thr Gly His Gln Asn  Ile Asn Gly Gln Glu  Leu Phe Phe
    1055                1060                1065

Asp Asn  Asn Gly Val Gln Val  Lys Gly Arg Thr Val  Asn Glu Asn
    1070                1075                1080

Gly Ala  Ile Arg Tyr Tyr Asp  Ala Asn Ser Gly Glu  Met Ala Arg
    1085                1090                1095

Asn Arg  Phe Ala Glu Ile Glu  Pro Gly Val Trp Ala  Tyr Phe Asn
    1100                1105                1110

Asn Asp  Gly Thr Ala Val Lys  Gly Ser Gln Asn Ile  Asn Gly Gln
    1115                1120                1125

Asp Leu  Tyr Phe Asp Gln Asn  Gly Arg Gln Val Lys  Gly Ala Leu
    1130                1135                1140

Ala Asn  Val Asp Gly Asn Leu  Arg Tyr Tyr Asp Val  Asn Ser Gly
    1145                1150                1155

Glu Leu  Tyr Arg Asn Arg Phe  His Glu Ile Asp Gly  Ser Trp Tyr
    1160                1165                1170

Tyr Phe  Asp Gly Asn Gly Asn  Ala Val Lys Gly Met  Val Asn Ile
    1175                1180                1185

Asn Gly  Gln Asn Leu Leu Phe  Asp Asn Asn Gly Lys  Gln Ile Lys
    1190                1195                1200

Gly His  Leu Val Arg Val Asn  Gly Val Val Arg Tyr  Phe Asp Pro
    1205                1210                1215

Asn Ser  Gly Glu Met Ala Val  Asn Arg Trp Val Glu  Val Ser Pro
    1220                1225                1230

Gly Trp  Trp Val Tyr Phe Asp  Gly Glu Gly Arg Gly  Gln Ile
    1235                1240                1245

<210> SEQ ID NO 7
```

```
<211> LENGTH: 4434
<212> TYPE: DNA
<213> ORGANISM: Streptococcus salivarius

<400> SEQUENCE: 7
atggacgaaa cgcaggataa gaccgtgacg cagagcaaca gcggcaccac cgcttccctg      60
gtcactagcc ctgaagccac gaaagaggcg gacaaacgca cgaacactaa agaggccgac     120
gttctgacgc ctgcaaaaga aacgaacgca gtcgagactg cgaccaccac taacacccag     180
gcgacggcgg aggccgccac gaccgcgacc accgcggacg tcgcggtggc tgcggtgccg     240
aacaaagaag cggtcgttac cacgcgatgct ccggcggtca cgaccgagaa agcggaagaa     300
cagccggcta ccgttaaagc agaagtcgtc aatacggaag tgaaagcgcc ggaagcggct     360
ctgaaagaca cgcgaggttga ggcagcgctg agcctgaaga acatcaagaa cattgatggc     420
aagtattact atgttaatga ggatggcagc cacaaagaga atttcgctat taccgtgaat     480
ggccagctgc tgtactttgg taaagacggt gcgctgacgt cctctagcac gtattctttt     540
accccaggca ctaccaatat cgtggacggt tttagcatta caaccgcgc ttacgacagc      600 agcgaggcga gctttgagct gatcgacggt tacttgaccg cagacagctg gtatcgtccg     660
gctagcatca tcaaagatgg tgttacgtgg caagcgtcca ccgccgagga ttttcgtccg     720
ctgctgatgg catggtggcc gaatgtggat acgcaggtga actatttgaa ttacatgtcc     780
aaagttttca acctggacgc gaaatactct agcaccgaca acaggaaac cctgaaagtg      840 gcagcaaaag acattcaaat caagattgaa caaagattc aagcggagaa gagcacgcag       900
tggctgcgtg aaactatcag cgcctttgtg aaacccagc cgcagtggaa caaagaaacc      960
gagaattaca gcaagggtgg tggtgaggac cacctgcaag gtggcgcact gctgtatgtt    1020
aacgacagcc gtaccccttg ggcgaatagc gattaccgtc gtctgaatcg caccgcaacc    1080
aatcagacgg gcacgatcga taagtctatt ctggacgagc agtctgaccc aaaccacatg    1140 ggcggttttcg acttctctgct ggcgaacgac gtcgacctga gcaatccggt cgtgcaggct    1200
gagcagctga atcaaatcca ctatctgatg aattgggtt ccattgtgat gggtgacaag     1260
gatgcgaact ttgacggcat tcgtgtcgat gcagttgaca acgtggacgc ggacatgttg    1320
caactgtata ccaattactt ccgtgagtac tacggtgtga acaagagcga agctaacgca    1380
ctggctcaca tcagcgttct ggaggcgtgg agcctgaatg ataatcatta caatgacaag    1440
accgatggtg cggcactggc aatggagaat aagcaacgtc tggcgctgtt gttttcgttg    1500
gcgaaaccga tcaaagagcg taccccggca gtgagcccgc tgtataacaa caccttcaat    1560
accacccagc gtgatgaaaa gaccgattgg attaacaaag acgtagcaa ggcttacaac     1620 gaagatggca cggtcaaaca atcgaccatc ggtaagtaca cgagaaata cggtgacgca    1680 tccggtaact acgttttcat ccgtgcccac gataacaacg tccaggacat catcgccgag    1740
atcatcaaga aagagatcaa cccgaaaagc gacggcttca ccatcaccga cgccgaaatg    1800
aagcaagcct ttgaaatcta taacaaagat atgctgtcga gcgacaaaaa gtataccctg    1860
aataacattc cggcagcgta tgccgtgatg ttgcagaata tggaaacgat tacccgcgtc    1920
tattacggtg atctgtatac ggacgacggt cactacatgg aaaccaaatc tccgtattac    1980
gataccatcg tgaatttgat gaagagccgt atcaagtatg tttcgggtgg ccaggcgcaa    2040
cgtagctatt ggctgccgac cgacggtaag atggacaata gcgacgttga gctgtaccgc    2100
acgaatgagg tttacacgag cgtgcgctat ggtaaggata tcatgaccgc taatgatacc    2160
gaaggctcta agtattcccg caccagcggc caagtcacct tggtcgcgaa caatccgaag    2220
```

```
ctgaatctgg accaaagcgc aagttgaat gtggagatgg gcaaaatcca tgcgaatcag      2280
aagtatcgcg cactgattgt cggcactgcg gacggcatta gaactttac ttccgacgcg      2340 gacgccattg cagcgggtta tgtgaaagaa accgatagca acggcgtgct gaccttcggt      2400
gctaacgaca ttaagggcta cgaaacgttt gatatgagcg gtttcgtggc ggtgtgggtt      2460
ccggtgggtg catctgacaa tcaggacatt cgtgttgcgc cgagcaccga ggcaaagaaa      2520
gaaggtgagc tgaccttgaa ggcgacggaa gcgtatgata ccagctgat ttacgaaggc      2580 tttagcaatt ccagacgat cccagatggc agcgatccgt ccgtgtatac gaaccgcaag      2640
attgcggaga acgtggatct gttcaaaagc tggggtgtca ccagctttga gatggcaccg      2700
caatttgtct cggcggatga tggcaccttt ctggatagcg ttattcagaa tggctacgcc      2760
ttcgccgacc gttatgacct ggccatgtcc aagaacaaca agtatggtag caaagaggac      2820
ctgcgtgatg cactgaaagc actgcataag gcgggtattc aagctatcgc agactgggtt      2880
ccagaccaga tctaccagct gccgggcaaa gaagttgtca ccgccacccg tacgatggt      2940 gctggccgta agatcgcaga cgcgattatc gaccattctc tgtatgttgc aaacagcaaa      3000
agcagcggca agattatca agcaaagtac ggtggcgagt tcctggccga gctgaaagcc      3060
aaatacccgg aaatgttcaa agttaacatg attagcacgg gtaagccgat tgatgactcc      3120
gtgaaattga gcaatggaa agccgagtac ttcaatggca ccaacgtttt ggaacgtggt      3180
gtcggctatg ttctgagcga cgaggcgacc ggtaagtatt tcacggtgac caaagaaggc      3240
aatttcattc cgctgcaact gacgggtaaa gagaaagtta tcacgggttt ctccagcgat      3300
ggtaagggta tcacctattt cggtacgagc ggtacgcagg cgaagtctgc gtttgttacc      3360
ttcaatggta acacctacta tttcgacgcg cgtggccaca tggttaccaa tagcgaatac      3420
agcccgaatg gcaaggacgt ctaccgtttt ctgccgaacg gtatcatgct gagcaatgcg      3480
ttttacattg atgcgaacgg taatacctac ctgtacaact ctaagggtca aatgtacaaa      3540
ggcggttaca cgaaattcga tgtttctgaa acggataagg acggtaaaga gtccaaggtc      3600
gtcaagttcc gctactttac gaacgaaggc gtcatggcca agggtgttac cgtcattgat      3660
ggttttaccc aatacttcgg tgaggacggc tttcaagcga aggataagct ggtcaccttc      3720
aagggcaaga cgtattactt cgacgcacac actggtaatg gtatcaaaga tacctggcgc      3780
aatatcaatg gtaaatggta ctatttcgac gcgaatggc ttgctgcgac cggtgcgcag      3840
gtgattaacg ccagaaact gtacttcaac gaggatggct cccaagtcaa aggcggcgtg      3900
gttaagaacg cagacggcac ctatagcaaa tacaaagaag gttttggtga gctggttact      3960
aacgagtttt tcacgactga tgcaatgtt tggtactacg ccggtgcaaa tggtaaaacc      4020
gttaccggtc cacaagtgat caacggccaa catttgtact tcaatgcgga cggttcccag      4080
gtgaagggtg cgttgtcaa aacgcggat ggcacctaca gcaagtacaa tgctagcact      4140
ggtgaacgtc tgacgaacga gttctttacg accggtgata caattggta ttacattggc      4200 gcaaacggta agagcgtgac gggtgaggtc aagattggtg atgatactta ctttttcgcg      4260
aaggatggca acaagttaa aggtcaaacc gtcagcgccg gtaatggtcg cattagctac      4320
tactacggtg acagcggcaa gcgtgcggtt agcacctgga ttgagattca gccgggtgtt      4380
tatgtgtatt tcgacaaaaa cggtttggcg taccctccgc gtgttctgaa ttaa           4434
```

<210> SEQ ID NO 8
<211> LENGTH: 1477
<212> TYPE: PRT

<213> ORGANISM: Streptococcus salivarius

<400> SEQUENCE: 8

```
Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
            20                  25                  30

Arg Thr Asn Thr Lys Glu Ala Asp Val Leu Thr Pro Ala Lys Glu Thr
        35                  40                  45

Asn Ala Val Glu Thr Ala Thr Thr Asn Thr Gln Ala Thr Ala Glu
50                  55                  60

Ala Ala Thr Thr Ala Thr Thr Ala Asp Val Ala Val Ala Ala Val Pro
65                  70                  75                  80

Asn Lys Glu Ala Val Val Thr Thr Asp Ala Pro Ala Val Thr Thr Glu
                85                  90                  95

Lys Ala Glu Glu Gln Pro Ala Thr Val Lys Ala Glu Val Val Asn Thr
            100                 105                 110

Glu Val Lys Ala Pro Glu Ala Ala Leu Lys Asp Ser Glu Val Glu Ala
        115                 120                 125

Ala Leu Ser Leu Lys Asn Ile Lys Asn Ile Asp Gly Lys Tyr Tyr Tyr
130                 135                 140

Val Asn Glu Asp Gly Ser His Lys Glu Asn Phe Ala Ile Thr Val Asn
145                 150                 155                 160

Gly Gln Leu Leu Tyr Phe Gly Lys Asp Gly Ala Leu Thr Ser Ser Ser
                165                 170                 175

Thr Tyr Ser Phe Thr Pro Gly Thr Thr Asn Ile Val Asp Gly Phe Ser
            180                 185                 190

Ile Asn Asn Arg Ala Tyr Asp Ser Ser Glu Ala Ser Phe Glu Leu Ile
        195                 200                 205

Asp Gly Tyr Leu Thr Ala Asp Ser Trp Tyr Arg Pro Ala Ser Ile Ile
210                 215                 220

Lys Asp Gly Val Thr Trp Gln Ala Ser Thr Ala Glu Asp Phe Arg Pro
225                 230                 235                 240

Leu Leu Met Ala Trp Trp Pro Asn Val Asp Thr Gln Val Asn Tyr Leu
                245                 250                 255

Asn Tyr Met Ser Lys Val Phe Asn Leu Asp Ala Lys Tyr Ser Ser Thr
            260                 265                 270

Asp Lys Gln Glu Thr Leu Lys Val Ala Ala Lys Asp Ile Gln Ile Lys
        275                 280                 285

Ile Glu Gln Lys Ile Gln Ala Glu Lys Ser Thr Gln Trp Leu Arg Glu
290                 295                 300

Thr Ile Ser Ala Phe Val Lys Thr Gln Pro Gln Trp Asn Lys Glu Thr
305                 310                 315                 320

Glu Asn Tyr Ser Lys Gly Gly Glu Asp His Leu Gln Gly Gly Ala
                325                 330                 335

Leu Leu Tyr Val Asn Asp Ser Arg Thr Pro Trp Ala Asn Ser Asp Tyr
            340                 345                 350

Arg Arg Leu Asn Arg Thr Ala Thr Asn Gln Thr Gly Thr Ile Asp Lys
        355                 360                 365

Ser Ile Leu Asp Glu Gln Ser Asp Pro Asn His Met Gly Gly Phe Asp
370                 375                 380

Phe Leu Leu Ala Asn Asp Val Asp Leu Ser Asn Pro Val Val Gln Ala
385                 390                 395                 400
```

-continued

Glu Gln Leu Asn Gln Ile His Tyr Leu Met Asn Trp Gly Ser Ile Val
                    405                 410                 415
Met Gly Asp Lys Asp Ala Asn Phe Asp Gly Ile Arg Val Asp Ala Val
            420                 425                 430
Asp Asn Val Asp Ala Asp Met Leu Gln Leu Tyr Thr Asn Tyr Phe Arg
        435                 440                 445
Glu Tyr Tyr Gly Val Asn Lys Ser Glu Ala Asn Ala Leu Ala His Ile
    450                 455                 460
Ser Val Leu Glu Ala Trp Ser Leu Asn Asp Asn His Tyr Asn Asp Lys
465                 470                 475                 480
Thr Asp Gly Ala Ala Leu Ala Met Glu Asn Lys Gln Arg Leu Ala Leu
            485                 490                 495
Leu Phe Ser Leu Ala Lys Pro Ile Lys Glu Arg Thr Pro Ala Val Ser
        500                 505                 510
Pro Leu Tyr Asn Asn Thr Phe Asn Thr Thr Gln Arg Asp Glu Lys Thr
    515                 520                 525
Asp Trp Ile Asn Lys Asp Gly Ser Lys Ala Tyr Asn Glu Asp Gly Thr
530                 535                 540
Val Lys Gln Ser Thr Ile Gly Lys Tyr Asn Glu Lys Tyr Gly Asp Ala
545                 550                 555                 560
Ser Gly Asn Tyr Val Phe Ile Arg Ala His Asp Asn Asn Val Gln Asp
            565                 570                 575
Ile Ile Ala Glu Ile Ile Lys Lys Glu Ile Asn Pro Lys Ser Asp Gly
        580                 585                 590
Phe Thr Ile Thr Asp Ala Glu Met Lys Gln Ala Phe Glu Ile Tyr Asn
    595                 600                 605
Lys Asp Met Leu Ser Ser Asp Lys Lys Tyr Thr Leu Asn Asn Ile Pro
610                 615                 620
Ala Ala Tyr Ala Val Met Leu Gln Asn Met Glu Thr Ile Thr Arg Val
625                 630                 635                 640
Tyr Tyr Gly Asp Leu Tyr Thr Asp Asp Gly His Tyr Met Glu Thr Lys
            645                 650                 655
Ser Pro Tyr Tyr Asp Thr Ile Val Asn Leu Met Lys Ser Arg Ile Lys
        660                 665                 670
Tyr Val Ser Gly Gly Gln Ala Gln Arg Ser Tyr Trp Leu Pro Thr Asp
    675                 680                 685
Gly Lys Met Asp Asn Ser Asp Val Glu Leu Tyr Arg Thr Asn Glu Val
690                 695                 700
Tyr Thr Ser Val Arg Tyr Gly Lys Asp Ile Met Thr Ala Asn Asp Thr
705                 710                 715                 720
Glu Gly Ser Lys Tyr Ser Arg Thr Ser Gly Gln Val Thr Leu Val Ala
            725                 730                 735
Asn Asn Pro Lys Leu Asn Leu Asp Gln Ser Ala Lys Leu Asn Val Glu
        740                 745                 750
Met Gly Lys Ile His Ala Asn Gln Lys Tyr Arg Ala Leu Ile Val Gly
    755                 760                 765
Thr Ala Asp Gly Ile Lys Asn Phe Thr Ser Asp Ala Asp Ile Ala
770                 775                 780
Ala Gly Tyr Val Lys Glu Thr Asp Ser Asn Gly Val Leu Thr Phe Gly
785                 790                 795                 800
Ala Asn Asp Ile Lys Gly Tyr Glu Thr Phe Asp Met Ser Gly Phe Val
            805                 810                 815
Ala Val Trp Val Pro Val Gly Ala Ser Asp Asn Gln Asp Ile Arg Val

-continued

```
                820                 825                 830
Ala Pro Ser Thr Glu Ala Lys Lys Glu Gly Glu Leu Thr Leu Lys Ala
                    835                 840                 845

Thr Glu Ala Tyr Asp Ser Gln Leu Ile Tyr Glu Gly Phe Ser Asn Phe
850                                 855                 860

Gln Thr Ile Pro Asp Gly Ser Asp Pro Ser Val Tyr Thr Asn Arg Lys
865                 870                 875                 880

Ile Ala Glu Asn Val Asp Leu Phe Lys Ser Trp Gly Val Thr Ser Phe
                885                 890                 895

Glu Met Ala Pro Gln Phe Val Ser Ala Asp Asp Gly Thr Phe Leu Asp
                900                 905                 910

Ser Val Ile Gln Asn Gly Tyr Ala Phe Ala Asp Arg Tyr Asp Leu Ala
                915                 920                 925

Met Ser Lys Asn Lys Tyr Gly Ser Lys Glu Asp Leu Arg Asp Ala
            930                 935                 940

Leu Lys Ala Leu His Lys Ala Gly Ile Gln Ala Ile Ala Asp Trp Val
945                 950                 955                 960

Pro Asp Gln Ile Tyr Gln Leu Pro Gly Lys Glu Val Val Thr Ala Thr
                965                 970                 975

Arg Thr Asp Gly Ala Gly Arg Lys Ile Ala Asp Ala Ile Ile Asp His
                980                 985                 990

Ser Leu Tyr Val Ala Asn Ser Lys Ser Ser Gly Lys Asp Tyr Gln Ala
            995                 1000                1005

Lys Tyr Gly Gly Glu Phe Leu Ala Glu Leu Lys Ala Lys Tyr Pro
    1010                1015                1020

Glu Met Phe Lys Val Asn Met Ile Ser Thr Gly Lys Pro Ile Asp
    1025                1030                1035

Asp Ser Val Lys Leu Lys Gln Trp Lys Ala Glu Tyr Phe Asn Gly
    1040                1045                1050

Thr Asn Val Leu Glu Arg Gly Val Gly Tyr Val Leu Ser Asp Glu
    1055                1060                1065

Ala Thr Gly Lys Tyr Phe Val Thr Lys Glu Gly Asn Phe Ile
    1070                1075                1080

Pro Leu Gln Leu Thr Gly Lys Glu Lys Val Ile Thr Gly Phe Ser
    1085                1090                1095

Ser Asp Gly Lys Gly Ile Thr Tyr Phe Gly Thr Ser Gly Thr Gln
    1100                1105                1110

Ala Lys Ser Ala Phe Val Thr Phe Asn Gly Asn Thr Tyr Tyr Phe
    1115                1120                1125

Asp Ala Arg Gly His Met Val Thr Asn Ser Glu Tyr Ser Pro Asn
    1130                1135                1140

Gly Lys Asp Val Tyr Arg Phe Leu Pro Asn Gly Ile Met Leu Ser
    1145                1150                1155

Asn Ala Phe Tyr Ile Asp Ala Asn Gly Asn Thr Tyr Leu Tyr Asn
    1160                1165                1170

Ser Lys Gly Gln Met Tyr Lys Gly Gly Tyr Thr Lys Phe Asp Val
    1175                1180                1185

Ser Glu Thr Asp Lys Asp Gly Lys Glu Ser Lys Val Val Lys Phe
    1190                1195                1200

Arg Tyr Phe Thr Asn Glu Gly Val Met Ala Lys Gly Val Thr Val
    1205                1210                1215

Ile Asp Gly Phe Thr Gln Tyr Phe Gly Glu Asp Gly Phe Gln Ala
    1220                1225                1230
```

```
Lys Asp Lys Leu Val Thr Phe Lys Gly Lys Thr Tyr Tyr Phe Asp
    1235                1240                1245
Ala His Thr Gly Asn Gly Ile Lys Asp Thr Trp Arg Asn Ile Asn
    1250                1255                1260
Gly Lys Trp Tyr Tyr Phe Asp Ala Asn Gly Val Ala Ala Thr Gly
    1265                1270                1275
Ala Gln Val Ile Asn Gly Gln Lys Leu Tyr Phe Asn Glu Asp Gly
    1280                1285                1290
Ser Gln Val Lys Gly Gly Val Lys Asn Ala Asp Gly Thr Tyr
    1295                1300                1305
Ser Lys Tyr Lys Glu Gly Phe Gly Glu Leu Val Thr Asn Glu Phe
    1310                1315                1320
Phe Thr Thr Asp Gly Asn Val Trp Tyr Tyr Ala Gly Ala Asn Gly
    1325                1330                1335
Lys Thr Val Thr Gly Ala Gln Val Ile Asn Gly Gln His Leu Tyr
    1340                1345                1350
Phe Asn Ala Asp Gly Ser Gln Val Lys Gly Gly Val Val Lys Asn
    1355                1360                1365
Ala Asp Gly Thr Tyr Ser Lys Tyr Asn Ala Ser Thr Gly Glu Arg
    1370                1375                1380
Leu Thr Asn Glu Phe Phe Thr Thr Gly Asp Asn Asn Trp Tyr Tyr
    1385                1390                1395
Ile Gly Ala Asn Gly Lys Ser Val Thr Gly Glu Val Lys Ile Gly
    1400                1405                1410
Asp Asp Thr Tyr Phe Phe Ala Lys Asp Gly Lys Gln Val Lys Gly
    1415                1420                1425
Gln Thr Val Ser Ala Gly Asn Gly Arg Ile Ser Tyr Tyr Tyr Gly
    1430                1435                1440
Asp Ser Gly Lys Arg Ala Val Ser Thr Trp Ile Glu Ile Gln Pro
    1445                1450                1455
Gly Val Tyr Val Tyr Phe Asp Lys Asn Gly Leu Ala Tyr Pro Pro
    1460                1465                1470
Arg Val Leu Asn
    1475

<210> SEQ ID NO 9
<211> LENGTH: 4311
<212> TYPE: DNA
<213> ORGANISM: Streptococcus downei

<400> SEQUENCE: 9
atggttgacg gcaaatacta ctactacgat caggacggca acgtaaagaa aaacttcgcg      60
gttagcgtgg gcgagaaaat ctattacttt gacgaaactg gcgcctacaa agacaccagc     120
aaagttgagg cggacaaaag cggcagcgac attagcaagg aagagactac cttcgcggca     180
aacaaccgcg cctacagcac cagcgcggag aatttttgagg cgatcgacaa ttatctgacc     240
gcggactcct ggtatcgtcc taaatccatc ctgaaggatg gcaaaacgtg gacggaaagc     300
agcaaagatg actttcgtcc gctgctgatg gcgtggtggc cggataccga aacgaagcgc     360
aattacgtga actacatgaa caaagttgtt ggcatcgaca agacctatac cgcggaaacc     420
agccaggccg acttgaccgc tgcggcggaa ctggtgcaag cacgcattga gcagaagatc     480
acgaccgaac agaacacgaa atggctgcgt gaggcaatct cggcatttgt taaaacgcaa     540
ccgcagtgga acggtgaaag cgagaagccg tacgacgatc acctgcaaaa cggtgctctg     600
```

```
aaatttgata atcagagcga cctgaccccg gatacgcaaa gcaactaccg tctgttgaac      660
cgtaccccga ctaatcagac gggtagcctg gacagccgct tcacttataa cgcgaacgac      720
cctttgggcg gttatgagct gctgctggca aatgacgtcg ataacagcaa tccgatcgtg      780
caggcggagc agctgaactg gctgcattac ctgctgaatt ttggtacgat ctacgccaaa      840
gatgccgacg ctaacttcga tagcattcgt gtggacgcgg ttgataacgt cgatgcggat      900
ctgctgcaaa ttagcagcga ttacctgaaa gcagcctacg gcattgataa gaataacaaa      960
aacgcgaaca accacgtgag cattgtcgaa gcctggagcg ataatgatac cccgtacctg     1020
catgacgatg gtgacaacct gatgaatatg gataacaaat ttcgcctgtc catgctgtgg     1080
tcgctggcca aaccgctgga caagcgtagc ggtctgaacc cgctgattca taacagcttg     1140
gtggatcgtg aagttgatga ccgcgaggtt gaaacggttc cgagctattc ttttgcacgt     1200
gcgcatgata gcgaggtcca ggacttgatc cgtgacatca tcaaggcaga gatcaatccg     1260
aacgcattcg gttatagctt tacccaagac gagattgacc aggcctttaa gatttacaat     1320
gaggatctga agaaaacgga taagaaatac acccactata atgtgccgtt gagctacacc     1380
ctgctgctga cgaataaggg tagcatccca cgtgtctact atggtgatat gtttaccgac     1440
gatggtcagt atatggcgaa caaaaccgtc aactatgacg ccattgaatc tctgctgaaa     1500
gcgcgtatga agtatgtcgc tggcggtcaa gcaatgcaga actaccaaat cggtaatggt     1560
gagatcctga ccagcgttcg ttatggtaag ggtgccctga acagagcga caaaggtgat     1620 gcgaccacgc gcaccagcgg tgtcggtgtc gttatgggca atcagccaaa ctttagcttg     1680
gacggcaaag tggtggctct gaacatgggc gcagctcatg cgaatcagga gtatcgtgcg     1740
ctgatggtta gcacgaaaga cggtgttgcc acgtatgcga ccgatgcaga tgcgagcaaa     1800
gccggtctgg tcaaacgtac cgacgaaaac ggctacctgt atttcctgaa tgacgacctg     1860
aagggtgtgg ccaatcctca ggtgagcggt tcttgcagg tgtgggttcc ggtgggtgcc     1920
gcggatgatc aagatatccg tgttgcagct agcgataccg catccaccga tggcaagagc     1980
ctgcaccaag acgccgcgat ggatagccgt gttatgtttg aaggcttctc taactttcag     2040
tcctttgcca cgaaagaaga ggaatatacc aacgtcgtta tcgccaacaa tgtggataag     2100
ttcgttagct ggggtatcac ggatttcgag atggccccac aatatgtttc cagcaccgac     2160
ggtcaattcc tggactctgt cattcagaac ggttatgctt ttacgaccg ttatgacttg     2220 ggcatgtcta aggcaaacaa atacggcacg gccgatcaac tggttaaggc cattaaggcc     2280
ctgcacgcga agggcctgaa ggttatggca gattgggtgc cggatcagat gtataccttc     2340
ccgaaacagg aagtcgtgac cgttacccgt accgacaaat ttggcaaacc gatcgcaggt     2400
tcccaaatca atcatagcct gtatgttacc gataccaagt ccagcggcga tgactatcag     2460
gccaaatatg gtggtgcgtt tctggacgag ctgaaggaga aatatccgga gctgttcacg     2520
aagaaacaaa tcagcacggg tcaagctatt gaccccgagc tgaaaatcaa acagtggtct     2580
gctaagtatt tcaatggctc caacatcctg ggtcgcggtg cggactacgt actgtcggat     2640
caggcgagca acaaatacct gaacgtgtct gacgataaac tgttcctgcc gaaaaccttg     2700
ctgggccaag ttgtcgagag cggtatccgc tttgacggca ctggttatgt gtacaactct     2760
agcactacgg gtgaaaaagt taccgattcc ttcattacgg aggcaggtaa tctgtactac     2820
ttcggtcaag acggctatat ggtgaccggc gcacagaaca ttaagggcag caactattac     2880
ttcctggcca atggtgcggc cctgcgtaac accgtttaca ccgatgcgca aggtcagaat     2940
```

```
cactattacg gcaacgacgg caagcgttat gagaatggtt accaacagtt cggcaacgat    3000
tcttggcgtt acttcaaaaa tggcgtgatg gcgctgggtc tgactacggt ggatggtcac    3060
gtgcagtatt tcgataaaga tggtgtccag gccaaggata agatcattgt cacccgcgat    3120
ggcaaagtcc gctatttcga ccagcacaac ggtaatgcgg ttactaacac gttcgttgcg    3180
gacaagacgg gtcactggta ctatctgggc aaagacggcg tcgcggttac cggtgcgcag    3240
actgtgggta acagcatttg tactttgaa gcgaacggtc aacaagtcaa gggtgacttc    3300
gtgacggcta agacggtaa actgtacttc tatgatgtgg acagcggcga catgtggacc    3360 aatacctttta tcgaggataa agcgggtaat tggttctacc tgggtaagga cggtgcggcc    3420
gtcaccggtg cacagacgat caaaggccag aaattgtatt tcaaagccaa cggtcagcaa    3480
gttaaaggtg acattgtcaa ggacgcggac ggtaagatcc gttattacga cgctcagacc    3540
ggtgaacagg tctttaacaa gtccgttagc gtcaacggta agacctacta tttcggtagc    3600
gacggcaccg cgcaaaccca ggcgaatccg aaaggccaaa cctttaagga tggtagcggc    3660
gttctgcgtt tctacaattt ggagggccag tatgtctcgg gcagcggctg gtacgaaacg    3720
gccgagcacg agtgggtata tgtgaaatcc ggtaagttc tgaccggtgc ccagacgatt    3780
ggtaatcaac gtgtttactt caaggacaat ggtcaccagt tgaaaggcca gctggtcacg    3840
ggtaatgacg gtaaattgcg ttactacgac gcgaacagcg tgatcaagc attcaacaaa    3900 tccgtcacgg ttaacggtaa aacctactac tttggcagcg atggtacggc gcagacgcag    3960
gctaatccta agggtcagac cttcaaagat ggtagcggcg tgctgcgttt ttacaacttg    4020
gaaggccaat acgtgtctgg cagcggttgg tacaagaatg cgcagggcca gtggctgtac    4080
gtgaaagatg gcaaggtcct gaccggtctg caaacggtcg gcaatcagaa ggtctacttc    4140
gacaaaaatg gcatccaagc aaagggtaag gccgttcgca cgtccgatgg taaagtgcgc    4200
tactttgatg agaatagcgg tagcatgatt acgaaccaat ggaagttcgt ttacggtcaa    4260
tactattact tcggttctga cggcgcagcg gtttaccgtg gttggaacta a              4311
```

<210> SEQ ID NO 10
<211> LENGTH: 1436
<212> TYPE: PRT
<213> ORGANISM: Streptococcus downei

<400> SEQUENCE: 10

```
Met Val Asp Gly Lys Tyr Tyr Tyr Asp Gln Asp Gly Asn Val Lys
1               5                   10                  15

Lys Asn Phe Ala Val Ser Val Gly Glu Lys Ile Tyr Tyr Phe Asp Glu
            20                  25                  30

Thr Gly Ala Tyr Lys Asp Thr Ser Lys Val Glu Ala Asp Lys Ser Gly
        35                  40                  45

Ser Asp Ile Ser Lys Glu Glu Thr Thr Phe Ala Ala Asn Asn Arg Ala
    50                  55                  60

Tyr Ser Thr Ser Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Ser Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
```

-continued

```
                130             135             140
Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
                195                 200                 205

Thr Pro Asp Thr Gln Ser Asn Tyr Arg Leu Leu Asn Arg Thr Pro Thr
        210                 215                 220

Asn Gln Thr Gly Ser Leu Asp Ser Arg Phe Thr Tyr Asn Ala Asn Asp
225                 230                 235                 240

Pro Leu Gly Gly Tyr Glu Leu Leu Ala Asn Asp Val Asp Asn Ser
                245                 250                 255

Asn Pro Ile Val Gln Ala Glu Gln Leu Asn Trp Leu His Tyr Leu Leu
            260                 265                 270

Asn Phe Gly Thr Ile Tyr Ala Lys Asp Ala Asp Ala Asn Phe Asp Ser
        275                 280                 285

Ile Arg Val Asp Ala Val Asp Asn Val Asp Ala Asp Leu Leu Gln Ile
        290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
                340                 345                 350

Lys Phe Arg Leu Ser Met Leu Trp Ser Leu Ala Lys Pro Leu Asp Lys
                355                 360                 365

Arg Ser Gly Leu Asn Pro Leu Ile His Asn Ser Leu Val Asp Arg Glu
        370                 375                 380

Val Asp Asp Arg Glu Val Glu Thr Val Pro Ser Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ala Phe Gly Tyr Ser Phe Thr Gln Asp Glu Ile
                420                 425                 430

Asp Gln Ala Phe Lys Ile Tyr Asn Glu Asp Leu Lys Lys Thr Asp Lys
                435                 440                 445

Lys Tyr Thr His Tyr Asn Val Pro Leu Ser Tyr Thr Leu Leu Leu Thr
                450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ala Gly Gln Ala Met
                500                 505                 510

Gln Asn Tyr Gln Ile Gly Asn Gly Glu Ile Leu Thr Ser Val Arg Tyr
                515                 520                 525

Gly Lys Gly Ala Leu Lys Gln Ser Asp Lys Gly Asp Ala Thr Thr Arg
        530                 535                 540

Thr Ser Gly Val Gly Val Val Met Gly Asn Gln Pro Asn Phe Ser Leu
545                 550                 555                 560
```

Asp Gly Lys Val Val Ala Leu Asn Met Gly Ala Ala His Ala Asn Gln
            565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
            595                 600                 605

Glu Asn Gly Tyr Leu Tyr Phe Leu Asn Asp Asp Leu Lys Gly Val Ala
            610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
            645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
            675                 680                 685

Tyr Thr Asn Val Val Ile Ala Asn Asn Val Asp Lys Phe Val Ser Trp
            690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
            725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
            755                 760                 765

Met Ala Asp Trp Val Pro Asp Gln Met Tyr Thr Phe Pro Lys Gln Glu
770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
            805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
            835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asp Tyr Val Leu Ser Asp
865                 870                 875                 880

Gln Ala Ser Asn Lys Tyr Leu Asn Val Ser Asp Asp Lys Leu Phe Leu
            885                 890                 895

Pro Lys Thr Leu Leu Gly Gln Val Val Glu Ser Gly Ile Arg Phe Asp
            900                 905                 910

Gly Thr Gly Tyr Val Tyr Asn Ser Ser Thr Thr Gly Glu Lys Val Thr
            915                 920                 925

Asp Ser Phe Ile Thr Glu Ala Gly Asn Leu Tyr Tyr Phe Gly Gln Asp
            930                 935                 940

Gly Tyr Met Val Thr Gly Ala Gln Asn Ile Lys Gly Ser Asn Tyr Tyr
945                 950                 955                 960

Phe Leu Ala Asn Gly Ala Ala Leu Arg Asn Thr Val Tyr Thr Asp Ala
            965                 970                 975

-continued

```
Gln Gly Gln Asn His Tyr Tyr Gly Asn Asp Gly Lys Arg Tyr Glu Asn
            980                 985                 990

Gly Tyr Gln Gln Phe Gly Asn Asp Ser Trp Arg Tyr Phe Lys Asn Gly
        995                1000                1005

Val Met Ala Leu Gly Leu Thr Thr Val Asp Gly His Val Gln Tyr
    1010                1015                1020

Phe Asp Lys Asp Gly Val Gln Ala Lys Asp Lys Ile Ile Val Thr
    1025                1030                1035

Arg Asp Gly Lys Val Arg Tyr Phe Asp Gln His Asn Gly Asn Ala
    1040                1045                1050

Val Thr Asn Thr Phe Val Ala Asp Lys Thr Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Tyr Asp Val
    1100                1105                1110

Asp Ser Gly Asp Met Trp Thr Asn Thr Phe Ile Glu Asp Lys Ala
    1115                1120                1125

Gly Asn Trp Phe Tyr Leu Gly Lys Asp Gly Ala Ala Val Thr Gly
    1130                1135                1140

Ala Gln Thr Ile Lys Gly Gln Lys Leu Tyr Phe Lys Ala Asn Gly
    1145                1150                1155

Gln Gln Val Lys Gly Asp Ile Val Lys Asp Ala Asp Gly Lys Ile
    1160                1165                1170

Arg Tyr Tyr Asp Ala Gln Thr Gly Glu Gln Val Phe Asn Lys Ser
    1175                1180                1185

Val Ser Val Asn Gly Lys Thr Tyr Tyr Phe Gly Ser Asp Gly Thr
    1190                1195                1200

Ala Gln Thr Gln Ala Asn Pro Lys Gly Gln Thr Phe Lys Asp Gly
    1205                1210                1215

Ser Gly Val Leu Arg Phe Tyr Asn Leu Glu Gly Gln Tyr Val Ser
    1220                1225                1230

Gly Ser Gly Trp Tyr Glu Thr Ala Glu His Glu Trp Val Tyr Val
    1235                1240                1245

Lys Ser Gly Lys Val Leu Thr Gly Ala Gln Thr Ile Gly Asn Gln
    1250                1255                1260

Arg Val Tyr Phe Lys Asp Asn Gly His Gln Val Lys Gly Gln Leu
    1265                1270                1275

Val Thr Gly Asn Asp Gly Lys Leu Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Ser Asp Gly Thr Ala Gln Thr Gln Ala Asn Pro
    1310                1315                1320

Lys Gly Gln Thr Phe Lys Asp Gly Ser Gly Val Leu Arg Phe Tyr
    1325                1330                1335

Asn Leu Glu Gly Gln Tyr Val Ser Gly Ser Gly Trp Tyr Lys Asn
    1340                1345                1350

Ala Gln Gly Gln Trp Leu Tyr Val Lys Asp Gly Lys Val Leu Thr
    1355                1360                1365

Gly Leu Gln Thr Val Gly Asn Gln Lys Val Tyr Phe Asp Lys Asn
```

|  |  |  |  |  | 1370 |  |  | 1375 |  |  |  | 1380 |  |
|---|---|---|---|---|---|---|---|---|---|---|---|---|---|
| Gly | Ile | Gln | Ala | Lys | Gly | Lys | Ala | Val | Arg | Thr | Ser | Asp | Gly | Lys |
|  |  |  | 1385 |  |  |  |  | 1390 |  |  |  |  | 1395 |  |

| Val | Arg | Tyr | Phe | Asp | Glu | Asn | Ser | Gly | Ser | Met | Ile | Thr | Asn | Gln |
|---|---|---|---|---|---|---|---|---|---|---|---|---|---|---|
|  | 1400 |  |  |  |  | 1405 |  |  |  |  | 1410 |  |  |  |

| Trp | Lys | Phe | Val | Tyr | Gly | Gln | Tyr | Tyr | Tyr | Phe | Gly | Ser | Asp | Gly |
|---|---|---|---|---|---|---|---|---|---|---|---|---|---|---|
| 1415 |  |  |  |  | 1420 |  |  |  |  | 1425 |  |  |  |  |

| Ala | Ala | Val | Tyr | Arg | Gly | Trp | Asn |
|---|---|---|---|---|---|---|---|
|  | 1430 |  |  |  |  | 1435 |  |

<210> SEQ ID NO 11
<211> LENGTH: 3942
<212> TYPE: DNA
<213> ORGANISM: Streptococcus mutans

<400> SEQUENCE: 11

| atgattgacg gcaaatacta ctactatgac aacaacggca agtacgcac caatttcacg | 60 |
|---|---|
| ttgatcgcgg acggtaaaat cctgcatttt gatgaaactg gcgcgtacac cgacactagc | 120 |
| attgataccg tgaacaagga tattgtcacg acgcgtagca acctgtataa gaaatacaat | 180 |
| caagtgtatg atcgcagcgc gcagagcttc gagcatgttg atcactacct gacggcggaa | 240 |
| tcttggtacc gtccgaaata cattctgaaa gatggcaaga cctggaccca gagcaccgag | 300 |
| aaggacttcc gtcctctgct gatgacctgg tggccgagcc aggaaacgca cgccagtat | 360 |
| gtcaacttca tgaacgccca gttgggtatc aacaaaacgt acgacgacac cagcaatcag | 420 |
| ctgcaattga acatcgctgc tgcaacgatc caagcaaaga tcgaagccaa atcacgacg | 480 |
| ctgaagaaca ccgattggct gcgtcaaacg atcagcgcgt tcgtcaaaac ccaaagcgct | 540 |
| tggaatagcg acagcgaaaa gccgtttgat gaccatctgc aaaacggtgc ggttctgtat | 600 |
| gataacgaag gtaaattgac gccgtatgcc aatagcaact atcgtattct gaaccgcacg | 660 |
| ccgaccaacc agaccggtaa gaaggacccg cgttataccg ccgacaacac gatcggcggc | 720 |
| tacgagtttc tgctggccaa cgacgtggat aatagcaacc cggtggttca ggccgagcag | 780 |
| ctgaactggc tgcacttcct gatgaacttt ggtaatatct acgcaaacga ccctgacgct | 840 |
| aacttcgact ccatccgcgt tgacgctgtc gataatgtgg acgccgatct gttacagatc | 900 |
| gcgggtgact atctgaaagc ggcaaagggc atccataaga tgacaaagc ggcgaacgac | 960 |
| cacctgtcca ttctggaagc gtggagcgac aatgacactc cgtatctgca tgatgatggc | 1020 |
| gacaacatga ttaacatgga taacaaactg cgcctgagcc tgctgttctc cctggcgaaa | 1080 |
| ccgctgaatc agcgtagcgg tatgaacccg ttgattacga cagcctggt caaccgtact | 1140 |
| gatgataatg ccgaaacggc ggcagtgcca agctactctt ttatccgtgc ccacgatagc | 1200 |
| gaggtccagg atttgattcg tgatatcatt aaggctgaga ttaacccgaa cgtcgtcggt | 1260 |
| tacagcttca cgatggaaga gattaagaag gcatttgaga tctacaataa ggacctgttg | 1320 |
| gccacggaga agaagtatac ccactataac accgcattga gctacgcgtt gctgctgacg | 1380 |
| aacaagagca gcgtgccgcg tgtctactat ggtgatatgt ttacggacga tggtcaatac | 1440 |
| atggcccaca agaccattaa ctacgaggca atcgaaaccc tgctgaaagc acgtatcaag | 1500 |
| tacgtgtccg gtggtcaggc tatgcgcaac cagcaagtgg gtaattcgga gatcatcacc | 1560 |
| agcgtgcgtt acggtaaagg tgcgctgaag gcgatggata cgggtgaccg cactacccgt | 1620 |
| acctctggtg tggcggtcat tgagggcaac aacccgagct gcgcctgaa ggcttctgat | 1680 |
| cgtgtggttg tgaatatggg tgcggcccac aaaaatcaag cctatcgccc gctgctgttg | 1740 |

```
acgaccgata acggcattaa ggcctatcac agcgaccaag aagcggcagg cctggtgcgt   1800
tacaccaacg accgtggcga actgatcttt accgcagccg acattaaggg ctacgcaaat   1860
ccgcaagtta gcggctacct gggcgtctgg gtccctgttg gcgcagcagc tgatcaggac   1920
gttcgtgttg cggcgagcac cgcgccaagc acggacggca agagcgttca ccagaacgcg   1980
gctctggaca gccgtgtgat gttcgagggt ttctcgaact tccaggcatt gctaccaag    2040 aaagaagagt ataccaatgt ggtcatcgct aagaatgtgg ataagttcgc ggagtggggt   2100
gtcaccgatt tcgagatggc tccgcaatac gtttctagca ccgacggtag cttttggat    2160 agcgtgattc aaaacggtta tgcttttacc gaccgttacg acctgggcat cagcaagccg   2220
aacaaatatg gcaccgcgga cgatctggtt aaagcgatta aggcattgca cagcaaaggc   2280
atcaaagtta tggcggattg ggttccggac cagatgtatg ccctgccgga aaagaggtt    2340 gtgacggcaa cccgtgttga caaatacggt acgccggtag ctggcagcca gatcaaaaac   2400
acgctgtacg tggtcgatgg taaatctagc ggtaaggacc agcaggcgaa gtacggtggt   2460
gccttcctgg aagagctgca agcgaagtat ccggaactgt tcgcgcgcaa acagattagc   2520
accggtgttc cgatggaccc gagcgtcaag attaagcaat ggagcgcaaa atacttcaac   2580
ggcacgaata tcctgggtcg tggtgctggt tacgtgctga agatcaggc aaccaacacc    2640 tactttaaca tcagcgacaa taaagagatc aatttcctgc caaagacgtt gctgaaccag   2700
gattctcaag ttggctttag ctacgacggt aagggctatg tgtactacag cacctcgggc   2760
taccaggcta aaaacacgtt catcagcgag ggtgacaagt ggtattactt cgacaataac   2820
ggttatatgg ttaccggcgc acagagcatt aatggtgtga actattactt cctgccgaat   2880
ggtttacagc tgcgtgatgc gattctgaaa atgaggacg gtacgtacgc gtattatggc    2940
aatgatggtc gccgctacga gaatggctat tatcagtta tgagcggtgt ttggcgccat    3000
ttcaataatg gcgagatgtc cgttggtctg accgtcattg acggtcaagt tcaatacttt   3060
gacgagatgg gttaccaggc gaaaggcaaa ttcgttacca ccgcggatgg taagatccgt   3120
tacttcgata gcagagcgg caatatgtat cgtaatcgtt tcattgagaa cgaagagggc    3180
aaatggctgt acctgggtga ggacggcgcg gcagtcaccg gtagccagac gatcaatggt   3240
cagcacctgt attttcgtgc taacggcgtt caggttaagg gtgagttcgt gaccgatcgt   3300
catggccgca tctcttatta cgacggcaac agcggtgatc agatccgcaa ccgtttcgtc   3360
cgcaatgcgc aaggccagtg gttttacttt gacaacaatg gctatgcagt aactggtgct   3420
cgtacgatca acgccagca cctgtatttc cgcgcgaacg tgttcaggt aaaaggtgag    3480 tttgttacgg accgccacgg ccgcattagc tattatgatg gtaatagcgg tgaccaaatt   3540
cgcaatcgtt tcgtgcgtaa tgcacagggt cagtggttct acttcgacaa taatggttat   3600
gcagtcacgg gtgcacgtac cattaacggc caacacctgt actttcgcgc caatggtgtg   3660
caagtgaaag cgaatttgt tactgatcgt tatggtcgta tcagctacta tgatggcaat    3720
tctggcgacc aaattcgcaa tcgctttgtt cgtaacgccc aaggtcaatg gttctatttc   3780
gacaacaacg gttacgcggt gaccggtgcc cgcacgatta atggtcaaca cttgtacttc   3840
cgtgccaacg gtgtccaggt gaagggtgaa tttgtgaccg accgctatgg tcgcatttct   3900
tactacgacg caaattccgg tgaacgcgtc cgtatcaatt aa                      3942
```

<210> SEQ ID NO 12
<211> LENGTH: 1313
<212> TYPE: PRT

-continued

<213> ORGANISM: Streptococcus mutans

<400> SEQUENCE: 12

```
Met Ile Asp Gly Lys Tyr Tyr Tyr Asp Asn Asn Gly Lys Val Arg
1               5                   10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
            35                  40                  45

Val Thr Thr Arg Ser Asn Leu Tyr Lys Lys Tyr Asn Gln Val Tyr Asp
            50                  55                  60

Arg Ser Ala Gln Ser Phe Glu His Val Asp His Tyr Leu Thr Ala Glu
65              70                  75                  80

Ser Trp Tyr Arg Pro Lys Tyr Ile Leu Lys Asp Gly Lys Thr Trp Thr
                85                  90                  95

Gln Ser Thr Glu Lys Asp Phe Arg Pro Leu Leu Met Thr Trp Trp Pro
            100                 105                 110

Ser Gln Glu Thr Gln Arg Gln Tyr Val Asn Phe Met Asn Ala Gln Leu
            115                 120                 125

Gly Ile Asn Lys Thr Tyr Asp Asp Thr Ser Asn Gln Leu Gln Leu Asn
130                 135                 140

Ile Ala Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
                165                 170                 175

Thr Gln Ser Ala Trp Asn Ser Asp Ser Glu Lys Pro Phe Asp Asp His
            180                 185                 190

Leu Gln Asn Gly Ala Val Leu Tyr Asp Asn Glu Gly Lys Leu Thr Pro
            195                 200                 205

Tyr Ala Asn Ser Asn Tyr Arg Ile Leu Asn Arg Thr Pro Thr Asn Gln
210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
                245                 250                 255

Gln Ala Glu Gln Leu Asn Trp Leu His Phe Leu Met Asn Phe Gly Asn
            260                 265                 270

Ile Tyr Ala Asn Asp Pro Asp Ala Asn Phe Asp Ser Ile Arg Val Asp
            275                 280                 285

Ala Val Asp Asn Val Asp Ala Asp Leu Leu Gln Ile Ala Gly Asp Tyr
290                 295                 300

Leu Lys Ala Ala Lys Gly Ile His Lys Asn Asp Lys Ala Ala Asn Asp
305                 310                 315                 320

His Leu Ser Ile Leu Glu Ala Trp Ser Asp Asn Asp Thr Pro Tyr Leu
                325                 330                 335

His Asp Asp Gly Asp Asn Met Ile Asn Met Asp Asn Lys Leu Arg Leu
            340                 345                 350

Ser Leu Leu Phe Ser Leu Ala Lys Pro Leu Asn Gln Arg Ser Gly Met
            355                 360                 365

Asn Pro Leu Ile Thr Asn Ser Leu Val Asn Arg Thr Asp Asp Asn Ala
            370                 375                 380

Glu Thr Ala Ala Val Pro Ser Tyr Ser Phe Ile Arg Ala His Asp Ser
385                 390                 395                 400
```

```
Glu Val Gln Asp Leu Ile Arg Asp Ile Ile Lys Ala Glu Ile Asn Pro
                405                 410                 415

Asn Val Val Gly Tyr Ser Phe Thr Met Glu Glu Ile Lys Lys Ala Phe
            420                 425                 430

Glu Ile Tyr Asn Lys Asp Leu Leu Ala Thr Glu Lys Lys Tyr Thr His
        435                 440                 445

Tyr Asn Thr Ala Leu Ser Tyr Ala Leu Leu Leu Thr Asn Lys Ser Ser
    450                 455                 460

Val Pro Arg Val Tyr Tyr Gly Asp Met Phe Thr Asp Asp Gly Gln Tyr
465                 470                 475                 480

Met Ala His Lys Thr Ile Asn Tyr Glu Ala Ile Glu Thr Leu Leu Lys
                485                 490                 495

Ala Arg Ile Lys Tyr Val Ser Gly Gly Gln Ala Met Arg Asn Gln Gln
            500                 505                 510

Val Gly Asn Ser Glu Ile Ile Thr Ser Val Arg Tyr Gly Lys Gly Ala
        515                 520                 525

Leu Lys Ala Met Asp Thr Gly Asp Arg Thr Thr Arg Thr Ser Gly Val
    530                 535                 540

Ala Val Ile Glu Gly Asn Asn Pro Ser Leu Arg Leu Lys Ala Ser Asp
545                 550                 555                 560

Arg Val Val Asn Met Gly Ala Ala His Lys Asn Gln Ala Tyr Arg
                565                 570                 575

Pro Leu Leu Leu Thr Thr Asp Asn Gly Ile Lys Ala Tyr His Ser Asp
            580                 585                 590

Gln Glu Ala Ala Gly Leu Val Arg Tyr Thr Asn Asp Arg Gly Glu Leu
        595                 600                 605

Ile Phe Thr Ala Ala Asp Ile Lys Gly Tyr Ala Asn Pro Gln Val Ser
    610                 615                 620

Gly Tyr Leu Gly Val Trp Val Pro Val Gly Ala Ala Asp Gln Asp
625                 630                 635                 640

Val Arg Val Ala Ala Ser Thr Ala Pro Ser Thr Asp Gly Lys Ser Val
                645                 650                 655

His Gln Asn Ala Ala Leu Asp Ser Arg Val Met Phe Glu Gly Phe Ser
            660                 665                 670

Asn Phe Gln Ala Phe Ala Thr Lys Lys Glu Glu Tyr Thr Asn Val Val
        675                 680                 685

Ile Ala Lys Asn Val Asp Lys Phe Ala Glu Trp Gly Val Thr Asp Phe
    690                 695                 700

Glu Met Ala Pro Gln Tyr Val Ser Ser Thr Asp Gly Ser Phe Leu Asp
705                 710                 715                 720

Ser Val Ile Gln Asn Gly Tyr Ala Phe Thr Asp Arg Tyr Asp Leu Gly
                725                 730                 735

Ile Ser Lys Pro Asn Lys Tyr Gly Thr Ala Asp Asp Leu Val Lys Ala
            740                 745                 750

Ile Lys Ala Leu His Ser Lys Gly Ile Lys Val Met Ala Asp Trp Val
        755                 760                 765

Pro Asp Gln Met Tyr Ala Leu Pro Glu Lys Glu Val Val Thr Ala Thr
    770                 775                 780

Arg Val Asp Lys Tyr Gly Thr Pro Val Ala Gly Ser Gln Ile Lys Asn
785                 790                 795                 800

Thr Leu Tyr Val Val Asp Gly Lys Ser Ser Gly Lys Asp Gln Gln Ala
                805                 810                 815

Lys Tyr Gly Gly Ala Phe Leu Glu Glu Leu Gln Ala Lys Tyr Pro Glu
```

```
                     820                 825                 830
Leu Phe Ala Arg Lys Gln Ile Ser Thr Gly Val Pro Met Asp Pro Ser
                835                 840                 845

Val Lys Ile Lys Gln Trp Ser Ala Lys Tyr Phe Asn Gly Thr Asn Ile
850                 855                 860

Leu Gly Arg Gly Ala Gly Tyr Val Leu Lys Asp Gln Ala Thr Asn Thr
865                 870                 875                 880

Tyr Phe Asn Ile Ser Asp Asn Lys Glu Ile Asn Phe Leu Pro Lys Thr
                885                 890                 895

Leu Leu Asn Gln Asp Ser Gln Val Gly Phe Ser Tyr Asp Gly Lys Gly
                900                 905                 910

Tyr Val Tyr Tyr Ser Thr Ser Gly Tyr Gln Ala Lys Asn Thr Phe Ile
                915                 920                 925

Ser Glu Gly Asp Lys Trp Tyr Tyr Phe Asp Asn Asn Gly Tyr Met Val
                930                 935                 940

Thr Gly Ala Gln Ser Ile Asn Gly Val Asn Tyr Tyr Phe Leu Pro Asn
945                 950                 955                 960

Gly Leu Gln Leu Arg Asp Ala Ile Leu Lys Asn Glu Asp Gly Thr Tyr
                965                 970                 975

Ala Tyr Tyr Gly Asn Asp Gly Arg Arg Tyr Glu Asn Gly Tyr Tyr Gln
                980                 985                 990

Phe Met Ser Gly Val Trp Arg His Phe Asn Asn Gly Glu Met Ser Val
                995                1000                1005

Gly Leu Thr Val Ile Asp Gly Gln Val Gln Tyr Phe Asp Glu Met
                1010                1015                1020

Gly Tyr Gln Ala Lys Gly Lys Phe Val Thr Thr Ala Asp Gly Lys
                1025                1030                1035

Ile Arg Tyr Phe Asp Lys Gln Ser Gly Asn Met Tyr Arg Asn Arg
                1040                1045                1050

Phe Ile Glu Asn Glu Glu Gly Lys Trp Leu Tyr Leu Gly Glu Asp
                1055                1060                1065

Gly Ala Ala Val Thr Gly Ser Gln Thr Ile Asn Gly Gln His Leu
                1070                1075                1080

Tyr Phe Arg Ala Asn Gly Val Gln Val Lys Gly Glu Phe Val Thr
                1085                1090                1095

Asp Arg His Gly Arg Ile Ser Tyr Tyr Asp Gly Asn Ser Gly Asp
                1100                1105                1110

Gln Ile Arg Asn Arg Phe Val Arg Asn Ala Gln Gly Gln Trp Phe
                1115                1120                1125

Tyr Phe Asp Asn Asn Gly Tyr Ala Val Thr Gly Ala Arg Thr Ile
                1130                1135                1140

Asn Gly Gln His Leu Tyr Phe Arg Ala Asn Gly Val Gln Val Lys
                1145                1150                1155

Gly Glu Phe Val Thr Asp Arg His Gly Arg Ile Ser Tyr Tyr Asp
                1160                1165                1170

Gly Asn Ser Gly Asp Gln Ile Arg Asn Arg Phe Val Arg Asn Ala
                1175                1180                1185

Gln Gly Gln Trp Phe Tyr Phe Asp Asn Asn Gly Tyr Ala Val Thr
                1190                1195                1200

Gly Ala Arg Thr Ile Asn Gly Gln His Leu Tyr Phe Arg Ala Asn
                1205                1210                1215

Gly Val Gln Val Lys Gly Glu Phe Val Thr Asp Arg Tyr Gly Arg
                1220                1225                1230
```

```
Ile Ser Tyr Tyr Asp Gly Asn  Ser Gly Asp Gln Ile  Arg Asn Arg
    1235                 1240                 1245

Phe Val Arg Asn Ala Gln Gly  Gln Trp Phe Tyr Phe  Asp Asn Asn
    1250                 1255                 1260

Gly Tyr Ala Val Thr Gly Ala  Arg Thr Ile Asn Gly  Gln His Leu
    1265                 1270                 1275

Tyr Phe Arg Ala Asn Gly Val  Gln Val Lys Gly Glu  Phe Val Thr
    1280                 1285                 1290

Asp Arg Tyr Gly Arg Ile Ser  Tyr Tyr Asp Ala Asn  Ser Gly Glu
    1295                 1300                 1305

Arg Val Arg Ile Asn
    1310

<210> SEQ ID NO 13
<211> LENGTH: 3972
<212> TYPE: DNA
<213> ORGANISM: Streptococcus dentirousetti

<400> SEQUENCE: 13
```

| | | | | | |
|---|---|---|---|---|---|
| atggttgacg | gcaaatacta | ctactacgat | gcagacggca | acgtaaagaa | aaacttcgcg | 60 |
| gttagcgttg | gcgatgccat | tttctatttt | gatgaaacgg | gtgcctacaa | agataccagc | 120 |
| aaagttgatg | cggataagac | cagctctagc | gtcaatcaga | ccacggaaac | gttcgcagcg | 180 |
| aataaccgtg | cgtatagcac | cgcagccgag | aactttgaag | cgattgataa | ctacctgact | 240 |
| gcggatagct | ggtatcgtcc | gaagtctatc | ttgaaagatg | gtacgacgtg | gaccgaaagc | 300 |
| accaaggatg | attttcgccc | gctgctgatg | gcgtggtggc | cggataccga | aaccaaacgt | 360 |
| aactacgtga | actatatgaa | caaggtggtc | ggtatcgaca | aaacgtacac | cgcggaaacg | 420 |
| tcccaagctg | acctgacggc | ggcagccgaa | ctggtgcagg | cgcgtatcga | gcagaaaatc | 480 |
| actagcgaaa | agaatacgaa | gtggctgcgt | gaggcgattt | ccgcgttcgt | taagactcaa | 540 |
| ccgcagtgga | atggcgagag | cgagaaacct | tatgatgacc | acctgcaaaa | tggtgcgctg | 600 |
| aagttcgaca | atgaaaccag | cctgaccccg | gatacgcaga | gcggctatcg | catcctgaac | 660 |
| cgtaccccga | cgaatcaaac | cggtagcctg | gacccgcgct | tcaccttaa | tcagaatgac | 720 |
| ccgctgggtg | gttatgagta | tttgctggct | aatgatgtcg | ataacagcaa | cccggtcgtt | 780 |
| caggccgaga | gcctgaactg | gctgcattac | ctgctgaatt | tggtagcat | ttacgcgaat | 840 |
| gatccggagg | ccaatttcga | cagcatccgt | gtggacgcgg | tggacaatgt | tgacgcagac | 900 |
| ctgctgcaaa | ttagctcgga | ttacctgaaa | tcggcgtaca | aaattgacaa | gaacaacaaa | 960 |
| aatgcgaacg | accacgttag | catcgtcgag | gcgtggagcg | acaatgatac | cccgtacctg | 1020 |
| aatgatgatg | cgacaatctc | gatgaacatg | gataacaagt | tcgtctgag | catgctgtgg | 1080 |
| agcctggcga | agccaaccaa | tgtccgtagc | ggcttgaatc | cgctgatcca | caacagcgtg | 1140 |
| gttgaccgtg | aggtggacga | ccgtgaagtt | gaggctaccc | cgaattacag | ctttgcacgc | 1200 |
| gcacacgaca | gcgaagttca | agatttgatt | cgcgacatca | tcaaagctga | gatcaaccca | 1260 |
| aacagcttcg | gttatagctt | tacccaagag | gaaatcgacc | aggccttcaa | gatctacaat | 1320 |
| gaggatttga | agaaaccaa | taagaagtat | acccactaca | acgtcccgct | gagctacacc | 1380 |
| ctgctgctga | cgaacaaggg | cagcattcca | cgcatttact | acggtgacat | gtttacggat | 1440 |
| gacggtcagt | atatggccaa | caaaaccgtt | aactatgacg | ccattgagag | cctgctgaaa | 1500 |
| gcacgtatga | agtatgttag | cggtggccaa | gcgatgcaga | attacaacat | cggcaacggc | 1560 |

```
gagattctga ccagcgtccg ttacggtaag ggtgccctga acagagcga caaaggcgat   1620 aagactactc gtaccagcgg tattggcgtt gtgatgggta accagagcaa tttcagcctg   1680
gagggcaagg tggtggccct gaatatgggt gcaacgcata ccaaacagaa gtatcgtgca   1740
ttgatggtgt ctacggaaac cggcgtggcg atttacaata gcgatgaaga agcagaggca   1800
gcaggcctga tcaaaacgac cgatgagaat ggttatttgt actttctgaa tgacgatctg   1860
aagggcgtgg ctaacccgca ggtcagcggc ttcctgcaag tgtgggttcc ggttggtgca   1920
ccggctgacc aggacattcg tgtggcggcg accgatgcgg cttctaccga cggtaagagc   1980
ctgcatcagg acgcagctct ggattctcgc gtcatgtttg aaggtttcag caacttccag   2040
agcttcgcaa ccaaggaaga ggaatacacc aacgttgtta ttgcaaagaa cgtggataag   2100
ttcgtgagct ggggtatcac cgacttcgag atggcaccgc agtacgttag ctctaccgat   2160 ggcaccttc tggatagcgt gattcaaaat ggctatgcct ttacggaccg ttacgacctg   2220
ggtatgagca agcaaacaa gtatggtact gctgaccaac tggtggccgc gattaaagcg   2280
ctgcatgcga agggtctgcg tgtgatggcg gattgggtcc cagatcaaat gtacactttc   2340
cctaagaagg aagtggttac cgttacccgt acggacaaat ttggcaatcc agtggcaggc   2400
agccaaatca ccacaccttt gtacgtcact gatactaagg gtagcggtga cgactaccag   2460
gcgaagtacg gtggcgcatt cctggatgaa ctgaagaaa agtacccgga gctgtttacc   2520
aagaagcaaa tcagcaccgg tcaggcaatc gacccgagcg tgaaaatcaa gcagtggagc   2580
gcgaagtact tcaacggtag caatatcttg ggtcgcggtg cgaactacgt gctgtccgac   2640
caggcgtcta acaagtactt taacgtgccc gaaggtaaag tctttctgcc agcggcgatg   2700
ctgggtaagg tcgtcgagag cggtatccgt ttcgacggta aaggttatat ctataacagc   2760
agcaccactg gcgaacaagt gaaggacagc ttcattaccg aagcgggtaa cttgtactat   2820
tttggcaaag atggttatat ggtcatgggt gcacagaata tccagggtgc taactactac   2880
ttcttggcga atggtgcggc cctgcgcaat agcatcctga cggatcagga tggcaaaagc   2940
cactattatg caaatgacgg caagcgttat gagaacggct actatcaatt cggtaacgac   3000
tcctggcgct attttgaaaa cggcgttatg gccgttggtt tgacgcgcgt tgcgggccac   3060
gaccaatact ttgataagga tggtatccaa gcgaagaata agatcattgt tacgcgtgac   3120
ggtaaggtcc gctacttcga cgaacacaac ggcaatgctg ccacgaatac gtttatcagc   3180
gatcaagccg gccattggta ctacctgggt aaagatggtg tcgccgtgac gggtgcgcag   3240
accgttggca gcaacacct gtacttcgag gctaacggcc aacaagtaaa aggcgatttt   3300
gttaccgcca aggacggtaa gttgtatttt ctggacggtg actctggcga catgtggacc   3360
gataccttcg tccaggataa ggctggtcat tggttctatc tgggcaaaga cggtgcggcg   3420
gtaaccggtg cccagaccgt ccgtggtcag aagctgtact tcaaagcgaa tggccagcag   3480
gttaagggtg acattgtgaa aggcgcggat ggtaaaatcc gttactatga tgcaaattcc   3540
ggtgaccagg tttacaatcg cacggtgaaa ggctccgacg gcaagaccta tatcattggt   3600
aatgacggcg tcgcaatcac gcaaaccatc gccaaaggcc agaccatcaa ggatggcagc   3660
gttctgcgct tctatagcat ggagggtcag ctggtgaccg gcagcggctg gtattccaac   3720
gcgaaaggtc aatggttgta tgtcaagaac ggtcaagtcc tgacgggttt gcagacggtg   3780
ggcagccagc gtgtgtactt tgacgcaaat ggtattcaag cgaaaggtaa agcagtgcgt   3840
acctccgatg gcaaactgcg ttacttcgat gcgaacagcg gcagcatgat caccaatcag   3900
tggaaagaag ttaatggtca gtactactat ttcgacaaca acggtgttgc gatctatcgc   3960
```
ggttggaact aa                                                         3972

<210> SEQ ID NO 14
<211> LENGTH: 1323
<212> TYPE: PRT
<213> ORGANISM: Streptococcus dentirousetti

<400> SEQUENCE: 14

```
Met Val Asp Gly Lys Tyr Tyr Tyr Asp Ala Asp Gly Asn Val Lys
1               5                   10                  15

Lys Asn Phe Ala Val Ser Val Gly Asp Ala Ile Phe Tyr Phe Asp Glu
            20                  25                  30

Thr Gly Ala Tyr Lys Asp Thr Ser Lys Val Asp Ala Asp Lys Thr Ser
        35                  40                  45

Ser Ser Val Asn Gln Thr Thr Glu Thr Phe Ala Ala Asn Asn Arg Ala
50                  55                  60

Tyr Ser Thr Ala Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Thr Thr
                85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
130                 135                 140

Leu Thr Ala Ala Ala Glu Leu Val Gln Ala Arg Ile Glu Gln Lys Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
        195                 200                 205

Thr Pro Asp Thr Gln Ser Gly Tyr Arg Ile Leu Asn Arg Thr Pro Thr
210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
        290                 295                 300

Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
                325                 330                 335

Thr Pro Tyr Leu Asn Asp Asp Gly Asp Asn Leu Met Asn Met Asp Asn
            340                 345                 350

Lys Phe Arg Leu Ser Met Leu Trp Ser Leu Ala Lys Pro Thr Asn Val
        355                 360                 365
```

```
Arg Ser Gly Leu Asn Pro Leu Ile His Asn Ser Val Val Asp Arg Glu
    370             375                 380
Val Asp Asp Arg Glu Val Glu Ala Thr Pro Asn Tyr Ser Phe Ala Arg
385                 390                 395                 400
Ala His Asp Ser Glu Val Gln Asp Leu Ile Arg Asp Ile Ile Lys Ala
                405                 410                 415
Glu Ile Asn Pro Asn Ser Phe Gly Tyr Ser Phe Thr Gln Glu Glu Ile
                420                 425                 430
Asp Gln Ala Phe Lys Ile Tyr Asn Glu Asp Leu Lys Lys Thr Asn Lys
            435                 440                 445
Lys Tyr Thr His Tyr Asn Val Pro Leu Ser Tyr Thr Leu Leu Leu Thr
    450                 455                 460
Asn Lys Gly Ser Ile Pro Arg Ile Tyr Tyr Gly Asp Met Phe Thr Asp
465                 470                 475                 480
Asp Gly Gln Tyr Met Ala Asn Lys Thr Val Asn Tyr Asp Ala Ile Glu
                485                 490                 495
Ser Leu Leu Lys Ala Arg Met Lys Tyr Val Ser Gly Gln Ala Met
            500                 505                 510
Gln Asn Tyr Asn Ile Gly Asn Gly Glu Ile Leu Thr Ser Val Arg Tyr
    515                 520                 525
Gly Lys Gly Ala Leu Lys Gln Ser Asp Lys Gly Asp Lys Thr Thr Arg
    530                 535                 540
Thr Ser Gly Ile Gly Val Val Met Gly Asn Gln Ser Asn Phe Ser Leu
545                 550                 555                 560
Glu Gly Lys Val Val Ala Leu Asn Met Gly Ala Thr His Thr Lys Gln
                565                 570                 575
Lys Tyr Arg Ala Leu Met Val Ser Thr Glu Thr Gly Val Ala Ile Tyr
    580                 585                 590
Asn Ser Asp Glu Glu Ala Glu Ala Ala Gly Leu Ile Lys Thr Thr Asp
            595                 600                 605
Glu Asn Gly Tyr Leu Tyr Phe Leu Asn Asp Asp Leu Lys Gly Val Ala
    610                 615                 620
Asn Pro Gln Val Ser Gly Phe Leu Gln Val Trp Val Pro Val Gly Ala
625                 630                 635                 640
Pro Ala Asp Gln Asp Ile Arg Val Ala Ala Thr Asp Ala Ala Ser Thr
                645                 650                 655
Asp Gly Lys Ser Leu His Gln Asp Ala Ala Leu Asp Ser Arg Val Met
            660                 665                 670
Phe Glu Gly Phe Ser Asn Phe Gln Ser Phe Ala Thr Lys Glu Glu Glu
    675                 680                 685
Tyr Thr Asn Val Val Ile Ala Lys Asn Val Asp Lys Phe Val Ser Trp
    690                 695                 700
Gly Ile Thr Asp Phe Glu Met Ala Pro Gln Tyr Val Ser Ser Thr Asp
705                 710                 715                 720
Gly Thr Phe Leu Asp Ser Val Ile Gln Asn Gly Tyr Ala Phe Thr Asp
                725                 730                 735
Arg Tyr Asp Leu Gly Met Ser Lys Ala Asn Lys Tyr Gly Thr Ala Asp
                740                 745                 750
Gln Leu Val Ala Ala Ile Lys Ala Leu His Ala Lys Gly Leu Arg Val
            755                 760                 765
Met Ala Asp Trp Val Pro Asp Gln Met Tyr Thr Phe Pro Lys Lys Glu
    770                 775                 780
```

Val Val Thr Val Thr Arg Thr Asp Lys Phe Gly Asn Pro Val Ala Gly
785                 790                 795                 800

Ser Gln Ile Asn His Thr Leu Tyr Val Thr Asp Thr Lys Gly Ser Gly
            805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
            835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asn Tyr Val Leu Ser Asp
865                 870                 875                 880

Gln Ala Ser Asn Lys Tyr Phe Asn Val Ala Glu Gly Lys Val Phe Leu
            885                 890                 895

Pro Ala Ala Met Leu Gly Lys Val Val Glu Ser Gly Ile Arg Phe Asp
            900                 905                 910

Gly Lys Gly Tyr Ile Tyr Asn Ser Ser Thr Thr Gly Glu Gln Val Lys
            915                 920                 925

Asp Ser Phe Ile Thr Glu Ala Gly Asn Leu Tyr Tyr Phe Gly Lys Asp
930                 935                 940

Gly Tyr Met Val Met Gly Ala Gln Asn Ile Gln Gly Ala Asn Tyr Tyr
945                 950                 955                 960

Phe Leu Ala Asn Gly Ala Ala Leu Arg Asn Ser Ile Leu Thr Asp Gln
            965                 970                 975

Asp Gly Lys Ser His Tyr Tyr Ala Asn Asp Gly Lys Arg Tyr Glu Asn
            980                 985                 990

Gly Tyr Tyr Gln Phe Gly Asn Asp Ser Trp Arg Tyr Phe Glu Asn Gly
            995                 1000                1005

Val Met Ala Val Gly Leu Thr Arg Val Ala Gly His Asp Gln Tyr
1010                1015                1020

Phe Asp Lys Asp Gly Ile Gln Ala Lys Asn Lys Ile Ile Val Thr
1025                1030                1035

Arg Asp Gly Lys Val Arg Tyr Phe Asp Glu His Asn Gly Asn Ala
1040                1045                1050

Ala Thr Asn Thr Phe Ile Ser Asp Gln Ala Gly His Trp Tyr Tyr
1055                1060                1065

Leu Gly Lys Asp Gly Val Ala Val Thr Gly Ala Gln Thr Val Gly
1070                1075                1080

Lys Gln His Leu Tyr Phe Glu Ala Asn Gly Gln Gln Val Lys Gly
1085                1090                1095

Asp Phe Val Thr Ala Lys Asp Gly Lys Leu Tyr Phe Leu Asp Gly
1100                1105                1110

Asp Ser Gly Asp Met Trp Thr Asp Thr Phe Val Gln Asp Lys Ala
1115                1120                1125

Gly His Trp Phe Tyr Leu Gly Lys Asp Gly Ala Ala Val Thr Gly
1130                1135                1140

Ala Gln Thr Val Arg Gly Gln Lys Leu Tyr Phe Lys Ala Asn Gly
1145                1150                1155

Gln Gln Val Lys Gly Asp Ile Val Lys Gly Ala Asp Gly Lys Ile
1160                1165                1170

Arg Tyr Tyr Asp Ala Asn Ser Gly Asp Gln Val Tyr Asn Arg Thr
1175                1180                1185

Val Lys Gly Ser Asp Gly Lys Thr Tyr Ile Ile Gly Asn Asp Gly

```
                    1190            1195                    1200
Val Ala Ile Thr Gln Thr Ile Ala Lys Gly Gln Thr Ile Lys Asp
        1205                1210                1215

Gly Ser Val Leu Arg Phe Tyr Ser Met Glu Gly Gln Leu Val Thr
        1220                1225                1230

Gly Ser Gly Trp Tyr Ser Asn Ala Lys Gly Gln Trp Leu Tyr Val
        1235                1240                1245

Lys Asn Gly Gln Val Leu Thr Gly Leu Gln Thr Val Gly Ser Gln
        1250                1255                1260

Arg Val Tyr Phe Asp Ala Asn Gly Ile Gln Ala Lys Gly Lys Ala
        1265                1270                1275

Val Arg Thr Ser Asp Gly Lys Leu Arg Tyr Phe Asp Ala Asn Ser
        1280                1285                1290

Gly Ser Met Ile Thr Asn Gln Trp Lys Glu Val Asn Gly Gln Tyr
        1295                1300                1305

Tyr Tyr Phe Asp Asn Asn Gly Val Ala Ile Tyr Arg Gly Trp Asn
        1310                1315                1320

<210> SEQ ID NO 15
<211> LENGTH: 4047
<212> TYPE: DNA
<213> ORGANISM: Streptococcus oralis

<400> SEQUENCE: 15
atgatcgacg gcaaaaacta ctacgtacag gatgatggca cggtaaagaa gaatttcgcg      60
gtagaactga tggtcgtat  cctgtatttt gatgcagaaa ccggcgctct ggttgatagc     120
aacgagtatc agttccaaca gggtacgagc agcctgaaca tgaattttc  tcagaagaac     180
gcattctatg gtacgaccga taaggatatt gagactgtgg atggctacct gaccgcagat     240
agctggtatc gcccgaaatt catcctgaag gatggcaaga cgtggaccgc gagcacggaa     300
acggatctgc gtccgctgtt gatggcatgg tggccggaca gcgtacccca aatcaactat     360
ctgaactaca tgaaccagca gggtctgggt gcgggtgcgt tgagaacaa  agtggagcag     420
gccctgctga cgggtgcaag ccaacaggta caacgcaaga tcgaagagaa gattggtaaa     480
gagggtgata ccaagtggct gcgcaccctg atgggtgcgt tcgtgaaaac gcaaccaaac     540
tggaatatca aaaccgagtc tgaaacgacc ggcacgaaaa aggaccatct gcaaggcggt     600
gcactgctgt atacgaacaa cgagaaatcc ccgcacgcgg acagcaaatt tcgtctgctg     660
aatcgtaccc cgaccagcca aaccggcacg ccgaagtatt tcatcgacaa gtctaacggt     720
ggctacgaat ttctgctggc gaacgatttt gacaatagca atcctgcggt acaagctgag     780
cagctgaatt ggctgcacta catgatgaac tttggcagca ttgttgcgaa tgatccgacc     840
gcgaatttcg acggcgttcg tgtggatgct gttgataacg tcaatgcgga cttgttgcaa     900
attgcaagcg attactttaa gagccgttac aaagtcggtg agagcgaaga agaagcgatc     960
aagcacctgt ccatcctgga agcatggagc gataacgacc cggactacaa caaagatacc    1020
aagggtgcac agttggcgat tgataacaaa ctgcgcctga gcctgctgta ctctttcatg    1080
cgtaatctga gcatccgtag cggtgttgaa ccgacgatta ccaatagcct gaatgaccgt    1140
tccagcgaaa agaagaacgg cgagcgtatg gcaaattaca tcttcgtgcg tgcccacgat    1200
agcgaggtcc aaacggtgat cgccgacatc attcgcgaaa acatcaatcc gaacaccgac    1260
ggcctgacgt ttacgatgga cgagctgaag caggcattca gatttacaa  cgaggacatg    1320
cgcaaggcgg acaaaaagta tacccagttt aacattccta ccgcacacgc gctgatgctg    1380
```

```
tctaataagg attctattac ccgcgtgtac tatggtgatc tgtatactga cgatggtcag    1440
tacatggaga agaaaagccc gtatcacgat gcgattgacg ctctgctgcg tgcacgtatt    1500
aaatacgtcg cgggtggcca ggatatgaaa gtgacctata tgggcgtgcc gcgtgaagcg    1560
gataagtgga gctataacgg cattctgacc agcgtgcgct atggcacggg cgctaacgaa    1620
gccacggatg agggcactgc ggaaacgcgc acgcaaggta tggcagtgat tgcgagcaat    1680
aatccaaatc tgaaactgaa tgaatgggac aagttgcaag tcaacatggg tgcggcgcat    1740
aagaatcaat attaccgtcc ggttctgctg accactaagg acggtatcag ccgttatctg    1800
accgatgaag aagtgcctca gagcctgtgg aaaaagacgg acgcaaacgg tattctgacc    1860
ttcgacatga atgatattgc tggctacagc aacgtgcaag ttagcggtta cctggccgtc    1920
tgggtcccgg tcggtgcgaa ggcggatcaa gatgcgcgca cgaccgcatc caagaagaaa    1980
aatgcgtcgg gtcaggtgta cgaaagcagc gcggctctgg atagccagct gatttacgaa    2040
ggtttcagca actttcaaga ctttgccact cgcgatgatc agtacacgaa caaggtcatt    2100
gcgaaaaacg tgaatctgtt caaagaatgg ggtgtgacca gcttcgagct gccgccgcag    2160
tacgtgagca gccaagatgg cacctttctg gacagcatta tccaaaacgg ctatgcattt    2220
gaagaccgtt acgatatggc gatgagcaag aataacaagt atggtagcct gaaagacctg    2280
ttgaacgcgc tgcgcgcact gcacagcgtc aacattcaag caatcgccga ttgggtgccg    2340
gaccaaattt acaacttgcc gggcaaagag gtggtgaccg caactcgtgt caacaactac    2400
ggcacctacc gtgagggtgc tgaaatcaaa gaaaagctgt atgtcgccaa tagcaagacc    2460
aacgaaaccg atttccaagg taaatacggt ggtgcgttcc tggatgagct gaaggcgaag    2520
tacccggaga ttttcgagcg tgtccaaatc agcaacggcc aaaagatgac taccgatgaa    2580
aagatcacca aatggagcgc gaaatacttt aatggcacca atattctggg tcgtggcgcg    2640
tactatgtcc tgaaagattg ggccagcaat gattacctga cgaaccgtaa cggcgagatt    2700
gttttgccga agcaactggt taacaagaat agctataccg gctttgtcag cgacgcgaac    2760
ggcacgaagt tctattctac ctctggctac caggcgaaga acagcttcat tcaagacgaa    2820
aacggtaatt ggtattactt tgacaaacgt ggttatctgg ttacgggcgc acacgagatt    2880
gatggcaagc atgtctactt cctgaaaaac ggtatccaac tgcgtgacag catccgtgag    2940
gatgagaacg taatcaata ctattacgac cagaccggcg cacaagtgct gaaccgttac    3000
tacacgacgg acgtcagaa ttggcgctat ttcgatgcga aggtgttat ggcacgcggc    3060 ctggtaaaga ttggtgacgg ccaacagttt ttcgatgaaa acggttacca ggtcaagggc    3120
aagattgtta gcgcaaaaga cggcaagctg cgctactttg ataaagactc tggcaatgct    3180
gtcattaatc gttcgcgca gggtgacaat ccgagcgact ggtactattt cggtgtggaa    3240
tttgctaaac tgacgggttt gcaaaagatc ggccagcaga cgctgtattt tgaccaagac    3300
ggtaagcaag tcaaaggtaa gatcgtaact ctgtcggaca aaagcattcg ttacttcgat    3360
gccaacagcg gtgaaatggc ggttggcaag ttcgcggaag gtgcaaagaa tgagtggtat    3420
tatttcgata aaaccggcaa agcggttact ggtttgcaga aaattggtaa gcagaccctg    3480
tactttgacc aggacggtaa acaggttaaa ggcaaggttg tcacgctggc tgataaaagc    3540
atccgctact tcgacgcaga ctccggcgag atggcggtcg gtaagtttgc agagggtgcg    3600
aagaacgagt ggtactatt tgatcagact ggcaaggccg tgactggttt gcaaaagatt    3660
gacaagcaaa ccttgtactt cgaccaggac ggtaaacaag tcaagggtaa gattgtgacg    3720
```

-continued

```
ttgagcgaca agtcgatccg ttactttgat gctaatagcg gtgagatggc tactaacaaa    3780
ttcgtcgagg gctcgcagaa tgaatggtac tacttcgatc aagcgggtaa ggctgttacg    3840
ggcttgcaac aggtcggtca gcaaactctg tacttcaccc aggatggtaa gcaagtgaag    3900
ggtaaggtcg tggacgtgaa cggtgttttct cgttatttcg acgcaaactc cggtgacatg    3960
gctcgttcta aatggattca actggaagat ggcagctgga tgtatttcga ccgtgacggt    4020
cgtggccaga attttggccg taactaa                                        4047
```

<210> SEQ ID NO 16
<211> LENGTH: 1348
<212> TYPE: PRT
<213> ORGANISM: Streptococcus oralis

<400> SEQUENCE: 16

```
Met Ile Asp Gly Lys Asn Tyr Tyr Val Gln Asp Gly Thr Val Lys
1               5                   10                  15

Lys Asn Phe Ala Val Glu Leu Asn Gly Arg Ile Leu Tyr Phe Asp Ala
            20                  25                  30

Glu Thr Gly Ala Leu Val Asp Ser Asn Glu Tyr Gln Phe Gln Gln Gly
        35                  40                  45

Thr Ser Ser Leu Asn Asn Glu Phe Ser Gln Lys Asn Ala Phe Tyr Gly
    50                  55                  60

Thr Thr Asp Lys Asp Ile Glu Thr Val Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Thr Asp Leu Arg Pro Leu Leu Met Ala Trp Trp Pro
            100                 105                 110

Asp Lys Arg Thr Gln Ile Asn Tyr Leu Asn Tyr Met Asn Gln Gln Gly
        115                 120                 125

Leu Gly Ala Gly Ala Phe Glu Asn Lys Val Glu Gln Ala Leu Leu Thr
    130                 135                 140

Gly Ala Ser Gln Gln Val Gln Arg Lys Ile Glu Glu Lys Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Lys Lys Asp His Leu Gln Gly Gly Ala Leu Leu Tyr Thr Asn Asn Glu
        195                 200                 205

Lys Ser Pro His Ala Asp Ser Lys Phe Arg Leu Leu Asn Arg Thr Pro
    210                 215                 220

Thr Ser Gln Thr Gly Thr Pro Lys Tyr Phe Ile Asp Lys Ser Asn Gly
225                 230                 235                 240

Gly Tyr Glu Phe Leu Leu Ala Asn Asp Phe Asn Ser Asn Pro Ala
                245                 250                 255

Val Gln Ala Glu Gln Leu Asn Trp Leu His Tyr Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Ser Glu Glu Glu Ala Ile
305                 310                 315                 320
```

```
Lys His Leu Ser Ile Leu Glu Ala Trp Ser Asp Asn Asp Pro Asp Tyr
                325                 330                 335

Asn Lys Asp Thr Lys Gly Ala Gln Leu Ala Ile Asp Asn Lys Leu Arg
            340                 345                 350

Leu Ser Leu Leu Tyr Ser Phe Met Arg Asn Leu Ser Ile Arg Ser Gly
        355                 360                 365

Val Glu Pro Thr Ile Thr Asn Ser Leu Asn Asp Arg Ser Ser Glu Lys
    370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
        435                 440                 445

Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
            500                 505                 510

Tyr Met Gly Val Pro Arg Glu Ala Asp Lys Trp Ser Tyr Asn Gly Ile
        515                 520                 525

Leu Thr Ser Val Arg Tyr Gly Thr Gly Ala Asn Glu Ala Thr Asp Glu
    530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Glu Val Pro Gln Ser
        595                 600                 605

Leu Trp Lys Lys Thr Asp Ala Asn Gly Ile Leu Thr Phe Asp Met Asn
    610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Thr Thr Ala
                645                 650                 655

Ser Lys Lys Lys Asn Ala Ser Gly Gln Val Tyr Glu Ser Ser Ala Ala
            660                 665                 670

Leu Asp Ser Gln Leu Ile Tyr Glu Gly Phe Ser Asn Phe Gln Asp Phe
        675                 680                 685

Ala Thr Arg Asp Asp Gln Tyr Thr Asn Lys Val Ile Ala Lys Asn Val
    690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735
```

```
Gly Tyr Ala Phe Glu Asp Arg Tyr Asp Met Ala Met Ser Lys Asn Asn
            740                 745                 750

Lys Tyr Gly Ser Leu Lys Asp Leu Leu Asn Ala Leu Arg Ala Leu His
        755                 760                 765

Ser Val Asn Ile Gln Ala Ile Ala Asp Trp Val Pro Asp Gln Ile Tyr
770                 775                 780

Asn Leu Pro Gly Lys Glu Val Val Thr Ala Thr Arg Val Asn Asn Tyr
785                 790                 795                 800

Gly Thr Tyr Arg Glu Gly Ala Glu Ile Lys Lys Leu Tyr Val Ala
            805                 810                 815

Asn Ser Lys Thr Asn Glu Thr Asp Phe Gln Gly Lys Tyr Gly Gly Ala
            820                 825                 830

Phe Leu Asp Glu Leu Lys Ala Lys Tyr Pro Glu Ile Phe Glu Arg Val
            835                 840                 845

Gln Ile Ser Asn Gly Gln Lys Met Thr Thr Asp Glu Lys Ile Thr Lys
            850                 855                 860

Trp Ser Ala Lys Tyr Phe Asn Gly Thr Asn Ile Leu Gly Arg Gly Ala
865                 870                 875                 880

Tyr Tyr Val Leu Lys Asp Trp Ala Ser Asn Asp Tyr Leu Thr Asn Arg
                885                 890                 895

Asn Gly Glu Ile Val Leu Pro Lys Gln Leu Val Asn Lys Asn Ser Tyr
            900                 905                 910

Thr Gly Phe Val Ser Asp Ala Asn Gly Thr Lys Phe Tyr Ser Thr Ser
            915                 920                 925

Gly Tyr Gln Ala Lys Asn Ser Phe Ile Gln Asp Glu Asn Gly Asn Trp
            930                 935                 940

Tyr Tyr Phe Asp Lys Arg Gly Tyr Leu Val Thr Gly Ala His Glu Ile
945                 950                 955                 960

Asp Gly Lys His Val Tyr Phe Leu Lys Asn Gly Ile Gln Leu Arg Asp
                965                 970                 975

Ser Ile Arg Glu Asp Glu Asn Gly Asn Gln Tyr Tyr Tyr Asp Gln Thr
            980                 985                 990

Gly Ala Gln Val Leu Asn Arg Tyr Tyr Thr Thr Asp Gly Gln Asn Trp
            995                 1000                1005

Arg Tyr Phe Asp Ala Lys Gly Val Met Ala Arg Gly Leu Val Lys
    1010                1015                1020

Ile Gly Asp Gly Gln Gln Phe Phe Asp Glu Asn Gly Tyr Gln Val
    1025                1030                1035

Lys Gly Lys Ile Val Ser Ala Lys Asp Gly Lys Leu Arg Tyr Phe
    1040                1045                1050

Asp Lys Asp Ser Gly Asn Ala Val Ile Asn Arg Phe Ala Gln Gly
    1055                1060                1065

Asp Asn Pro Ser Asp Trp Tyr Tyr Phe Gly Val Glu Phe Ala Lys
    1070                1075                1080

Leu Thr Gly Leu Gln Lys Ile Gly Gln Gln Thr Leu Tyr Phe Asp
    1085                1090                1095

Gln Asp Gly Lys Gln Val Lys Gly Lys Ile Val Thr Leu Ser Asp
    1100                1105                1110

Lys Ser Ile Arg Tyr Phe Asp Ala Asn Ser Gly Glu Met Ala Val
    1115                1120                1125

Gly Lys Phe Ala Glu Gly Ala Lys Asn Glu Trp Tyr Tyr Phe Asp
    1130                1135                1140

Lys Thr Gly Lys Ala Val Thr Gly Leu Gln Lys Ile Gly Lys Gln
```

```
         1145                1150                1155
Thr Leu Tyr Phe Asp Gln Asp Gly Lys Gln Val Lys Gly Lys Val
         1160                1165                1170
Val Thr Leu Ala Asp Lys Ser Ile Arg Tyr Phe Asp Ala Asp Ser
         1175                1180                1185
Gly Glu Met Ala Val Gly Lys Phe Ala Glu Gly Ala Lys Asn Glu
         1190                1195                1200
Trp Tyr Tyr Phe Asp Gln Thr Gly Lys Ala Val Thr Gly Leu Gln
         1205                1210                1215
Lys Ile Asp Lys Gln Thr Leu Tyr Phe Asp Gln Asp Gly Lys Gln
         1220                1225                1230
Val Lys Gly Lys Ile Val Thr Leu Ser Asp Lys Ser Ile Arg Tyr
         1235                1240                1245
Phe Asp Ala Asn Ser Gly Glu Met Ala Thr Asn Lys Phe Val Glu
         1250                1255                1260
Gly Ser Gln Asn Glu Trp Tyr Tyr Phe Asp Gln Ala Gly Lys Ala
         1265                1270                1275
Val Thr Gly Leu Gln Gln Val Gly Gln Gln Thr Leu Tyr Phe Thr
         1280                1285                1290
Gln Asp Gly Lys Gln Val Lys Gly Lys Val Val Asp Val Asn Gly
         1295                1300                1305
Val Ser Arg Tyr Phe Asp Ala Asn Ser Gly Asp Met Ala Arg Ser
         1310                1315                1320
Lys Trp Ile Gln Leu Glu Asp Gly Ser Trp Met Tyr Phe Asp Arg
         1325                1330                1335
Asp Gly Arg Gly Gln Asn Phe Gly Arg Asn
         1340                1345
```

<210> SEQ ID NO 17
<211> LENGTH: 4047
<212> TYPE: DNA
<213> ORGANISM: Streptococcus sanguinis

<400> SEQUENCE: 17

```
atgattgatg gtaaaaagta ttacgtacag gacgacggca cggttaagaa gaatttcgcg    60
gttgagctga tggcaagat  cctgtacttc gatgcagaga ctggtgcgtt gattgacagc   120
gcggagtatc aattccaaca aggcaccagc agcctgaata tgagttcac  tcaaaagaac   180
gccttttacg gtacgaccga taaggatgtg gaaaccattg atggttactt gaccgccgat   240
tcctggtatc gtccgaagtt cattctgaaa gatggcaaaa cctggacggc gagcacggaa   300
attgacttgc gtccgttgtt gatggcgtgg tggccggaca acagaccca  ggttagctac   360
ctgaattaca tgaaccagca aggcttgggt gcaggcgcct tcgaaaacaa gtagagcag   420
gcaattctga ccggtgcgtc ccaacaggta caacgtaaaa tcgaagaacg catcggtaaa   480
gagggtgata ccaagtggct gcgtacccctg atgggtgcat tgtaaagac  ccagccgaac   540
tggaacatta agaccgagtc cgaaaccact ggcacgaata agatcatct  gcaaggtggc   600
gcactgctgt atagcaattc cgacaagacg agccatgcca actctaagta ccgtatcctg   660
aaccgcaccc cgaccaacca aacgggcacg ccgaaatact ttattgacaa gagcaatggt   720
ggttatgaat ttctgctggc gaatgacttt gacaatagca atccggcagt gcaagcggaa   780
cagctgaact ggttgcactt tatgatgaat tttggctcca tcgttgcaaa tgatccgacg   840
gccaacttcg acggcgtccg cgttgacgct gtggataacg tgaatgcgga tctgttgcaa   900
```

```
attgcgagcg actatttcaa gagccgctat aaagtcggcg aaagcgaaga agaggccatt    960
aagcacctgt ccatcctgga agcgtggagc gacaacgacc cggactacaa caaggatact   1020
aaaggtgccc aactgccgat cgacaacaaa ctgcgtctga gcctgctgta ctccttcatg   1080
cgtaagctga gcatccgtag cggcgtcgag ccgaccatca ccaactctct gaatgatcgc   1140
agcacggaga agaagaatgg tgagcgtatg gcaaactata tcttcgttcg tgcacatgat   1200
agcgaggtgc aaacggtcat cgccgacatt atccgtgaga acatcaatcc gaataccgac   1260
ggcctgacgt tcacgatgga tgaactgaag caggccttta aaatttacaa tgaggatatg   1320
cgtaaagccg acaaaaagta cacgcagttc aatatcccga ccgcgcacgc gctgatgctg   1380
agcaacaaag attctatcac ccgcgtttac tacggtgacc tgtatacgga tgacggtcag   1440
tatatggaaa agaaaagccc gtatcacgac gccattgacg ctctgctgcg tgcgcgtatc   1500
aaatatgttg cgggtggtca ggacatgaag gtgacctata tgggcgtgcc gcgtgaggca   1560
gataaatgga gctataacgg catcctgacc agcgttcgtt atggtacggg tgccaacgag   1620
gcaaccgacg agggtacggc agaaacccgt acccagggca tggccgtcat tgccagcaac   1680
aatccgaacc tgaaactgaa cgagtgggac aagttgcagg tcaacatggg tgcagctcac   1740
aaaaaccaat actatcgtcc ggtgctgctg accaccaagg acggcatctc cgctacctg    1800
accgacgaag aagtcccgca gagcctgtgg aaaaagaccg atgcgaacgg catcttgacg   1860
tttgacatga atgatattgc gggttacagc aacgtccaag tgagcggtta tctggccgtc   1920
tgggttcctg tgggtgcgaa ggcggaccag gacgctcgtg ttacggcatc taagaagaaa   1980
aatgcctctg gccaagtttta cgaaagcagc gcagccctgg actcccagct gatctatgag   2040
ggcttcagca attttcagga ctttgccacc cgtgacgacc agtacactaa caaggttatc   2100
gcgaaaaacg tcaatctgtt taagagtgg ggcgtcacca gcttcgaatt gccgccacag   2160
tatgtgagca gccaagacgg tacgttcctg gatagcatca tccagaatgg ttatgcattc   2220
gaagatcgct atgatatggc gatgagcaaa acaataagt acggtagctt gaacgacctg   2280
ttgaacgcct tgcgtgcact gcatagcgtg aatatccaag cgattgcgga ttgggtgccg   2340
gaccagattt acaatctgcc gggtaaagaa gttgtcactg caacccgtgt taacaattat   2400
ggcacgtatc gtgagggtag cgagattaaa gagaacctgt acgttgctaa caccaaaacc   2460
aatggtacgg actaccaagg taagtatggt ggtgcgttct tggacgagct gaaagccaaa   2520
taccctgaga tttttgagcg cgtccaaatc agcaacggcc agaagatgac caccgacgag   2580
aagattacga aatggtccgc caaacacttt aacggcacga acattctggg tcgtggtgcg   2640
tattatgtgc tgaaagactg ggcgagcaac gagtacctga ataacaaaaa tggcgagatg   2700
gttctgccga agcagctggt taataaaaat gcatataccg gcttcgtcag cgacgcgagc   2760
ggcaccaaat actattctac cagcggctat caggctcgta atagctttat tcaagatgaa   2820
aatggtaatt ggtactactt caataaccgt ggttatttgg tgacgggtgc acaggaaatc   2880
gacggtaagc aactgtattt cctgaaaaac ggcattcagc tgcgtgattc tctgcgtgag   2940
gacgaaaacg gcaaccagta ttactatgat aagacgggtg cgcaagttct gaatcgttat   3000
tacactacga acggccaaaa ttggcgctac ttcgacgtta aaggcgtcat ggcccgtggt   3060
ctggtcacga tgggtggtaa ccaacaattc tttgaccaaa acggttacca ggttaaaggc   3120
aaaattgcgc gtgcaaaaga cggtaaactg cgttacttcg ataaagacag cggtaatgcg   3180
gcagctaacc gtttcgccca aggcgataac cctagcgact ggtactattt cggtgcagat   3240
ggtgttgcgg ttacgggcct gcaaaaggtt ggtcagcaaa ctctgtactt tgatcaggac   3300
```

```
ggcaagcagg tgaaaggtaa agttgttacc ttggcggaca aaagcattcg ttatttcgat    3360
gcaaacagcg gcgagatggc ggtgaacaag tttgtggaag gtgctaagaa cgtgtggtac    3420
tacttcgatc aagcaggcaa agcggtgacc ggcctgcaaa ccatcaataa acaagtgctg    3480
tatttcgacc aggatggtaa acaagtcaaa ggtaaggtgg tcacgctggc tgataagtct    3540
atccgctact tcgacgcgaa cagcggtgag atggcagtgg gcaaattcgc cgaaggcgca    3600
aagaatgagt ggtattactt tgaccaggcg ggcaaggctg ttaccggtct gcaaaagatc    3660
ggccaacaga cgctgtattt cgaccagaac ggtaaacagg ttaagggtaa agtggtcacc    3720
ctggcggata gagcatccg ctatttcgac gctaactctg gcgaaatggc aagcaataag    3780
ttcgttgagg gtgccaaaaa tgaatggtac tatttcgatc aggctggcaa ggcagtgacg    3840
ggtctgcaac aaattggcca gcagaccctg tattttgacc agaatggcaa acaggtgaag    3900
ggtaagattg tgtatgttaa tggtgcgaat cgctactttg atgccaatag cggtgaaatg    3960
gcgcgtaaca gtggattca gctggaagat ggcagctgga tgtattttga ccgcaatggt    4020
cgtggtcgtc gtttcggttg gaactaa                                         4047
```

<210> SEQ ID NO 18
<211> LENGTH: 1348
<212> TYPE: PRT
<213> ORGANISM: Streptococcus sanguinis

<400> SEQUENCE: 18

```
Met Ile Asp Gly Lys Lys Tyr Tyr Val Gln Asp Gly Thr Val Lys
1               5                   10                  15

Lys Asn Phe Ala Val Glu Leu Asn Gly Lys Ile Leu Tyr Phe Asp Ala
                20                  25                  30

Glu Thr Gly Ala Leu Ile Asp Ser Ala Glu Tyr Gln Phe Gln Gln Gly
            35                  40                  45

Thr Ser Ser Leu Asn Asn Glu Phe Thr Gln Lys Asn Ala Phe Tyr Gly
        50                  55                  60

Thr Thr Asp Lys Asp Val Glu Thr Ile Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Ile Asp Leu Arg Pro Leu Leu Met Ala Trp Trp Pro
            100                 105                 110

Asp Lys Gln Thr Gln Val Ser Tyr Leu Asn Tyr Met Asn Gln Gly
        115                 120                 125

Leu Gly Ala Gly Ala Phe Glu Asn Lys Val Glu Gln Ala Ile Leu Thr
    130                 135                 140

Gly Ala Ser Gln Gln Val Gln Arg Lys Ile Glu Glu Arg Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Ser Asn Ser Asp
        195                 200                 205

Lys Thr Ser His Ala Asn Ser Lys Tyr Arg Ile Leu Asn Arg Thr Pro
    210                 215                 220

Thr Asn Gln Thr Gly Thr Pro Lys Tyr Phe Ile Asp Lys Ser Asn Gly
225                 230                 235                 240
```

```
Gly Tyr Glu Phe Leu Leu Ala Asn Asp Phe Asp Asn Ser Asn Pro Ala
                245                 250                 255

Val Gln Ala Glu Gln Leu Asn Trp Leu His Phe Met Met Asn Phe Gly
        260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Ser Glu Glu Ala Ile
305                 310                 315                 320

Lys His Leu Ser Ile Leu Glu Ala Trp Ser Asn Asp Pro Asp Tyr
                325                 330                 335

Asn Lys Asp Thr Lys Gly Ala Gln Leu Pro Ile Asp Asn Lys Leu Arg
                340                 345                 350

Leu Ser Leu Leu Tyr Ser Phe Met Arg Lys Leu Ser Ile Arg Ser Gly
            355                 360                 365

Val Glu Pro Thr Ile Thr Asn Ser Leu Asn Asp Arg Ser Thr Glu Lys
        370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Arg Glu Asn Ile Asn
                405                 410                 415

Pro Asn Thr Asp Gly Leu Thr Phe Thr Met Asp Glu Leu Lys Gln Ala
                420                 425                 430

Phe Lys Ile Tyr Asn Glu Asp Met Arg Lys Ala Asp Lys Lys Tyr Thr
        435                 440                 445

Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
                500                 505                 510

Tyr Met Gly Val Pro Arg Glu Ala Asp Lys Trp Ser Tyr Asn Gly Ile
        515                 520                 525

Leu Thr Ser Val Arg Tyr Gly Thr Gly Ala Asn Glu Ala Thr Asp Glu
    530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
                580                 585                 590

Lys Asp Gly Ile Ser Arg Tyr Leu Thr Asp Glu Glu Val Pro Gln Ser
            595                 600                 605

Leu Trp Lys Lys Thr Asp Ala Asn Gly Ile Leu Thr Phe Asp Met Asn
        610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Val Thr Ala
                645                 650                 655
```

-continued

Ser Lys Lys Lys Asn Ala Ser Gly Gln Val Tyr Glu Ser Ala Ala
            660                 665                 670

Leu Asp Ser Gln Leu Ile Tyr Glu Gly Phe Ser Asn Phe Gln Asp Phe
        675                 680                 685

Ala Thr Arg Asp Asp Gln Tyr Thr Asn Lys Val Ile Ala Lys Asn Val
    690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735

Gly Tyr Ala Phe Glu Asp Arg Tyr Asp Met Ala Met Ser Lys Asn Asn
            740                 745                 750

Lys Tyr Gly Ser Leu Asn Asp Leu Leu Asn Ala Leu Arg Ala Leu His
        755                 760                 765

Ser Val Asn Ile Gln Ala Ile Ala Asp Trp Val Pro Asp Gln Ile Tyr
    770                 775                 780

Asn Leu Pro Gly Lys Glu Val Val Thr Ala Thr Arg Val Asn Asn Tyr
785                 790                 795                 800

Gly Thr Tyr Arg Glu Gly Ser Glu Ile Lys Glu Asn Leu Tyr Val Ala
                805                 810                 815

Asn Thr Lys Thr Asn Gly Thr Asp Tyr Gln Gly Lys Tyr Gly Gly Ala
            820                 825                 830

Phe Leu Asp Glu Leu Lys Ala Lys Tyr Pro Glu Ile Phe Glu Arg Val
        835                 840                 845

Gln Ile Ser Asn Gly Gln Lys Met Thr Thr Asp Glu Lys Ile Thr Lys
    850                 855                 860

Trp Ser Ala Lys His Phe Asn Gly Thr Asn Ile Leu Gly Arg Gly Ala
865                 870                 875                 880

Tyr Tyr Val Leu Lys Asp Trp Ala Ser Asn Glu Tyr Leu Asn Asn Lys
                885                 890                 895

Asn Gly Glu Met Val Leu Pro Lys Gln Leu Val Asn Lys Asn Ala Tyr
            900                 905                 910

Thr Gly Phe Val Ser Asp Ala Ser Gly Thr Lys Tyr Tyr Ser Thr Ser
        915                 920                 925

Gly Tyr Gln Ala Arg Asn Ser Phe Ile Gln Asp Glu Asn Gly Asn Trp
    930                 935                 940

Tyr Tyr Phe Asn Asn Arg Gly Tyr Leu Val Thr Gly Ala Gln Glu Ile
945                 950                 955                 960

Asp Gly Lys Gln Leu Tyr Phe Leu Lys Asn Gly Ile Gln Leu Arg Asp
                965                 970                 975

Ser Leu Arg Glu Asp Glu Asn Gly Asn Gln Tyr Tyr Asp Lys Thr
            980                 985                 990

Gly Ala Gln Val Leu Asn Arg Tyr Tyr Thr Thr Asp Gly Gln Asn Trp
        995                 1000                1005

Arg Tyr Phe Asp Val Lys Gly Val Met Ala Arg Gly Leu Val Thr
        1010                1015                1020

Met Gly Gly Asn Gln Gln Phe Phe Asp Gln Asn Gly Tyr Gln Val
        1025                1030                1035

Lys Gly Lys Ile Ala Arg Ala Lys Asp Gly Lys Leu Arg Tyr Phe
        1040                1045                1050

Asp Lys Asp Ser Gly Asn Ala Ala Ala Asn Arg Phe Ala Gln Gly
        1055                1060                1065

Asp Asn Pro Ser Asp Trp Tyr Tyr Phe Gly Ala Asp Gly Val Ala

| | | | |
|---|---|---|---|
| | 1070 | 1075 | 1080 |

Val Thr Gly Leu Gln Lys Val Gly Gln Gln Thr Leu Tyr Phe Asp
　　　 1085　　　　　　　　 1090　　　　　　　　 1095

Gln Asp Gly Lys Gln Val Lys Gly Lys Val Val Thr Leu Ala Asp
　 1100　　　　　　　　 1105　　　　　　　　 1110

Lys Ser Ile Arg Tyr Phe Asp Ala Asn Ser Gly Glu Met Ala Val
　 1115　　　　　　　　 1120　　　　　　　　 1125

Asn Lys Phe Val Glu Gly Ala Lys Asn Val Trp Tyr Tyr Phe Asp
　 1130　　　　　　　　 1135　　　　　　　　 1140

Gln Ala Gly Lys Ala Val Thr Gly Leu Gln Thr Ile Asn Lys Gln
　 1145　　　　　　　　 1150　　　　　　　　 1155

Val Leu Tyr Phe Asp Gln Asp Gly Lys Gln Val Lys Gly Lys Val
　 1160　　　　　　　　 1165　　　　　　　　 1170

Val Thr Leu Ala Asp Lys Ser Ile Arg Tyr Phe Asp Ala Asn Ser
　 1175　　　　　　　　 1180　　　　　　　　 1185

Gly Glu Met Ala Val Gly Lys Phe Ala Glu Gly Ala Lys Asn Glu
　 1190　　　　　　　　 1195　　　　　　　　 1200

Trp Tyr Tyr Phe Asp Gln Ala Gly Lys Ala Val Thr Gly Leu Gln
　 1205　　　　　　　　 1210　　　　　　　　 1215

Lys Ile Gly Gln Gln Thr Leu Tyr Phe Asp Gln Asn Gly Lys Gln
　 1220　　　　　　　　 1225　　　　　　　　 1230

Val Lys Gly Lys Val Val Thr Leu Ala Asp Lys Ser Ile Arg Tyr
　 1235　　　　　　　　 1240　　　　　　　　 1245

Phe Asp Ala Asn Ser Gly Glu Met Ala Ser Asn Lys Phe Val Glu
　 1250　　　　　　　　 1255　　　　　　　　 1260

Gly Ala Lys Asn Glu Trp Tyr Tyr Phe Asp Gln Ala Gly Lys Ala
　 1265　　　　　　　　 1270　　　　　　　　 1275

Val Thr Gly Leu Gln Gln Ile Gly Gln Gln Thr Leu Tyr Phe Asp
　 1280　　　　　　　　 1285　　　　　　　　 1290

Gln Asn Gly Lys Gln Val Lys Gly Lys Ile Val Tyr Val Asn Gly
　 1295　　　　　　　　 1300　　　　　　　　 1305

Ala Asn Arg Tyr Phe Asp Ala Asn Ser Gly Glu Met Ala Arg Asn
　 1310　　　　　　　　 1315　　　　　　　　 1320

Lys Trp Ile Gln Leu Glu Asp Gly Ser Trp Met Tyr Phe Asp Arg
　 1325　　　　　　　　 1330　　　　　　　　 1335

Asn Gly Arg Gly Arg Arg Phe Gly Trp Asn
　 1340　　　　　　　　 1345

<210> SEQ ID NO 19
<211> LENGTH: 4023
<212> TYPE: DNA
<213> ORGANISM: unknown
<220> FEATURE:
<223> OTHER INFORMATION: unknown Streptococcus sp. C150

<400> SEQUENCE: 19

| | |
|---|---|
| atgatcgacg gcaaatacta ctacgtaaac gaggacggca gccacaaaga gaatttcgcg | 60 |
| atcacggtta atggtcaact gctgtatttt ggtaaggatg gcgcgctgac cagcagcagc | 120 |
| acgtacagct tcacccaagg cactaccaat attgtggacg ttttagcat taacaaccgt | 180 |
| gcgtatgact ccagcgaggc ctctttcgag ctgattgacg ttatctgac tgcggactct | 240 |
| tggtaccgtc cggcgagcat tatcaaagac ggtgtgacgt ggcaagcatc caccgccgag | 300 |
| gacttccgcc cgttgctgat ggcgtggtgg ccgaacgttg atactcaggt gaactacctg | 360 |
| aactacatgt ccaaagtctt taatctggat gctaaataca gctcgactga taaacaggaa | 420 |

-continued

| | |
|---|---|
| accctgaagg tggcggcgaa agatatccag atcaaaattg aacaaaagat tcaggcggaa | 480 |
| aagtccacgc aatggctgcg tgaaacgatc agcgcctttg taaaaaccca gccgcaatgg | 540 |
| aacaaagaga ctgagaacta cagcaagggc ggtggtgagg accatctgca aggtggtgcc | 600 |
| ctgctgtatg ttaatgactc tcgtaccccg tgggcgaaca gcaactatcg tttgctgaac | 660 |
| cgcacggcga ccaaccagac cggtacgatc gacaagagca tcctggacga gcagagcgat | 720 |
| ccgaatcaca tgggtggttt tgatttcttg ctggctaatg acgttgactt gagcaatccg | 780 |
| gtcgtccagg cggaacaact gaatcagatc cactacctga tgaattgggg ttctattgtc | 840 |
| atgggtgata aagacgcgaa ttttgacggt attcgtgtag acgcggtgga taatgttgat | 900 |
| gcggacatgc tgcaattgta caccaactat ttccgcgaat actatggtgt caacaaaagc | 960 |
| gaggcaaacg cgctggcgca cattagcgtc ctggaagcct ggagcctgaa tgacaaccat | 1020 |
| tacaatgata agactgatgt tgcggcgctg gcaatggaga ataagcagcg cttggcactg | 1080 |
| ttgtttagcc tggcgaaacc gattaaagaa cgcacgcctg ccgtgtctcc gctgtacaac | 1140 |
| aatacgttta acaccactca gcgtgatgaa aagacggact ggatcaataa agatggttcg | 1200 |
| aaagcctaca atgaggatgg cactgtcaag aaaagcacca tcggcaagta taacgagaag | 1260 |
| tatggtgatg ctagcggcaa ctacgttttc atccgcgctc acgacaataa cgtgcaagac | 1320 |
| atcatcgcgg agatcattaa gaaagagatt aacgagaaat ctgacggttt taccattacg | 1380 |
| gattcggaga tgaagcgtgc atttgagatc tataacaaag acatgctgtc taatgacaaa | 1440 |
| aagtacacgc tgaataacat cccggcggcg tacgcggtta tgctgcaaaa catggaaacg | 1500 |
| attcccgcg tgtattacgg cgatctgtac acggacgacg gtaattacat ggaagcgaaa | 1560 |
| agcccgtact acgatacgat tgttaacttg atgaagtctc gcatcaaata cgtgagcggt | 1620 |
| ggccaggcgc agcgcagcta ctggctgccg accgatggta agatggataa gtcggatgtt | 1680 |
| gagctgtacc gtacgaacga agtgtacacg agcgtccgtt acggcaaaga cattatgacc | 1740 |
| gccgatgaca cgcaaggtag caaatacagc cgtaccagcg gtcaggtgac cctggtcgtc | 1800 |
| aacaacccaa aactgacctt ggaccaaagc gcaaagctga acgtggttat gggcaagatt | 1860 |
| catgctaatc agaagtaccg cgcactgatt gtcggtaccc cgaacggtat taagaatttc | 1920 |
| accagcgacg cagaggctat tgccgcaggc tatgtcaaag aaaccgatgg caatggcgtg | 1980 |
| ctgaccttcg gtgcaaacga catcaagggt tatgaaactt tcgatatgag cggcttcgtc | 2040 |
| gctgtttggg ttccggtcgg tgcgagcgac gaccaagata ttcgtgtggc ggcgtctacg | 2100 |
| gcagcaaaga aagagggtga gctgacgctg aaagcgaccg aagcctatga ctcccaactg | 2160 |
| atctatgaag gctttagcaa tttccagacc atcccagatg gcagcgatcc ttctgtttat | 2220 |
| accaatcgta gatcgcgga aaatgttgat ttgttcaaga gctggggtgt cacgagcttc | 2280 |
| gaaatggctc cgcagttcgt ttctgcggac gatggcacgt ttctggacag cgtcattcaa | 2340 |
| aacggctatg cgttcgcaga ccgttatgat ctggccatga gcaaaaacaa taagtacggt | 2400 |
| agcaaagaag atctgcgtaa cgcgctgaag gcactgcaca aagcaggcat tcaggcgatt | 2460 |
| gcagattggg tgccagacca aatctaccag ctgcctggca agaagttgt tactgccacc | 2520 |
| cgcacggacg gtgctggtcg caaaatcagc gatgcaatca tcgatcattc cctgtacgtt | 2580 |
| gcgaactcca agagctccgg taaggactac caagcgaagt acggtggcga gttcttggcg | 2640 |
| gaactgaagg cgaaataccc ggaaatgttc aaagtgaaca tgattagcac cggcaaaccg | 2700 |
| attgatgata gcgtgaaact gaagcagtgg aaagcagaat acttcaacgg caccaatgtg | 2760 |

```
ctggatcgcg gtgtcggtta tgttctgagc gatgaggcaa ccggtaagta tttcaccgtt    2820
accaaagagg gtaactttat cccgttgcag ctgaagggta caagaaggt gattaccggc     2880 ttttccagcg acggtaaggg cattacctat ttcggtacta gcggtaacca agctaaatcc    2940
gcgttcgtca cttttaacgg taacacgtac tacttcgacg cacgtggcca catggttacc    3000
aacggtgagt actcgccgaa tggtaaagat gtgtatcgtt ttctgccgaa cggcattatg    3060
ctgagcaacg cgttctatgt tgacggcaat ggcaacacct acctgtacaa ctccaaaggc    3120
caaatgtata aggtggcta tagcaaattt gacgtcacgg aaacgaagga cggtaaagag    3180
agcaaagttg tcaagttccg ctactttacg aacgagggcg tgatggcgaa aggtgtcacg    3240
gttgtggatg gcttcactca gtactttaac gaggatggca ttcaaagcaa agacgagctg    3300
gtcacttaca atggcaagac ctattacttc gaagcacaca cgggcaatgc cattaagaat    3360
acgtggcgta atatcaaggg caatggtac cattttgatg ctaacggtgt cgcggctact    3420
ggcgcacagg ttatcaacgg tcagcacctg tacttcaatg aagatggctc tcaagtaaaa    3480
ggtagcatcg tcaaaaacgc tgatggtacg ttcagcaagt acaaggacag ctctggcgat    3540
ctggtggtga acgagttttt cacgacgggt gataacgtct ggtactatgc tggtgccaat    3600
ggcaaaacgg ttactggtgc acaggtgatt aatggccagc acttgttctt caaagaggat    3660
ggcagccagg tcaagggcga ctttgtgaag aatagcgacg gcacctactc caagtatgac    3720
gctgcgagcg cgaacgtct gaccaacgag ttcttcacta cgggcgacaa tcattggtac    3780
tatattggcg ccaacggtaa gaccgttacc ggtgaagtta agattggtga cgacacgtat    3840
ttcttcgcaa aagacggtaa gcaactgaaa ggtcaaatcg ttaccacccg tagcggtcgt    3900
atcagctact actttggtga tagcggtaag aaggctatta gcacgtgggt ggagatccag    3960
ccgggtgtgt ttgttttctt cgacaaaaac ggcctggctt acccaccgga gaatatgaac    4020
tga                                                                 4023
```

<210> SEQ ID NO 20
<211> LENGTH: 1340
<212> TYPE: PRT
<213> ORGANISM: unknown
<220> FEATURE:
<223> OTHER INFORMATION: unknown Streptococcus sp. C150

<400> SEQUENCE: 20

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Gln Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
```

```
              130                 135                 140
Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
            195                 200                 205

Thr Pro Trp Ala Asn Ser Asn Tyr Arg Leu Leu Asn Arg Thr Ala Thr
210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
                260                 265                 270

Leu Met Asn Trp Gly Ser Ile Val Met Gly Asp Lys Asp Ala Asn Phe
            275                 280                 285

Asp Gly Ile Arg Val Asp Ala Val Asp Asn Val Asp Ala Asp Met Leu
        290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Val Ala Ala Leu Ala Met
                340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Lys Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Glu Lys Ser Asp Gly Phe Thr Ile Thr Asp Ser Glu Met
450                 455                 460

Lys Arg Ala Phe Glu Ile Tyr Asn Lys Asp Met Leu Ser Asn Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly Asn Tyr Met Glu Ala Lys Ser Pro Tyr Tyr Asp Thr Ile Val
        515                 520                 525

Asn Leu Met Lys Ser Arg Ile Lys Tyr Val Ser Gly Gly Gln Ala Gln
530                 535                 540

Arg Ser Tyr Trp Leu Pro Thr Asp Gly Lys Met Asp Lys Ser Asp Val
545                 550                 555                 560
```

```
Glu Leu Tyr Arg Thr Asn Glu Val Tyr Thr Ser Val Arg Tyr Gly Lys
            565                 570                 575

Asp Ile Met Thr Ala Asp Thr Gln Gly Ser Lys Tyr Ser Arg Thr
        580                 585                 590

Ser Gly Gln Val Thr Leu Val Val Asn Asn Pro Lys Leu Thr Leu Asp
        595                 600                 605

Gln Ser Ala Lys Leu Asn Val Val Met Gly Lys Ile His Ala Asn Gln
        610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
                660                 665                 670

Thr Phe Asp Met Ser Gly Phe Val Ala Val Trp Val Pro Val Gly Ala
        675                 680                 685

Ser Asp Asp Gln Asp Ile Arg Val Ala Ala Ser Thr Ala Ala Lys Lys
        690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
                740                 745                 750

Lys Ser Trp Gly Val Thr Ser Phe Glu Met Ala Pro Gln Phe Val Ser
                755                 760                 765

Ala Asp Asp Gly Thr Phe Leu Asp Ser Val Ile Gln Asn Gly Tyr Ala
        770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
                820                 825                 830

Gly Lys Glu Val Val Thr Ala Thr Arg Thr Asp Gly Ala Gly Arg Lys
            835                 840                 845

Ile Ser Asp Ala Ile Ile Asp His Ser Leu Tyr Val Ala Asn Ser Lys
        850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
            915                 920                 925

Leu Ser Asp Glu Ala Thr Gly Lys Tyr Phe Thr Val Thr Lys Glu Gly
        930                 935                 940

Asn Phe Ile Pro Leu Gln Leu Lys Gly Asn Lys Lys Val Ile Thr Gly
945                 950                 955                 960

Phe Ser Ser Asp Gly Lys Gly Ile Thr Tyr Phe Gly Thr Gly Ser Asn
                965                 970                 975
```

Gln Ala Lys Ser Ala Phe Val Thr Phe Asn Gly Asn Thr Tyr Tyr Phe
                980                 985                 990

Asp Ala Arg Gly His Met Val Thr Asn Gly Glu Tyr Ser Pro Asn Gly
            995                1000                1005

Lys Asp Val Tyr Arg Phe Leu Pro Asn Gly Ile Met Leu Ser Asn
        1010                1015                1020

Ala Phe Tyr Val Asp Gly Asn Gly Asn Thr Tyr Leu Tyr Asn Ser
        1025                1030                1035

Lys Gly Gln Met Tyr Lys Gly Gly Tyr Ser Lys Phe Asp Val Thr
        1040                1045                1050

Glu Thr Lys Asp Gly Lys Glu Ser Lys Val Val Lys Phe Arg Tyr
        1055                1060                1065

Phe Thr Asn Glu Gly Val Met Ala Lys Gly Val Thr Val Val Asp
        1070                1075                1080

Gly Phe Thr Gln Tyr Phe Asn Glu Asp Gly Ile Gln Ser Lys Asp
        1085                1090                1095

Glu Leu Val Thr Tyr Asn Gly Lys Thr Tyr Tyr Phe Glu Ala His
        1100                1105                1110

Thr Gly Asn Ala Ile Lys Asn Thr Trp Arg Asn Ile Lys Gly Lys
        1115                1120                1125

Trp Tyr His Phe Asp Ala Asn Gly Val Ala Ala Thr Gly Ala Gln
        1130                1135                1140

Val Ile Asn Gly Gln His Leu Tyr Phe Asn Glu Asp Gly Ser Gln
        1145                1150                1155

Val Lys Gly Ser Ile Val Lys Asn Ala Asp Gly Thr Phe Ser Lys
        1160                1165                1170

Tyr Lys Asp Ser Ser Gly Asp Leu Val Val Asn Glu Phe Phe Thr
        1175                1180                1185

Thr Gly Asp Asn Val Trp Tyr Tyr Ala Gly Ala Asn Gly Lys Thr
        1190                1195                1200

Val Thr Gly Ala Gln Val Ile Asn Gly Gln His Leu Phe Phe Lys
        1205                1210                1215

Glu Asp Gly Ser Gln Val Lys Gly Asp Phe Val Lys Asn Ser Asp
        1220                1225                1230

Gly Thr Tyr Ser Lys Tyr Asp Ala Ala Ser Gly Glu Arg Leu Thr
        1235                1240                1245

Asn Glu Phe Phe Thr Thr Gly Asp Asn His Trp Tyr Tyr Ile Gly
        1250                1255                1260

Ala Asn Gly Lys Thr Val Thr Gly Glu Val Lys Ile Gly Asp Asp
        1265                1270                1275

Thr Tyr Phe Phe Ala Lys Asp Gly Lys Gln Leu Lys Gly Gln Ile
        1280                1285                1290

Val Thr Thr Arg Ser Gly Arg Ile Ser Tyr Tyr Phe Gly Asp Ser
        1295                1300                1305

Gly Lys Lys Ala Ile Ser Thr Trp Val Glu Ile Gln Pro Gly Val
        1310                1315                1320

Phe Val Phe Phe Asp Lys Asn Gly Leu Ala Tyr Pro Pro Glu Asn
        1325                1330                1335

Met Asn
    1340

<210> SEQ ID NO 21

<400> SEQUENCE: 21

000

<210> SEQ ID NO 22
<400> SEQUENCE: 22

000

<210> SEQ ID NO 23
<400> SEQUENCE: 23

000

<210> SEQ ID NO 24
<400> SEQUENCE: 24

000

<210> SEQ ID NO 25
<211> LENGTH: 4308
<212> TYPE: DNA
<213> ORGANISM: Streptococcus sobrinus

<400> SEQUENCE: 25

```
atggttgacg gcaaatacta ctattatgat caggatggca acgttaagaa gaatttcgcg     60
gttagcgttg gtgacaagat ctactacttt gacgagactg gtgcctacaa agacacctct    120
aaagtggacg cggacaagtc tagcagcgcc gttagccaaa atgcgacgat ctttgcggct    180
aacaatcgtg cgtatagcac ctctgctgag aactttgagg ccgttgataa ctatctgacg    240
gcagatagct ggtatcgtcc taaatctatt ctgaaagatg caagacgtg gaccgagtcg     300
ggtaaggacg acttccgtcc gctgctgatg gcgtggtggc cggacacgga gactaaacgc    360
aattacgtga attacatgaa cctggttgtc ggcatcgaca agacgtacac cgcggaaacc    420
tctcaagcag atttgaccgc agcggcggag ctggtccagg cgcgtattga acagaaaatc    480
accacggaac agaatacgaa atggctgcgc gaggcgatct ctgctttcgt caagacccag    540
ccgcagtgga atggtgaaag cgagaagccg tatgacgacc acctgcaaaa cggtgctctg    600
aaattcgata tcagagcga cctgaccccg gacacccaga gcaactatcg cctgctgaat    660
cgcacccga ctaaccagac tggcagcctg acagccgtt tcacctataa tgcgaacgat    720
ccgttgggtg gctacgaatt tctgctggct aacgacgtgg ataatagcaa ccctgtggtg    780
caggcagaac aactgaactg gttgcattac ctgttgaatt ttggtagcat ttacgcgaaa    840
gatgcggatg caaacttcga ttccatccgt gtggacgccg tggacaacgt cgatgcagat    900
ctgttgcaga ttagcagcga ttacctgaag gcagcctatg gcattgacaa gaacaataag    960
aacgcgaaca accatgttag cattgttgag gcttggagcg ataacgatac gccgtacctg   1020
cacgatgacg gtgataacct gatgaacatg gacaataagt tccgcttgag catgctgtgg   1080
agcctggcca agccgctgga caagcgcagc ggtctgaatc ctctgattca taacagcctg   1140
gtggaccgtg aggttgatga ccgtgaagtg gaaacggttc cgagctactc ttttgcgcgt   1200
gcgcatgatt ccgaggtcca agacattatc cgcgacatta tcaaggccga aatcaacccg   1260
aatagctttg ttatagctt cacccaagaa gagattgacc aggcgtttaa gatctataat   1320
gaagatctga agaaaaccga caagaaatac acccactata atgtcccgtt gagctatact   1380
ttgctgctga cgaataaagg ttcgattccg cgtgtgtatt acggtgatat gttcaccgat   1440
```

```
gatggtcaat acatggcgaa caaaacggtt aactatgatg ccattgagtc gctgctgaaa   1500
gcgcgcatga agtacgttag cggcggtcaa gcgatgcaaa actatcaaat cggcaatggt   1560
gagattctga ccagcgttcg ttatggtaag ggtgcattga agcaatccga caagggtgac   1620
gcgaccacgc gtacgtccgg tgtgggcgtc gtgatgggca accagccgaa ctttagcctg   1680
gacggcaagg tggtggcatt gaacatgggt gccgctcatg caaatcagga gtatcgtgcg   1740
ctgatggtga gcaccaagga tggcgttgcc acgtatgcca ccgacgcgga cgcaagcaag   1800
gcaggtctgg tcaaacgcac cgatgaaaat ggttatttgt actttctgaa cgacgatctg   1860
aagggtgtga caaacccaca agtcagcggt ttcttgcagg tgtgggtccc agtgggtgcg   1920
gctgacgatc aggacattcg tgttgcagcg agcgacacgg ctagcacgga cggtaagtcc   1980
ctgcatcaag atgcggcaat ggatagccgt gttatgtttg agggttttag caacttccag   2040
agctttgcaa ccaaagaaga gagtacacc aacgtagtta ttgcgaacaa cgtggacaaa   2100
ttcgttagct ggggtattac cgactttgag atggcaccgc aatatgtcag ctccaccgat   2160
ggccagtttc tggatagcgt tatccagaat ggttacgcgt tcaccgaccg ttatgatctg   2220
ggtatgagca aagccaacaa atacggtacc gcggatcagc tggttaaagc aatcaaagcg   2280
ttgcacgcga agggtctgaa ggtgatggcg gactgggttc agaccagat gtacacgttt   2340
ccgaagcagg aagttgtcac tgtcacgcgc accgacaaat ttggtaagcc gattgcgggc   2400
agccaaatca atcacagcct gtacgtgacg gacaccaaat ccagcggtga tgattaccag   2460
gccaaatatg gtggtgcgtt cctggatgag ctgaaagaga ataccccgga gctgttcacc   2520
aaaaagcaga tctcgaccgg tcaggcgatc gacccgagcg tgaagattaa gcagtggagc   2580
gcgaaatact ttaatggtag caacattctg ggtcgtggtg ccgactacgt cctgtccgat   2640
caagttagca acaagtattt caatgtggcc agcgacacgc tgtttctgcc gtctagcctg   2700
ttgggtaagg ttgtcgaaag cggtattcgt tacgatggca aaggttatat ctataacagc   2760
agcgcgactg gcgaccaagt caaggcgtct tttatcacgg aagcaggcaa tctgtactac   2820
ttcggcaaag acggttacat ggttactggt gcgcagacca ttaacggtgc gaattacttc   2880
ttcttggaaa atggtacggc cctgcgtaat accatctaca ccgatgcaca gggcaactcc   2940
cactattatg ctaatgatgg caagcgttac gagaacggtt accagcagtt cggcaacgat   3000
tggcgttact tcaaagatgg taacatggcc gtcggtctga ccacggtgga tggtaacgtt   3060
cagtatttcg acaaggacgg tgtccaagct aaagacaaga ttattgtgac ccgcgatggt   3120
aaggtgcgct actttgatca acacaatggc aacgcggtca cgaataccct tatcgccgac   3180
aagaccggtc actggtacta cctgggcaaa gatggcgtcg cggtcaccgg cgctcaaacc   3240
gtcggtaagc aaaaactgta ttttgagcg aacggtgagc aggtgaaagg cgactttgtg   3300
actagccatg aaggcaaact gtacttttat gatgttgaca gcggcgacat gtggaccgat   3360
accttcatcg aggataaggc cggcaactgg ttctacctgg gtaaagacgg cgcagcagtt   3420
agcggtgcac agaccattcg cggtcaaaag ctgtacttca aggcgtacgg tcaacaggtc   3480
aaaggtgaca tcgttaaagg caccgacggc aagatccgtt actacgatgc gaaatccggc   3540
gagcaggttt tcaataagac ggtcaaagcc gctgatggca aaacctatgt gatcggcaac   3600
aatggtgtgg cggtcgatcc gagcgttgtt aagggtcaga cgttcaaaga cgccagcggc   3660
gcactgcgtt tttacaatct gaaaggtcaa ctggttacgg gctccggttg gtatgaaacg   3720
gccaatcacg attgggtgta tattcagagc ggtaaagcac tgaccggtga gcaaaccatc   3780
```

-continued

```
aatggtcagc acctgtactt taaagaagat ggccaccaag ttaaaggtca gctggtcacc   3840
cgtacggacg gcaaagtgcg ttactatgac gcaaattctg gcgatcaagc gttcaacaag   3900
tccgtgacgg ttaacggcaa aacgtattac ttcggtaatg atggtaccgc gcaaaccgcg   3960
ggtaacccga aaggccaaat cttcaaggac ggcagcgttc tgcgtttcta tagcatggaa   4020
ggccagctgg taattggcag cggctggtat tccaacgcgc aaggccaatg gctgtatgtg   4080
aagaatggta agtgttgac cggttttgcag accgtcggtt cccagcgcgt gtactttgat   4140
gagaatggca ttcaagcaaa aggcaaagcg ttcgcacga gcgacggcaa aattcgctac   4200
ttcgacgaga acagcggtag catgatcacc aatcaatgga agtttgttta cggtcaatac   4260
tattactttg gtaatgacgg tgcggcaatc taccgtggtt ggaattaa                4308
```

<210> SEQ ID NO 26
<211> LENGTH: 1435
<212> TYPE: PRT
<213> ORGANISM: Streptococcus sobrinus

<400> SEQUENCE: 26

```
Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
                20                  25                  30

Thr Gly Ala Tyr Lys Asp Thr Ser Lys Val Asp Ala Asp Lys Ser Ser
            35                  40                  45

Ser Ala Val Ser Gln Asn Ala Thr Ile Phe Ala Ala Asn Asn Arg Ala
        50                  55                  60

Tyr Ser Thr Ser Ala Glu Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Leu
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Lys Asp Ala Asp Ala Asn Phe Asp Ser
        275                 280                 285
```

```
Ile Arg Val Asp Ala Val Asp Asn Val Asp Ala Asp Leu Leu Gln Ile
    290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
        355                 360                 365

Arg Ser Gly Leu Asn Pro Ile His Asn Ser Leu Val Asp Arg Glu
    370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asp Lys
        435                 440                 445

Lys Tyr Thr His Tyr Asn Val Pro Leu Ser Tyr Thr Leu Leu Leu Thr
    450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
    530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Asn Asn Val Asp Lys Phe Val Ser Trp
    690                 695                 700
```

```
Gly Ile Thr Asp Phe Glu Met Ala Pro Gln Tyr Val Ser Thr Asp
705                 710                 715                 720

Gly Gln Phe Leu Asp Ser Val Ile Gln Asn Gly Tyr Ala Phe Thr Asp
            725                 730                 735

Arg Tyr Asp Leu Gly Met Ser Lys Ala Asn Lys Tyr Gly Thr Ala Asp
                740                 745                 750

Gln Leu Val Lys Ala Ile Lys Ala Leu His Ala Lys Gly Leu Lys Val
            755                 760                 765

Met Ala Asp Trp Val Pro Asp Gln Met Tyr Thr Phe Pro Lys Gln Glu
770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
                820                 825                 830

Glu Lys Tyr Pro Glu Leu Phe Thr Lys Lys Gln Ile Ser Thr Gly Gln
                835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
            900                 905                 910

Gly Lys Gly Tyr Ile Tyr Asn Ser Ser Ala Thr Gly Asp Gln Val Lys
            915                 920                 925

Ala Ser Phe Ile Thr Glu Ala Gly Asn Leu Tyr Tyr Phe Gly Lys Asp
930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                965                 970                 975

Gln Gly Asn Ser His Tyr Tyr Ala Asn Asp Gly Lys Arg Tyr Glu Asn
                980                 985                 990

Gly Tyr Gln Gln Phe Gly Asn Asp Trp Arg Tyr Phe Lys Asp Gly Asn
                995                 1000                1005

Met Ala Val Gly Leu Thr Thr Val Asp Gly Asn Val Gln Tyr Phe
    1010                1015                1020

Asp Lys Asp Gly Val Gln Ala Lys Asp Lys Ile Ile Val Thr Arg
    1025                1030                1035

Asp Gly Lys Val Arg Tyr Phe Asp Gln His Asn Gly Asn Ala Val
    1040                1045                1050

Thr Asn Thr Phe Ile Ala Asp Lys Thr Gly His Trp Tyr Tyr Leu
    1055                1060                1065

Gly Lys Asp Gly Val Ala Val Thr Gly Ala Gln Thr Val Gly Lys
    1070                1075                1080

Gln Lys Leu Tyr Phe Glu Ala Asn Gly Glu Gln Val Lys Gly Asp
    1085                1090                1095

Phe Val Thr Ser His Glu Gly Lys Leu Tyr Phe Tyr Asp Val Asp
    1100                1105                1110

Ser Gly Asp Met Trp Thr Asp Thr Phe Ile Glu Asp Lys Ala Gly
```

Asn Trp Phe Tyr Leu Gly Lys Asp Gly Ala Ala Val Ser Gly Ala
   1130                1135                1140

Gln Thr Ile Arg Gly Gln Lys Leu Tyr Phe Lys Ala Tyr Gly Gln
   1145                1150                1155

Gln Val Lys Gly Asp Ile Val Lys Gly Thr Asp Gly Lys Ile Arg
   1160                1165                1170

Tyr Tyr Asp Ala Lys Ser Gly Glu Gln Val Phe Asn Lys Thr Val
   1175                1180                1185

Lys Ala Ala Asp Gly Lys Thr Tyr Val Ile Gly Asn Asn Gly Val
   1190                1195                1200

Ala Val Asp Pro Ser Val Val Lys Gly Gln Thr Phe Lys Asp Ala
   1205                1210                1215

Ser Gly Ala Leu Arg Phe Tyr Asn Leu Lys Gly Gln Leu Val Thr
   1220                1225                1230

Gly Ser Gly Trp Tyr Glu Thr Ala Asn His Asp Trp Val Tyr Ile
   1235                1240                1245

Gln Ser Gly Lys Ala Leu Thr Gly Glu Gln Thr Ile Asn Gly Gln
   1250                1255                1260

His Leu Tyr Phe Lys Glu Asp Gly His Gln Val Lys Gly Gln Leu
   1265                1270                1275

Val Thr Arg Thr Asp Gly Lys Val Arg Tyr Tyr Asp Ala Asn Ser
   1280                1285                1290

Gly Asp Gln Ala Phe Asn Lys Ser Val Thr Val Asn Gly Lys Thr
   1295                1300                1305

Tyr Tyr Phe Gly Asn Asp Gly Thr Ala Gln Thr Ala Gly Asn Pro
   1310                1315                1320

Lys Gly Gln Ile Phe Lys Asp Gly Ser Val Leu Arg Phe Tyr Ser
   1325                1330                1335

Met Glu Gly Gln Leu Val Ile Gly Ser Gly Trp Tyr Ser Asn Ala
   1340                1345                1350

Gln Gly Gln Trp Leu Tyr Val Lys Asn Gly Lys Val Leu Thr Gly
   1355                1360                1365

Leu Gln Thr Val Gly Ser Gln Arg Val Tyr Phe Asp Glu Asn Gly
   1370                1375                1380

Ile Gln Ala Lys Gly Lys Ala Val Arg Thr Ser Asp Gly Lys Ile
   1385                1390                1395

Arg Tyr Phe Asp Glu Asn Ser Gly Ser Met Ile Thr Asn Gln Trp
   1400                1405                1410

Lys Phe Val Tyr Gly Gln Tyr Tyr Tyr Phe Gly Asn Asp Gly Ala
   1415                1420                1425

Ala Ile Tyr Arg Gly Trp Asn
   1430                1435

<210> SEQ ID NO 27
<211> LENGTH: 4023
<212> TYPE: DNA
<213> ORGANISM: Streptococcus salivarius PS4

<400> SEQUENCE: 27
atgattgacg gcaaatacta ctacgtaaac aaagatggct cgcacaaaga gaatttcgca    60
attaccgtga atggtcagtt gttgtatttc ggtaaggacg gtgcattgac gtctagcagc   120
acctacagct ttacgcaggg caccaccaac atcgttgatg gctttagcaa aaacaaccgt   180

-continued

```
gcgtacgatt ccagcgaggc gagctttgaa ctgatcgacg gttatctgac cgcggactcc      240
tggtatcgtc cggtgagcat tatcaaggac ggcgttacgt ggcaagccag caccaaagag      300
gactttcgcc cgctgctgat ggcctggtgg ccgaatgttg acacccaggt caactacctg      360
aattacatgt cgaaggtgtt taacctggac gcgaagtata cgagcaccga caaacaggtt      420
gacctgaatc gcgcagccaa ggacattcag gttaagattg agcaaaagat tcaggccgag      480
aagagcactc aatggctgcg tgaagcgatt tcggccttcg tcaaaaccca gccgcagtgg      540
aataaagaaa cggagaactt ctccaagggt ggtggtgagg atcatctgca aggtggtgca      600
ctgctgtacg ttaacgaccc gcgtaccccg tgggctaact ccaactaccg cctgctgaat      660
cgtactgcga ccaaccagac cggcacgatc gacaagagcg ttctggacga acagagcgat      720
cctaaccaca tgggcggctt cgattttctg ctggcgaatg acgtcgatac cagcaatccg      780
gtggtgcagg cggaacaact gaatcagatc cactacctga tgaattgggg ttccattgtt      840
atgggcgaca aagatgcaaa cttcgatggt atccgcgtgg acgcggtcga taacgttgac      900
gcagatatgc tgcaactgta caccaactac tttcgtgagt attatggcgt gaacaaaagc      960
gaggcaaacg cttggcgca catctcggtg ctggaagcgt ggagcttgaa tgataatcac     1020
tataatgaca agactgacgg tgcggccctg gcgatggaga caaacagcg tttggccctg     1080 ctgtttagct tggcgaaacc gatcaaagaa cgtaccccctg cggtgagccc gctgtacaac     1140
aacactttca cacgacgca gcgtgacgaa agaccgatt ggattaacaa agacggtagc     1200
aaagcctata tgaggacgg caccgtcaag cagtccacca tcggcaagta caacgagaaa     1260 tacgcgacg cgtccggcaa ttatgtgttc attcgcgccc acgataacaa cgtccaagac     1320
attattgcag agatcattaa gaaagaaatc aatccgaaaa gcgacggttt caccattacc     1380
gacgccgaaa tgaaaaaggc attcgaaatc tacaacaaag atatgctgtc ctctgataag     1440
aaatacaccc tgaacaacat cccagcggcc tacgcggtga tgctgcaaaa catggaaacc     1500
attactcgtg tgtattacgg cgatctgtat accgacgatg ccattacat ggaaaccaag     1560 agcccgtact acgacaccat tgtgaacctg atgaagaacc gtatcaaata cgtgtccggt     1620
ggtcaagcgc aacgttccta ttggctgccg accgacggta agatggataa agcgatgtc     1680 gaactgtatc gcaccaacga ggtgtacacc agcgtccgtt acggtaagga catcatgact     1740
gccgatgaca cccaaggtag caagtacagc cgtaccagcg gtcaggtgac cctggtggtg     1800
aacaacccga gctgtctttt ggataagagc gcgaagctgg acgtcgaaat gggcaagatc     1860
catgcaaacc agaaataccg tgctctgatc gtgggtacgc cgaacggcat caaaaacttc     1920
acgagcgacg ccgaggcaat cgcggctggc tacgtgaaag aaaccgacgg caatggtgtg     1980
ctgaccttcg gtgcaaatga catcaaaggt tacgaaacgt ttgacatgag cggtttcgtt     2040
gcagtttggg ttccggtagg tgcaagcgat gatcaagaca tccgtgtcgc cgcaagcacc     2100
gcggcaaaga aagaaggtga gctgactttg aaggcaactg aggcgtatga ctctcagctg     2160
atttacgaag gttttttcgaa ttttcagacc attccggatg gtagcgatcc gagcgtttac     2220
accaatcgta agatcgcgga aaatgttgat ttgttcaaga gctggggtgt gacctctttc     2280 gaaatgcgc cacagtttgt gagcgcgac gacggtacgt ttctggacag cgttatccag     2340
aacggctatg cgtttgcgga ccgttatgat ctggcgatgt ccaaaaacaa taagtacggt     2400
tcgaaagaag atctgcgtaa cgcgttgaag ctttgcaca aggccggcat ccaagccatt     2460
gcggactggg ttccggatca gatctaccaa ctgccgggca aagaagtagt gaccgccact     2520
cgtaccgatg gtgccggtcg taagattagc gatgcaatta tcgatcacag cctgtacgtc     2580
```

```
gcaaacagca agtcgtctgg caaagactat caagctaaat acggtggtga gttcctggcc    2640
gagctgaaag caaagtaccc ggaaatgttt aaagtcaaca tgattagcac gggtaaaccg    2700
atcgacgact ctgtcaaact gaagcaatgg aaggcggagt actttaacgg tacgaatgtt    2760
ctggaccgtg gtgttggtta cgtcctgagc gatgaggcga cgggcaagta ctttaccgtt    2820
acgaaagagg gtaactttat cccactgcaa ttgaaaggta cgagaaagt tatcacgggc    2880 ttcagctctg acggcaaggg cattacctat ttcggcacct cgggtaatca agcgaaaagc    2940
gcttttgtca cgttcaatgg taatacctac tattttgacg cgcgtggcca catggttacc    3000
aacggcgaat atagccctaa tggtaaggat gtgtatcgtt tcctgccgaa tggtattatg    3060
ttgagcaatg cattctacgt tgacggtaac ggcaatacct acctgtacaa ctccaagggc    3120
caaatgtaca aggtggtta tagcaaattc gacgttacgg aaaccaaaga tggtaaagag    3180
agcaaagtgg tgaaatttcg ctactttacc aatgaaggtg tgatggcaaa aggtgttacc    3240
gtggtggacg gcttcactca atacttcaac gaagatggca ttcagagcaa ggacgaactg    3300
gtgacctaca atggtaaaac ctattacttc gaagcgcata ccggtaatgc gatcaaaaac    3360
acgtggcgca atatcaaggg taagtggtat cactttgatg cgaatggcgt ggcggcaacg    3420
ggtgcacagg ttatcaatgg tcagcacctg tactttaatg aggatggttc ccaggtgaag    3480 ggtgcgtcg tgaagaatgc ggatggtacc ttcagcaagt ataaagatgg ttccggtgac    3540
ctggtggtca atgagttctt cactactggt gataacgtgt ggtactacgc tggtgccaac    3600
ggcaaaactg tgacgggtgc ccaggtcatc aatggccaac acctgttttt caaagaggac    3660
ggtagccagg ttaagggtga tttcgttaag aacagcgacg gcacctactc taagtatgat    3720
gcggccagcg cgaacgcct gacgaatgag ttttccacga ccggtgacaa ccactggtac    3780
tatattggtg ccaatggcaa aaccgttacc ggcgaagtca agatcggtga tgatacgtac    3840
ttcttcgcaa aagatggcaa gcagctgaag ggccagatcg tgacgacccg cagcggtcgt    3900
atcagctact acttcggcga ctctggtaag aaggcgatta gcacctgggt ggagattcag    3960
ccgggtgttt tcgtgtttttt cgacaaaaat ggcctggcat atccgccgga aacatgaat    4020 taa                                                                  4023
```

<210> SEQ ID NO 28
<211> LENGTH: 1340
<212> TYPE: PRT
<213> ORGANISM: Streptococcus salivarius PS4

<400> SEQUENCE: 28

```
Met Ile Asp Gly Lys Tyr Tyr Val Asn Lys Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Gln Gly Thr
            35                  40                  45

Thr Asn Ile Val Asp Gly Phe Ser Lys Asn Asn Arg Ala Tyr Asp Ser
        50                  55                  60

Ser Glu Ala Ser Phe Glu Leu Ile Asp Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Lys Glu Asp Phe Arg Pro Leu Leu Met Ala Trp Trp Pro Asn
                100                 105                 110
```

```
Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Val Asp Leu Asn Arg
        130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Ala Ile Ser Ala Phe Val Lys Thr
                165                 170                 175

Gln Pro Gln Trp Asn Lys Glu Thr Glu Asn Phe Ser Lys Gly Gly Gly
                180                 185                 190

Glu Asp His Leu Gln Gly Gly Ala Leu Leu Tyr Val Asn Asp Pro Arg
                195                 200                 205

Thr Pro Trp Ala Asn Ser Asn Tyr Arg Leu Leu Asn Arg Thr Ala Thr
        210                 215                 220

Asn Gln Thr Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Thr Ser Asn Pro Val Val Gln Ala Glu Gln Leu Asn Gln Ile His Tyr
                260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
        290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
                340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
                420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
450                 455                 460

Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
                500                 505                 510

Asp Gly His Tyr Met Glu Thr Lys Ser Pro Tyr Tyr Asp Thr Ile Val
        515                 520                 525
```

```
Asn Leu Met Lys Asn Arg Ile Lys Tyr Val Ser Gly Gln Ala Gln
    530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Ser Leu Asp
        595                 600                 605

Lys Ser Ala Lys Leu Asp Val Glu Met Gly Lys Ile His Ala Asn Gln
610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Ala Ser Thr Ala Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ser Asp Ala Ile Asp His Ser Leu Tyr Val Ala Asn Ser Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
930                 935                 940

Asn Phe Ile Pro Leu Gln Leu Lys Gly Asn Glu Lys Val Ile Thr Gly
```

-continued

```
            945                 950                 955                 960
        Phe Ser Ser Asp Gly Lys Gly Ile Thr Tyr Phe Gly Thr Ser Gly Asn
                        965                 970                 975
        Gln Ala Lys Ser Ala Phe Val Thr Phe Asn Gly Asn Thr Tyr Tyr Phe
                        980                 985                 990
        Asp Ala Arg Gly His Met Val Thr Asn Gly Glu Tyr Ser Pro Asn Gly
                        995                 1000                1005
        Lys Asp Val Tyr Arg Phe Leu Pro Asn Gly Ile Met Leu Ser Asn
            1010                1015                1020
        Ala Phe Tyr Val Asp Gly Asn Gly Asn Thr Tyr Leu Tyr Asn Ser
            1025                1030                1035
        Lys Gly Gln Met Tyr Lys Gly Gly Tyr Ser Lys Phe Asp Val Thr
            1040                1045                1050
        Glu Thr Lys Asp Gly Lys Glu Ser Lys Val Val Lys Phe Arg Tyr
            1055                1060                1065
        Phe Thr Asn Glu Gly Val Met Ala Lys Gly Val Thr Val Val Asp
            1070                1075                1080
        Gly Phe Thr Gln Tyr Phe Asn Glu Asp Gly Ile Gln Ser Lys Asp
            1085                1090                1095
        Glu Leu Val Thr Tyr Asn Gly Lys Thr Tyr Tyr Phe Glu Ala His
            1100                1105                1110
        Thr Gly Asn Ala Ile Lys Asn Thr Trp Arg Asn Ile Lys Gly Lys
            1115                1120                1125
        Trp Tyr His Phe Asp Ala Asn Gly Val Ala Ala Thr Gly Ala Gln
            1130                1135                1140
        Val Ile Asn Gly Gln His Leu Tyr Phe Asn Glu Asp Gly Ser Gln
            1145                1150                1155
        Val Lys Gly Gly Val Val Lys Asn Ala Asp Gly Thr Phe Ser Lys
            1160                1165                1170
        Tyr Lys Asp Gly Ser Gly Asp Leu Val Val Asn Glu Phe Phe Thr
            1175                1180                1185
        Thr Gly Asp Asn Val Trp Tyr Tyr Ala Gly Ala Asn Gly Lys Thr
            1190                1195                1200
        Val Thr Gly Ala Gln Val Ile Asn Gly Gln His Leu Phe Phe Lys
            1205                1210                1215
        Glu Asp Gly Ser Gln Val Lys Gly Asp Phe Val Lys Asn Ser Asp
            1220                1225                1230
        Gly Thr Tyr Ser Lys Tyr Asp Ala Ala Ser Gly Glu Arg Leu Thr
            1235                1240                1245
        Asn Glu Phe Phe Thr Thr Gly Asp Asn His Trp Tyr Tyr Ile Gly
            1250                1255                1260
        Ala Asn Gly Lys Thr Val Thr Gly Glu Val Lys Ile Gly Asp Asp
            1265                1270                1275
        Thr Tyr Phe Phe Ala Lys Asp Gly Lys Gln Leu Lys Gly Gln Ile
            1280                1285                1290
        Val Thr Thr Arg Ser Gly Arg Ile Ser Tyr Tyr Phe Gly Asp Ser
            1295                1300                1305
        Gly Lys Lys Ala Ile Ser Thr Trp Val Glu Ile Gln Pro Gly Val
            1310                1315                1320
        Phe Val Phe Phe Asp Lys Asn Gly Leu Ala Tyr Pro Pro Glu Asn
            1325                1330                1335
        Met Asn
            1340
```

<210> SEQ ID NO 29
<211> LENGTH: 4026
<212> TYPE: DNA
<213> ORGANISM: Streptococcus salivarius K12

<400> SEQUENCE: 29

| | | | | | |
|---|---|---|---|---|---|
| atgacggacg | gtaaatacta | ttatgtaaat | gaggacggca | gccacaaaga gaatttcgca | 60 |
| attacggtaa | acgtcaact | gttgtacttt | ggcaaggacg | gcgctctgac gagcagcagc | 120 |
| acgcacagct | tcacgccggg | tactacgaat | attgtggacg | gtttctcgat caacaaccgt | 180 |
| gcgtacgata | gcagcgaagc | gagctttgag | ctgatcaacg | gttacctgac ggcggattcc | 240 |
| tggtatcgcc | cggtttctat | catcaaggat | ggcgtcacgt | ggcaggcaag cactgccgag | 300 |
| gattttcgtc | cgctgttgat | ggcctggtgg | ccgaacgttg | atacccaggt gaactatctg | 360 |
| aactatatgt | ccaaggtctt | taacctggaa | gccaagtaca | ccagcaccga taaacaggct | 420 |
| gatctgaacc | gtgctgcaaa | ggatatccag | gtcaagatcg | aacagaagat ccaggcggaa | 480 |
| aagagcacgc | agtggctgcg | tgagactatc | tccgcgtttg | ttaaaaccca gccgcaatgg | 540 |
| aacaaagaga | ctgagaatta | ctccaagggt | ggtggcgaag | atcatctgca aggcggtgcg | 600 |
| ctgttgtacg | tgaacgacag | ccgtaccccg | tgggcgaata | gcaattaccg cctgctgaat | 660 |
| cgcacggcaa | cgaaccagac | cggtaccatt | aacaagtcgg | tgttggacga gcaatccgat | 720 |
| ccaaatcaca | tgggtggctt | cgacttcctg | ctggcaaacg | atgtggatct gagcaatcct | 780 |
| gttgtgcagg | ccgagcagct | gaatcaaatc | cattatctga | tgaactgggg cagcattgtt | 840 |
| atgggtgaca | agacgcgaa | ttttgatggt | atccgtgtgg | acgccgttga caacgtgaac | 900 |
| gctgacatgt | tgcagctgta | cacgaactac | tttcgtgagt | attacggcgt caacaaaagc | 960 |
| gaagcgcaag | cgctggcgca | cattagcgtt | ctggaagcgt | ggagcttgaa cgataaccac | 1020 |
| tataacgaca | aaaccgatgg | tgcggcactg | gcgatggaga | taagcaacg tctggccttg | 1080 |
| ctgttctctc | tggccaagcc | gatcaaagat | cgtactccgg | cagtgagccc actgtataac | 1140 |
| aatactttca | ataccaccca | acgtgacttc | aagacggatt | ggattaacaa ggacggtagc | 1200 |
| accgcctaca | tgaggatgg | caccgcgaaa | caatctacca | tcggtaagta caatgagaaa | 1260 |
| tatggtgatg | caagcggtaa | ctatgtgttt | attcgtgccc | atgacaataa cgtccaagac | 1320 |
| attattgcgg | agatcattaa | gaaagaaatc | aataagaaga | gcgatggttt taccatcagc | 1380 |
| gatagcgaaa | tgaaacaggc | gttcgaaatc | tacaacaaag | atatgctgag cagcaataag | 1440 |
| aaatacactc | tgaataacat | tccggcagcg | tacgccgtga | tgctgcaaaa catggagact | 1500 |
| atcacccgtg | tgtattatgg | tgacctgtac | accgacgacg | gtcactatat ggaaaccaag | 1560 |
| agcccgtatc | atgacaccat | tgtgaacctg | atgaaaaacc | gtatcaagta cgtttctggt | 1620 |
| ggccaggccc | aacgctccta | ttggctgccg | accgacggta | aaatggacaa tagcgatgtc | 1680 |
| gaactgtacc | gtactagcga | ggtctatacc | agcgttcgct | acggtaagga cattatgacg | 1740 |
| gcggatgaca | ccgagggtag | caagtactcc | cgcacgagcg | gtcaggttac cctggttgtt | 1800 |
| aacaacccga | agctgactct | gcatgaaagc | gccaaactga | acgtcgagat gggtaagatc | 1860 |
| cacgcaaaacc | agaaataccg | tgcgctgatt | gtgggtaccg | ccgatggcat caaaaacttt | 1920 |
| acgtctgatg | ccgaagcgat | cgcggcaggc | tacgtaaaag | aaacggacag caatggtgtt | 1980 |
| ctgaccttcg | gcgcaaatga | tatcaaaggt | tacgagactt | tcgatatgag cggtttcgtc | 2040 |
| gcagtttggg | tgccggtggg | tgcgagcgat | gatcaggaca | tccgcgtggc gccgtcgacg | 2100 |

```
gaagcgaaga aagaaggtga actgacgctg aaagccacgg aagcgtatga tagccagttg    2160
atttatgaag gcttctccaa tttccagacc attccggatg gcagcgaccc gagcgtttat    2220
accaaccgca aaattgctga gaatgttgat ctgtttaagt cctggggtgt cactagcttc    2280
gaaatggctc cgcagtttgt ttcggcggac gacggcacct tcctggatag cgttatccag    2340
aacggttacg cctttgcgga ccgttatgat ttggccatga gcaagaacaa caagtacggt    2400
tctaaagagg atctgcgcga cgcactgaaa gcgctgcaca agctggcat tcaggcaatc    2460 gcggactggg tcccagacca aatctaccaa ctgccaggca agaagtggt tacggcgacg    2520 cgcacggacg gtgcgggtcg caagatcgcg gacgccatca ttgatcatag cctgtatgtt    2580
gctaactcca agagctccgg tcgcgattac caagcgcagt atggtggcga gtttctggca    2640
gagctgaaag cgaagtaccc gaaaatgttc acggaaaaca tgattagcac gggtaagccg    2700
atcgatgaca gcgtcaaact gaagcaatgg aaagccaagt atttcaatgg tacgaatgtg    2760
ctggaccgtg gtgtcggtta cgtcctgtcc gacgaggcga ccggcaaata cttcaccgtt    2820
accaaagagg gtaacttcat tccgctgcaa ctgaccggca tgaaaaagc ggtgaccggt    2880 ttcagcaacg acggcaaggg tatcacctac tttggtacga gcggtaatca ggccaagagc    2940
gcgttcgtca cctttaacgg caatacgtac tatttcgacg cgcgtggcca catggtcacg    3000
aacggcgagt atagcccgaa cggcaaagat gtctaccgtt ttctgccaaa tggtattatg    3060
ttgtcgaacg cgttttatgt cgacgcaaac ggtaatacgt acttgtacaa ctacaagggc    3120
cagatgtaca aggtggtta tacgaaattt gatgtcaccg aaactgataa agatggtaat    3180
gagagcaagg tggtcaagtt tcgttatttc accaatgagg cgtcatggc taagggtctg    3240 accgtcattg acggtagcac ccagtacttt ggtgaggatg ttttcaaac gaaggacaag    3300 ctggcgacct ataaaggtaa gacttattac ttcgaggcac acacgggcaa tgcgatcaaa    3360
aacacctggc gtaacatcga cggtaagtgg tatcacttcg atgagaatgg cgttgccgcg    3420
accggtgcac aagtgattaa cggtcaaaaa ctgtatttca acgaggatgg ctcgcaagtg    3480
aagggcggtg ttgttaagaa cgccgacggt acctacagca atacaaaga gggcagcggt    3540 gagctggtta ccaacgagtt tttcacgacc gacggtaatg tgtggtacta tgctggtgcg    3600
gatggcaaga ctgtgaccgg tgctcaggtc attaatggtc agcacctgta ctttaaagaa    3660
gatggcagcc aggtgaaagg tggtgtggtg aaaaacgcgg acggtacgta cagcaagtat    3720
gacgccgcca ccggtgaacg cttgaccaat gagttcttta ccacgggcga taacaattgg    3780
tactatattg gttctaatgg taagaccgta accggtgaag tcaaaatcgg tgcggacacc    3840
tattactttg ccaaagatgg caaacaggtc aagggccaaa ccgtcaccgc aggcaatggc    3900
cgcatctcct attactacgg cgattctggt aagaaagcaa tcagcacgtg gatcgaaatt    3960
caaccgggta tctatgtcta ttttgataag acgggcatcg cgtacccacc gcgtgtgctg    4020
aattaa                                                                4026
```

<210> SEQ ID NO 30
<211> LENGTH: 1341
<212> TYPE: PRT
<213> ORGANISM: Streptococcus salivarius K12

<400> SEQUENCE: 30

```
Met Thr Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30
```

```
Asp Gly Ala Leu Thr Ser Ser Thr His Ser Phe Thr Pro Gly Thr
         35                  40                  45

Thr Asn Ile Val Asp Gly Phe Ser Ile Asn Asn Arg Ala Tyr Asp Ser
 50                  55                  60

Ser Glu Ala Ser Phe Glu Leu Ile Asn Gly Tyr Leu Thr Ala Asp Ser
 65                  70                  75                  80

Trp Tyr Arg Pro Val Ser Ile Ile Lys Asp Gly Val Thr Trp Gln Ala
             85                  90                  95

Ser Thr Ala Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
         115                 120                 125

Leu Glu Ala Lys Tyr Thr Ser Thr Asp Lys Gln Ala Asp Leu Asn Arg
 130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
             165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
         195                 200                 205

Thr Pro Trp Ala Asn Ser Asn Tyr Arg Leu Leu Asn Arg Thr Ala Thr
 210                 215                 220

Asn Gln Thr Gly Thr Ile Asn Lys Ser Val Leu Asp Glu Gln Ser Asp
225                 230                 235                 240

Pro Asn His Met Gly Gly Phe Asp Phe Leu Leu Ala Asn Asp Val Asp
             245                 250                 255

Leu Ser Asn Pro Val Val Gln Ala Glu Gln Leu Asn Gln Ile His Tyr
                260                 265                 270

Leu Met Asn Trp Gly Ser Ile Val Met Gly Asp Lys Asp Ala Asn Phe
         275                 280                 285

Asp Gly Ile Arg Val Asp Ala Val Asp Asn Val Asn Ala Asp Met Leu
290                 295                 300

Gln Leu Tyr Thr Asn Tyr Phe Arg Glu Tyr Tyr Gly Val Asn Lys Ser
305                 310                 315                 320

Glu Ala Gln Ala Leu Ala His Ile Ser Val Leu Glu Ala Trp Ser Leu
             325                 330                 335

Asn Asp Asn His Tyr Asn Asp Lys Thr Asp Gly Ala Ala Leu Ala Met
                340                 345                 350

Glu Asn Lys Gln Arg Leu Ala Leu Leu Phe Ser Leu Ala Lys Pro Ile
         355                 360                 365

Lys Asp Arg Thr Pro Ala Val Ser Pro Leu Tyr Asn Asn Thr Phe Asn
370                 375                 380

Thr Thr Gln Arg Asp Phe Lys Thr Asp Trp Ile Asn Lys Asp Gly Ser
385                 390                 395                 400

Thr Ala Tyr Asn Glu Asp Gly Thr Ala Lys Gln Ser Thr Ile Gly Lys
             405                 410                 415

Tyr Asn Glu Lys Tyr Gly Asp Ala Ser Gly Asn Tyr Val Phe Ile Arg
                420                 425                 430

Ala His Asp Asn Asn Val Gln Asp Ile Ile Ala Glu Ile Ile Lys Lys
         435                 440                 445
```

```
Glu Ile Asn Lys Lys Ser Asp Gly Phe Thr Ile Ser Asp Ser Glu Met
450                 455                 460
Lys Gln Ala Phe Glu Ile Tyr Asn Lys Asp Met Leu Ser Ser Asn Lys
465                 470                 475                 480
Lys Tyr Thr Leu Asn Asn Ile Pro Ala Ala Tyr Ala Val Met Leu Gln
                485                 490                 495
Asn Met Glu Thr Ile Thr Arg Val Tyr Tyr Gly Asp Leu Tyr Thr Asp
                500                 505                 510
Asp Gly His Tyr Met Glu Thr Lys Ser Pro Tyr His Asp Thr Ile Val
                515                 520                 525
Asn Leu Met Lys Asn Arg Ile Lys Tyr Val Ser Gly Gly Gln Ala Gln
530                 535                 540
Arg Ser Tyr Trp Leu Pro Thr Asp Gly Lys Met Asp Asn Ser Asp Val
545                 550                 555                 560
Glu Leu Tyr Arg Thr Ser Glu Val Tyr Thr Ser Val Arg Tyr Gly Lys
                565                 570                 575
Asp Ile Met Thr Ala Asp Asp Thr Glu Gly Ser Lys Tyr Ser Arg Thr
                580                 585                 590
Ser Gly Gln Val Thr Leu Val Val Asn Asn Pro Lys Leu Thr Leu His
                595                 600                 605
Glu Ser Ala Lys Leu Asn Val Glu Met Gly Lys Ile His Ala Asn Gln
610                 615                 620
Lys Tyr Arg Ala Leu Ile Val Gly Thr Ala Asp Gly Ile Lys Asn Phe
625                 630                 635                 640
Thr Ser Asp Ala Glu Ala Ile Ala Ala Gly Tyr Val Lys Glu Thr Asp
                645                 650                 655
Ser Asn Gly Val Leu Thr Phe Gly Ala Asn Asp Ile Lys Gly Tyr Glu
                660                 665                 670
Thr Phe Asp Met Ser Gly Phe Val Ala Val Trp Val Pro Val Gly Ala
                675                 680                 685
Ser Asp Asp Gln Asp Ile Arg Val Ala Pro Ser Thr Glu Ala Lys Lys
                690                 695                 700
Glu Gly Glu Leu Thr Leu Lys Ala Thr Glu Ala Tyr Asp Ser Gln Leu
705                 710                 715                 720
Ile Tyr Glu Gly Phe Ser Asn Phe Gln Thr Ile Pro Asp Gly Ser Asp
                725                 730                 735
Pro Ser Val Tyr Thr Asn Arg Lys Ile Ala Glu Asn Val Asp Leu Phe
                740                 745                 750
Lys Ser Trp Gly Val Thr Ser Phe Glu Met Ala Pro Gln Phe Val Ser
                755                 760                 765
Ala Asp Asp Gly Thr Phe Leu Asp Ser Val Ile Gln Asn Gly Tyr Ala
770                 775                 780
Phe Ala Asp Arg Tyr Asp Leu Ala Met Ser Lys Asn Asn Lys Tyr Gly
785                 790                 795                 800
Ser Lys Glu Asp Leu Arg Asp Ala Leu Lys Ala Leu His Lys Ala Gly
                805                 810                 815
Ile Gln Ala Ile Ala Asp Trp Val Pro Asp Gln Ile Tyr Gln Leu Pro
                820                 825                 830
Gly Lys Glu Val Val Thr Ala Thr Arg Thr Asp Gly Ala Gly Arg Lys
                835                 840                 845
Ile Ala Asp Ala Ile Ile Asp His Ser Leu Tyr Val Ala Asn Ser Lys
850                 855                 860
Ser Ser Gly Arg Asp Tyr Gln Ala Gln Tyr Gly Gly Glu Phe Leu Ala
```

```
            865                 870                 875                 880
         Glu Leu Lys Ala Lys Tyr Pro Lys Met Phe Thr Glu Asn Met Ile Ser
                         885                 890                 895
         Thr Gly Lys Pro Ile Asp Asp Ser Val Lys Leu Lys Gln Trp Lys Ala
                         900                 905                 910
         Lys Tyr Phe Asn Gly Thr Asn Val Leu Asp Arg Gly Val Gly Tyr Val
                         915                 920                 925
         Leu Ser Asp Glu Ala Thr Gly Lys Tyr Phe Val Thr Lys Glu Gly
         930                 935                 940
         Asn Phe Ile Pro Leu Gln Leu Thr Gly Asn Glu Lys Ala Val Thr Gly
         945                 950                 955                 960
         Phe Ser Asn Asp Gly Lys Gly Ile Thr Tyr Phe Gly Thr Ser Gly Asn
                         965                 970                 975
         Gln Ala Lys Ser Ala Phe Val Thr Phe Asn Gly Asn Thr Tyr Tyr Phe
                         980                 985                 990
         Asp Ala Arg Gly His Met Val Thr  Asn Gly Glu Tyr Ser  Pro Asn Gly
                         995                 1000                1005
         Lys Asp Val Tyr Arg Phe Leu  Pro Asn Gly Ile Met  Leu Ser Asn
             1010                1015                1020
         Ala Phe Tyr Val Asp Ala Asn  Gly Asn Thr Tyr Leu  Tyr Asn Tyr
             1025                1030                1035
         Lys Gly Gln Met Tyr Lys Gly  Gly Tyr Thr Lys Phe  Asp Val Thr
             1040                1045                1050
         Glu Thr Asp Lys Asp Gly Asn  Glu Ser Lys Val Val  Lys Phe Arg
             1055                1060                1065
         Tyr Phe Thr Asn Glu Gly Val  Met Ala Lys Gly Leu  Thr Val Ile
             1070                1075                1080
         Asp Gly Ser Thr Gln Tyr Phe  Gly Glu Asp Gly Phe  Gln Thr Lys
             1085                1090                1095
         Asp Lys Leu Ala Thr Tyr Lys  Gly Lys Thr Tyr Tyr  Phe Glu Ala
             1100                1105                1110
         His Thr Gly Asn Ala Ile Lys  Asn Thr Trp Arg Asn  Ile Asp Gly
             1115                1120                1125
         Lys Trp Tyr His Phe Asp Glu  Asn Gly Val Ala Ala  Thr Gly Ala
             1130                1135                1140
         Gln Val Ile Asn Gly Gln Lys  Leu Tyr Phe Asn Glu  Asp Gly Ser
             1145                1150                1155
         Gln Val Lys Gly Gly Val Val  Lys Asn Ala Asp Gly  Thr Tyr Ser
             1160                1165                1170
         Lys Tyr Lys Glu Gly Ser Gly  Glu Leu Val Thr Asn  Glu Phe Phe
             1175                1180                1185
         Thr Thr Asp Gly Asn Val Trp  Tyr Tyr Ala Gly Ala  Asp Gly Lys
             1190                1195                1200
         Thr Val Thr Gly Ala Gln Val  Ile Asn Gly Gln His  Leu Tyr Phe
             1205                1210                1215
         Lys Glu Asp Gly Ser Gln Val  Lys Gly Gly Val Val  Lys Asn Ala
             1220                1225                1230
         Asp Gly Thr Tyr Ser Lys Tyr  Asp Ala Ala Thr Gly  Glu Arg Leu
             1235                1240                1245
         Thr Asn Glu Phe Phe Thr Thr  Gly Asp Asn Asn Trp  Tyr Tyr Ile
             1250                1255                1260
         Gly Ser Asn Gly Lys Thr Val  Thr Gly Glu Val Lys  Ile Gly Ala
             1265                1270                1275
```

```
Asp Thr Tyr Tyr Phe Ala Lys Asp Gly Lys Gln Val Lys Gly Gln
    1280                1285                1290

Thr Val Thr Ala Gly Asn Gly Arg Ile Ser Tyr Tyr Gly Asp
    1295                1300                1305

Ser Gly Lys Lys Ala Ile Ser Thr Trp Ile Glu Ile Gln Pro Gly
    1310                1315                1320

Ile Tyr Val Tyr Phe Asp Lys Thr Gly Ile Ala Tyr Pro Pro Arg
    1325                1330                1335

Val Leu Asn
    1340

<210> SEQ ID NO 31

<400> SEQUENCE: 31

000

<210> SEQ ID NO 32

<400> SEQUENCE: 32

000

<210> SEQ ID NO 33
<211> LENGTH: 4026
<212> TYPE: DNA
<213> ORGANISM: Streptococcus salivarius JIM8777

<400> SEQUENCE: 33
atgatcgacg gcaaatacta ctatgtaaac gaggacggca gccacaaaga gaatttcgcg     60
attacggtaa acgtcagct gctgtacttt ggtaaggacg tgctctgac gagcagctcc      120 acgtacagct ttaccccggg tacgaccaat attgtcgatg gcttcagcat taacaaccgt    180
gcgtatgaca gcagcgaggc atcctttgag ctgatcgatg ttatttgac cgcggatagc     240 tggtatcgtc cggcgagcat cattaaggac ggcgttacgt ggcaggcctc gaccgcagaa    300
gattttcgtc cgctgctgat ggcttggtgg ccgaatgttg acacccaggt gaattatctg    360
aattacatgt ccaaggtttt caacctggat gcaaagtaca ccagcaccga caagcaggaa    420
accctgaacg tggctgcgaa agatatccaa gtcaagattg agcaaaagat tcaggcagag    480
aaatctaccc agtggctgcg tgaaacgatt agcgcgtttg ttaaaactca gccgcaatgg    540
aataaagaaa cggaaaacta ttccaagggt ggtggcgagg accatctgca aggcggtgcc    600
ctgttgtacg ttaacgattc gcgcacccc tgggcgaact cgaactatcg cttgctgaac    660
cataccgcta ccaatcaaaa aggcactatt gacaaatctg tcctggacga gcagagcgac    720
ccgaaccaca tgggcggttt cgattttctg ctggcgaacg acgtcgacct gagcaacccg    780
gtggtgcagg ccgaacaact gaaccagatt cactacctga tgaattgggg tagcatcgtg    840
atgggtgata aagatgcgaa ctttgacggc attcgtgtcg atgcggtcga taacgtggac    900
gccgacatgt tgcagctgta cacgaactac tttcgtgagt actacggcgt taacaagagc    960
gaagcaaatg ccctggcgca tatcagcgtt ctggaagcgt ggagcctgaa tgacaatcac   1020
tataacgata agacggacgg tgcggccctg gcaatggaga ataaacaacg tctggcgctg   1080
ctgttcagcc tggcgaaacc gatcaaagag cgtacgccgg ctgtgagccc actgtataac   1140
aacaccttca atactacgca gcgtgacgag aaaacggact ggattaacaa agacggtagc   1200
aaagcgtata acgaggatgg taccgtcaag caatcgacca ttggtaagta caatgagaag   1260
```

```
tatggcgacg caagcggtaa ttacgtgttc attcgtgccc acgacaacaa tgttcaagac    1320
atcatcgccg aaatcatcaa gaaagagatc aaccctaaga gcgacggttt caccatcacc    1380
gacgcagaga tgaagaaggc ctttgaaatc tacaacaagg acatgttgag cagcgataag    1440
aagtatactc tgaacaacat tccggctgcg tacgcggtga tgttgcagaa tatggaaacc    1500
atcacgcgtg tttactatgg tgatctgtat accgataatg caactacat ggaaacgaaa     1560 agcccgtact atgacaccat tgttaatctg atgaagaatc gcatcaagta tgtgtctggc    1620
ggtcaagcgc agcgttctta ctggctgccg accgatggta agatggacaa tagcgatgtg    1680
gaactgtacc gcaccaacga ggtatacgct tctgtgcgct atggtaaaga cattatgacc    1740
gccgatgata ccgagggttc caagtactcc cgtacgagcg ccaagttac cttggtggca     1800 aacaacccga aattgaccct ggaccaaagc gcgaaactga agtggagat gggtaagatc     1860 cacgcaaatc aaaagtaccg tgcactgatt gtcggtaccg ccgacggtat caagaatttc    1920
accagcgatg cggatgcgat tgcagcaggc tatgttaaag agactgatag caatggtgtg    1980
ctgacgtttg gtgcgaacga cattaaaggc tatgaaacgt tgacatgag cggtttcgtt     2040 gcggtgtggg tgcctgtggg tgctagcgat gatcaggata tccgtgtcgc gccgagcacc    2100
gaggcaaaga aagaaggtga gctgacgttg aaagcgaccg aggcctatga cagccagttg    2160
atttacgaag gtttcagcaa tttccaaacc attccagacg gttccgatcc gagcgtctac    2220
accaatcgca aaatcgcgga aaacgttgat ctgttcaaaa gctggggtgt gaccagcttc    2280
gaaatggcac cgcaattcgt tagcgcggac gatggtacgt tcttggacag cgttatccaa    2340
aatggctatg cgttcgccga tcgttatgac ttggcgatga gcaaaaacaa caaatacggc    2400
agcaaagagg atctgcgcga cgccctgaaa gcgctgcata agcgggtat tcaagccatc     2460 gctgactggg ttccggacca gatctaccag ctgccgggta agaagtcgt taccgcgacc     2520 cgcaccgatg cgctggccg taagatcgcg gatgcaatta tcgatcatag cttgtatgtg     2580
gccaatacta aaagctccgg taaggattac caggcgaaat atggtggtga atttctggct    2640
gagctgaagg ccaaataccc ggagatgttc aaggtcaaca tgattagcac cggcaaacct    2700
attgatgact ctgtcaaatt gaaacaatgg aaggcagagt atttcaatgg cactaacgtc    2760
ctggaacgtg gtgttggtta cgtgctgagc gacgaggcga ccggtaaata cttcaccgtt    2820
acgaaggacg gcaatttcat cccgctgcaa ctgaccggta tgagaaggt tgtgacgggt     2880 ttttctaatg acggtaaggg cattacctac ttcggtacct cgggtaccca ggcaaagagc    2940
gcattcgtga cgtttaacgg taacacctac tactttgatg cacgcggcca catggtgacg    3000
aacggcgagt acagcccgaa cggcaaggat gtttatcgct tcctgccgaa tggcatcatg    3060
ctgtccaatg cgtttacgt cgatgcaaat ggtaatactt acctgtacaa cagcaagggt    3120
cagatgtata agggcggtta taccaagttc gacgttactg aaacggacaa ggacggtaaa    3180
gagagcaaag tagtgaagtt tcgttatttc acgaacgaag cgtcatggc gaaaggtgtc     3240 accgttattg atggctttac ccagtatttc ggtgaagatg gctttcaagc gaaggacaag    3300
ctggtgacct ttaagggcaa aacctactat tttgacgcgc acacgggcaa cgccatcaag    3360
aacacctggc gtaatatcga cggtaagtgg tatcattttg atgcgaacgg tgtggcggcg    3420
accggcgcac aggtcattaa tggtcaaaaa ctgtacttta atgaggacgg tagccaagtc    3480
aaaggtggcg tcgtcaagaa tgcagatggc acctatagca aatacaaaga gggctccggt    3540
gagctggtta ccaacgagtt ctttaccacg gatggtaacg tctggtacta tgctggtgcg    3600
```

```
aatggcaaga ccgttaccgg tgcacaggtt atcaacggcc agcacctgta cttcaatgcg   3660
gatggctctc aagtgaaggg cggtgtcgtc aaaaacgcgg acggtacgta ctccaaatac   3720
gatgccgcga ccggtgaacg tctgaccaat gagttttca cgactggtga caacaattgg    3780
tactacatcg gcgccaacgg taagacggtt acgggcgaag tgaaaattgg cgacgatacg   3840
tactacttcg caaaagatgg taaacaggtg aaaggtcaga cggtttccgc tggtaatggc   3900
cgcatcagct actattacgg tgactctggt aaacgtgcgg ttagcacgtg ggttgaaatt   3960
caaccgggcg tgtatgtcta ttttgataag aatggcctgg catatccacc gcgcgttttg   4020
aattaa                                                              4026
```

<210> SEQ ID NO 34
<211> LENGTH: 1341
<212> TYPE: PRT
<213> ORGANISM: Streptococcus salivarius JIM8777

<400> SEQUENCE: 34

```
Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Glu Thr Leu Asn Val
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn His Thr Ala Thr
    210                 215                 220

Asn Gln Lys Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
```

-continued

```
             290                 295                 300
Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
                340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Pro Lys Ser Asp Gly Phe Thr Ile Thr Asp Ala Glu Met
450                 455                 460

Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asn Gly Asn Tyr Met Glu Thr Lys Ser Pro Tyr Tyr Asp Thr Ile Val
            515                 520                 525

Asn Leu Met Lys Asn Arg Ile Lys Tyr Val Ser Gly Gly Gln Ala Gln
530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Ala Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Ala Asn Asn Pro Lys Leu Thr Leu Asp
            595                 600                 605

Gln Ser Ala Lys Leu Lys Val Glu Met Gly Lys Ile His Ala Asn Gln
610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
            675                 680                 685

Ser Asp Asp Gln Asp Ile Arg Val Ala Pro Ser Thr Glu Ala Lys Lys
            690                 695                 700

Glu Gly Glu Leu Thr Leu Lys Ala Thr Glu Ala Tyr Asp Ser Gln Leu
705                 710                 715                 720
```

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Thr Lys
    850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Glu Arg Gly Val Gly Tyr Val
        915                 920                 925

Leu Ser Asp Glu Ala Thr Gly Lys Tyr Phe Thr Val Thr Lys Asp Gly
    930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
        995                 1000                1005

Lys Asp Val Tyr Arg Phe Leu Pro Asn Gly Ile Met Leu Ser Asn
    1010                1015                1020

Ala Phe Tyr Val Asp Ala Asn Gly Asn Thr Tyr Leu Tyr Asn Ser
    1025                1030                1035

Lys Gly Gln Met Tyr Lys Gly Gly Tyr Thr Lys Phe Asp Val Thr
    1040                1045                1050

Glu Thr Asp Lys Asp Gly Lys Glu Ser Lys Val Val Lys Phe Arg
    1055                1060                1065

Tyr Phe Thr Asn Glu Gly Val Met Ala Lys Gly Val Thr Val Ile
    1070                1075                1080

Asp Gly Phe Thr Gln Tyr Phe Gly Glu Asp Gly Phe Gln Ala Lys
    1085                1090                1095

Asp Lys Leu Val Thr Phe Lys Gly Lys Thr Tyr Tyr Phe Asp Ala
    1100                1105                1110

His Thr Gly Asn Ala Ile Lys Asn Thr Trp Arg Asn Ile Asp Gly
    1115                1120                1125

-continued

```
Lys Trp Tyr His Phe Asp Ala Asn Gly Val Ala Ala Thr Gly Ala
    1130                1135                1140
Gln Val Ile Asn Gly Gln Lys Leu Tyr Phe Asn Glu Asp Gly Ser
    1145                1150                1155
Gln Val Lys Gly Gly Val Val Lys Asn Ala Asp Gly Thr Tyr Ser
    1160                1165                1170
Lys Tyr Lys Glu Gly Ser Gly Glu Leu Val Thr Asn Glu Phe Phe
    1175                1180                1185
Thr Thr Asp Gly Asn Val Trp Tyr Tyr Ala Gly Ala Asn Gly Lys
    1190                1195                1200
Thr Val Thr Gly Ala Gln Val Ile Asn Gly Gln His Leu Tyr Phe
    1205                1210                1215
Asn Ala Asp Gly Ser Gln Val Lys Gly Gly Val Val Lys Asn Ala
    1220                1225                1230
Asp Gly Thr Tyr Ser Lys Tyr Asp Ala Ala Thr Gly Glu Arg Leu
    1235                1240                1245
Thr Asn Glu Phe Phe Thr Thr Gly Asp Asn Asn Trp Tyr Tyr Ile
    1250                1255                1260
Gly Ala Asn Gly Lys Thr Val Thr Gly Glu Val Lys Ile Gly Asp
    1265                1270                1275
Asp Thr Tyr Tyr Phe Ala Lys Asp Gly Lys Gln Val Lys Gly Gln
    1280                1285                1290
Thr Val Ser Ala Gly Asn Gly Arg Ile Ser Tyr Tyr Tyr Gly Asp
    1295                1300                1305
Ser Gly Lys Arg Ala Val Ser Thr Trp Val Glu Ile Gln Pro Gly
    1310                1315                1320
Val Tyr Val Tyr Phe Asp Lys Asn Gly Leu Ala Tyr Pro Pro Arg
    1325                1330                1335
Val Leu Asn
    1340

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000
```

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59
<211> LENGTH: 1242
<212> TYPE: PRT
<213> ORGANISM: Streptococcus sp. C150

<400> SEQUENCE: 59

```
Met Ile Asn Gly Lys Glu Tyr Tyr Val Glu Asp Asp Gly Thr Val Arg
1               5                   10                  15

Lys Asn Tyr Val Leu Glu Arg Asn Gly Gly Ser Gln Tyr Phe Asn Ala
                20                  25                  30

Glu Thr Gly Glu Leu Ser Asn Gln Lys Asp Tyr Arg Phe Asp Lys Asn
            35                  40                  45

Gly Gly Thr Gly Ser Ala Ala Asp Ser Thr Thr Asn Thr Asn Val Thr
        50                  55                  60

Val Asn Gly Asp Lys Asn Ala Phe Tyr Gly Thr Thr Glu Lys Asp Ile
65                  70                  75                  80

Glu Leu Val Asp Gly Tyr Phe Thr Ala Asn Thr Trp Tyr Arg Pro Lys
```

```
                    85                  90                  95
Glu Ile Leu Lys Asp Gly Lys Glu Trp Thr Ala Ser Thr Glu Asn Asp
            100                 105                 110

Lys Arg Pro Leu Leu Thr Val Trp Trp Pro Ser Lys Ala Ile Gln Ala
            115                 120                 125

Ser Tyr Leu Asn Tyr Met Arg Glu Glu Gly Leu Gly Thr Asn Gln Thr
            130                 135                 140

Phe Thr Ser Tyr Ser Ser Gln Thr Gln Met Asp Gln Ala Ala Leu Glu
145                 150                 155                 160

Val Gln Lys Arg Ile Glu Glu Arg Ile Ala Arg Glu Gly Asn Thr Asp
                165                 170                 175

Trp Leu Arg Thr Thr Ile Lys Asn Phe Val Lys Thr Gln Pro Gly Trp
                180                 185                 190

Asn Ser Thr Ser Glu Asn Leu Asp Asn Ser Asp His Leu Gln Gly Gly
                195                 200                 205

Ala Leu Leu Tyr Asn Asn Ser Asn Arg Thr Ser Tyr Ala Asn Ser Asp
            210                 215                 220

Tyr Arg Leu Leu Asn Arg Thr Pro Thr Gln Gln Asp Gly Thr Arg Arg
225                 230                 235                 240

Tyr Phe Lys Asp Asn Ser Ser Gly Gly Phe Glu Phe Leu Leu Ala Asn
                245                 250                 255

Asp Ile Asp Asn Ser Asn Pro Ala Val Gln Ala Glu Gln Leu Asn Trp
                260                 265                 270

Leu His Tyr Ile Met Asn Ile Gly Ser Leu Thr Gly Gly Ser Glu Asp
            275                 280                 285

Glu Asn Phe Asp Gly Val Arg Val Asp Ala Val Asp Asn Val Asn Ala
            290                 295                 300

Asp Leu Leu Gln Ile Ala Ser Asp Tyr Phe Lys Ala Lys Tyr Gly Val
305                 310                 315                 320

Glu Lys Ser Glu Glu Ala Ile Lys His Leu Ser Ile Leu Glu Ala
                325                 330                 335

Trp Ser His Asn Asp Ala Tyr Tyr Asn Glu Asp Thr Lys Gly Ala Gln
                340                 345                 350

Leu Pro Met Asp Asp Pro Leu Arg Leu Ala Met Val Phe Ser Phe Leu
            355                 360                 365

Arg Pro Ile Gly Asn Arg Ser Gly Leu Glu Pro Leu Ile Thr Asn Ser
            370                 375                 380

Leu Asn Asp Arg Ser Glu Ser Lys Lys Asn Thr Lys Arg Met Ala Asn
385                 390                 395                 400

Tyr Thr Phe Val Arg Ala His Asp Ser Glu Val Gln Ser Val Ile Gly
                405                 410                 415

Gln Ile Ile Lys Asn Glu Ile Asn Pro Gln Ser Thr Gly Asn Thr Phe
            420                 425                 430

Thr Leu Asp Glu Met Lys Lys Ala Phe Lys Ile Tyr Asn Ala Asp Met
435                 440                 445

Arg Ser Ala Asn Lys Arg Tyr Thr Gln Tyr Asn Ile Pro Ser Ala Tyr
            450                 455                 460

Ala Phe Met Leu Thr Asn Lys Asp Thr Val Pro Arg Val Tyr Tyr Gly
465                 470                 475                 480

Asp Leu Tyr Thr Asp Asp Gly Gln Tyr Met Ala Gln Lys Ser Pro Tyr
                485                 490                 495

His Asp Ala Ile Ser Thr Leu Leu Gln Ala Arg Ile Arg Tyr Ala Ala
            500                 505                 510
```

```
Gly Gly Gln Asp Met Lys Met Ser Tyr Val Gly Ser Gly Asn Thr Asn
        515                 520                 525

Gly Trp Asp Ala Ser Gly Val Leu Thr Ser Val Arg Tyr Gly Lys Gly
    530                 535                 540

Ala Asn Asn Ala Ser Asp Ala Gly Thr Ala Glu Thr Arg Asn Gln Gly
545                 550                 555                 560

Met Ala Val Ile Leu Ser Asn Gln Pro Ala Leu Arg Leu Asn Ser Asn
                565                 570                 575

Leu Thr Ile Asn Met Gly Ala Ala His Arg Asn Gln Ala Tyr Arg Pro
            580                 585                 590

Leu Leu Leu Thr Thr Ser Asn Gly Val Ala Ser Tyr Leu Asn Asp Gly
        595                 600                 605

Asp Ala Asn Gly Ile Val Lys Tyr Thr Asp Ala Asn Gly Tyr Leu Thr
        610                 615                 620

Phe Asn Pro Gly Glu Ile Ser Gly Val Arg Asn Ala Gln Val Asp Gly
625                 630                 635                 640

Tyr Leu Ala Val Trp Val Pro Leu Gly Ala Ser Glu Asn Gln Asp Val
                645                 650                 655

Arg Val Ala Ala Ser Lys Ser Lys Asn Ser Ser Gly Leu Val Tyr Asp
            660                 665                 670

Ser Ser Ala Ala Leu Asp Ser Gln Val Ile Tyr Glu Gly Phe Ser Asn
        675                 680                 685

Phe Gln Asp Phe Val Gln Asp Pro Ser Gln Tyr Thr Asn Lys Lys Ile
        690                 695                 700

Ala Glu Asn Ala Asn Leu Phe Lys Ser Trp Gly Ile Thr Ser Phe Glu
705                 710                 715                 720

Phe Ala Pro Gln Tyr Val Ser Ser Asp Gly Thr Phe Leu Asp Ser
                725                 730                 735

Val Ile Gln Asn Gly Tyr Ala Phe Ser Asp Arg Tyr Asp Ile Gly Met
            740                 745                 750

Ser Lys Asp Asn Lys Tyr Gly Ser Leu Ala Asp Leu Lys Ala Ala Leu
        755                 760                 765

Lys Ser Leu His Ala Val Gly Ile Ser Ala Ile Ala Asp Trp Val Pro
    770                 775                 780

Asp Gln Ile Tyr Asn Leu Pro Gly Asp Glu Val Val Thr Ala Thr Arg
785                 790                 795                 800

Val Asn Asn Tyr Gly Glu Thr Lys Asp Gly Ala Ile Ile Asp His Ser
                805                 810                 815

Leu Tyr Val Ala Lys Thr Arg Thr Phe Gly Asn Asp Tyr Gln Gly Lys
            820                 825                 830

Tyr Gly Gly Ala Tyr Leu Asp Glu Leu Lys Arg Leu Tyr Pro Gln Phe
        835                 840                 845

Phe Asp Arg Val Gln Ile Ser Thr Gly Lys Arg Leu Thr Thr Asp Glu
        850                 855                 860

Lys Ile Thr Lys Trp Ser Ala Lys Tyr Met Asn Gly Thr Asn Ile Leu
865                 870                 875                 880

Asp Arg Gly Ser Glu Tyr Val Leu Lys Asn Gly Leu Ser Gly Tyr Tyr
                885                 890                 895

Gly Thr Asn Gly Gly Lys Val Ser Leu Pro Lys Val Val Gly Ser Asn
            900                 905                 910

Gln Ser Thr Asn Asn Asn Gln Asn Gly Asp Gly Ser Gly Arg Phe
        915                 920                 925
```

```
Glu Lys Ser Trp Gly Ser Val Tyr Tyr Arg Tyr Asn Asp Gly Gln Arg
930                 935                 940

Ala Arg Asn Ala Phe Ile Lys Asp Asn Asp Gly Asn Val Tyr Tyr Phe
945                 950                 955                 960

Asp Asn Thr Gly Arg Met Ala Ile Gly Glu Lys Thr Ile Asp Gly Lys
            965                 970                 975

Gln Tyr Phe Phe Leu Ala Asn Gly Val Gln Leu Arg Asp Gly Tyr Arg
            980                 985                 990

Gln Asn Arg Arg Gly Gln Val Phe Tyr Tyr Asp Glu Asn Gly Ile Met
        995                 1000                1005

Ser Gln Thr Gly Lys Pro Ser Pro Lys Pro Glu Pro Lys Pro Asp
    1010                1015                1020

Asn Asn Thr Phe Ser Arg Asn Gln Phe Ile Gln Ile Gly Asn Asn
    1025                1030                1035

Val Trp Ala Tyr Tyr Asp Gly Asn Gly Lys Arg Val Ile Gly Arg
    1040                1045                1050

Gln Asn Ile Asn Gly Gln Glu Leu Phe Phe Asp Asn Asn Gly Val
    1055                1060                1065

Gln Val Lys Gly Arg Thr Ala Gln Val Asp Gly Val Thr Arg Tyr
    1070                1075                1080

Phe Asp Ala Asn Ser Gly Glu Met Ala Arg Asn Arg Phe Ala Glu
    1085                1090                1095

Val Glu Pro Gly Val Trp Ala Tyr Phe Asn Asn Asp Gly Ala Ala
    1100                1105                1110

Val Thr Gly Ser Gln Asn Ile Asn Gly Gln Thr Leu Tyr Phe Asp
    1115                1120                1125

Gln Asn Gly His Gln Val Lys Gly Ala Leu Val Thr Val Asp Gly
    1130                1135                1140

Asn Leu Arg Tyr Tyr Asp Ala Asn Ser Gly Asp Leu Tyr Arg Asn
    1145                1150                1155

Arg Phe Gln Glu Val Asn Gly Ser Trp Tyr Tyr Phe Asp Gly Asn
    1160                1165                1170

Gly Asn Ala Val Lys Gly Met Val Asn Ile Asn Gly Gln Asn Leu
    1175                1180                1185

Leu Phe Asp Asn Asp Gly Lys Gln Val Lys Gly His Leu Val Arg
    1190                1195                1200

Val Asn Gly Val Ile Arg Tyr Tyr Asp Pro Asn Ser Gly Glu Met
    1205                1210                1215

Ala Val Asn Arg Trp Val Glu Ile Ser Ser Gly Trp Trp Val Tyr
    1220                1225                1230

Phe Asp Gly Glu Gly Arg Gly Gln Ile
    1235                1240

<210> SEQ ID NO 60
<211> LENGTH: 1518
<212> TYPE: PRT
<213> ORGANISM: Streptococcus salivarius

<400> SEQUENCE: 60

Met Glu Asn Lys Ile His Tyr Lys Leu His Val Lys Lys Gln Trp
1               5                   10                  15

Val Thr Ile Ala Val Ala Ser Val Ala Leu Ala Thr Val Leu Gly Gly
                20                  25                  30

Leu Ser Val Thr Thr Ser Ser Val Ser Ala Asp Glu Thr Gln Asp Lys
            35                  40                  45
```

```
Thr Val Thr Gln Ser Asn Ser Gly Thr Thr Ala Ser Leu Val Thr Ser
     50                  55                  60
Pro Glu Ala Thr Lys Glu Ala Asp Lys Arg Thr Asn Thr Lys Glu Ala
 65                  70                  75                  80
Asp Val Leu Thr Pro Ala Lys Glu Thr Asn Ala Val Glu Thr Ala Thr
                 85                  90                  95
Thr Thr Asn Thr Gln Ala Thr Ala Glu Ala Ala Thr Thr Ala Thr Thr
            100                 105                 110
Ala Asp Val Ala Val Ala Ala Val Pro Asn Lys Glu Ala Val Val Thr
        115                 120                 125
Thr Asp Ala Pro Ala Val Thr Thr Glu Lys Ala Glu Glu Gln Pro Ala
    130                 135                 140
Thr Val Lys Ala Glu Val Val Asn Thr Glu Val Lys Ala Pro Glu Ala
145                 150                 155                 160
Ala Leu Lys Asp Ser Glu Val Glu Ala Ala Leu Ser Leu Lys Asn Ile
                165                 170                 175
Lys Asn Ile Asp Gly Lys Tyr Tyr Val Asn Glu Asp Gly Ser His
            180                 185                 190
Lys Glu Asn Phe Ala Ile Thr Val Asn Gly Gln Leu Leu Tyr Phe Gly
        195                 200                 205
Lys Asp Gly Ala Leu Thr Ser Ser Ser Thr Tyr Ser Phe Thr Pro Gly
    210                 215                 220
Thr Thr Asn Ile Val Asp Gly Phe Ser Ile Asn Asn Arg Ala Tyr Asp
225                 230                 235                 240
Ser Ser Glu Ala Ser Phe Glu Leu Ile Asp Gly Tyr Leu Thr Ala Asp
                245                 250                 255
Ser Trp Tyr Arg Pro Ala Ser Ile Ile Lys Asp Gly Val Thr Trp Gln
            260                 265                 270
Ala Ser Thr Ala Glu Asp Phe Arg Pro Leu Leu Met Ala Trp Trp Pro
        275                 280                 285
Asn Val Asp Thr Gln Val Asn Tyr Leu Asn Tyr Met Ser Lys Val Phe
    290                 295                 300
Asn Leu Asp Ala Lys Tyr Ser Ser Thr Asp Lys Gln Glu Thr Leu Lys
305                 310                 315                 320
Val Ala Ala Lys Asp Ile Gln Ile Lys Ile Glu Gln Lys Ile Gln Ala
                325                 330                 335
Glu Lys Ser Thr Gln Trp Leu Arg Glu Thr Ile Ser Ala Phe Val Lys
            340                 345                 350
Thr Gln Pro Gln Trp Asn Lys Glu Thr Glu Asn Tyr Ser Lys Gly Gly
        355                 360                 365
Gly Glu Asp His Leu Gln Gly Gly Ala Leu Leu Tyr Val Asn Asp Ser
    370                 375                 380
Arg Thr Pro Trp Ala Asn Ser Asp Tyr Arg Arg Leu Asn Arg Thr Ala
385                 390                 395                 400
Thr Asn Gln Thr Gly Thr Ile Asp Lys Ser Ile Leu Asp Glu Gln Ser
                405                 410                 415
Asp Pro Asn His Met Gly Gly Phe Asp Phe Leu Leu Ala Asn Asp Val
            420                 425                 430
Asp Leu Ser Asn Pro Val Val Gln Ala Glu Gln Leu Asn Gln Ile His
        435                 440                 445
Tyr Leu Met Asn Trp Gly Ser Ile Val Met Gly Asp Lys Asp Ala Asn
    450                 455                 460
```

```
Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
            485                 490                 495

Ser Glu Ala Asn Ala Leu Ala His Ile Ser Val Leu Glu Ala Trp Ser
        500                 505                 510

Leu Asn Asp Asn His Tyr Asn Asp Lys Thr Asp Gly Ala Ala Leu Ala
    515                 520                 525

Met Glu Asn Lys Gln Arg Leu Ala Leu Leu Phe Ser Leu Ala Lys Pro
530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
            565                 570                 575

Ser Lys Ala Tyr Asn Glu Asp Gly Thr Val Lys Gln Ser Thr Ile Gly
        580                 585                 590

Lys Tyr Asn Glu Lys Tyr Gly Asp Ala Ser Gly Asn Tyr Val Phe Ile
    595                 600                 605

Arg Ala His Asp Asn Asn Val Gln Asp Ile Ile Ala Glu Ile Ile Lys
610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
            645                 650                 655

Lys Lys Tyr Thr Leu Asn Asn Ile Pro Ala Ala Tyr Ala Val Met Leu
        660                 665                 670

Gln Asn Met Glu Thr Ile Thr Arg Val Tyr Tyr Gly Asp Leu Tyr Thr
    675                 680                 685

Asp Asp Gly His Tyr Met Glu Thr Lys Ser Pro Tyr Tyr Asp Thr Ile
690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asp Asn Ser Asp
            725                 730                 735

Val Glu Leu Tyr Arg Thr Asn Glu Val Tyr Thr Ser Val Arg Tyr Gly
        740                 745                 750

Lys Asp Ile Met Thr Ala Asn Asp Thr Glu Gly Ser Lys Tyr Ser Arg
    755                 760                 765

Thr Ser Gly Gln Val Thr Leu Val Ala Asn Asn Pro Lys Leu Asn Leu
770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
            805                 810                 815

Phe Thr Ser Asp Ala Asp Ala Ile Ala Ala Gly Tyr Val Lys Glu Thr
        820                 825                 830

Asp Ser Asn Gly Val Leu Thr Phe Gly Ala Asn Asp Ile Lys Gly Tyr
    835                 840                 845

Glu Thr Phe Asp Met Ser Gly Phe Val Ala Val Trp Val Pro Val Gly
850                 855                 860

Ala Ser Asp Asn Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
```

-continued

```
              885                 890                 895
Leu Ile Tyr Glu Gly Phe Ser Asn Phe Gln Thr Ile Pro Asp Gly Ser
              900                 905                 910
Asp Pro Ser Val Tyr Thr Asn Arg Lys Ile Ala Glu Asn Val Asp Leu
              915                 920                 925
Phe Lys Ser Trp Gly Val Thr Ser Phe Glu Met Ala Pro Gln Phe Val
              930                 935                 940
Ser Ala Asp Asp Gly Thr Phe Leu Asp Ser Val Ile Gln Asn Gly Tyr
945                 950                 955                 960
Ala Phe Ala Asp Arg Tyr Asp Leu Ala Met Ser Lys Asn Asn Lys Tyr
              965                 970                 975
Gly Ser Lys Glu Asp Leu Arg Asp Ala Leu Lys Ala Leu His Lys Ala
              980                 985                 990
Gly Ile Gln Ala Ile Ala Asp Trp Val Pro Asp Gln Ile Tyr Gln Leu
              995                1000                1005
Pro Gly Lys Glu Val Val Thr Ala Thr Arg Thr Asp Gly Ala Gly
              1010                1015                1020
Arg Lys Ile Ala Asp Ala Ile Ile Asp His Ser Leu Tyr Val Ala
              1025                1030                1035
Asn Ser Lys Ser Ser Gly Lys Asp Tyr Gln Ala Lys Tyr Gly Gly
              1040                1045                1050
Glu Phe Leu Ala Glu Leu Lys Ala Lys Tyr Pro Glu Met Phe Lys
              1055                1060                1065
Val Asn Met Ile Ser Thr Gly Lys Pro Ile Asp Asp Ser Val Lys
              1070                1075                1080
Leu Lys Gln Trp Lys Ala Glu Tyr Phe Asn Gly Thr Asn Val Leu
              1085                1090                1095
Glu Arg Gly Val Gly Tyr Val Leu Ser Asp Glu Ala Thr Gly Lys
              1100                1105                1110
Tyr Phe Thr Val Thr Lys Glu Gly Asn Phe Ile Pro Leu Gln Leu
              1115                1120                1125
Thr Gly Lys Glu Lys Val Ile Thr Gly Phe Ser Ser Asp Gly Lys
              1130                1135                1140
Gly Ile Thr Tyr Phe Gly Thr Ser Gly Thr Gln Ala Lys Ser Ala
              1145                1150                1155
Phe Val Thr Phe Asn Gly Asn Thr Tyr Tyr Phe Asp Ala Arg Gly
              1160                1165                1170
His Met Val Thr Asn Ser Glu Tyr Ser Pro Asn Gly Lys Asp Val
              1175                1180                1185
Tyr Arg Phe Leu Pro Asn Gly Ile Met Leu Ser Asn Ala Phe Tyr
              1190                1195                1200
Ile Asp Ala Asn Gly Asn Thr Tyr Leu Tyr Asn Ser Lys Gly Gln
              1205                1210                1215
Met Tyr Lys Gly Gly Tyr Thr Lys Phe Asp Val Ser Glu Thr Asp
              1220                1225                1230
Lys Asp Gly Lys Glu Ser Lys Val Val Lys Phe Arg Tyr Phe Thr
              1235                1240                1245
Asn Glu Gly Val Met Ala Lys Gly Val Thr Val Ile Asp Gly Phe
              1250                1255                1260
Thr Gln Tyr Phe Gly Glu Asp Gly Phe Gln Ala Lys Asp Lys Leu
              1265                1270                1275
Val Thr Phe Lys Gly Lys Thr Tyr Tyr Phe Asp Ala His Thr Gly
              1280                1285                1290
```

```
Asn Gly Ile Lys Asp Thr Trp Arg Asn Ile Asn Gly Lys Trp Tyr
            1295                1300                1305

Tyr Phe Asp Ala Asn Gly Val Ala Ala Thr Gly Ala Gln Val Ile
    1310                1315                1320

Asn Gly Gln Lys Leu Tyr Phe Asn Glu Asp Gly Ser Gln Val Lys
1325                1330                1335

Gly Gly Val Val Lys Asn Ala Asp Gly Thr Tyr Ser Lys Tyr Lys
1340                1345                1350

Glu Gly Phe Gly Glu Leu Val Thr Asn Glu Phe Phe Thr Thr Asp
    1355                1360                1365

Gly Asn Val Trp Tyr Tyr Ala Gly Ala Asn Gly Lys Thr Val Thr
    1370                1375                1380

Gly Ala Gln Val Ile Asn Gly Gln His Leu Tyr Phe Asn Ala Asp
    1385                1390                1395

Gly Ser Gln Val Lys Gly Val Val Lys Asn Ala Asp Gly Thr
    1400                1405                1410

Tyr Ser Lys Tyr Asn Ala Ser Thr Gly Glu Arg Leu Thr Asn Glu
    1415                1420                1425

Phe Phe Thr Thr Gly Asp Asn Trp Tyr Tyr Ile Gly Ala Asn
    1430                1435                1440

Gly Lys Ser Val Thr Gly Glu Val Lys Ile Gly Asp Asp Thr Tyr
    1445                1450                1455

Phe Phe Ala Lys Asp Gly Lys Gln Val Lys Gly Gln Thr Val Ser
    1460                1465                1470

Ala Gly Asn Gly Arg Ile Ser Tyr Tyr Tyr Gly Asp Ser Gly Lys
    1475                1480                1485

Arg Ala Val Ser Thr Trp Ile Glu Ile Gln Pro Gly Val Tyr Val
    1490                1495                1500

Tyr Phe Asp Lys Asn Gly Leu Ala Tyr Pro Pro Arg Val Leu Asn
    1505                1510                1515

<210> SEQ ID NO 61
<211> LENGTH: 1528
<212> TYPE: PRT
<213> ORGANISM: Streptococcus salivarius K12

<400> SEQUENCE: 61

Met Thr Asn Lys Ile Thr Gly Lys Ile Ile Met Glu Asn Lys Val His
1               5                   10                  15

Tyr Lys Leu His Lys Val Lys Ser Gln Trp Val Thr Ile Ala Val Ala
            20                  25                  30

Ser Ala Ala Leu Ala Thr Val Val Gly Gly Leu Ser Ala Thr Thr Ser
        35                  40                  45

Ser Val Ser Ala Asp Glu Thr Gln Asp Lys Ile Val Thr Gln Pro Asn
    50                  55                  60

Leu Asp Thr Thr Ala Asp Leu Val Thr Ser Thr Glu Ala Thr Lys Glu
65                  70                  75                  80

Val Asp Lys Arg Thr Asn Thr Lys Glu Ala Asp Val Leu Thr Pro Ala
                85                  90                  95

Lys Glu Thr Asn Ala Val Glu Thr Ala Thr Thr Asn Thr Gln Ala
                100                 105                 110

Thr Ala Glu Ala Ala Thr Thr Ala Thr Thr Ser Asp Val Ala Val Ala
            115                 120                 125

Ala Val Pro Asn Lys Glu Ala Val Val Thr Thr Asp Ala Pro Ala Val
```

```
                130             135             140
Thr Thr Glu Lys Ala Glu Gln Pro Ala Thr Val Lys Ala Glu Val
145             150             155             160

Val Asn Thr Glu Val Lys Ala Pro Gln Ala Ala Leu Lys Asp Ser Glu
                165             170             175

Val Glu Ala Ala Leu Ser Leu Lys Asn Ile Lys Tyr Thr Asp Gly Lys
            180             185             190

Tyr Tyr Tyr Val Asn Glu Asp Gly Ser His Lys Glu Asn Phe Ala Ile
            195             200             205

Thr Val Asn Gly Gln Leu Leu Tyr Phe Gly Lys Asp Gly Ala Leu Thr
        210             215             220

Ser Ser Ser Thr His Ser Phe Thr Pro Gly Thr Thr Asn Ile Val Asp
225             230             235             240

Gly Phe Ser Ile Asn Asn Arg Ala Tyr Asp Ser Ser Glu Ala Ser Phe
            245             250             255

Glu Leu Ile Asn Gly Tyr Leu Thr Ala Asp Ser Trp Tyr Arg Pro Val
            260             265             270

Ser Ile Ile Lys Asp Gly Val Thr Trp Gln Ala Ser Thr Ala Glu Asp
            275             280             285

Phe Arg Pro Leu Leu Met Ala Trp Trp Pro Asn Val Asp Thr Gln Val
        290             295             300

Asn Tyr Leu Asn Tyr Met Ser Lys Val Phe Asn Leu Glu Ala Lys Tyr
305             310             315             320

Thr Ser Thr Asp Lys Gln Ala Asp Leu Asn Arg Ala Ala Lys Asp Ile
            325             330             335

Gln Val Lys Ile Glu Gln Lys Ile Gln Ala Glu Lys Ser Thr Gln Trp
            340             345             350

Leu Arg Glu Thr Ile Ser Ala Phe Val Lys Thr Gln Pro Gln Trp Asn
        355             360             365

Lys Glu Thr Glu Asn Tyr Ser Lys Gly Gly Glu Asp His Leu Gln
        370             375             380

Gly Gly Ala Leu Leu Tyr Val Asn Asp Ser Arg Thr Pro Trp Ala Asn
385             390             395             400

Ser Asn Tyr Arg Leu Leu Asn Arg Thr Ala Thr Asn Gln Thr Gly Thr
            405             410             415

Ile Asn Lys Ser Val Leu Asp Glu Gln Ser Asp Pro Asn His Met Gly
            420             425             430

Gly Phe Asp Phe Leu Leu Ala Asn Asp Val Asp Leu Ser Asn Pro Val
        435             440             445

Val Gln Ala Glu Gln Leu Asn Gln Ile His Tyr Leu Met Asn Trp Gly
450             455             460

Ser Ile Val Met Gly Asp Lys Asp Ala Asn Phe Asp Gly Ile Arg Val
465             470             475             480

Asp Ala Val Asp Asn Val Asn Ala Asp Met Leu Gln Leu Tyr Thr Asn
            485             490             495

Tyr Phe Arg Glu Tyr Tyr Gly Val Asn Lys Ser Glu Ala Gln Ala Leu
            500             505             510

Ala His Ile Ser Val Leu Glu Ala Trp Ser Leu Asn Asp Asn His Tyr
        515             520             525

Asn Asp Lys Thr Asp Gly Ala Ala Leu Ala Met Glu Asn Lys Gln Arg
        530             535             540

Leu Ala Leu Leu Phe Ser Leu Ala Lys Pro Ile Lys Asp Arg Thr Pro
545             550             555             560
```

```
Ala Val Ser Pro Leu Tyr Asn Asn Thr Phe Asn Thr Thr Gln Arg Asp
            565                 570                 575

Phe Lys Thr Asp Trp Ile Asn Lys Asp Gly Ser Thr Ala Tyr Asn Glu
            580                 585                 590

Asp Gly Thr Ala Lys Gln Ser Thr Ile Gly Lys Tyr Asn Glu Lys Tyr
            595                 600                 605

Gly Asp Ala Ser Gly Asn Tyr Val Phe Ile Arg Ala His Asp Asn Asn
            610                 615                 620

Val Gln Asp Ile Ile Ala Glu Ile Ile Lys Lys Glu Ile Asn Lys Lys
625                 630                 635                 640

Ser Asp Gly Phe Thr Ile Ser Asp Ser Glu Met Lys Gln Ala Phe Glu
            645                 650                 655

Ile Tyr Asn Lys Asp Met Leu Ser Ser Asn Lys Lys Tyr Thr Leu Asn
            660                 665                 670

Asn Ile Pro Ala Ala Tyr Ala Val Met Leu Gln Asn Met Glu Thr Ile
            675                 680                 685

Thr Arg Val Tyr Tyr Gly Asp Leu Tyr Thr Asp Asp Gly His Tyr Met
            690                 695                 700

Glu Thr Lys Ser Pro Tyr His Asp Thr Ile Val Asn Leu Met Lys Asn
705                 710                 715                 720

Arg Ile Lys Tyr Val Ser Gly Gly Gln Ala Gln Arg Ser Tyr Trp Leu
            725                 730                 735

Pro Thr Asp Gly Lys Met Asp Asn Ser Asp Val Glu Leu Tyr Arg Thr
            740                 745                 750

Ser Glu Val Tyr Thr Ser Val Arg Tyr Gly Lys Asp Ile Met Thr Ala
            755                 760                 765

Asp Asp Thr Glu Gly Ser Lys Tyr Ser Arg Thr Ser Gly Gln Val Thr
            770                 775                 780

Leu Val Val Asn Asn Pro Lys Leu Thr Leu His Glu Ser Ala Lys Leu
785                 790                 795                 800

Asn Val Glu Met Gly Lys Ile His Ala Asn Gln Lys Tyr Arg Ala Leu
            805                 810                 815

Ile Val Gly Thr Ala Asp Gly Ile Lys Asn Phe Thr Ser Asp Ala Glu
            820                 825                 830

Ala Ile Ala Ala Gly Tyr Val Lys Glu Thr Asp Ser Asn Gly Val Leu
            835                 840                 845

Thr Phe Gly Ala Asn Asp Ile Lys Gly Tyr Glu Thr Phe Asp Met Ser
            850                 855                 860

Gly Phe Val Ala Val Trp Val Pro Val Gly Ala Ser Asp Asp Gln Asp
865                 870                 875                 880

Ile Arg Val Ala Pro Ser Thr Glu Ala Lys Lys Glu Gly Glu Leu Thr
            885                 890                 895

Leu Lys Ala Thr Glu Ala Tyr Asp Ser Gln Leu Ile Tyr Glu Gly Phe
            900                 905                 910

Ser Asn Phe Gln Thr Ile Pro Asp Gly Ser Asp Pro Ser Val Tyr Thr
            915                 920                 925

Asn Arg Lys Ile Ala Glu Asn Val Asp Leu Phe Lys Ser Trp Gly Val
            930                 935                 940

Thr Ser Phe Glu Met Ala Pro Gln Phe Val Ser Ala Asp Asp Gly Thr
945                 950                 955                 960

Phe Leu Asp Ser Val Ile Gln Asn Gly Tyr Ala Phe Ala Asp Arg Tyr
            965                 970                 975
```

```
Asp Leu Ala Met Ser Lys Asn Asn Lys Tyr Gly Ser Lys Glu Asp Leu
            980                 985                 990

Arg Asp Ala Leu Lys Ala Leu His  Lys Ala Gly Ile Gln  Ala Ile Ala
        995                 1000                1005

Asp Trp Val Pro Asp Gln Ile  Tyr Gln Leu Pro Gly  Lys Glu Val
    1010            1015                1020

Val Thr Ala Thr Arg Thr Asp  Gly Ala Gly Arg Lys  Ile Ala Asp
    1025            1030                1035

Ala Ile Ile Asp His Ser Leu  Tyr Val Ala Asn Ser  Lys Ser Ser
    1040            1045                1050

Gly Arg Asp Tyr Gln Ala Gln  Tyr Gly Gly Glu Phe  Leu Ala Glu
    1055            1060                1065

Leu Lys Ala Lys Tyr Pro Lys  Met Phe Thr Glu Asn  Met Ile Ser
    1070            1075                1080

Thr Gly Lys Pro Ile Asp Asp  Ser Val Lys Leu Lys  Gln Trp Lys
    1085            1090                1095

Ala Lys Tyr Phe Asn Gly Thr  Asn Val Leu Asp Arg  Gly Val Gly
    1100            1105                1110

Tyr Val Leu Ser Asp Glu Ala  Thr Gly Lys Tyr Phe  Thr Val Thr
    1115            1120                1125

Lys Glu Gly Asn Phe Ile Pro  Leu Gln Leu Thr Gly  Asn Glu Lys
    1130            1135                1140

Ala Val Thr Gly Phe Ser Asn  Asp Gly Lys Gly Ile  Thr Tyr Phe
    1145            1150                1155

Gly Thr Ser Gly Asn Gln Ala  Lys Ser Ala Phe Val  Thr Phe Asn
    1160            1165                1170

Gly Asn Thr Tyr Tyr Phe Asp  Ala Arg Gly His Met  Val Thr Asn
    1175            1180                1185

Gly Glu Tyr Ser Pro Asn Gly  Lys Asp Val Tyr Arg  Phe Leu Pro
    1190            1195                1200

Asn Gly Ile Met Leu Ser Asn  Ala Phe Tyr Val Asp  Ala Asn Gly
    1205            1210                1215

Asn Thr Tyr Leu Tyr Asn Tyr  Lys Gly Gln Met Tyr  Lys Gly Gly
    1220            1225                1230

Tyr Thr Lys Phe Asp Val Thr  Glu Thr Asp Lys Asp  Gly Asn Glu
    1235            1240                1245

Ser Lys Val Val Lys Phe Arg  Tyr Phe Thr Asn Glu  Gly Val Met
    1250            1255                1260

Ala Lys Gly Leu Thr Val Ile  Asp Gly Ser Thr Gln  Tyr Phe Gly
    1265            1270                1275

Glu Asp Gly Phe Gln Thr Lys  Asp Lys Leu Ala Thr  Tyr Lys Gly
    1280            1285                1290

Lys Thr Tyr Tyr Phe Glu Ala  His Thr Gly Asn Ala  Ile Lys Asn
    1295            1300                1305

Thr Trp Arg Asn Ile Asp Gly  Lys Trp Tyr His Phe  Asp Glu Asn
    1310            1315                1320

Gly Val Ala Ala Thr Gly Ala  Gln Val Ile Asn Gly  Gln Lys Leu
    1325            1330                1335

Tyr Phe Asn Glu Asp Gly Ser  Gln Val Lys Gly Gly  Val Val Lys
    1340            1345                1350

Asn Ala Asp Gly Thr Tyr Ser  Lys Tyr Lys Glu Gly  Ser Gly Glu
    1355            1360                1365

Leu Val Thr Asn Glu Phe Phe  Thr Thr Asp Gly Asn  Val Trp Tyr
```

```
                1370                1375                1380

Tyr Ala Gly Ala Asp Gly Lys Thr Val Thr Gly Ala Gln Val Ile
    1385                1390                1395

Asn Gly Gln His Leu Tyr Phe Lys Glu Asp Gly Ser Gln Val Lys
1400                1405                1410

Gly Gly Val Val Lys Asn Ala Asp Gly Thr Tyr Ser Lys Tyr Asp
    1415                1420                1425

Ala Ala Thr Gly Glu Arg Leu Thr Asn Glu Phe Phe Thr Thr Gly
    1430                1435                1440

Asp Asn Asn Trp Tyr Tyr Ile Gly Ser Asn Gly Lys Thr Val Thr
    1445                1450                1455

Gly Glu Val Lys Ile Gly Ala Asp Thr Tyr Tyr Phe Ala Lys Asp
    1460                1465                1470

Gly Lys Gln Val Lys Gly Gln Thr Val Thr Ala Gly Asn Gly Arg
    1475                1480                1485

Ile Ser Tyr Tyr Tyr Gly Asp Ser Gly Lys Lys Ala Ile Ser Thr
    1490                1495                1500

Trp Ile Glu Ile Gln Pro Gly Ile Tyr Val Tyr Phe Asp Lys Thr
    1505                1510                1515

Gly Ile Ala Tyr Pro Pro Arg Val Leu Asn
    1520                1525

<210> SEQ ID NO 62
<211> LENGTH: 1518
<212> TYPE: PRT
<213> ORGANISM: Streptococcus salivarius SK126

<400> SEQUENCE: 62

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
                20                  25                  30

Leu Ser Val Thr Thr Ser Ser Val Ser Ala Asp Glu Thr Gln Asp Lys
            35                  40                  45

Thr Val Thr Gln Ser Asn Ser Gly Thr Thr Ala Ser Leu Val Thr Ser
        50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Thr Ala Thr Thr
            100                 105                 110

Ala Asp Val Ala Val Ala Val Pro Asn Lys Glu Ala Val Val Thr
            115                 120                 125

Thr Asp Ala Pro Ala Val Thr Thr Glu Lys Ala Glu Glu Gln Pro Ala
        130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Tyr Val Asn Glu Asp Gly Ser His
            180                 185                 190

Lys Glu Asn Phe Ala Ile Thr Val Asn Gly Gln Leu Leu Tyr Phe Gly
        195                 200                 205
```

```
Lys Asp Gly Ala Leu Thr Ser Ser Thr Tyr Ser Phe Thr Pro Gly
    210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
                260                 265                 270

Ala Ser Thr Ala Glu Asp Phe Arg Pro Leu Leu Met Ala Trp Trp Pro
                275                 280                 285

Asn Val Asp Thr Gln Val Asn Tyr Leu Asn Tyr Met Ser Lys Val Phe
    290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Gln Lys Ile Gln Ala
                325                 330                 335

Glu Lys Ser Thr Gln Trp Leu Arg Glu Thr Ile Ser Ala Phe Val Lys
                340                 345                 350

Thr Gln Pro Gln Trp Asn Lys Glu Thr Glu Asn Tyr Ser Lys Gly Gly
                355                 360                 365

Gly Glu Asp His Leu Gln Gly Gly Ala Leu Leu Tyr Val Asn Asp Ser
    370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
                405                 410                 415

Asp Pro Asn His Met Gly Gly Phe Asp Phe Leu Leu Ala Asn Asp Val
                420                 425                 430

Asp Leu Ser Asn Pro Val Val Gln Ala Glu Gln Leu Asn Gln Ile His
                435                 440                 445

Tyr Leu Met Asn Trp Gly Ser Ile Val Met Gly Asp Lys Asp Ala Asn
    450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
                485                 490                 495

Ser Glu Ala Asn Ala Leu Ala His Ile Ser Val Leu Glu Ala Trp Ser
                500                 505                 510

Leu Asn Asp Asn His Tyr Asn Asp Lys Thr Asp Gly Ala Ala Leu Ala
                515                 520                 525

Met Glu Asn Lys Gln Arg Leu Ala Leu Leu Phe Ser Leu Ala Lys Pro
    530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
                565                 570                 575

Ser Lys Ala Tyr Asn Glu Asp Gly Thr Val Lys Gln Ser Thr Ile Gly
                580                 585                 590

Lys Tyr Asn Glu Lys Tyr Gly Asp Ala Ser Gly Asn Tyr Val Phe Ile
                595                 600                 605

Arg Ala His Asp Asn Asn Val Gln Asp Ile Ile Ala Glu Ile Ile Lys
    610                 615                 620

Lys Glu Ile Asn Pro Lys Ser Asp Gly Phe Thr Ile Thr Asp Ala Glu
```

-continued

```
            625                 630                 635                 640
        Met Lys Gln Ala Phe Glu Ile Tyr Asn Lys Asp Met Leu Ser Ser Asp
                        645                 650                 655

Lys Lys Tyr Thr Leu Asn Asn Ile Pro Ala Ala Tyr Ala Val Met Leu
                        660                 665                 670

Gln Asn Met Glu Thr Ile Thr Arg Val Tyr Tyr Gly Asp Leu Tyr Thr
                        675                 680                 685

Asp Asp Gly His Tyr Met Glu Thr Lys Ser Pro Tyr Tyr Asp Thr Ile
                        690                 695                 700

Val Asn Leu Met Lys Ser Arg Ile Lys Tyr Val Ser Gly Gln Ala
        705                 710                 715                 720

Gln Arg Ser Tyr Trp Leu Pro Thr Asp Gly Lys Met Asp Asn Ser Asp
                        725                 730                 735

Val Glu Leu Tyr Arg Thr Asn Glu Val Tyr Thr Ser Val Arg Tyr Gly
                        740                 745                 750

Lys Asp Ile Met Thr Ala Asn Asp Thr Glu Gly Ser Lys Tyr Ser Arg
                        755                 760                 765

Thr Ser Gly Gln Val Thr Leu Val Ala Asn Asn Pro Lys Leu Thr Leu
        770                 775                 780

Asp Gln Ser Ala Lys Leu Asn Val Glu Met Gly Lys Ile His Ala Asn
        785                 790                 795                 800

Gln Lys Tyr Arg Ala Leu Ile Val Gly Thr Ala Asp Gly Ile Lys Asn
                        805                 810                 815

Phe Thr Ser Asp Ala Asp Ala Ile Ala Ala Gly Tyr Val Lys Glu Thr
                        820                 825                 830

Asp Ser Asn Gly Val Leu Thr Phe Gly Ala Asn Asp Ile Lys Gly Tyr
                        835                 840                 845

Glu Thr Phe Asp Met Ser Gly Phe Val Ala Val Trp Val Pro Val Gly
                        850                 855                 860

Ala Ser Asp Asp Gln Asp Ile Arg Val Ala Pro Ser Thr Glu Ala Lys
        865                 870                 875                 880

Lys Glu Gly Glu Leu Thr Leu Lys Ala Thr Glu Ala Tyr Asp Ser Gln
                        885                 890                 895

Leu Ile Tyr Glu Gly Phe Ser Asn Phe Gln Thr Ile Pro Asp Gly Ser
                        900                 905                 910

Asp Pro Ser Val Tyr Thr Asn Arg Lys Ile Ala Glu Asn Val Asp Leu
                        915                 920                 925

Phe Lys Ser Trp Gly Val Thr Ser Phe Glu Met Ala Pro Gln Phe Val
        930                 935                 940

Ser Ala Asp Asp Gly Thr Phe Leu Asp Ser Val Ile Gln Asn Gly Tyr
        945                 950                 955                 960

Ala Phe Ala Asp Arg Tyr Asp Leu Ala Met Ser Lys Asn Asn Lys Tyr
                        965                 970                 975

Gly Ser Lys Glu Asp Leu Arg Asp Ala Leu Lys Ala Leu His Lys Ala
                        980                 985                 990

Gly Ile Gln Ala Ile Ala Asp Trp Val Pro Asp Gln Ile Tyr Gln Leu
                        995                 1000                1005

Pro Gly Lys Glu Val Val Thr Ala Thr Arg Thr Asp Gly Ala Gly
                    1010                1015                1020

Arg Lys Ile Ala Asp Ala Ile Ile Asp His Ser Leu Tyr Val Ala
                    1025                1030                1035

Asn Thr Lys Ser Ser Gly Lys Asp Tyr Gln Ala Lys Tyr Gly Gly
                    1040                1045                1050
```

-continued

```
Glu Phe Leu Ala Glu Leu Lys Ala Lys Tyr Pro Glu Met Phe Lys
    1055                1060                1065

Val Asn Met Ile Ser Thr Gly Lys Pro Ile Asp Asp Ser Val Lys
    1070                1075                1080

Leu Lys Gln Trp Lys Ala Glu Tyr Phe Asn Gly Thr Asn Val Leu
    1085                1090                1095

Glu Arg Gly Val Gly Tyr Val Leu Ser Asp Glu Ala Thr Gly Lys
    1100                1105                1110

Tyr Phe Thr Val Thr Lys Asp Gly Asn Phe Ile Pro Leu Gln Leu
    1115                1120                1125

Thr Gly Asn Glu Lys Val Val Thr Gly Phe Ser Asn Asp Gly Lys
    1130                1135                1140

Gly Ile Thr Tyr Phe Gly Thr Ser Gly Thr Gln Ala Lys Ser Ala
    1145                1150                1155

Phe Val Thr Phe Asn Gly Asn Thr Tyr Tyr Phe Asp Ala Arg Gly
    1160                1165                1170

His Met Val Thr Asn Gly Glu Tyr Ser Pro Asn Gly Lys Asp Val
    1175                1180                1185

Tyr Arg Phe Leu Pro Asn Gly Ile Met Leu Ser Asn Ala Phe Tyr
    1190                1195                1200

Val Asp Ala Asn Gly Asn Thr Tyr Leu Tyr Asn Ser Lys Gly Gln
    1205                1210                1215

Met Tyr Lys Gly Gly Tyr Thr Lys Phe Asp Val Thr Glu Thr Asp
    1220                1225                1230

Lys Asp Gly Lys Glu Ser Lys Val Val Lys Phe Arg Tyr Phe Thr
    1235                1240                1245

Asn Glu Gly Val Met Ala Lys Gly Val Thr Val Ile Asp Gly Phe
    1250                1255                1260

Thr Gln Tyr Phe Gly Glu Asp Gly Phe Gln Ala Lys Asp Lys Leu
    1265                1270                1275

Val Thr Phe Lys Gly Lys Thr Tyr Tyr Phe Asp Ala His Thr Gly
    1280                1285                1290

Asn Ala Ile Lys Asp Thr Trp Arg Asn Ile Asn Gly Lys Trp Tyr
    1295                1300                1305

His Phe Asp Ala Asn Gly Val Ala Ala Thr Gly Ala Gln Val Ile
    1310                1315                1320

Asn Gly Gln Lys Leu Tyr Phe Asn Glu Asp Gly Ser Gln Val Lys
    1325                1330                1335

Gly Gly Val Val Lys Asn Ala Asp Gly Thr Tyr Ser Lys Tyr Lys
    1340                1345                1350

Glu Gly Ser Gly Glu Leu Val Thr Asn Glu Phe Phe Thr Thr Asp
    1355                1360                1365

Gly Asn Val Trp Tyr Tyr Ala Gly Ala Asn Gly Lys Thr Val Thr
    1370                1375                1380

Gly Ala Gln Val Ile Asn Gly Gln His Leu Tyr Phe Asn Ala Asp
    1385                1390                1395

Gly Ser Gln Val Lys Gly Gly Val Val Lys Asn Ala Asp Gly Thr
    1400                1405                1410

Tyr Ser Lys Tyr Asp Ala Ser Thr Gly Glu Arg Leu Thr Asn Glu
    1415                1420                1425

Phe Phe Thr Thr Gly Asp Asn Asn Trp Tyr Tyr Ile Gly Ala Asn
    1430                1435                1440
```

```
Gly Lys Ser Val Thr Gly Glu Val Lys Ile Gly Asp Asp Thr Tyr
    1445                1450                1455

Phe Phe Ala Lys Asp Gly Lys Gln Val Lys Gly Gln Thr Val Ser
    1460                1465                1470

Ala Gly Asn Gly Arg Ile Ser Tyr Tyr Tyr Gly Asp Ser Gly Lys
    1475                1480                1485

Arg Ala Val Ser Thr Trp Ile Glu Ile Gln Pro Gly Val Tyr Val
    1490                1495                1500

Tyr Phe Asp Lys Asn Gly Ile Ala Tyr Pro Pro Arg Val Leu Asn
    1505                1510                1515

<210> SEQ ID NO 63
<211> LENGTH: 1431
<212> TYPE: PRT
<213> ORGANISM: Streptococcus salivarius PS4

<400> SEQUENCE: 63

Met Thr Lys Glu Thr Asn Thr Val Asp Ala Thr Thr Asn Thr
1               5                   10                  15

Gln Ala Ala Asp Ala Ala Thr Lys Thr Ala Asp Ala Ala Val Thr
                20                  25                  30

Ala Leu Pro Asn Lys Glu Ala Val Thr Thr Asp Ala Pro Ala Val
                35                  40                  45

Thr Thr Glu Lys Ala Ala Glu Gln Pro Ala Thr Val Lys Ser Glu Val
    50                  55                  60

Val Asn Thr Glu Val Lys Ala Pro Glu Ala Ala Leu Lys Asp Ser Glu
65                  70                  75                  80

Val Glu Ala Ala Leu Ser Leu Lys Asn Ile Lys Asn Ile Asp Gly Lys
                85                  90                  95

Tyr Tyr Tyr Val Asn Lys Asp Gly Ser His Lys Glu Asn Phe Ala Ile
                100                 105                 110

Thr Val Asn Gly Gln Leu Leu Tyr Phe Gly Lys Asp Gly Ala Leu Thr
                115                 120                 125

Ser Ser Ser Thr Tyr Ser Phe Thr Gln Gly Thr Thr Asn Ile Val Asp
                130                 135                 140

Gly Phe Ser Lys Asn Asn Arg Ala Tyr Asp Ser Ser Glu Ala Ser Phe
145                 150                 155                 160

Glu Leu Ile Asp Gly Tyr Leu Thr Ala Asp Ser Trp Tyr Arg Pro Val
                165                 170                 175

Ser Ile Ile Lys Asp Gly Val Thr Trp Gln Ala Ser Thr Lys Glu Asp
                180                 185                 190

Phe Arg Pro Leu Leu Met Ala Trp Trp Pro Asn Val Asp Thr Gln Val
                195                 200                 205

Asn Tyr Leu Asn Tyr Met Ser Lys Val Phe Asn Leu Asp Ala Lys Tyr
                210                 215                 220

Thr Ser Thr Asp Lys Gln Val Asp Leu Asn Arg Ala Ala Lys Asp Ile
225                 230                 235                 240

Gln Val Lys Ile Glu Gln Lys Ile Gln Ala Glu Lys Ser Thr Gln Trp
                245                 250                 255

Leu Arg Glu Ala Ile Ser Ala Phe Val Lys Thr Gln Pro Gln Trp Asn
                260                 265                 270

Lys Glu Thr Glu Asn Phe Ser Lys Gly Gly Gly Glu Asp His Leu Gln
                275                 280                 285

Gly Gly Ala Leu Leu Tyr Val Asn Asp Pro Arg Thr Pro Trp Ala Asn
                290                 295                 300
```

```
Ser Asn Tyr Arg Leu Leu Asn Arg Thr Ala Thr Asn Gln Thr Gly Thr
305                 310                 315                 320

Ile Asp Lys Ser Val Leu Asp Glu Gln Ser Asp Pro Asn His Met Gly
            325                 330                 335

Gly Phe Asp Phe Leu Leu Ala Asn Asp Val Asp Thr Ser Asn Pro Val
        340                 345                 350

Val Gln Ala Glu Gln Leu Asn Gln Ile His Tyr Leu Met Asn Trp Gly
    355                 360                 365

Ser Ile Val Met Gly Asp Lys Asp Ala Asn Phe Asp Gly Ile Arg Val
370                 375                 380

Asp Ala Val Asp Asn Val Asp Ala Asp Met Leu Gln Leu Tyr Thr Asn
385                 390                 395                 400

Tyr Phe Arg Glu Tyr Tyr Gly Val Asn Lys Ser Glu Ala Asn Ala Leu
            405                 410                 415

Ala His Ile Ser Val Leu Glu Ala Trp Ser Leu Asn Asp Asn His Tyr
        420                 425                 430

Asn Asp Lys Thr Asp Gly Ala Ala Leu Ala Met Glu Asn Lys Gln Arg
    435                 440                 445

Leu Ala Leu Leu Phe Ser Leu Ala Lys Pro Ile Lys Glu Arg Thr Pro
450                 455                 460

Ala Val Ser Pro Leu Tyr Asn Asn Thr Phe Asn Thr Thr Gln Arg Asp
465                 470                 475                 480

Glu Lys Thr Asp Trp Ile Asn Lys Asp Gly Ser Lys Ala Tyr Asn Glu
            485                 490                 495

Asp Gly Thr Val Lys Gln Ser Thr Ile Gly Lys Tyr Asn Glu Lys Tyr
        500                 505                 510

Gly Asp Ala Ser Gly Asn Tyr Val Phe Ile Arg Ala His Asp Asn Asn
    515                 520                 525

Val Gln Asp Ile Ile Ala Glu Ile Lys Lys Glu Ile Asn Pro Lys
530                 535                 540

Ser Asp Gly Phe Thr Ile Thr Asp Ala Glu Met Lys Lys Ala Phe Glu
545                 550                 555                 560

Ile Tyr Asn Lys Asp Met Leu Ser Ser Asp Lys Lys Tyr Thr Leu Asn
            565                 570                 575

Asn Ile Pro Ala Ala Tyr Ala Val Met Leu Gln Asn Met Glu Thr Ile
        580                 585                 590

Thr Arg Val Tyr Tyr Gly Asp Leu Tyr Thr Asp Asp Gly His Tyr Met
    595                 600                 605

Glu Thr Lys Ser Pro Tyr Tyr Asp Thr Ile Val Asn Leu Met Lys Asn
610                 615                 620

Arg Ile Lys Tyr Val Ser Gly Gln Ala Gln Arg Ser Tyr Trp Leu
625                 630                 635                 640

Pro Thr Asp Gly Lys Met Asp Lys Ser Asp Val Glu Leu Tyr Arg Thr
            645                 650                 655

Asn Glu Val Tyr Thr Ser Val Arg Tyr Gly Lys Asp Ile Met Thr Ala
        660                 665                 670

Asp Asp Thr Gln Gly Ser Lys Tyr Ser Arg Thr Ser Gly Gln Val Thr
    675                 680                 685

Leu Val Val Asn Asn Pro Lys Leu Ser Leu Asp Lys Ser Ala Lys Leu
690                 695                 700

Asp Val Glu Met Gly Lys Ile His Ala Asn Gln Lys Tyr Arg Ala Leu
705                 710                 715                 720
```

```
Ile Val Gly Thr Pro Asn Gly Ile Lys Asn Phe Thr Ser Asp Ala Glu
            725                 730                 735
Ala Ile Ala Ala Gly Tyr Val Lys Glu Thr Asp Gly Asn Gly Val Leu
            740                 745                 750
Thr Phe Gly Ala Asn Asp Ile Lys Gly Tyr Glu Thr Phe Asp Met Ser
            755                 760                 765
Gly Phe Val Ala Val Trp Val Pro Val Gly Ala Ser Asp Asp Gln Asp
            770                 775                 780
Ile Arg Val Ala Ala Ser Thr Ala Lys Lys Glu Gly Glu Leu Thr
785             790                 795                 800
Leu Lys Ala Thr Glu Ala Tyr Asp Ser Gln Leu Ile Tyr Gly Phe
                805                 810                 815
Ser Asn Phe Gln Thr Ile Pro Asp Gly Ser Asp Pro Ser Val Tyr Thr
            820                 825                 830
Asn Arg Lys Ile Ala Glu Asn Val Asp Leu Phe Lys Ser Trp Gly Val
            835                 840                 845
Thr Ser Phe Glu Met Ala Pro Gln Phe Val Ser Ala Asp Asp Gly Thr
            850                 855                 860
Phe Leu Asp Ser Val Ile Gln Asn Gly Tyr Ala Phe Ala Asp Arg Tyr
865             870                 875                 880
Asp Leu Ala Met Ser Lys Asn Asn Lys Tyr Gly Ser Lys Glu Asp Leu
                885                 890                 895
Arg Asn Ala Leu Lys Ala Leu His Lys Ala Gly Ile Gln Ala Ile Ala
                900                 905                 910
Asp Trp Val Pro Asp Gln Ile Tyr Gln Leu Pro Gly Lys Glu Val Val
                915                 920                 925
Thr Ala Thr Arg Thr Asp Gly Ala Gly Arg Lys Ile Ser Asp Ala Ile
            930                 935                 940
Ile Asp His Ser Leu Tyr Val Ala Asn Ser Lys Ser Ser Gly Lys Asp
945             950                 955                 960
Tyr Gln Ala Lys Tyr Gly Gly Glu Phe Leu Ala Glu Leu Lys Ala Lys
                965                 970                 975
Tyr Pro Glu Met Phe Lys Val Asn Met Ile Ser Thr Gly Lys Pro Ile
            980                 985                 990
Asp Asp Ser Val Lys Leu Lys Gln Trp Lys Ala Glu Tyr Phe Asn Gly
            995                 1000                1005
Thr Asn Val Leu Asp Arg Gly Val Gly Tyr Val Leu Ser Asp Glu
    1010                1015                1020
Ala Thr Gly Lys Tyr Phe Thr Val Thr Lys Glu Gly Asn Phe Ile
    1025                1030                1035
Pro Leu Gln Leu Lys Gly Asn Glu Lys Val Ile Thr Gly Phe Ser
    1040                1045                1050
Ser Asp Gly Lys Gly Ile Thr Tyr Phe Gly Thr Ser Gly Asn Gln
    1055                1060                1065
Ala Lys Ser Ala Phe Val Thr Phe Asn Gly Asn Thr Tyr Tyr Phe
    1070                1075                1080
Asp Ala Arg Gly His Met Val Thr Asn Gly Glu Tyr Ser Pro Asn
    1085                1090                1095
Gly Lys Asp Val Tyr Arg Phe Leu Pro Asn Gly Ile Met Leu Ser
    1100                1105                1110
Asn Ala Phe Tyr Val Asp Gly Asn Gly Asn Thr Tyr Leu Tyr Asn
    1115                1120                1125
Ser Lys Gly Gln Met Tyr Lys Gly Gly Tyr Ser Lys Phe Asp Val
```

```
            1130                1135               1140

Thr Glu Thr Lys Asp Gly Lys Glu Ser Lys Val Val Lys Phe Arg
        1145                1150               1155

Tyr Phe Thr Asn Glu Gly Val Met Ala Lys Gly Val Thr Val Val
    1160                1165               1170

Asp Gly Phe Thr Gln Tyr Phe Asn Glu Asp Gly Ile Gln Ser Lys
1175                1180               1185

Asp Glu Leu Val Thr Tyr Asn Gly Lys Thr Tyr Tyr Phe Glu Ala
    1190                1195               1200

His Thr Gly Asn Ala Ile Lys Asn Thr Trp Arg Asn Ile Lys Gly
    1205                1210               1215

Lys Trp Tyr His Phe Asp Ala Asn Gly Val Ala Ala Thr Gly Ala
    1220                1225               1230

Gln Val Ile Asn Gly Gln His Leu Tyr Phe Asn Glu Asp Gly Ser
    1235                1240               1245

Gln Val Lys Gly Gly Val Val Lys Asn Ala Asp Gly Thr Phe Ser
    1250                1255               1260

Lys Tyr Lys Asp Gly Ser Gly Asp Leu Val Val Asn Glu Phe Phe
    1265                1270               1275

Thr Thr Gly Asp Asn Val Trp Tyr Tyr Ala Gly Ala Asn Gly Lys
    1280                1285               1290

Thr Val Thr Gly Ala Gln Val Ile Asn Gly Gln His Leu Phe Phe
    1295                1300               1305

Lys Glu Asp Gly Ser Gln Val Lys Gly Asp Phe Val Lys Asn Ser
    1310                1315               1320

Asp Gly Thr Tyr Ser Lys Tyr Asp Ala Ala Ser Gly Glu Arg Leu
    1325                1330               1335

Thr Asn Glu Phe Phe Thr Thr Gly Asp Asn His Trp Tyr Tyr Ile
    1340                1345               1350

Gly Ala Asn Gly Lys Thr Val Thr Gly Glu Val Lys Ile Gly Asp
    1355                1360               1365

Asp Thr Tyr Phe Phe Ala Lys Asp Gly Lys Gln Leu Lys Gly Gln
    1370                1375               1380

Ile Val Thr Thr Arg Ser Gly Arg Ile Ser Tyr Tyr Phe Gly Asp
    1385                1390               1395

Ser Gly Lys Lys Ala Ile Ser Thr Trp Val Glu Ile Gln Pro Gly
    1400                1405               1410

Val Phe Val Phe Phe Asp Lys Asn Gly Leu Ala Tyr Pro Pro Glu
    1415                1420               1425

Asn Met Asn
    1430

<210> SEQ ID NO 64
<211> LENGTH: 1532
<212> TYPE: PRT
<213> ORGANISM: unknown
<220> FEATURE:
<223> OTHER INFORMATION: unknown Streptococcus sp. C150

<400> SEQUENCE: 64

Met Glu Asn Lys Val His Tyr Lys Leu His Lys Val Lys Lys Gln Trp
1               5                   10                  15

Val Thr Ile Ala Val Ala Ser Ala Ala Leu Ala Thr Val Val Gly Gly
            20                  25                  30

Leu Ser Ala Thr Thr Ser Ser Val Ser Ala Asp Glu Thr Gln Asp Lys
```

-continued

```
                35                  40                  45
Thr Val Thr Gln Pro Asn Ser Asp Thr Thr Ala Asp Leu Val Thr Ser
 50                  55                  60
Thr Glu Ala Thr Lys Glu Val Asp Lys Arg Thr Asn Thr Lys Glu Ala
 65                  70                  75                  80
Asp Val Leu Thr Pro Ala Lys Glu Thr Asn Thr Val Glu Thr Ala Ala
                 85                  90                  95
Thr Thr Asn Thr Gln Ala Thr Ala Glu Ala Ala Lys Thr Ala Thr Thr
                100                 105                 110
Thr Asn Thr Gln Ala Thr Ala Glu Val Ala Lys Thr Ala Thr Thr Ala
                115                 120                 125
Asp Val Ala Val Ala Val Pro Asn Lys Glu Ala Val Val Thr Thr
                130                 135                 140
Asp Ala Pro Ala Val Thr Thr Glu Lys Ala Glu Gln Pro Ala Thr
145                 150                 155                 160
Val Lys Ala Glu Val Val Asn Thr Glu Val Lys Ala Pro Glu Ala Ala
                165                 170                 175
Leu Lys Asp Ser Glu Val Glu Ala Ala Leu Ser Leu Lys Asn Ile Lys
                180                 185                 190
Asn Ile Asp Gly Lys Tyr Tyr Tyr Val Asn Glu Asp Gly Ser His Lys
                195                 200                 205
Glu Asn Phe Ala Ile Thr Val Asn Gly Gln Leu Leu Tyr Phe Gly Lys
                210                 215                 220
Asp Gly Ala Leu Thr Ser Ser Thr Tyr Ser Phe Thr Gln Gly Thr
225                 230                 235                 240
Thr Asn Ile Val Asp Gly Phe Ser Ile Asn Asn Arg Ala Tyr Asp Ser
                245                 250                 255
Ser Glu Ala Ser Phe Glu Leu Ile Asp Gly Tyr Leu Thr Ala Asp Ser
                260                 265                 270
Trp Tyr Arg Pro Ala Ser Ile Ile Lys Asp Gly Val Thr Trp Gln Ala
                275                 280                 285
Ser Thr Ala Glu Asp Phe Arg Pro Leu Leu Met Ala Trp Trp Pro Asn
                290                 295                 300
Val Asp Thr Gln Val Asn Tyr Leu Asn Tyr Met Ser Lys Val Phe Asn
305                 310                 315                 320
Leu Asp Ala Lys Tyr Ser Ser Thr Asp Lys Gln Glu Thr Leu Lys Val
                325                 330                 335
Ala Ala Lys Asp Ile Gln Ile Lys Ile Glu Gln Lys Ile Gln Ala Glu
                340                 345                 350
Lys Ser Thr Gln Trp Leu Arg Glu Thr Ile Ser Ala Phe Val Lys Thr
                355                 360                 365
Gln Pro Gln Trp Asn Lys Thr Glu Asn Tyr Ser Lys Gly Gly
                370                 375                 380
Glu Asp His Leu Gln Gly Gly Ala Leu Leu Tyr Val Asn Asp Ser Arg
385                 390                 395                 400
Thr Pro Trp Ala Asn Ser Asn Tyr Arg Leu Leu Asn Arg Thr Ala Thr
                405                 410                 415
Asn Gln Thr Gly Thr Ile Asp Lys Ser Ile Leu Asp Glu Gln Ser Asp
                420                 425                 430
Pro Asn His Met Gly Gly Phe Asp Phe Leu Leu Ala Asn Asp Val Asp
                435                 440                 445
Leu Ser Asn Pro Val Val Gln Ala Glu Gln Leu Asn Gln Ile His Tyr
450                 455                 460
```

```
Leu Met Asn Trp Gly Ser Ile Val Met Gly Asp Lys Asp Ala Asn Phe
465                 470                 475                 480

Asp Gly Ile Arg Val Asp Ala Val Asp Asn Val Asp Ala Asp Met Leu
                485                 490                 495

Gln Leu Tyr Thr Asn Tyr Phe Arg Glu Tyr Tyr Gly Val Asn Lys Ser
            500                 505                 510

Glu Ala Asn Ala Leu Ala His Ile Ser Val Leu Glu Ala Trp Ser Leu
            515                 520                 525

Asn Asp Asn His Tyr Asn Asp Lys Thr Asp Val Ala Ala Leu Ala Met
            530                 535                 540

Glu Asn Lys Gln Arg Leu Ala Leu Leu Phe Ser Leu Ala Lys Pro Ile
545                 550                 555                 560

Lys Glu Arg Thr Pro Ala Val Ser Pro Leu Tyr Asn Asn Thr Phe Asn
                565                 570                 575

Thr Thr Gln Arg Asp Glu Lys Thr Asp Trp Ile Asn Lys Asp Gly Ser
            580                 585                 590

Lys Ala Tyr Asn Glu Asp Gly Thr Val Lys Lys Ser Thr Ile Gly Lys
            595                 600                 605

Tyr Asn Glu Lys Tyr Gly Asp Ala Ser Gly Asn Tyr Val Phe Ile Arg
610                 615                 620

Ala His Asp Asn Asn Val Gln Asp Ile Ile Ala Glu Ile Ile Lys Lys
625                 630                 635                 640

Glu Ile Asn Glu Lys Ser Asp Gly Phe Thr Ile Thr Asp Ser Glu Met
                645                 650                 655

Lys Arg Ala Phe Glu Ile Tyr Asn Lys Asp Met Leu Ser Asn Asp Lys
                660                 665                 670

Lys Tyr Thr Leu Asn Asn Ile Pro Ala Ala Tyr Ala Val Met Leu Gln
            675                 680                 685

Asn Met Glu Thr Ile Thr Arg Val Tyr Tyr Gly Asp Leu Tyr Thr Asp
            690                 695                 700

Asp Gly Asn Tyr Met Glu Ala Lys Ser Pro Tyr Tyr Asp Thr Ile Val
705                 710                 715                 720

Asn Leu Met Lys Ser Arg Ile Lys Tyr Val Ser Gly Gly Gln Ala Gln
                725                 730                 735

Arg Ser Tyr Trp Leu Pro Thr Asp Gly Lys Met Asp Lys Ser Asp Val
                740                 745                 750

Glu Leu Tyr Arg Thr Asn Glu Val Tyr Thr Ser Val Arg Tyr Gly Lys
            755                 760                 765

Asp Ile Met Thr Ala Asp Asp Thr Gln Gly Ser Lys Tyr Ser Arg Thr
            770                 775                 780

Ser Gly Gln Val Thr Leu Val Val Asn Asn Pro Lys Leu Thr Leu Asp
785                 790                 795                 800

Gln Ser Ala Lys Leu Asn Val Val Met Gly Lys Ile His Ala Asn Gln
                805                 810                 815

Lys Tyr Arg Ala Leu Ile Val Gly Thr Pro Asn Gly Ile Lys Asn Phe
                820                 825                 830

Thr Ser Asp Ala Glu Ala Ile Ala Ala Gly Tyr Val Lys Glu Thr Asp
            835                 840                 845

Gly Asn Gly Val Leu Thr Phe Gly Ala Asn Asp Ile Lys Gly Tyr Glu
            850                 855                 860

Thr Phe Asp Met Ser Gly Phe Val Ala Val Trp Val Pro Val Gly Ala
865                 870                 875                 880
```

```
Ser Asp Asp Gln Asp Ile Arg Val Ala Ala Ser Thr Ala Ala Lys Lys
            885                 890                 895

Glu Gly Glu Leu Thr Leu Lys Ala Thr Glu Ala Tyr Asp Ser Gln Leu
        900                 905                 910

Ile Tyr Glu Gly Phe Ser Asn Phe Gln Thr Ile Pro Asp Gly Ser Asp
    915                 920                 925

Pro Ser Val Tyr Thr Asn Arg Lys Ile Ala Glu Asn Val Asp Leu Phe
930                 935                 940

Lys Ser Trp Gly Val Thr Ser Phe Glu Met Ala Pro Gln Phe Val Ser
945                 950                 955                 960

Ala Asp Asp Gly Thr Phe Leu Asp Ser Val Ile Gln Asn Gly Tyr Ala
            965                 970                 975

Phe Ala Asp Arg Tyr Asp Leu Ala Met Ser Lys Asn Asn Lys Tyr Gly
        980                 985                 990

Ser Lys Glu Asp Leu Arg Asn Ala Leu Lys Ala Leu His Lys Ala Gly
    995                 1000                1005

Ile Gln Ala Ile Ala Asp Trp Val Pro Asp Gln Ile Tyr Gln Leu
    1010                1015                1020

Pro Gly Lys Glu Val Val Thr Ala Thr Arg Thr Asp Gly Ala Gly
    1025                1030                1035

Arg Lys Ile Ser Asp Ala Ile Ile Asp His Ser Leu Tyr Val Ala
    1040                1045                1050

Asn Ser Lys Ser Ser Gly Lys Asp Tyr Gln Ala Lys Tyr Gly Gly
    1055                1060                1065

Glu Phe Leu Ala Glu Leu Lys Ala Lys Tyr Pro Glu Met Phe Lys
    1070                1075                1080

Val Asn Met Ile Ser Thr Gly Lys Pro Ile Asp Ser Val Lys
    1085                1090                1095

Leu Lys Gln Trp Lys Ala Glu Tyr Phe Asn Gly Thr Asn Val Leu
    1100                1105                1110

Asp Arg Gly Val Gly Tyr Val Leu Ser Asp Glu Ala Thr Gly Lys
    1115                1120                1125

Tyr Phe Thr Val Thr Lys Glu Gly Asn Phe Ile Pro Leu Gln Leu
    1130                1135                1140

Lys Gly Asn Lys Lys Val Ile Thr Gly Phe Ser Ser Asp Gly Lys
    1145                1150                1155

Gly Ile Thr Tyr Phe Gly Thr Ser Gly Asn Gln Ala Lys Ser Ala
    1160                1165                1170

Phe Val Thr Phe Asn Gly Asn Thr Tyr Tyr Phe Asp Ala Arg Gly
    1175                1180                1185

His Met Val Thr Asn Gly Glu Tyr Ser Pro Asn Gly Lys Asp Val
    1190                1195                1200

Tyr Arg Phe Leu Pro Asn Gly Ile Met Leu Ser Asn Ala Phe Tyr
    1205                1210                1215

Val Asp Gly Asn Gly Asn Thr Tyr Leu Tyr Asn Ser Lys Gly Gln
    1220                1225                1230

Met Tyr Lys Gly Gly Tyr Ser Lys Phe Asp Val Thr Glu Thr Lys
    1235                1240                1245

Asp Gly Lys Glu Ser Lys Val Val Lys Phe Arg Tyr Phe Thr Asn
    1250                1255                1260

Glu Gly Val Met Ala Lys Gly Val Thr Val Val Asp Gly Phe Thr
    1265                1270                1275

Gln Tyr Phe Asn Glu Asp Gly Ile Gln Ser Lys Asp Glu Leu Val
```

```
                    1280                1285                1290

Thr Tyr Asn Gly Lys Thr Tyr Tyr Phe Glu Ala His Thr Gly Asn
                    1295                1300                1305

Ala Ile Lys Asn Thr Trp Arg Asn Ile Lys Gly Lys Trp Tyr His
                    1310                1315                1320

Phe Asp Ala Asn Gly Val Ala Ala Thr Gly Ala Gln Val Ile Asn
                    1325                1330                1335

Gly Gln His Leu Tyr Phe Asn Glu Asp Gly Ser Gln Val Lys Gly
                    1340                1345                1350

Ser Ile Val Lys Asn Ala Asp Gly Thr Phe Ser Lys Tyr Lys Asp
                    1355                1360                1365

Ser Ser Gly Asp Leu Val Val Asn Glu Phe Phe Thr Thr Gly Asp
                    1370                1375                1380

Asn Val Trp Tyr Tyr Ala Gly Ala Asn Gly Lys Thr Val Thr Gly
                    1385                1390                1395

Ala Gln Val Ile Asn Gly Gln His Leu Phe Phe Lys Glu Asp Gly
                    1400                1405                1410

Ser Gln Val Lys Gly Asp Phe Val Lys Asn Ser Asp Gly Thr Tyr
                    1415                1420                1425

Ser Lys Tyr Asp Ala Ala Ser Gly Glu Arg Leu Thr Asn Glu Phe
                    1430                1435                1440

Phe Thr Thr Gly Asp Asn His Trp Tyr Tyr Ile Gly Ala Asn Gly
                    1445                1450                1455

Lys Thr Val Thr Gly Glu Val Lys Ile Gly Asp Asp Thr Tyr Phe
                    1460                1465                1470

Phe Ala Lys Asp Gly Lys Gln Leu Lys Gly Gln Ile Val Thr Thr
                    1475                1480                1485

Arg Ser Gly Arg Ile Ser Tyr Tyr Phe Gly Asp Ser Gly Lys Lys
                    1490                1495                1500

Ala Ile Ser Thr Trp Val Glu Ile Gln Pro Gly Val Phe Val Phe
                    1505                1510                1515

Phe Asp Lys Asn Gly Leu Ala Tyr Pro Pro Glu Asn Met Asn
                    1520                1525                1530

<210> SEQ ID NO 65
<211> LENGTH: 1341
<212> TYPE: PRT
<213> ORGANISM: Streptococcus salivarius

<400> SEQUENCE: 65

Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Pro Gly Thr
            35                  40                  45

Thr Asn Ile Val Asp Gly Phe Ser Ile Asn Asn Arg Ala Tyr Asp Ser
        50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
                100                 105                 110
```

```
Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
        195                 200                 205

Thr Pro Trp Ala Asn Ser Asp Tyr Arg Arg Leu Asn Arg Thr Ala Thr
        210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
                260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
        290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
                340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
                420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
        450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
                500                 505                 510

Asp Gly His Tyr Met Glu Thr Lys Ser Pro Tyr Tyr Asp Thr Ile Val
        515                 520                 525

Asn Leu Met Lys Ser Arg Ile Lys Tyr Val Ser Gly Gly Gln Ala Gln
```

```
            530                 535                 540
Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Asn Leu Asp
        595                 600                 605

Gln Ser Ala Lys Leu Asn Val Glu Met Gly Lys Ile His Ala Asn Gln
610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asn Gln Asp Ile Arg Val Ala Pro Ser Thr Glu Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Ser Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Glu Arg Gly Val Gly Tyr Val
        915                 920                 925

Leu Ser Asp Glu Ala Thr Gly Lys Tyr Phe Thr Val Thr Lys Glu Gly
930                 935                 940

Asn Phe Ile Pro Leu Gln Leu Thr Gly Lys Glu Lys Val Ile Thr Gly
945                 950                 955                 960
```

```
Phe Ser Ser Asp Gly Lys Gly Ile Thr Tyr Phe Gly Thr Ser Gly Thr
                965                 970                 975
Gln Ala Lys Ser Ala Phe Val Thr Phe Asn Gly Asn Thr Tyr Tyr Phe
            980                 985                 990
Asp Ala Arg Gly His Met Val Thr Asn Ser Glu Tyr Ser Pro Asn Gly
        995                 1000                1005
Lys Asp Val Tyr Arg Phe Leu Pro Asn Gly Ile Met Leu Ser Asn
    1010                1015                1020
Ala Phe Tyr Ile Asp Ala Asn Gly Asn Thr Tyr Leu Tyr Asn Ser
    1025                1030                1035
Lys Gly Gln Met Tyr Lys Gly Gly Tyr Thr Lys Phe Asp Val Ser
    1040                1045                1050
Glu Thr Asp Lys Asp Gly Lys Glu Ser Lys Val Val Lys Phe Arg
    1055                1060                1065
Tyr Phe Thr Asn Glu Gly Val Met Ala Lys Gly Val Thr Val Ile
    1070                1075                1080
Asp Gly Phe Thr Gln Tyr Phe Gly Glu Asp Gly Phe Gln Ala Lys
    1085                1090                1095
Asp Lys Leu Val Thr Phe Lys Gly Lys Thr Tyr Tyr Phe Asp Ala
    1100                1105                1110
His Thr Gly Asn Gly Ile Lys Asp Thr Trp Arg Asn Ile Asn Gly
    1115                1120                1125
Lys Trp Tyr Tyr Phe Asp Ala Asn Gly Val Ala Ala Thr Gly Ala
    1130                1135                1140
Gln Val Ile Asn Gly Gln Lys Leu Tyr Phe Asn Glu Asp Gly Ser
    1145                1150                1155
Gln Val Lys Gly Gly Val Val Lys Asn Ala Asp Gly Thr Tyr Ser
    1160                1165                1170
Lys Tyr Lys Glu Gly Phe Gly Glu Leu Val Thr Asn Glu Phe Phe
    1175                1180                1185
Thr Thr Asp Gly Asn Val Trp Tyr Tyr Ala Gly Ala Asn Gly Lys
    1190                1195                1200
Thr Val Thr Gly Ala Gln Val Ile Asn Gly Gln His Leu Tyr Phe
    1205                1210                1215
Asn Ala Asp Gly Ser Gln Val Lys Gly Gly Val Val Lys Asn Ala
    1220                1225                1230
Asp Gly Thr Tyr Ser Lys Tyr Asn Ala Ser Thr Gly Glu Arg Leu
    1235                1240                1245
Thr Asn Glu Phe Phe Thr Thr Gly Asp Asn Asn Trp Tyr Tyr Ile
    1250                1255                1260
Gly Ala Asn Gly Lys Ser Val Thr Gly Glu Val Lys Ile Gly Asp
    1265                1270                1275
Asp Thr Tyr Phe Phe Ala Lys Asp Gly Lys Gln Val Lys Gly Gln
    1280                1285                1290
Thr Val Ser Ala Gly Asn Gly Arg Ile Ser Tyr Tyr Tyr Gly Asp
    1295                1300                1305
Ser Gly Lys Arg Ala Val Ser Thr Trp Ile Glu Ile Gln Pro Gly
    1310                1315                1320
Val Tyr Val Tyr Phe Asp Lys Asn Gly Leu Ala Tyr Pro Pro Arg
    1325                1330                1335
Val Leu Asn
    1340
```

```
<210> SEQ ID NO 66

<400> SEQUENCE: 66

000

<210> SEQ ID NO 67
<211> LENGTH: 93
<212> TYPE: DNA
<213> ORGANISM: Unknown
<220> FEATURE:
<223> OTHER INFORMATION: terminator sequence added to pHYT

<400> SEQUENCE: 67
ggttaccttg aatgtatata aacattctca aagggatttc taataaaaaa cgctcggttg      60
ccgccgggcg tttttatgc atcgatggaa ttc                                   93
```

ENGINEERED GLUCOSYLTRANSFERASES

This application claims the benefit of U.S. Provisional Application No. 62/557,834 (filed Sep. 13, 2017), which is incorporated herein by reference in its entirety.

FIELD

The present disclosure is in the field of enzyme catalysis. For example, the disclosure pertains to glucosyltransferase enzymes with modified amino acid sequences. Such modified enzymes synthesize products with increased molecular weight.

REFERENCE TO SEQUENCE LISTING SUBMITTED ELECTRONICALLY

The official copy of the sequence listing is submitted electronically via EFS-Web as an ASCII formatted sequence listing with a file named 20180911_CL6159WOPCT_SequenceListing_ST25 created on Sep. 11, 2018, and having a size of about 315 kilobytes and is filed concurrently with the specification. The sequence listing contained in this ASCII-formatted document is part of the specification and is herein incorporated by reference in its entirety.

BACKGROUND

Driven by a desire to use polysaccharides in various applications, researchers have explored for polysaccharides that are biodegradable and that can be made economically from renewably sourced feedstocks. One such polysaccharide is alpha-1,3-glucan, an insoluble glucan polymer characterized by having alpha-1,3-glycosidic linkages. This polymer has been prepared, for example, using a glucosyltransferase enzyme isolated from *Streptococcus salivarius* (Simpson et al., *Microbiology* 141:1451-1460, 1995). Also for example, U.S. Pat. No. 7,000,000 disclosed the preparation of a spun fiber from enzymatically produced alpha-1,3-glucan. Various other glucan materials have also been studied for developing new or enhanced applications. For example, U.S. Patent Appl. Publ. No. 2015/0232819 discloses enzymatic synthesis of several insoluble glucans having mixed alpha-1,3 and -1,6 linkages.

While these and other advances have been made in producing glucan polymers using glucosyltransferase enzymes, less attention appears to have been drawn to enhancing the molecular weight of insoluble glucan products synthesized by such enzymes. Addressing this technological gap, disclosed herein are glucosyltransferases with modified amino acid sequences that produce higher molecular weight insoluble glucan products.

SUMMARY

In one embodiment, the present disclosure concerns a non-native glucosyltransferase comprising at least one amino acid substitution at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62, wherein the non-native glucosyltransferase synthesizes insoluble alpha-glucan comprising 1,3-linkages, and the molecular weight of the insoluble alpha-glucan is higher than the molecular weight of insoluble alpha-glucan synthesized by a second glucosyltransferase that only differs from the non-native glucosyltransferase at the substitution position(s).

In another embodiment, the present disclosure concerns a polynucleotide comprising a nucleotide sequence encoding a non-native glucosyltransferase as presently disclosed, optionally wherein one or more regulatory sequences are operably linked to the nucleotide sequence, and preferably wherein the one or more regulatory sequences include a promoter sequence.

In another embodiment, the present disclosure concerns a reaction composition comprising water, sucrose, and a non-native glucosyltransferase as presently disclosed.

In another embodiment, the present disclosure concerns a method of producing insoluble alpha-glucan comprising: (a) contacting at least water, sucrose, and a non-native glucosyltransferase enzyme as presently disclosed, whereby insoluble alpha-glucan is produced; and (b) optionally, isolating the insoluble alpha-glucan produced in step (a).

In another embodiment, the present disclosure concerns a method of preparing a polynucleotide sequence encoding a non-native glucosyltransferase, the method comprising: (a) identifying a polynucleotide sequence encoding a parent glucosyltransferase that (i) comprises an amino acid sequence that is at least about 40% identical to SEQ ID NO:4 or positions 55-960 of SEQ ID NO:4, and (ii) synthesizes insoluble alpha-glucan comprising 1,3-linkages; and (b) modifying the polynucleotide sequence identified in step (a) to substitute at least one amino acid of the parent glucosyltransferase at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62, thereby providing a polynucleotide sequence encoding a non-native glucosyltransferase that synthesizes insoluble alpha-glucan with a molecular weight that is higher than the molecular weight of insoluble alpha-glucan synthesized by the parent glucosyltransferase.

BRIEF DESCRIPTION OF THE SEQUENCES

TABLE 1

Summary of Nucleic Acid and Protein SEQ ID Numbers[b]

| Description | Nucleic acid SEQ ID NO. | Protein SEQ ID NO. |
|---|---|---|
| GTF 0874, *Streptococcus sobrinus*. The first 156 amino acids of the protein are deleted compared to GENBANK Identification No. 450874; a start methionine is included. | 1[a] | 2 (1435 aa) |
| GTF 6855, *Streptococcus salivarius* SK126. The first 178 amino acids of the protein are deleted compared to GENBANK Identification No. 228476855 (Acc. No. ZP_04061500.1); a start methionine is included. | 3[a] | 4 (1341 aa) |

TABLE 1-continued

Summary of Nucleic Acid and Protein SEQ ID Numbers[b]

| Description | Nucleic acid SEQ ID NO. | Protein SEQ ID NO. |
|---|---|---|
| GTF 2379, *Streptococcus salivarius*. The first 203 amino acids of the protein are deleted compared to GENBANK Identification No. 662379; a start methionine is included. | 5[a] | 6 (1247 aa) |
| GTF 7527 or GTFJ, *Streptococcus salivarius*. The first 42 amino acids of the protein are deleted compared to GENBANK Identification No. 47527; a start methionine is included. | 7[a] | 8 (1477 aa) |
| GTF 1724, *Streptococcus downei*. The first 162 amino acids of the protein are deleted compared to GENBANK Identification No. 121724; a start methionine is included. | 9[a] | 10 (1436 aa) |
| GTF 0544, *Streptococcus mutans*. The first 164 amino acids of the protein are deleted compared to GENBANK Identification No. 290580544; a start methionine is included. | 11[a] | 12 (1313 aa) |
| GTF 5926, *Streptococcus dentirousetti*. The first 144 amino acids of the protein are deleted compared to GENBANK Identification No. 167735926; a start methionine is included. | 13[a] | 14 (1323 aa) |
| GTF 4297, *Streptococcus oralis*. The first 228 amino acids of the protein are deleted compared to GENBANK Identification No. 7684297; a start methionine is included. | 15[a] | 16 (1348 aa) |
| GTF 5618, *Streptococcus sanguinis*. The first 223 amino acids of the protein are deleted compared to GENBANK Identification No. 328945618; a start methionine is included. | 17[a] | 18 (1348 aa) |
| GTF 2765, unknown *Streptococcus* sp. C150. The first 193 amino acids of the protein are deleted compared to GENBANK Identification No. 322372765; a start methionine is included. | 19[a] | 20 (1340 aa) |
| GTF 0427, *Streptococcus sobrinus*. The first 156 amino acids of the protein are deleted compared to GENBANK Identification No. 940427; a start methionine is included. | 25[a] | 26 (1435 aa) |
| GTF 2919, *Streptococcus salivarius* PS4. The first 92 amino acids of the protein are deleted compared to GENBANK Identification No. 383282919; a start methionine is included. | 27[a] | 28 (1340 aa) |
| GTF 2678, *Streptococcus salivarius* K12. The first 188 amino acids of the protein are deleted compared to GENBANK Identification No. 400182678; a start methionine is included. | 29[a] | 30 (1341 aa) |
| GTF 3929, *Streptococcus salivarius* JIM8777. The first 178 amino acids of the protein are deleted compared to GENBANK Identification No. 387783929; a start methionine is included. | 33[a] | 34 (1341 aa) |
| GTF 3298, *Streptococcus* sp. C150. The first 209 amino acids of the protein are deleted compared to GENBANK Identification No. 322373298; a start methionine is included. | | 59 (1242 aa) |
| Wild type GTFJ, *Streptococcus salivarius*. GENBANK Identification No. 47527. | | 60 (1518 aa) |
| Wild type GTF corresponding to GTF 2678, *Streptococcus salivarius* K12. | | 61 (1528 aa) |
| Wild type GTF corresponding to GTF 6855, *Streptococcus salivarius* SK126. | | 62 (1518 aa) |
| Wild type GTF corresponding to GTF 2919, *Streptococcus salivarius* PS4. | | 63 (1431 aa) |
| Wild type GTF corresponding to GTF 2765, unknown *Streptococcus* sp. C150. | | 64 (1532 aa) |
| Shorter version of GTF 7527, *Streptococcus salivarius*, (also referred to as "7527-NT" herein. The first 178 amino acids of the protein are deleted compared to GENBANK Identification No. 47527; a start methionine is included. | | 65 (1341 aa) |
| Terminator sequence added to pHY300PLK to derive the pHYT vector. | 67 | |

[a]This DNA coding sequence is codon-optimized for expression in *E. coli*, and is merely disclosed as an example of a suitable coding sequence.
[b]SEQ ID NOs: 21-24, 31, 32, 35-58 and 66 are intentionally not included in this table and merely serve as placeholders.

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like.

The terms "alpha-glucan", "alpha-glucan polymer" and the like are used interchangeably herein. An alpha-glucan is a polymer comprising glucose monomeric units linked together by alpha-glycosidic linkages. In typical embodiments, an alpha-glucan herein comprises at least about 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages. Examples of alpha-glucan polymers herein include alpha-1,3-glucan.

The terms "poly alpha-1,3-glucan", "alpha-1,3-glucan", "alpha-1,3-glucan polymer" and the like are used interchangeably herein. Alpha-1,3-glucan is a polymer comprising glucose monomeric units linked together by glycosidic linkages, typically wherein at least about 50% of the glycosidic linkages are alpha-1,3. Alpha-1,3-glucan in certain embodiments comprises at least 90% or 95% alpha-1,3 glycosidic linkages. Most or all of the other linkages in alpha-1,3-glucan herein typically are alpha-1,6, though some linkages may also be alpha-1,2 and/or alpha-1,4.

The terms "glycosidic linkage", "glycosidic bond", "linkage" and the like are used interchangeably herein and refer to the covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. The term "alpha-1,6-glycosidic linkage" as used herein refers to the covalent bond that joins alpha-D-glucose molecules to each other through carbons 1 and 6 on adjacent alpha-D-glucose rings. The glycosidic linkages of a glucan polymer herein can also be referred to as "glucosidic linkages". Herein, "alpha-D-glucose" will be referred to as "glucose".

The glycosidic linkage profile of an alpha-glucan herein can be determined using any method known in the art. For example, a linkage profile can be determined using methods using nuclear magnetic resonance (NMR) spectroscopy (e.g., $^{13}$C NMR or $^{1}$H NMR). These and other methods that can be used are disclosed in, for example, Food *Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The "molecular weight" of large alpha-glucan polymers herein can be represented as weight-average molecular weight (Mw) or number-average molecular weight (Mn), the units of which are in Daltons or grams/mole. Alternatively, the molecular weight of large alpha-glucan polymers can be represented as $DP_w$ (weight average degree of polymerization) or $DP_n$ (number average degree of polymerization). The molecular weight of smaller alpha-glucan polymers such as oligosaccharides typically can be provided as "DP" (degree of polymerization), which simply refers to the number of glucoses comprised within the alpha-glucan. Various means are known in the art for calculating these various molecular weight measurements such as with high-pressure liquid chromatography (HPLC), size exclusion chromatography (SEC), or gel permeation chromatography (GPC).

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The terms "leucrose" and "D-glucopyranosyl-alpha(1-5)-D-fructopyranose" are used interchangeably herein and refer to a disaccharide containing an alpha-1,5 glucosyl-fructose linkage.

The terms "glucosyltransferase", "glucosyltransferase enzyme", "GTF", "glucansucrase" and the like are used interchangeably herein. The activity of a glucosyltransferase herein catalyzes the reaction of the substrate sucrose to make the products alpha-glucan and fructose. Other products (by-products) of a GTF reaction can include glucose, various soluble gluco-oligosaccharides, and leucrose. Wild type forms of glucosyltransferase enzymes generally contain (in the N-terminal to C-terminal direction) a signal peptide (which is typically removed by cleavage processes), a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37:D233-238, 2009).

The term "glucosyltransferase catalytic domain" herein refers to the domain of a glucosyltransferase enzyme that provides alpha-glucan-synthesizing activity to a glucosyltransferase enzyme. A glucosyltransferase catalytic domain typically does not require the presence of any other domains to have this activity.

The terms "enzymatic reaction", "glucosyltransferase reaction", "glucan synthesis reaction", "reaction composition", "reaction formulation" and the like are used interchangeably herein and generally refer to a reaction that initially comprises water, sucrose, at least one active glucosyltransferase enzyme, and optionally other components. Components that can be further present in a glucosyltransferase reaction typically after it has commenced include fructose, glucose, leucrose, soluble gluco-oligosaccharides (e.g., DP2-DP7) (such may be considered as products or by-products, depending on the glucosyltransferase used), and/or insoluble alpha-glucan product(s) of DP8 or higher (e.g., DP100 and higher). It would be understood that certain glucan products, such as alpha-1,3-glucan with a degree of polymerization (DP) of at least 8 or 9, are water-insoluble and thus not dissolved in a glucan synthesis reaction, but rather may be present out of solution (e.g., by virtue of having precipitated from the reaction). It is in a glucan synthesis reaction where the step of contacting water, sucrose and a glucosyltransferase enzyme is performed. The term "under suitable reaction conditions" as used herein refers to reaction conditions that support conversion of sucrose to alpha-glucan product(s) via glucosyltransferase enzyme activity.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "aqueous conditions", "aqueous reaction conditions", "aqueous setting", "aqueous system" and the like are used interchangeably herein. Aqueous conditions herein refer to a solution or mixture in which the solvent is at least about 60 wt % water, for example. A glucosyltransferase reaction herein is performed under aqueous conditions.

The terms "soluble", "aqueous-soluble", "water-soluble" and the like as used herein characterize a glucan that has the capability of dissolving in water and/or an aqueous solution herein. Examples of soluble glucans herein are certain oligosaccharides, such as alpha-1,3-glucan with a DP less than 8. In contrast, a glucan that is "insoluble", "aqueous-insoluble", "water-insoluble" (and like terms) does not dissolve (or does not appreciably dissolve) in water and/or an aqueous solution herein. Optionally, the conditions for determining solubility include a water/solution temperature range of about 1 to 85° C. (e.g., 20-25° C.) and/or a pH range of about 4-9 (e.g., 6-8).

The terms "polynucleotide", "polynucleotide sequence", "nucleic acid molecule" and the like are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene can refer to a gene that is introduced into the host organism by gene transfer. Foreign/heterologous genes can comprise native genes inserted into a non-native organism, native genes introduced into a new location within the native host, or chimeric genes. Polynucleotide sequences in certain embodiments disclosed herein are heterologous. A "transgene" is a gene that has been introduced into the genome by a gene delivery procedure (e.g., transformation). A "codon-optimized" open reading frame has its frequency of codon usage designed to mimic the frequency of preferred codon usage of the host cell.

As used herein, the term "polypeptide" is defined as a chain of amino acid residues, usually having a defined sequence. As used herein the term polypeptide is interchangeable with the terms "peptides" and "proteins". Typical amino acids contained in polypeptides herein include (respective three- and one-letter codes shown parenthetically): alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), valine (Val, V).

The term "heterologous" means not naturally found in the location of interest. For example, a heterologous gene can be one that is not naturally found in a host organism, but that is introduced into the host organism by gene transfer. As another example, a nucleic acid molecule that is present in a chimeric gene can be characterized as being heterologous, as such a nucleic acid molecule is not naturally associated with the other segments of the chimeric gene (e.g., a promoter can be heterologous to a coding sequence).

A "non-native" amino acid sequence or polynucleotide sequence comprised in a cell or organism herein does not occur in a native (natural) counterpart of such cell or organism. Such an amino acid sequence or polynucleotide sequence can also be referred to as being heterologous to the cell or organism.

"Regulatory sequences" as used herein refer to nucleotide sequences located upstream of a gene's transcription start site (e.g., promoter), 5' untranslated regions, introns, and 3' non-coding regions, and which may influence the transcription, processing or stability, and/or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". A promoter may alternatively be inducible. One or more promoters herein may be heterologous to a coding region herein.

A "strong promoter" as used herein refers to a promoter that can direct a relatively large number of productive initiations per unit time, and/or is a promoter driving a higher level of gene transcription than the average transcription level of the genes in a cell.

The terms "3' non-coding sequence", "transcription terminator", "terminator" and the like as used herein refer to DNA sequences located downstream of a coding sequence. This includes polyadenylation recognition sequences and other sequences encoding regulatory signals capable of affecting mRNA processing or gene expression.

As used herein, a first nucleic acid sequence is "hybridizable" to a second nucleic acid sequence when a single-stranded form of the first nucleic acid sequence can anneal to the second nucleic acid sequence under suitable annealing conditions (e.g., temperature, solution ionic strength). Hybridization and washing conditions are well known and exemplified in Sambrook J, Fritsch E F and Maniatis T, *Molecular Cloning: A Laboratory Manual*, 2nd ed., Cold Spring Harbor Laboratory: Cold Spring Harbor, N.Y. (1989), which is incorporated herein by reference, particularly Chapter 11 and Table 11.1.

The term "DNA manipulation technique" refers to any technique in which the sequence of a DNA polynucleotide sequence is modified. Although the DNA polynucleotide sequence being modified can be used as a substrate itself for modification, it does not have to be physically in hand for certain techniques (e.g., a sequence stored in a computer can be used as the basis for the manipulation technique). A DNA manipulation technique can be used to delete and/or mutate one or more DNA sequences in a longer sequence. Examples of a DNA manipulation technique include recombinant DNA techniques (restriction and ligation, molecular cloning), polymerase chain reaction (PCR), and synthetic DNA methods (e.g., oligonucleotide synthesis and ligation). Regarding synthetic DNA techniques, a DNA manipulation technique can entail observing a DNA polynucleotide in silico, determining desired modifications (e.g., one or more deletions) of the DNA polynucleotide, and synthesizing a DNA polynucleotide that contains the desired modifications.

The term "in silico" herein means in or on an information storage and/or processing device such as a computer; done or produced using computer software or simulation, i.e., virtual reality.

The terms "upstream" and "downstream" as used herein with respect to polynucleotides refer to "5' of" and "3' of", respectively.

The term "expression" as used herein refers to (i) transcription of RNA (e.g., mRNA or a non-protein-coding RNA) from a coding region, and/or (ii) translation of a polypeptide from mRNA. Expression of a coding region of a polynucleotide sequence can be up-regulated or down-regulated in certain embodiments.

The term "operably linked" as used herein refers to the association of two or more nucleic acid sequences such that the function of one is affected by the other. For example, a promoter is operably linked with a coding sequence when it is capable of affecting the expression of that coding sequence. That is, the coding sequence is under the transcriptional control of the promoter. A coding sequence can be operably linked to one (e.g., promoter) or more (e.g., promoter and terminator) regulatory sequences, for example.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules. Host organisms/cells herein containing a transforming nucleic acid sequence can be referred to as "transgenic", "recombinant", "transformed", "engineered", as a "transformant", and/or as being "modified for exogenous gene expression", for example.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Biology* (von Heinje, G., Ed.) Academic (1987); and 5) *Sequence Analysis Primer* (Gribskov, M. and Devereux, J., Eds.) Stockton: NY (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, Wis.), for example. Multiple alignment of sequences can be performed, for example, using the Clustal method of alignment which encompasses several varieties of the algorithm including the Clustal V method of alignment (described by Higgins and Sharp, *CABIOS.* 5:151-153 (1989); Higgins, D. G. et al., *Comput. Appl. Biosci.*, 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4. Additionally, the Clustal W method of alignment can be used (described by Higgins and Sharp, *CABIOS.* 5:151-153 (1989); Higgins, D. G. et al., *Comput. Appl. Biosci.* 8:189-191(1992); Thompson, J. D. et al, 15 *Nucleic Acids Research,* 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergent Seqs (%)=30/30, DNA Transition Weight=0.5, Protein Weight Matrix=Gonnet Series, DNA Weight Matrix=IUB.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

The terms "aligns with", "corresponds with", and the like can be used interchangeably herein. Some embodiments herein relate to a glucosyltransferase comprising at least one amino acid substitution at a position corresponding with at least one particular amino acid residue of SEQ ID NO:62. An amino acid position of a glucosyltransferase or subsequence thereof (e.g., catalytic domain or catalytic domain plus glucan-binding domains) (can refer to such an amino acid position or sequence as a "query" position or sequence) can be characterized to correspond with a particular amino acid residue of SEQ ID NO:62 (can refer to such an amino acid position or sequence as a "subject" position or sequence) if (1) the query sequence can be aligned with the subject sequence (e.g., where an alignment indicates that the query sequence and the subject sequence [or a subsequence of the subject sequence] are at least about 30%, 40%, 50%, 60%, 70%, 80%, or 90% identical), and (2) if the query amino acid position directly aligns with (directly lines up against) the subject amino acid position in the alignment of (1). In general, one can align a query amino acid sequence with a subject sequence (SEQ ID NO:62 or a subsequence of SEQ ID NO:62) using any alignment algorithm, tool and/or software described disclosed herein (e.g., BLASTP, ClustalW, ClustalV, Clustal-Omega, EMBOSS) to determine percent identity. Just for further example, one can align a query sequence with a subject sequence herein using the Needleman-Wunsch algorithm (Needleman and Wunsch, *J. Mol. Biol.* 48:443-453, 1970) as implemented in the Needle program of the European Molecular Biology Open Software Suite (EMBOSS [e.g., version 5.0.0 or later], Rice et al., *Trends Genet.* 16:276-277, 2000). The parameters of such an EMBOSS alignment can comprise, for example: gap open penalty of 10, gap extension penalty of 0.5, EBLOSUM62 (EMBOSS version of BLOSUM62) substitution matrix.

The numbering of particular amino acid residues of SEQ ID NO:62 herein (e.g., Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, Ile-1453) is with respect to the full-length amino acid sequence of SEQ ID NO:62. The first amino acid (i.e., position 1, Met-1) of SEQ ID NO:62 is at the start of the signal peptide. Unless otherwise disclosed, substitutions herein are with respect to the full-length amino acid sequence of SEQ ID NO:62.

A "non-native glucosyltransferase" herein ("mutant", "variant", "modified" and like terms can likewise be used to describe such a glucosyltransferase) has at least one amino acid substitution at a position corresponding with a particular amino acid residue of SEQ ID NO:62. Such at least one amino acid substitution typically is in place of the amino acid residue(s) that normally (natively) occurs at the same position in the native counterpart (parent) of the non-native glucosyltransferase (i.e., although SEQ ID NO:62 is used as a reference for position, an amino acid substitution herein is with respect to the native counterpart of a non-native glucosyltransferase) (considered another way, when aligning the sequence of a non-native glucosyltransferase with SEQ ID NO:62, determining whether a substitution exists at a particular position does not depend in-and-of-itself on the respective amino acid residue in SEQ ID NO:62, but rather depends on what amino acid exists at the subject position within the native counterpart of the non-native glucosyltransferase). The amino acid normally occurring at the relevant site in the native counterpart glucosyltransferase often (but not always) is the same as (or conserved with) the particular amino acid residue of SEQ ID NO:62 for which the alignment is made. A non-native glucosyltransferase optionally can have other amino acid changes (mutations, deletions, and/or insertions) relative to its native counterpart sequence.

It may be instructive to illustrate a substitution/alignment herein. SEQ ID NO:12 (GTF 0544) is a truncated form of a *Streptococcus sobrinus* glucosyltransferase. It is noted that Leu-193 of SEQ ID NO:12 corresponds with Leu-373 of SEQ ID NO:62 (alignment not shown). If SEQ ID NO:12 is mutated at position 193 to substitute the Leu residue with a different residue (e.g., Gln), then it can be stated that the position 193-mutated version of SEQ ID NO:12 represents a non-native glucosyltransferase having an amino acid substitution at a position corresponding with Leu-373 of SEQ ID NO:62, for example.

The term "isolated" means a substance (or process) in a form or environment that does not occur in nature. Non-limiting examples of isolated substances include (1) any non-naturally occurring substance (e.g., a non-native glucosyltransferase herein), (2) any substance including, but not limited to, any host cell, enzyme, variant, nucleic acid, protein, peptide, cofactor, or carbohydrate/saccharide that is at least partially removed from one or more or all of the naturally occurring constituents with which it is associated in nature; (3) any substance modified by the hand of man relative to that substance found in nature (e.g., a non-native glucosyltransferase herein); or (4) any substance modified by increasing the amount of the substance relative to other components with which it is naturally associated. It is believed that the embodiments (e.g., enzymes and reaction compositions) disclosed herein are synthetic/man-made, and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein. These terms can be used to characterize the "over-expression" or "up-regulation" of a polynucleotide encoding a protein, for example.

While advances have been made in producing insoluble glucan polymers using glucosyltransferase enzymes, less attention appears to have been drawn to enhancing the molecular weight of insoluble glucan products synthesized by such enzymes. Addressing this technological gap, disclosed herein are glucosyltransferases with modified amino acid sequences that produce higher molecular weight insoluble glucan products.

Certain embodiments of the present disclosure concern a non-native glucosyltransferase comprising at least one amino acid substitution at a position corresponding with amino acid residue(s) Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62, wherein the non-native glucosyltransferase synthesizes insoluble alpha-glucan comprising 1,3-linkages, and the molecular weight of this alpha-glucan is higher than the molecular weight of insoluble alpha-glucan synthesized by a second glucosyltransferase that only differs from the non-native glucosyltransferase at the substitution position(s). Thus, in general, mutant glucosyltransferase enzymes are disclosed herein that can synthesize higher molecular weight insoluble alpha-glucan having alpha-1,3 linkages.

A non-native glucosyltransferase herein synthesizes insoluble alpha-glucan comprising 1,3-linkages. In some aspects, at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% of the glycosidic linkages of such an alpha-glucan can be alpha-1,3 linkages. The linkage profile of an alpha-glucan can optionally be characterized as having a range between any two of these values. The other linkages in any of these aspects having 30%-99% alpha-1,3 linkages can be alpha-1,6, and/or not include any alpha-1,4 or alpha-1,2 linkages, for example.

Alpha-glucan in some aspects can have, for example, less than 10%, 9%, 8%, 7%, 6%, 5%, 4%, 3%, 2%, 1%, or 0.5% of alpha-1,2 or alpha-1,4 glycosidic linkages. In another embodiment, an alpha-glucan only has alpha-1,3 and optionally alpha-1,6 linkages (i.e., no alpha-1,2 or alpha-1,4 linkages).

Alpha-glucan in some aspects can be linear/unbranched (no branch points). Alternatively, there can be branches in an alpha-glucan herein. For example, an alpha-glucan can have less than about 10%, 9%, 8%, 7%, 6%, 5%, 4%, 3%, 2%, or 1% branch points as a percent of the linkages in the polymer.

In certain aspects, an alpha-glucan can have a molecular weight in $DP_w$ or $DP_n$ of at least about 100. For example, the $DP_w$ or $DP_n$ can be about, or at least about, 100, 150, 200, 250, 300, 350, 400, 450, 500, 550, 600, 650, 700, 750, 800, 850, 900, 950, 1000, 1100, or 1200. The molecular weight of an alpha-glucan can optionally be expressed as a range between any two of these values (e.g., 100-1200, 400-1200, 700-1200, 100-1000, 400-1000, 700-1000). Molecular weight herein can be measured following any suitable method, including those methods disclosed in the present Examples (below) or as disclosed in U.S. Pat. Appl. Publ. Nos. 2017/0002335, 2015/0064748, or 2015/0232819, for example.

In certain aspects, the polydispersity index (PDI, which equals $DP_w/DP_n$) of alpha-1,3-glucan produced by a non-native glucosyltransferase can be the same as, or similar to, the PDI of alpha-1,3-glucan produced by a second glucosyltransferase (e.g., parent glucosyltransferase) that only differs from the non-native glucosyltransferase at the substitution position(s). The PDI can be at or below about 2.5, 2.4, 2.3, 2.2, 2.1, or 2.0, or range from about 2.0-2.5, 2.0-2.4, 2.0-2.3, 2.0-2.2, 2.1-2.5, 2.1-2.4, 2.1-2.3, or 2.1-2.2, for example. Amino acid substitutions providing a non-native glucosyltransferase herein can optionally be characterized to allow enzymatic synthesis of alpha-1,3-glucan with preserved PDI, but with increased molecular weight.

An alpha-glucan produced by a non-native glucosyltransferase herein is water-insoluble. Alpha-1,3-glucan is generally insoluble at a $DP_w$ of 8 or 9 and above in neutral (e.g., pH 6-8) aqueous conditions.

Any of the foregoing linkage profiles and/or molecular weight profiles, for example, can be combined herein to appropriately characterize an alpha-glucan product of a non-native glucosyltransferase of the present disclosure. In some aspects, the linkage and/or molecular weight profile of an alpha-glucan product can be as disclosed in any of the following publications, all of which are incorporated herein by reference: U.S. Pat. Nos. 7,000,000 and 8,871,474, U.S. Patent Appl. Publ. No. 2015/0232819.

A non-native glucosyltransferase, for example, can comprise the amino acid sequence of any glucosyltransferase disclosed in the following publications that is capable of producing insoluble alpha-glucan as presently disclosed, but with the exception that the non-native glucosyltransferase comprises at least one amino acid substitution at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62: U.S. Pat. Nos. 7,000,000 and 8,871,474; and U.S. Patent Appl. Publ. Nos. 2015/0232819 and 2017/0002335, all of which are incorporated herein by reference. In some aspects, such a non-native glucosyltransferase (i) has at least one of the foregoing substitutions, and (ii) comprises an amino acid sequence that is at least about 90%, 91%, 92%, 93%, 94%, 95%, 96%, 97%, 98%, 99%, or 99.5% identical to the amino acid sequence of the respective counterpart/parent glucosyltransferase not having the at least one substitution.

In some aspects, a non-native glucosyltransferase (i) comprises at least one amino acid substitution at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62, and (ii) comprises or consists of an amino acid sequence that is at least about 90%, 91%, 92%, 93%, 94%, 95%, 96%, 97%, 98%, 99%, or 99.5% identical to SEQ ID NO:2, 4, 6, 8, 10, 12, 14, 16, 18, 20, 26, 28, 30, 34, or 59. Certain information regarding insoluble alpha-glucan products of glucosyltransferases with most of these amino acid sequences is provided in Table 2.

TABLE 2

GTF Enzymes and Related Alpha-Glucan Products[a]

| GTF ID | SEQ ID NO. | Reducing Sugars | Insoluble Product | % alpha-1,3 | % alpha-1,6 | $DP_n$ |
|---|---|---|---|---|---|---|
| 0874 | 2 | yes | yes | 100 | 0 | 60 |
| 6855 | 4 | yes | yes | 100 | 0 | 440 |
| 2379 | 6 | yes | yes | 37 | 63 | 310 |
| 7527 | 8 | yes | yes | 100 | 0 | 440 |
| 1724 | 10 | yes | yes | 100 | 0 | 250 |
| 0544 | 12 | yes | yes | 62 | 36 | 980 |
| 5926 | 14 | yes | yes | 100 | 0 | 260 |
| 4297 | 16 | yes | yes | 31 | 67 | 800 |
| 5618 | 18 | yes | yes | 34 | 66 | 1020 |
| 2765 | 20 | yes | yes | 100 | 0 | 280 |
| 0427 | 26 | yes | yes | 100 | 0 | 120 |
| 2919 | 28 | yes | yes | 100 | 0 | 250 |
| 2678 | 30 | yes | yes | 100 | 0 | 390 |
| 3929 | 34 | yes | yes | 100 | 0 | 280 |

[a]GTF reactions and product analyses were performed as follows. Reactions were prepared comprising sucrose (50 g/L), potassium phosphate buffer (pH 6.5, 20 mM) and a GTF enzyme (2.5% bacterial cell extract by volume; extracts prepared according to U.S. application Pub. No. 2017/0002335, in a manner similar to procedure disclosed in U.S. Pat. No. 8,871,474). After 24-30 hours at 22-25° C., insoluble product was harvested by centrifugation, washed three times with water, washed once with ethanol, and dried at 50° C. for 24-30 hours. Approximate linkages and $DP_n$ are shown for each insoluble product. Linkages and $DP_n$ were determined by $^{13}C$ NMR and SEC, respectively.

In some aspects, a non-native glucosyltransferase (i) comprises at least one amino acid substitution at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62, and (ii) comprises or consists of a glucosyltransferase catalytic domain that is at least about 90%, 91%, 92%, 93%, 94%, 95%, 96%, 97%, 98%, 99%, or 99.5% identical to amino acid residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20. Such a non-native glucosyltransferase, for instance, is believed to be able to produce alpha-glucan that is water-insoluble and comprise at least about 50% (e.g., ≥90% or ≥95%) alpha-1,3 linkages, and optionally further have a $DP_w$ of at least 100. It is noted that a glucosyltransferase with amino acid positions 54-957 of SEQ ID NO:65 can produce alpha-1,3-glucan with 100% alpha-1,3 linkages and a $DP_w$ of at least 400 (data not shown, refer to Table 6 of U.S. Pat. Appl. Publ. No. 2017/0002335, which is incorporated herein by reference), for example. It is further noted that SEQ ID NOs:65 (GTF 7527), 30 (GTF 2678), 4 (GTF 6855), 28 (GTF 2919), and 20 (GTF 2765) each represent a glucosyltransferase that, compared to its respective wild type counterpart, lacks the signal peptide domain and all or a substantial portion of the variable domain. Thus, each of these glucosyltransferase enzymes has a catalytic domain followed by a glucan-binding domain. The approximate location of catalytic domain sequences in these enzymes is as follows: 7527 (residues 54-957 of SEQ ID NO:65), 2678 (residues 55-960 of SEQ ID NO:30), 6855 (residues 55-960 of SEQ ID NO:4), 2919 (residues 55-960 of SEQ ID NO:28), 2765 (residues 55-960 of SEQ ID NO:20). The amino acid sequences of the catalytic domains (approx.) of GTFs 2678, 6855, 2919 and 2765 have about 94.9%, 99.0%, 95.5% and 96.4% identity, respectively, with the approximate catalytic domain sequence of GTF 7527 (i.e., amino acids 54-957 of SEQ ID NO:65). Each of these particular glucosyltransferases (GTFs 2678, 6855, 2919 and 2765) can produce alpha-1,3-glucan with 100% alpha-1,3 linkages and a $DP_w$ of at least 400 (data not shown, refer to Table 4 of U.S. Pat. Appl. Publ. No. 2017/0002335). Based on this activity, and the relatedness (high percent identity) of the foregoing catalytic domains, it is contemplated that a non-native glucosyltransferase herein having one of the foregoing catalytic domains further with at least one amino acid substitution as presently disclosed can produce insoluble alpha-glucan comprising at least about 50% (e.g., ≥90% or ≥95%) alpha-1,3 linkages and a $DP_w$ of at least 100.

In some aspects, a non-native glucosyltransferase (i) comprises at least one amino acid substitution at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62, and (ii) comprises or consists of an amino acid sequence that is at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:62 or a subsequence thereof such as SEQ ID NO:4 (without start methionine thereof) or positions 55-960 of SEQ ID NO:4 (approximate catalytic domain).

Although it is believed that a non-native glucosyltransferase in certain aspects need only have a catalytic domain, the non-native glucosyltransferase can be comprised within a larger amino acid sequence. For example, a catalytic domain may be linked at its C-terminus to a glucan-binding domain, and/or linked at its N-terminus to a variable domain and/or signal peptide.

Although amino acid substitutions in a non-native glucosyltransferase are generally disclosed herein with respect to the corresponding positions in SEQ ID NO:62, such substitutions can alternatively be stated simply with respect to its position number in the sequence of the non-native glucosyltransferase itself, as convenience may dictate.

Still further examples of non-native glucosyltransferases can be any as disclosed herein and that include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example. A non-native glucosyltransferase herein typically lacks an N-terminal signal peptide; such an enzyme can optionally be characterized as being mature if its signal peptide was removed during a secretion process.

A non-native glucosyltransferase herein can be derived from any microbial source, for example, such as bacteria. Examples of bacterial glucosyltransferases are those derived from a *Streptococcus* species, *Leuconostoc* species, or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

A non-native glucosyltransferase herein can be prepared by fermentation of an appropriately engineered microbial strain, for example. Recombinant enzyme production by fermentation is well known in the art using microbial species such as *E. coli, Bacillus* strains (e.g., *B. subtilis*), *Ralstonia eutropha, Pseudomonas fluorescens, Saccharomyces cerevisiae, Pichia pastoris, Hansenula polymorpha*, and species of *Aspergillus* (e.g., *A. awamori*) and *Trichoderma* (e.g., *T. reesei*) (e.g., see Adrio and Demain, *Biomolecules* 4:117-139, 2014, which is incorporated herein by reference). A nucleotide sequence encoding a non-native glucosyltransferase amino acid sequence is typically linked to a heterologous promoter sequence to create an expression cassette for the enzyme, and/or is codon-optimized accordingly. Such an expression cassette may be incorporated in a suitable plasmid or integrated into the microbial host chromosome, using methods well known in the art. The expression cassette may include a transcriptional terminator nucleotide sequence following the amino acid coding sequence. The expression cassette may also include, between the promoter sequence and glucosyltransferase amino acid coding sequence, a nucleotide sequence encoding a signal peptide (e.g., heterologous signal peptide) that is designed for direct secretion of the glucosyltransferase enzyme. At the end of fermentation, cells may be ruptured accordingly (generally when a signal peptide for secretion is not employed) and the glucosyltransferase enzyme can be isolated using methods such as precipitation, filtration, and/or concentration. Alternatively, a lysate or extract comprising a glucosyltransferase can be used without further isolation. If the glucosyltransferase was secreted (i.e., it is present in the fermentation broth), it can optionally be used as isolated from, or as comprised in, the fermentation broth. The activity of a glucosyltransferase enzyme can be confirmed by biochemical assay, such as measuring its conversion of sucrose to glucan polymer.

A non-native glucosyltransferase herein can comprise at least one amino acid substitution at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62. In some aspects, the amino acid substitution at a position corresponding with amino acid residue Asn-531 of SEQ ID NO:62 can be with a Gly, Leu, or Met residue. In some aspects, the amino acid substitution at a position corresponding with amino acid residue Arg-534 of SEQ ID NO:62 can be with a Lys, Gly, Ile, Leu, or Met residue. In some aspects, the amino acid substitution at a position corresponding with amino acid residue Thr-563 of SEQ ID NO:62 can be with an Ala residue. In some aspects, the amino acid substitution at a position corresponding with amino acid residue Glu-567 of SEQ ID NO:62 can be with a Gln residue. In some aspects, the amino acid substitution at a position corresponding with amino acid residue Val-586 of SEQ ID NO:62 can be with a Thr residue. In some aspects, the amino acid substitution at a position corresponding with amino acid residue Gln-588 of SEQ ID NO:62 can be with a Leu residue. In some aspects, the amino acid substitution at a position corresponding with amino acid residue Ile-591 of SEQ ID NO:62 can be with a Val, Lys, or Arg residue. In some aspects, the amino acid substitution at a position corresponding with amino acid residue Lys-593 of SEQ ID NO:62 can be with a Met residue. In some aspects, the amino acid substitution at a position corresponding with amino acid residue Ile-608 of SEQ ID NO:62 can be with a Tyr residue. In some aspects, the amino acid substitution at a position corresponding with amino acid residue Ala-610 of SEQ ID NO:62 can be with a Cys or Thr residue. In some aspects, the amino acid substitution at a position corresponding with amino acid residue Leu-661 of SEQ ID NO:62 can be with a Pro residue. In some aspects, the amino acid substitution at a position corresponding with amino acid residue Arg-722 of SEQ ID NO:62 can be with a His or Asn residue. In some aspects, the amino acid substitution at a position corresponding with amino acid residue Thr-728 of SEQ ID NO:62 can be with a Ser residue. In some aspects, the amino acid substitution at a position corresponding with amino acid residue Met-732 of SEQ ID NO:62 can be with a Leu residue. In some aspects, the amino acid substitution at a position corresponding with amino acid residue Arg-741 of SEQ ID NO:62 can be with a Ser, Ala, Pro, Gln, or Thr residue. In some aspects, the amino acid substitution at a position corresponding with amino acid residue Asn-743 of SEQ ID NO:62 can be with a Ser, Thr, or Asp residue. In some aspects, the amino acid substitution at a position corresponding with amino acid residue Ala-777 of SEQ ID NO:62 can be with an Asn residue. In some aspects, the amino acid substitution at a position corresponding with amino acid residue Tyr-848 of SEQ ID NO:62 can be with a Glu residue. In some aspects, the amino acid substitution at a position corresponding with amino acid residue Ile-1453 of SEQ ID NO:62 can be with a Gly or Met residue.

A non-native glucosyltransferase in certain embodiments can comprise, in addition to any of the above-listed substitution(s), or alternatively to the above-listed substitution(s), at least one amino acid substitution at a position corresponding with amino acid residue Phe-424, Asn-475, Trp-511, Arg-609, Asn-614, or Asn-1214 of SEQ ID NO:62. Such a non-native glucosyltransferase can be based on any of the above-disclosed glucosyltransferase/catalytic domain amino acid sequences (and percent identities thereto), for example. In some aspects, the amino acid substitution at a position corresponding with amino acid residue Phe-424 of SEQ ID NO:62 can be with an Ala, Val, Leu, Glu, or Gln residue. In some aspects, the amino acid substitution at a position corresponding with amino acid residue Asn-475 of SEQ ID NO:62 can be with a Gln or Ser residue. In some aspects, the amino acid substitution at a position corresponding with amino acid residue Trp-511 of SEQ ID NO:62 can be with a Tyr residue. In some aspects, the amino acid substitution at a position corresponding with amino acid residue Arg-609 of SEQ ID NO:62 can be with a His residue. In some aspects, the amino acid substitution at a position corresponding with amino acid residue Asn-614 of SEQ ID NO:62 can be with a Phe residue. In some aspects, the amino acid substitution at a position corresponding with amino acid residue Asn-1214 of SEQ ID NO:62 can be with a Leu or Ile residue.

A non-native glucosyltransferase herein can comprise one, two, three, four, five, six, seven, eight, nine, or more of the presently disclosed amino acid substitutions, for instance. A non-native glucosyltransferase in some aspects can comprise at least one amino acid substitution at a position corresponding with amino acid residue Gln-588, Arg-741, or Arg-722 of SEQ ID NO:62. In some aspects, a non-native glucosyltransferase can comprise substitutions at one of these sites (e.g., Q588), two of these sites (e.g., Q588 and R741), or all three of these sites (Q588, R741 and Arg-722). Such an amino acid substitution(s) can be any of those as disclosed above, for example (e.g., Q588L, R741S, R722H). In some aspects, a non-native glucosyltransferase can comprise substitutions at one, two or all three of these sites, and have a total number of the presently disclosed substitutions as disclosed above.

Suitable substitution sites, and examples of particular substitutions at these sites, can include those as listed in Table 3 in Example 1 (below) that are associated with an increase in the molecular weight ($DP_w$) of alpha-1,3-glucan product by at least about 5%, 10%, 15%, 20%, 25%, 30%, 35%, 40%, 45%, 50%, 55%, or 60%, for example. In some alternative aspects, a substitution site, and example(s) of particular substitution(s) at such site, can include any of those as listed in Table 3 in Example 1 (below) that are associated with a feature that endows a benefit to a glucosyltransferase that synthesizes insoluble alpha-1,3-glucan. The foregoing substitutions as listed in Table 3 are as they correspond with the listed residue position number in SEQ ID NO:62. In some aspects, one or more substitutions are conserved or non-conserved substitutions; such conservation (or not) can be, for instance, with respect to the amino acid that occurs in the native glucosyltransferase from which the non-native glucosyltransferase is derived.

A non-native glucosyltransferase herein can synthesize insoluble alpha-glucan comprising 1,3-linkages with a molecular weight higher than the molecular weight of insoluble alpha-glucan comprising 1,3-linkages synthesized by a second glucosyltransferase (or, simply, "another" glucosyltransferase) (e.g., parent glucosyltransferase) that only differs from the non-native glucosyltransferase at the substitution position(s). A second glucosyltransferase herein, for example, can be comprised of all of, or mostly, native amino acid sequence. Thus, while a second glucosyltransferase herein can be a native glucosyltransferase in some aspects, it can be a prior-modified glucosyltransferase in other aspects (e.g., a glucosyltransferase with one or more other amino acid substitutions differing from the substitution[s] of the present disclosure). In some embodiments, a second glucosyltransferase to which a non-native glucosyltransferase is compared has a native amino acid residue(s) at the substitution position(s). Determining whether an amino acid residue is native can be done by comparing the second glucosyltransferase amino acid sequence to the native/wild type glucosyltransferase amino acid sequence from which the second glucosyltransferase is derived.

In some aspects, a non-native glucosyltransferase herein can synthesize insoluble alpha-glucan with a molecular weight that is at least about 5%, 10%, 15%, 20%, 25%, 30%, 35%, 40%, 45%, 50%, 55%, or 60% higher than the molecular weight of insoluble alpha-glucan synthesized by a second glucosyltransferase. Such a determination can be made with respect to any glucan synthesis reaction/process as disclosed herein (e.g., taking into account initial sucrose conc., temperature, pH, and/or reaction time), and using any suitable measurement technique (e.g., SEC). Typically, a comparison between non-native and second glucosyltransferases herein can be made under identical or similar reaction conditions. The molecular weight of insoluble alpha-glucan can be expressed as $DP_w$, for example.

Some embodiments disclosed herein concern a polynucleotide comprising a nucleotide sequence that encodes a non-native glucosyltransferase as presently disclosed (e.g., a non-native glucosyltransferase comprising at least one amino acid substitution at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62). Optionally, one or more regulatory sequences are operably linked to the nucleotide sequence, and preferably a promoter sequence is included as a regulatory sequence.

A polynucleotide comprising a nucleotide sequence encoding a non-native glucosyltransferase herein can be a vector or construct useful for transferring a nucleotide sequence into a cell, for example. Examples of a suitable vector/construct can be selected from a plasmid, yeast artificial chromosome (YAC), cosmid, phagemid, bacterial artificial chromosome (BAC), virus, or linear DNA (e.g., linear PCR product). A polynucleotide sequence in some aspects can be capable of existing transiently (i.e., not integrated into the genome) or stably (i.e., integrated into the genome) in a cell. A polynucleotide sequence in some aspects can comprise, or lack, one or more suitable marker sequences (e.g., selection or phenotype marker).

A polynucleotide sequence in certain embodiments can comprise one or more regulatory sequences operably linked to the nucleotide sequence encoding a non-native glucosyltransferase. For example, a nucleotide sequence encoding a non-native glucosyltransferase may be in operable linkage with a promoter sequence (e.g., a heterologous promoter). A promoter sequence can be suitable for expression in a cell (e.g., bacterial cell such as E. coli or Bacillus; eukaryotic cell such as a fungus, yeast, insect, or mammalian cell) or in an in vitro protein expression system, for example. Examples of other suitable regulatory sequences include transcription terminator sequences.

Some aspects herein are drawn to a cell comprising a polynucleotide sequence as presently disclosed; such a cell can be any type disclosed herein (e.g., bacterial cell such as E. coli or Bacillus; eukaryotic cell such as a fungus, yeast, insect, or mammalian cell). A cell can optionally express a non-native glucosyltransferase encoded by the polynucleotide sequence. In some aspects, the polynucleotide sequence exists transiently (i.e., not integrated into the genome) or stably (i.e., integrated into the genome) in the cell.

Some embodiments disclosed herein concern reaction compositions comprising water, sucrose, and one or more non-native glucosyltransferases herein (e.g., a non-native glucosyltransferase comprising at least one amino acid substitution at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62). Such a reaction composition produces, at least, alpha-glucan comprising 1,3-linkages as disclosed.

The temperature of a reaction composition herein can be controlled, if desired, and can be about 5-50° C., 20-40° C., 30-40° C., 20-30° C., 20-25° C., 20° C., 25° C., 30° C., 35° C., or 40° C., for example.

The initial concentration of sucrose in a reaction composition herein can be about 20-400 g/L, 75-175 g/L, or 50-150 g/L, for example. In some aspects, the initial sucrose concentration is at least about 50, 75, 100, 150 or 200 g/L, or is about 50-600 g/L, 100-500 g/L, 50-100 g/L, 100-200 g/L, 150-450 g/L, 200-450 g/L, or 250-600 g/L. "Initial concentration of sucrose" refers to the sucrose concentration in a reaction composition just after all the reaction components have been added/combined (e.g., at least water, sucrose, non-native glucosyltransferase enzyme).

The pH of a reaction composition in certain embodiments can be about 4.0-9.0, 4.0-8.5, 4.0-8.0, 5.0-8.0, 5.5-7.5, or 5.5-6.5. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. The buffer concentration in a reaction composition herein can be about 0.1-300 mM, 0.1-100 mM, 10-100 mM, 10 mM, 20 mM, or 50 mM, for example.

A reaction composition can be contained within any vessel (e.g., an inert vessel/container) suitable for applying one or more of the reaction conditions disclosed herein. An inert vessel in some aspects can be of stainless steel, plastic, or glass (or comprise two or more of these components) and be of a size suitable to contain a particular reaction. For example, the volume/capacity of an inert vessel (and/or the volume of a reaction composition herein), can be about, or at least about, 1, 10, 50, 100, 500, 1000, 2500, 5000, 10000, 12500, 15000, or 20000 liters. An inert vessel can optionally be equipped with a stirring device.

A reaction composition herein can contain one, two, or more glucosyltransferase enzymes, for example, just as long that at least one of the enzymes is a non-native glucosyltransferase as presently disclosed. In some embodiments, only one or two glucosyltransferase enzymes is/are comprised in a reaction composition. A glucosyltransferase reaction herein can be, and typically is, cell-free (e.g., no whole cells present).

Any of the features disclosed herein (e.g., above and in the below Examples) regarding a reaction composition can characterize appropriate aspects of a glucan production method herein, and vice versa.

The present disclosure also concerns a method for producing insoluble alpha-glucan, the method comprising: (a) contacting at least water, sucrose, and at least one non-native glucosyltransferase as disclosed herein that produces insoluble alpha-glucan, whereby insoluble alpha-glucan is produced; and b) optionally, isolating the insoluble alpha-glucan produced in step (a). Conducting such a method, which can optionally be characterized as a glucan synthesis method, is typically also performed when conducting a reaction composition herein.

A glucan synthesis method as presently disclosed comprises contacting at least water, sucrose, and a non-native glucosyltransferase herein that produces insoluble alpha-glucan. These and optionally other reagents can be added altogether or in any order as discussed below. This step can optionally be characterized as providing a reaction composition comprising water, sucrose and a non-native glucosyltransferase enzyme that synthesizes insoluble alpha-glucan. The contacting step herein can be performed in any number of ways. For example, the desired amount of sucrose can first be dissolved in water (optionally, other components may also be added at this stage of preparation, such as buffer components), followed by addition of glucosyltransferase enzyme. The solution may be kept still, or agitated via stirring or orbital shaking, for example. A glucan synthesis method can be performed by batch, fed-batch, continuous mode, or by any variation of these modes.

Completion of a reaction in certain embodiments can be determined visually (e.g., no more accumulation of insoluble glucan), and/or by measuring the amount of sucrose left in the solution (residual sucrose), where a percent sucrose consumption of at least about 90%, 95%, or 99% can indicate reaction completion. A reaction of the disclosed process can be conducted for about 1 hour to about 2, 4, 6, 8, 10, 12, 14, 16, 18, 20, 22, 24, 36, 48, 60, 72, 96, 120, 144, or 168 hours, for example.

The molecular weight of insoluble alpha-glucan produced in some aspects of a glucan synthesis method herein can be at least about 5%, 10%, 15%, 20%, 25%, 30%, 35%, 40%, 45%, 50%, 55%, or 60% higher than the molecular weight of insoluble alpha-glucan synthesized by a second glucosyltransferase. Such molecular weight enhancement in some aspects is achieved in a reaction conducted for about 16-24 hours (e.g., ~20 hours).

Insoluble alpha-glucan produced in a method herein can optionally be isolated. In certain embodiments, isolating insoluble alpha-glucan can include at least conducting a step of centrifugation and/or filtration. Isolation can optionally further comprise washing alpha-glucan one, two, or more times with water or other aqueous liquid, and/or drying the alpha-glucan product.

An isolated alpha-glucan product herein, as provided in a dry form, can comprise no more than 2.0, 1.5, 1.0, 0.5, 0.25, 0.10, 0.05, or 0.01 wt % water, for example. In some aspects, an alpha-glucan product is provided in an amount of at least 1 gram (e.g., at least about 2.5, 5, 10, 25, 50, 100, 250, 500, 750, 1000, 2500, 5000, 7500, 10000, 25000, 50000, or 100000 g); such an amount can be a dry amount, for example.

Any of the disclosed conditions for synthesizing an alpha-glucan, such as the foregoing or those described in the below Examples, can be applied to practicing a reaction composition as presently disclosed (and vice versa), and/or used to characterize features/activity of a non-native glucosyltransferase, accordingly.

The present disclosure also concerns a method of preparing a polynucleotide sequence encoding a non-native glucosyltransferase herein. This method comprises:

(a) identifying a polynucleotide sequence encoding a parent glucosyltransferase that (i) comprises an amino acid sequence that is at least about 40% identical to SEQ ID NO:4 or positions 55-960 of SEQ ID NO:4, and (ii) synthesizes insoluble alpha-glucan comprising 1,3-linkages; and (b) modifying the polynucleotide sequence identified in step (a) to substitute at least one amino acid of the parent glucosyltransferase at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62, thereby providing a polynucleotide sequence encoding a non-native glucosyltransferase that synthesizes insoluble alpha-glucan with a molecular weight that is higher than the molecular weight of insoluble alpha-glucan synthesized by the parent glucosyltransferase.

Such a method can optionally further comprise using a polynucleotide prepared in this manner in a method of expressing the non-native glucosyltransferase encoded by the polynucleotide. Such an expression method can follow any heterologous protein expression method as known in the art, for example. The present method of preparing a polynucleotide can optionally alternatively be characterized as a method of increasing the product molecular weight of a glucosyltransferase.

Identification step (a) herein can, in some instances, comprise identifying an amino acid sequence of a parent glucosyltransferase enzyme. A polynucleotide sequence could be determined from this amino acid sequence according to the genetic code (codons), such as the genetic code used in the species from which the parent glucosyltransferase was identified.

Identifying a polynucleotide encoding a parent glucosyltransferase herein can be performed (a) in silico, (b) with a method comprising a nucleic acid hybridization step, (c) with a method comprising a protein sequencing step, and/or (d) with a method comprising a protein binding step, for example.

Regarding in silico detection, the amino acid sequences of candidate parent glucosyltransferase enzymes (and/or nucleotide sequences encoding such glucosyltransferase enzymes) stored in a computer or database (e.g., public databases such as GENBANK, EMBL, REFSEQ, GENE-PEPT, SWISS-PROT, PIR, PDB) can be reviewed in silico to identify a glucosyltransferase enzyme comprising an amino acid sequence with a percent sequence identity as described above for a parent glucosyltransferase. Such review could comprise using any means known in the art such as through use of an alignment algorithm or software as described above (e.g., BLASTN, BLASTP, ClustalW, ClustalV, Clustal-Omega, EMBOSS).

Identifying a parent glucosyltransferase as disclosed above can optionally be performed via a method comprising a nucleic acid hybridization step. Such a method can comprise using DNA hybridization (e.g., Southern blot, dot blot), RNA hybridization (e.g., northern blot), or any other method that has a nucleic acid hybridization step (e.g., DNA sequencing, PCR, RT-PCR, all of which may comprise hybridization of an oligonucleotide), for example. A polynucleotide sequence encoding SEQ ID NO:4 or a subsequence thereof (e.g., positions 55-960 of SEQ ID NO:4) can be used as a probe, for example, in such a hybridization. Conditions and parameters for carrying out hybridization methods in general are well known and disclosed, for example, in Sambrook J, Fritsch E F and Maniatis T, *Molecular Cloning: A Laboratory Manual*, Cold Spring Harbor Laboratory: Cold Spring Harbor, N.Y. (1989); Silhavy T J, Bennan M L and Enquist L W, *Experiments with Gene Fusions*, Cold Spring Harbor Laboratory: Cold Spring Harbor, N.Y. (1984); Ausubel F M et al., *Current Protocols in Molecular Biology*, published by Greene Publishing Assoc. and Wiley-Interscience, Hoboken, N.J. (1987); and Innis M A, Gelfand D H, Sninsky J J and White T J (Editors), *PCR Protocols: A Guide to Methods and Applications*, Academic Press, Inc., San Diego, Calif. (1990).

Identifying a parent glucosyltransferase as disclosed above can optionally be performed via a method comprising a protein sequencing step. Such a protein sequencing step can comprise one or more procedures such as N-terminal amino acid analysis, C-terminal amino acid analysis, Edman degradation, or mass spectrometry, for example.

Identifying a parent glucosyltransferase as disclosed above can optionally be performed via a method comprising a protein binding step. Such a protein binding step can be performed using an antibody that binds to a motif or epitope within SEQ ID NO:4 (e.g., within positions 55-960 of SEQ ID NO:4), for example.

A polynucleotide identified in step (a) (i.e., before its modification in step [b]) can, in some aspects, encode a glucosyltransferase comprising an amino acid sequence that is identical to, or at least 90%, 91%, 92%, 93%, 94%, 95%, 96%, 97%, 98%, or 99% identical to, the amino acid sequence of any glucosyltransferase disclosed in Table 1. An alpha-glucan as produced by such a glucosyltransferase can be as disclosed herein, for example.

A method of preparing a polynucleotide sequence encoding a non-native glucosyltransferase herein comprises step (b) of modifying the polynucleotide sequence (encoding a parent glucosyltransferase) identified in step (a). Such modification substitutes at least one amino acid of the parent glucosyltransferase at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62. The non-native glucosyltransferase (encoded by the modified polynucleotide sequence) resulting from such one or more substitutions can be optionally be characterized as a "child glucosyltransferase" herein.

A parent glucosyltransferase enzyme herein can comprise an amino acid sequence that is at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:4 (optionally without start methionine thereof) or positions 55-960 of SEQ ID NO:4 (approximate catalytic domain), for example. It is noted simply for reference purposes that SEQ ID NO:4 without its start methionine is a subsequence of SEQ ID NO:62.

A suitable modification of a polynucleotide in step (b) can be made following any DNA manipulation technique known in the art. Modifying step (b) can optionally be performed in silico, followed by synthesis of the polynucleotide sequence encoding a non-native glucosyltransferase. For example, a polynucleotide sequence identified in step (a) can be manipulated in silico using a suitable sequence manipulation program/software (e.g., VECTOR NTI, Life Technologies, Carlsbad, Calif.; DNAStrider; DNASTAR, Madison, Wis.). Following such virtual manipulation, the modified polynucleotide sequence can be artificially synthesized by any suitable technique (e.g., annealing-based connection of oligonucleotides, or any technique disclosed in Hughes et al., *Methods Enzymol.* 498:277-309, which is incorporated herein by reference). It should be appreciated that the foregoing methodology is not believed to necessarily rely on having a pre-existing polynucleotide (encoding a parent glucosyltransferase) in hand.

Modifying step (b) can optionally be performed using a physical copy of a polynucleotide sequence identified in step (a) encoding a parent glucosyltransferase. As an example, such a polynucleotide can serve as a template for amplification using primers designed in a manner such that the amplified product encodes a non-native glucosyltransferase herein (e.g., refer to Innis et al., ibid.).

The amino acid substitutions in this method can be any of those combinations of substitutions as disclosed herein. Essentially any non-native glucosyltransferase as presently disclosed can be encoded by a polynucleotide as prepared by this method, for instance.

Non-limiting examples of compositions and methods disclosed herein include:

1. A non-native glucosyltransferase comprising at least one amino acid substitution at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62, wherein the non-native glucosyltransferase synthesizes insoluble alpha-glucan comprising 1,3-linkages, and the molecular weight of the insoluble alpha-glucan is higher than the molecular weight of insoluble alpha-glucan synthesized by a second glucosyltransferase that only differs from the non-native glucosyltransferase at the substitution position(s).

2. The non-native glucosyltransferase of embodiment 1, wherein: (i) the amino acid substitution at the position corresponding with amino acid residue Asn-531 is with a Gly, Leu, or Met residue; (ii) the amino acid substitution at the position corresponding with amino acid residue Arg-534 is with a Lys, Gly, Ile, Leu, or Met residue; (iii) the amino acid substitution at the position corresponding with amino acid residue Thr-563 is with an Ala residue; (iv) the amino acid substitution at the position corresponding with amino acid residue Glu-567 is with a Gln residue; (v) the amino acid substitution at the position corresponding with amino acid residue Val-586 is with a Thr residue; (vi) the amino acid substitution at the position corresponding with amino acid residue Gln-588 is with a Leu residue; (vii) the amino acid substitution at the position corresponding with amino acid residue Ile-591 is with a Val, Lys, or Arg residue; (viii) the amino acid substitution at the position corresponding with amino acid residue Lys-593 is with a Met residue; (ix) the amino acid substitution at the position corresponding with amino acid residue Ile-608 is with a Tyr residue; (x) the amino acid substitution at the position corresponding with amino acid residue Ala-610 is with a Cys or Thr residue; (xi) the amino acid substitution at the position corresponding with amino acid residue Leu-661 is with a Pro residue; (xii) the amino acid substitution at the position corresponding with amino acid residue Arg-722 is with a His or Asn residue; (xiii) the amino acid substitution at the position corresponding with amino acid residue Thr-728 is with a Ser residue; (xiv) the amino acid substitution at the position corresponding with amino acid residue Met-732 is with a Leu residue; (xv) the amino acid substitution at the position corresponding with amino acid residue Arg-741 is with a Ser, Ala, Pro, Gln, or Thr residue; (xvi) the amino acid substitution at the position corresponding with amino acid residue Asn-743 is with a Ser, Thr, or Asp residue; (xvii) the amino acid substitution at the position corresponding with amino acid residue Ala-777 is with an Asn residue; (xviii) the amino acid substitution at the position corresponding with amino acid residue Tyr-848 is with a Glu residue; and/or (xix) the amino acid substitution at the position corresponding with amino acid residue Ile-1453 is with a Gly or Met residue.

3. The non-native glucosyltransferase of embodiment 1 or 2, comprising at least one amino acid substitution at a position corresponding with amino acid residue Gln-588, Arg-741, or Arg-722 of SEQ ID NO:62; optionally wherein: (i) the amino acid substitution at the position corresponding with amino acid residue Gln-588 is with a Leu residue; (ii) the amino acid substitution at the position corresponding with amino acid residue Arg-741 is with a Ser residue; and/or (iii) the amino acid substitution at the position corresponding with amino acid residue Arg-722 is with a His residue.

4. The non-native glucosyltransferase of embodiment 3, comprising two or more amino acid substitutions at positions corresponding with amino acid residues Gln-588, Arg-741, or Arg-722 of SEQ ID NO:62.

5. The non-native glucosyltransferase of embodiment 1, 2, 3, or 4, wherein the insoluble alpha-glucan produced by the non-native glucosyltransferase comprises at least about 50% alpha-1,3 linkages, and optionally wherein it has a weight average degree of polymerization ($DP_w$) of at least 100.

6. The non-native glucosyltransferase of embodiment 1, 2, 3, 4, or 5, wherein the insoluble alpha-glucan produced by the non-native glucosyltransferase has a $DP_w$ of at least 650.

7. The non-native glucosyltransferase of embodiment 5 or 6, comprising a catalytic domain that is at least about 90% identical to residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20.

8. The non-native glucosyltransferase of embodiment 5, 6, or 7, comprising an amino acid sequence that is at least about 90% identical to SEQ ID NO:4, SEQ ID NO:65, SEQ ID NO:30, SEQ ID NO:28, or SEQ ID NO:20.

9. The non-native glucosyltransferase of embodiment 1, 2, 3, 4, 5, 6, 7, or 8, wherein the insoluble alpha-glucan produced by the non-native glucosyltransferase comprises at least about 90% (or at least 95%) alpha-1,3 linkages.

10. The non-native glucosyltransferase of embodiment 1, 2, 3, 4, 5, 6, 7, 8, or 9, wherein the molecular weight of the insoluble alpha-glucan produced by the non-native glucosyltransferase is at least about 10% higher than the molecular weight of insoluble alpha-glucan synthesized by the second glucosyltransferase.

11. A polynucleotide comprising a nucleotide sequence encoding a non-native glucosyltransferase according to any one of embodiments 1-10, optionally wherein one or more regulatory sequences are operably linked to the nucleotide sequence, and preferably wherein the one or more regulatory sequences include a promoter sequence.

12. A reaction composition comprising water, sucrose, and a non-native glucosyltransferase according to any one of embodiments 1-10.

13. A method of producing insoluble alpha-glucan comprising: (a) contacting at least water, sucrose, and a non-native glucosyltransferase enzyme according to any one of embodiments 1-10, whereby insoluble alpha-glucan is produced; and (b) optionally, isolating the insoluble alpha-glucan produced in step (a).

14. A method of preparing a polynucleotide sequence encoding a non-native glucosyltransferase (e.g., of any one of embodiments 1-10), the method comprising: (a) identifying a polynucleotide sequence encoding a parent glucosyltransferase that (i) comprises an amino acid sequence that is at least about 40% identical to SEQ ID NO:4 or positions 55-960 of SEQ ID NO:4, and (ii) synthesizes insoluble alpha-glucan comprising 1,3-linkages; and (b) modifying the polynucleotide sequence identified in step (a) to substitute at least one amino acid of the parent glucosyltransferase at a position corresponding with amino acid residue Asn-531, Arg-534, Thr-563, Glu-567, Val-586, Gln-588, Ile-591, Lys-593, Ile-608, Ala-610, Leu-661, Arg-722, Thr-728, Met-732, Arg-741, Asn-743, Ala-777, Tyr-848, or Ile-1453 of SEQ ID NO:62, thereby providing a polynucleotide sequence encoding a non-native glucosyltransferase that synthesizes insoluble alpha-glucan with a molecular weight that is higher than the molecular weight of insoluble alpha-glucan synthesized by the parent glucosyltransferase.

15. The method of embodiment 14, wherein the identifying step is performed: (a) in silico, (b) with a method comprising a nucleic acid hybridization step, (c) with a method comprising a protein sequencing step, and/or (d) with a method comprising a protein binding step; and/or wherein the modifying step is performed: (e) in silico, followed by synthesis of the polynucleotide sequence encoding the non-native glucosyltransferase enzyme, or (f) using a physical copy of the polynucleotide sequence encoding the parent glucosyltransferase.

EXAMPLES

The present disclosure is further exemplified in the following Examples. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Analysis of Amino Acid Sites Affecting Glucosyltransferase Alpha-Glucan Product Molecular Weight This Example describes screening for glucosyltransferase variants that produce alpha-glucan with increased molecular weight. This screening was performed using a site evaluation library (SEL).

The amino acid sequence of the glucosyltransferase used to prepare amino acid substitutions in this Example was SEQ ID NO:4 (GTF 6855), which essentially is an N-terminally truncated (signal peptide and variable region removed) version of the full-length wild type glucosyltransferase (represented by SEQ ID NO:62) from *Streptococcus salivarius* SK126 (see Table 1). Substitutions made in SEQ ID NO:4 can be characterized as substituting for native amino acid residues, as each amino acid residue/position of SEQ ID NO:4 (apart from the Met-1 residue of SEQ ID NO:4) corresponds accordingly with an amino acid residue/position within SEQ ID NO:62. In reactions comprising at least sucrose and water, the glucosyltransferase of SEQ ID NO:4 typically produces alpha-glucan having about 100% alpha-1,3 linkages and a $DP_w$ of 400 or greater (e.g., refer to U.S. Pat. Nos. 8,871,474 and 9,169,506, and U.S. Pat. Appl. Publ. No. 2017/0002336, which are incorporated herein by reference). This alpha-glucan product, which is insoluble, can be isolated following enzymatic synthesis via filtration, for example.

To summarize this Example, GTF 6855 variants (each with a single amino acid substitution) from SELs were each bacterially expressed, purified, and normalized to a concentration of 100 ppm. Each enzyme preparation was then screened (in triplicate) using sucrose as substrate in alpha-1,3-glucan synthesis reactions. Alpha-1,3-glucan polymer obtained in each reaction was analyzed for length ($DP_w$) using size exclusion chromatography (SEC).

Plasmids for individually expressing various single amino acid-substituted variants of GTF 6855 (SEQ ID NO:4) in a *Bacillus subtilis* host were prepared. Such plasmids were prepared as follows. A DNA expression cassette having (operably linked in 5'-to-3' order) the *B. subtilis* aprE promoter, a codon-optimized sequence encoding SEQ ID NO:4 (GTF 6855), and a BPN' terminator was synthesized. This expression cassette was cloned into the pHYT replicating shuttle vector (forming pHYT-GTF6855) and transformed into *B. subtilis* CBS12-1. The pHYT vector was derived from pHY300PLK (Takara) by adding a terminator sequence (SEQ ID NO:67) after the tetracycline resistance gene using the BstEII and EcoRI sites. The HindIII site in pHY300PLK had been removed by cloning a linker sequence (not shown) into the BamHI and HindIII sites. The pHYT-GTF6855 plasmid was amplified and used for generating SELs. The resulting plasmids encoding single-amino acid substituted GTFs were sequenced to verify each substitution.

To produce GTF 6855 (SEQ ID NO:4) and single amino acid-substituted variants thereof, *B. subtilis* individually transformed with pHYT-GTF6855 or mutated versions thereof were cultivated in Tryptone Soya Broth (Oxoid Ltd., UK) and Grant's II medium. Heart infusion agar plates (Difco Laboratories, MI) were used to select transformants. Plasmid integrity was maintained by the addition of 25 µg/mL tetracycline. Each GTF targeted for expression was detected in the growth medium after incubation for about 6 hours at 37° C. After centrifugation and filtration, culture supernatants with expressed GTF were obtained. GTF enzyme present in the supernatant was purified to apparent homogeneity by affinity chromatography using washed (2×MILLIQ 1×25 mM $NaH_2PO_4$ pH 5.7 with intermediate centrifugation steps 100×g) SUPERDEX 200 resin (GE Healthcare). Each GTF was eluted with a 15% solution of Dextran T1 (Pharmacosmos) in 25 mM $NaH_2PO_4$ pH 5.7 by centrifugation 100×g. Each purified GTF was dialyzed against 25 mM $NaH_2PO_4$ pH 5.7 buffer (at least 100×) using a Harvard Apparatus 96-well DISPODIALYZER (10000-Dalton MWCO).

After dialysis, GTF enzyme concentration was determined by OD280 using purified GTF 6855 as a standard. Normalization of each purified GTF to 100 ppm was achieved by diluting appropriately with 25 mM $NaH_2PO_4$ pH 5.7. Protein concentration for each sample was confirmed using an AGILENT 1200 (Agilent Technologies) HPLC equipped with an AGILENT BIO SEC3 guard-column column (3 µm 100 Å (4.6×50 mm). Five (5) µL of sample was injected onto the column for each determination. Compounds were eluted with isocratic flow of 25 mM $KH_2PO_4$ pH 6.8+0.1 M NaCl for 1.3 min at 0.5 mL/min flow rate.

Each GTF (GTF 6855 and each variant thereof) was entered into a reaction with sucrose to produce alpha-glucan. Each reaction was performed as follows: 37.5 µL of 100 ppm enzyme sample (ppm based on a BSA calibration curve) was added to 262.5 µL of 86 g/L sucrose (75 g/L final) in 20 mM $Na_2HPO_4/NaH_2PO_4$ pH 5.7 and incubated overnight (about 20 hours) at 30° C. After this incubation, each reaction was quenched by incubation for 1 hour at 80° C. Appropriate analyses indicated that each variant enzyme listed in Table 3 below was able to perform a glucosyltransferase reaction producing alpha-1,3-glucan (data not shown).

A 100-µL aliquot of each quenched reaction was diluted 20× in DMSO/2% LiCl and filtered via centrifugation through a 0.2-µm PALL GHP membrane (4000 g×30 min× 30° C.) in preparation for SEC analysis. Alpha-1,3-glucan polymer size was approximated using a WATERS APC-SEC system equipped with a WATERS ACQUITY APC-XT 450-A 2.5-µm 4.6×30 mm column. The column was held at 55° C. with a flow-rate of 0.65 mL/min of DMSO/0.25% LiCl mobile-phase. Dextran analytical standards with molecular weights of 80, 165, 325 and 750 kD were used to approximate alpha-1,3-glucan $DP_w$'s of 280, 480, 660 and 880, respectively, via elution peak apexes.

The molecular weight ($DP_w$) and polydispersity index (PDI) of alpha-1,3-glucan produced in each reaction (~20 hours) as measured via the above methodology are provided in Table 3.

TABLE 3

Insoluble Alpha-1,3-Glucan Produced by GTF 6855 (SEQ ID NO: 4) and Single Amino Acid-Substituted Variants thereof

| GTF | Alpha-1,3-Glucan | |
|---|---|---|
| | $DP_w$ | PDI |
| Plate 1[a] | | |
| 6855[b] | 611 | 2.2 |
| 6855[b] | 635 | 2.1 |
| 6855[b] | 633 | 2.1 |
| 6855[b] | 626 | 2.1 |
| V186A[c] | 589 | 2.0 |
| V186M | 580 | 2.0 |
| E194C | 580 | 2.3 |
| L434N | 613 | 2.2 |
| A472C | 530 | 1.8 |
| A472S | 374 | 2.2 |
| A510E | 654 | 2.0 |
| A510I | 621 | 2.1 |
| A510V | 655 | 2.1 |
| M529L | 558 | 2.1 |
| R534G | 711 | 2.2 |
| R534I | 789 | 2.3 |
| R534L | 763 | 2.3 |
| R534M | 776 | 2.2 |
| G576H | 436 | 2.3 |
| Q588L | 817 | 2.1 |
| I591K | 816 | 2.0 |
| I591R | 832 | 2.0 |
| Y605W | 524 | 1.9 |
| F607N | 561 | 2.0 |
| F607W | 624 | 2.0 |
| A610C | 799 | 2.4 |
| N613I | 555 | 2.1 |
| N613M | 587 | 2.1 |
| N613T | 526 | 2.0 |
| N613V | 578 | 2.0 |
| K625A | 638 | 2.3 |
| K625M | 623 | 2.2 |
| A510E | 622 | 2.0 |
| S631T | 532 | 2.1 |
| T635H | 539 | 2.1 |
| T635W | 528 | 2.1 |
| I636H | 521 | 2.1 |
| Y848E | 843 | 2.0 |
| D947G | 408 | 2.1 |
| F951Y | 325 | 2.0 |
| E849M | 610 | 2.4 |

TABLE 3-continued

Insoluble Alpha-1,3-Glucan Produced by GTF 6855 (SEQ ID NO: 4) and Single Amino Acid-Substituted Variants thereof

| GTF | Alpha-1,3-Glucan $DP_w$ | PDI |
|---|---|---|
| Q1007A | 394 | 1.9 |
| D1003G | 486 | 2.1 |
| A1022M | 303 | 1.8 |
| D1028L | 416 | 1.9 |
| D1028Q | 537 | 2.1 |
| A1057H | 624 | 2.3 |
| N1096A | 562 | 2.2 |
| Y1104M | 611 | 2.2 |
| N1122K | 614 | 2.3 |
| E1132A | 589 | 2.2 |
| E1132H | 611 | 2.2 |
| E1132K | 610 | 2.2 |
| E1132R | 622 | 2.1 |
| V1135K | 612 | 2.3 |
| V1188E | 641 | 2.2 |
| L1212N | 630 | 2.0 |
| E1250R | 606 | 2.0 |
| T1381E | 612 | 2.1 |
| T1431M | 625 | 2.0 |
| A1442R | 609 | 2.0 |
| E1450F | 611 | 2.0 |
| E1450W | 618 | 2.0 |
| Dead[d] | | |
| Blank[e] | | |
| Blank[e] | | |
| Plate 2[a] | | |
| 6855[b] | 622 | 2.1 |
| 6855[b] | 628 | 2.1 |
| 6855[b] | 634 | 2.1 |
| 6855[b] | 619 | 2.2 |
| I1453M[c] | 635 | 2.1 |
| V1491F | 604 | 2.0 |
| P1499Y | 587 | 2.0 |
| Y219C | 591 | 2.0 |
| E243H | 631 | 2.1 |
| A377I | 514 | 2.1 |
| I411F | 586 | 2.3 |
| I411S | 591 | 2.1 |
| D425Q | 681 | 2.1 |
| L428V | 577 | 2.0 |
| M529N | 560 | 2.1 |
| N531G | 977 | 2.2 |
| G576R | 416 | 1.8 |
| Y580H | 554 | 2.1 |
| K593M | 792 | 1.9 |
| I608Y | 708 | 1.9 |
| N613G | 644 | 2.0 |
| N613L | 618 | 2.0 |
| D617E | 419 | 2.1 |
| E621T | 603 | 2.1 |
| I627W | 506 | 2.2 |
| S631D | 521 | 2.0 |
| S631E | 545 | 2.0 |
| S631R | 521 | 2.1 |
| G633W | 493 | 2.2 |
| F634A | 523 | 2.1 |
| T635E | 561 | 2.2 |
| T635I | 648 | 2.1 |
| T635Y | 518 | 2.1 |
| R722H | 793 | 2.5 |
| T728S | 769 | 2.4 |
| M732L | 791 | 2.4 |
| A777N | 755 | 2.4 |
| A510E | 625 | 2.2 |
| N904E | 554 | 2.5 |
| K930G | 637 | 2.5 |
| K930V | 582 | 2.3 |
| D947F | 619 | 2.6 |
| D947I | 610 | 2.4 |
| D947K | 559 | 2.5 |
| D947N | 635 | 2.6 |
| D947Q | 635 | 2.9 |
| D947S | 603 | 2.7 |
| D947V | 621 | 2.5 |
| D947Y | 624 | 2.6 |
| Q1007S | 578 | 2.6 |
| D1003N | 570 | 2.6 |
| I1026H | 621 | 2.6 |
| D1028A | 568 | 2.1 |
| D1028M | 535 | 2.1 |
| V1037A | 591 | 2.2 |
| K1041A | 583 | 2.1 |
| K1041M | 648 | 2.3 |
| D1080M | 554 | 2.2 |
| F1244P | 589 | 2.2 |
| F1244Q | 534 | 1.9 |
| E1250H | 553 | 2.1 |
| E1250K | 591 | 2.2 |
| T1431Q | 663 | 2.2 |
| E1450D | 585 | 2.2 |
| G1484P | 627 | 2.2 |
| I1453G | 881 | 2.1 |
| W1437N | 654 | 2.3 |
| R722N | 766 | 2.2 |
| Dead[d] | | |
| Blank[e] | | |
| Blank[e] | | |

[a]Glucan synthesis reactions were run in microtiter plate format (two plates).
[b]GTF 6855, SEQ ID NO: 4. Reactions with this GTF were run in quadruplicate per plate.
[c]Each listed GTF with a substitution is a version of GTF 6855 comprising a substitution at a respective position, where the position number is in correspondence with the residue numbering of SEQ ID NO: 62. The wild type residue is listed first (before residue position number) and the substituting residue is listed second (after the residue position number) (this "wild type residue-position number-variant residue" annotation format applies throughout the present disclosure).
[d]GTF with destroyed activity was entered into the reaction. Alpha-1,3-glucan was not detected.
[e]No GTF was added to the reaction. Alpha-1,3-glucan was not detected.

Based on the data in Table 3, individual substitutions at amino acid positions Y848, I591, Q588, A610, R534, N531, I1453, K593, M732, T728, R722, A777, and I608, for example, in GTF 6855 (SEQ ID NO:4) each result in an enzyme that produces insoluble alpha-1,3-glucan with a $DP_w$ at least 10% greater than the average $DP_w$ of insoluble alpha-1,3-glucan produced by the parent non-substituted enzyme (GTF 6855, SEQ ID NO:4). Interestingly, these higher $DP_w$ alpha-1,3-glucan products generally had a PDI that was the same as, or similar to, the average PDI (2.1-2.2) of alpha-1,3-glucan produced by the parent non-substituted enzyme (GTF 6855, SEQ ID NO:4), meaning that the increase in molecular weight likely did not compromise polymer uniformity.

In a similar SEL study (not all data shown), individual substitutions in GTF 6855 (SEQ ID NO:4) at the following amino acid positions appeared to also have an enhancing effect on insoluble alpha-1,3-glucan molecular weight (substituting residue, resulting $DP_w$): N614 (P, 1054), R609 (H, 1052), F424 (A, 1051; V, 1023; L, 942; E, 937; Q, 725), W511 (Y, 1020), N475 (Q, 975; S, 954), A610 (T, 972; C, 959), Y848 (E, 922), N1214 (L, 918; I, 863), N531 (L, 879; M, 724; G, 714), I591 (K, 840; R, 824), R534 (K, 759), Q588 (L, 734), and R722 (H, 701) (non-substituted GTF 6855 produced insoluble alpha-1,3-glucan with $DP_w$ 487).

One or more substitutions at any of the foregoing sites in this example are expected to allow for production of insoluble alpha-1,3-glucan with a $DP_w$ significantly higher than the $DP_w$ of alpha-1,3-glucan produced by a parent non-substituted glucosyltransferase.

Example 2

Generating Glucosyltransferase Variants that Produce Alpha-Glucan Products of Higher Molecular Weight This Example describes another screening for glucosyltransferase variants that produce alpha-glucan with increased molecular weight.

Saturation mutagenesis was performed on GTF 6855 (SEQ ID NO:4) to provide a multitude of single amino acid-substituted variants of this glucosyltransferase. Each variant was entered into a glucan synthesis reaction with parameters that were the same as, or similar to, the following: vessel, 250-mL bottom-indented shake flask agitated at 120 rpm; initial pH, 5.7; reaction volume, 50 mL; sucrose, 75 g/L; GTF, 1.5 mL lysate of E. coli cells heterologously expressing enzyme; $KH_2PO_4$, 5 mM; temperature, 30° C.; time, about 20 hours. The molecular weight ($DP_w$) of alpha-1,3-glucan produced in each reaction (as measured via SEC methodology similar to that disclosed in Example 1) is provided in Table 4.

TABLE 4

Molecular Weight of Insoluble Alpha-1,3-Glucan Produced by GTF 6855 (SEQ ID NO: 4) and Single Amino Acid-Substituted Variants thereof

| GTF | Alpha-1,3-Glucan $DP_w$ |
|---|---|
| 6855[a] | 558 |
| E567Q | 1001 |
| I591V | 859 |
| L661P | 842 |
| N743D | 700 |
| N743S | 937 |
| N743T | 874 |
| R741A | 831 |
| R741P | 871 |
| R741Q | 886 |
| R741S | 887 |
| R741T | 693 |
| T563A | 910 |
| V586T | 874 |

[a]GTF 6855, SEQ ID NO: 4. The reaction with this GTF was performed separately under the same conditions as described above.

Based on the data in Table 4, it is apparent, for example, that each listed single amino acid substitution in GTF 6855 (SEQ ID NO:4) results in an enzyme that produces insoluble alpha-1,3-glucan with increased molecular weight ($DP_w$). Thus, one or more substitutions at the positions indicated in Table 4 are expected to allow for production of insoluble alpha-1,3-glucan with a $DP_w$ significantly higher than the $DP_w$ of alpha-1,3-glucan produced by a parent non-substituted glucosyltransferase.

Example 3

Analysis of the Effects of Amino Acid Substitution Combinations on Glucosyltransferase Alpha-Glucan Synthesis Activity This Example describes the effects of introducing multiple amino acid substitutions to a glucosyltransferase and determining their effect on its alpha-glucan synthesis function. This analysis indicates, for example, that amino acid substitutions identified above to enhance alpha-glucan product molecular weight can be included in substitution combinations that likewise impart this molecular weight enhancement.

Briefly, certain combinations of amino acid substitutions were made to SEQ ID NO:4 (GTF 6855, see Table 1 and Example 1 for description of this glucosyltransferase) by site-directed mutagenesis of appropriate DNA templates contained in a plasmid. The plasmid sequences encoding each modified glucosyltransferase were individually sequenced to confirm the intended codon changes. Each combination of substitutions is listed in Table 5 below; appropriate analyses indicated that each modified enzyme was able to perform a glucosyltransferase reaction producing alpha-1,3-glucan (data not shown).

Expression plasmids encoding the modified glucosyltransferases were individually used to transform a B. subtilis strain containing nine protease deletions (amyE::xylRPxylAcomK-ermC, degUHy32, oppA, ΔspoIIE3501, ΔaprE, ΔnprE, Δepr, ΔispA, Δbpr, Δvpr, ΔwprA, Δmpr-ybfJ, ΔnprB). Transformed cells were spread onto LB plates supplemented with 5 μg/mL chloramphenicol. Colonies growing on these plates were streaked several times onto LB plates with 25 μg/mL chloramphenicol. Each resulting Bacillus strain for expressing a particular variant glucosyltransferase was then grown for 6-8 hours in LB medium containing 25 μg/mL chloramphenicol, and then subcultured into Grants II medium at 30° C. for 2-3 days. The cultures were spun at 15000 g for 30 minutes at 4° C., and the supernatants were filtered through 0.22-μm filters. The filtered supernatants, each of which contained an expressed secreted variant glucosyltransferase, were aliquoted and frozen at −80° C., and later used (below) for analyzing alpha-1,3-glucan synthesis activity.

The same amount of each variant enzyme, activity-wise, was entered into a glucan synthesis reaction with parameters that were the same as, or similar to, the following: vessel, 500-mL jacketed reactor with Teflon®-pitched blade turbine (45-degree angle) on a glass stir rod and agitated at 50-200 rpm; initial pH, 5.5; reaction volume, 500 mL; sucrose, 108 g/L; $KH_2PO_4$, 1 mM; temperature, 39° C.; time, about 18-24 hours; filtrate from a previous alpha-1,3-glucan synthesis reaction, 50 vol %. The molecular weight ($DP_w$) of alpha-1,3-glucan produced in each reaction (as measured via methodology similar to that disclosed in Example 1) is provided in Table 5.

TABLE 5

Alpha-1,3 Glucan Products of GTF 6855 (SEQ ID NO: 4) Variants with Multiple Amino Acid Substitutions

| GTF[a] | | | | | | | | | | Alpha-1,3-Glucan[b] $DP_w$ |
|---|---|---|---|---|---|---|---|---|---|---|
| A510D | Q588L | F607Y | R741S | D948G | R722H | T877K | | M1253I | K1277N | 844 |
| A510D | Q588L | F607Y | R741S | D948G | R722H | T877K | V1188E | M1253I | Q957P | 744 |
| A510D | Q588L | F607Y | R741S | D948G | | T877K | V1188E | M1253I | Q957P | 812 |
| A510D | Q588L | F607Y | R741S | D948G | | | | M1253I | | 750 |
| A510D | Q588L | F607W | R741S | D948G | | | | | | 752 |

TABLE 5-continued

Alpha-1,3 Glucan Products of GTF 6855 (SEQ ID NO: 4) Variants with Multiple Amino Acid Substitutions

| GTF[a] | | | | | | | | | | | | | Alpha-1,3-Glucan[b] DP$_w$ |
|---|---|---|---|---|---|---|---|---|---|---|---|---|---|
| | Q588L | F607Y | R741S | D948G | | | | | | | | | 705 |
| A510D | Q588L | F607Y | R741S | D948G | N628D | T635A | | T877K | | M1253I | F929L | R1172C | 855 |
| A510D | Q588L | F607W | R741S | D948G | S631T | S710G | R722H | T877K | V1188E | M1253I | | | 863 |
| A510D | Q588L | F607W | R741S | D948G | S631T | S710G | R722H | T877K | V1188E | | | | 812 |
| A510D | Q588L | F607W | R741S | D948G | S631T | S710G | | T877K | V1188E | M1253I | | | 727 |
| A510D | Q588L | F607Y | R741S | D948G | | | | | | | | | 697 |
| A510D | Q588L | F607Y | R741S | D948G | | | | | V1188E | | | | 703 |
| A510D | Q588L | F607W | R741S | D948G | S631T | S710G | | | V1188E | | | | 676 |
| A510D | Q588L | F607W | R741S | D948G | | S710G | R722H | T877K | | M1253I | | | 963 |
| A510D | Q588L | F607Y | R741S | D948G | S631T | | R722H | T877K | V1188E | M1253I | | | 906 |
| A510D | Q588L | F607W | R741S | D948G | S631T | | | T877K | V1188E | M1253I | | | 781 |
| A510D | Q588L | F607W | R741S | D948G | S631T | | | | V1188E | | | | 687 |
| A510D | Q588L | F607Y | R741S | D948G | S631T | | R722H | T877K | V1188E | M1253I | | | 961 |
| A510D | Q588L | F607W | R741S | D948G | | | | | V1188E | M1253I | | | 781 |

[a] Each listed GTF is a version of GTF 6855 (SEQ ID NO: 4) comprising substitutions at respective positions, where each position number is in correspondence with the residue numbering of SEQ ID NO: 62.
[b] Insoluble alpha-1,3-glucan product.

Based on the data in Table 5, it is apparent that introduction of multiple amino acid substitutions to GTF 6855 (SEQ ID NO:4), including substitutions that enhance molecular weight, can be employed in efforts to produce higher molecular weight insoluble alpha-1,3-glucan; for example, compare these DP$_w$ values to those of GTF 6855 (SEQ ID NO:4) without substitutions shown in Table 3.

It is apparent, for example, that a glucosyltransferase with multiple substitutions, including those at positions corresponding to positions Gln-588, Arg-741, and/or Arg-722 of SEQ ID NO:62, can increase the molecular weight of insoluble alpha-glucan produced by the glucosyltransferase.

What is claimed is:

1. A non-native glucosyltransferase comprising at least one amino acid substitution at a position corresponding with amino acid residue Asn-531, Arg-534, Thr-563, Gln-588, Ile-591, Lys-593, Ile-608, Ala-610, Leu-661, Arg-722, Thr-728, Met-732, Arg-741, Tyr-848, or Ile-1453 of SEQ ID NO:62, wherein the non-native glucosyltransferase synthesizes insoluble alpha-glucan comprising 1,3-linkages, and the molecular weight of said insoluble alpha-glucan is higher than the molecular weight of insoluble alpha-glucan synthesized by a second glucosyltransferase that only differs from the non-native glucosyltransferase at the substitution position(s);

wherein the non-native glucosyltransferase comprises a catalytic domain that is at least 90% identical to residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20.

2. The non-native glucosyltransferase of claim 1, wherein:
(i) the amino acid substitution at the position corresponding with amino acid residue Asn-531 is with a Gly, Leu, or Met residue;
(ii) the amino acid substitution at the position corresponding with amino acid residue Arg-534 is with a Lys, Gly, Ile, Leu, or Met residue;
(iii) the amino acid substitution at the position corresponding with amino acid residue Thr-563 is with an Ala residue;
(iv) the amino acid substitution at the position corresponding with amino acid residue Gln-588 is with a Leu residue;
(v) the amino acid substitution at the position corresponding with amino acid residue Ile-591 is with a Val, Lys, or Arg residue;
(vi) the amino acid substitution at the position corresponding with amino acid residue Lys-593 is with a Met residue;
(vii) the amino acid substitution at the position corresponding with amino acid residue Ile-608 is with a Tyr residue;
(viii) the amino acid substitution at the position corresponding with amino acid residue Ala-610 is with a Cys or Thr residue;
(ix) the amino acid substitution at the position corresponding with amino acid residue Leu-661 is with a Pro residue;
(x) the amino acid substitution at the position corresponding with amino acid residue Arg-722 is with a His or Asn residue;
(xi) the amino acid substitution at the position corresponding with amino acid residue Thr-728 is with a Ser residue;
(xii) the amino acid substitution at the position corresponding with amino acid residue Met-732 is with a Leu residue;
(xiii) the amino acid substitution at the position corresponding with amino acid residue Arg-741 is with a Ser, Ala, Pro, Gln, or Thr residue;
(xiv) the amino acid substitution at the position corresponding with amino acid residue Tyr-848 is with a Glu residue; and/or
(xv) the amino acid substitution at the position corresponding with amino acid residue Ile-1453 is with a Gly or Met residue.

3. The non-native glucosyltransferase of claim 1, comprising at least one amino acid substitution at a position corresponding with amino acid residue Gln-588, Arg-741, or Arg-722 of SEQ ID NO:62.

4. The non-native glucosyltransferase of claim 3, comprising two or more amino acid substitutions at positions corresponding with amino acid residues Gln-588, Arg-741, or Arg-722 of SEQ ID NO:62.

5. The non-native glucosyltransferase of claim 1, wherein the insoluble alpha-glucan comprises at least 50% alpha-1,3 linkages.

6. The non-native glucosyltransferase of claim 5, wherein the insoluble alpha-glucan has a $DP_w$ of at least 100.

7. The non-native glucosyltransferase of claim 1, comprising a catalytic domain that is at least 92% identical to residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20.

8. The non-native glucosyltransferase of claim 1, comprising an amino acid sequence that is at least 90% identical to SEQ ID NO:4, SEQ ID NO:65, SEQ ID NO:30, SEQ ID NO:28, or SEQ ID NO:20.

9. The non-native glucosyltransferase of claim 5, wherein the insoluble alpha-glucan comprises at least 90% alpha-1,3 linkages.

10. The non-native glucosyltransferase of claim 1, wherein the molecular weight of said insoluble alpha-glucan is at least 10% higher than the molecular weight of insoluble alpha-glucan synthesized by said second glucosyltransferase.

11. A polynucleotide comprising a nucleotide sequence encoding a non-native glucosyltransferase according to claim 1, wherein one or more regulatory sequences are operably linked to the nucleotide sequence.

12. A reaction composition comprising water, sucrose, and a non-native glucosyltransferase according to claim 1.

13. A method of producing insoluble alpha-glucan comprising:
   contacting at least water, sucrose, and a non-native glucosyltransferase enzyme according to claim 1, whereby insoluble alpha-glucan is produced.

14. The method of claim 13, wherein the method further comprises isolating the insoluble alpha-glucan.

15. The polynucleotide of claim 11, wherein said one or more regulatory sequences include a promoter sequence.

16. The non-native glucosyltransferase of claim 3, wherein:
   (i) the amino acid substitution at the position corresponding with amino acid residue Gln-588 is with a Leu residue,
   (ii) the amino acid substitution at the position corresponding with amino acid residue Arg-741 is with a Ser residue, and/or
   (iii) the amino acid substitution at the position corresponding with amino acid residue Arg-722 is with a His residue.

17. The non-native glucosyltransferase of claim 16, comprising two or more amino acid substitutions at positions corresponding with amino acid residues Gln-588, Arg-741, or Arg-722 of SEQ ID NO:62.

18. The non-native glucosyltransferase of claim 6, wherein the insoluble alpha-glucan has a $DP_w$ of at least 650.

19. The non-native glucosyltransferase of claim 7, comprising a catalytic domain that is at least 95% identical to residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20.

20. The non-native glucosyltransferase of claim 19, comprising a catalytic domain that is at least 95% identical to residues 55-960 of SEQ ID NO:4 or residues 54-957 of SEQ ID NO:65.

21. The non-native glucosyltransferase of claim 19, comprising a catalytic domain that is at least 97% identical to residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20.

22. The non-native glucosyltransferase of claim 21, comprising a catalytic domain that is at least 97% identical to residues 55-960 of SEQ ID NO:4 or residues 54-957 of SEQ ID NO:65.

23. The non-native glucosyltransferase of claim 8, comprising an amino acid sequence that is at least 92% identical to SEQ ID NO:4, SEQ ID NO:65, SEQ ID NO:30, SEQ ID NO:28, or SEQ ID NO:20.

24. The non-native glucosyltransferase of claim 23, comprising an amino acid sequence that is at least 95% identical to SEQ ID NO:4, SEQ ID NO:65, SEQ ID NO:30, SEQ ID NO:28, or SEQ ID NO:20.

25. The non-native glucosyltransferase of claim 24, comprising an amino acid sequence that is at least 95% identical to SEQ ID NO:4 or SEQ ID NO:65.

26. The non-native glucosyltransferase of claim 24, comprising an amino acid sequence that is at least 97% identical to SEQ ID NO:4, SEQ ID NO:65, SEQ ID NO:30, SEQ ID NO:28, or SEQ ID NO:20.

27. The non-native glucosyltransferase of claim 26, comprising an amino acid sequence that is at least 97% identical to SEQ ID NO:4 or SEQ ID NO:65.

* * * * *